US012790346B2

(12) United States Patent
Yi et al.

(10) Patent No.: US 12,790,346 B2
(45) Date of Patent: Nov. 10, 2026

(54) SUBSTITUTED PYRAZINE COMPOUND, PHARMACEUTICAL COMPOSITION COMPRISING SAME, AND USE THEREOF

(71) Applicant: Sichuan Kelun-Biotech Biopharmaceutical Co., Ltd., Chengdu (CN)

(72) Inventors: Lei Yi, Chengdu (CN); Qiang Tian, Chengdu (CN); Shoujun Chen, Chengdu (CN); Liqiang Song, Chengdu (CN); Taijin Wang, Chengdu (CN); Qian Liu, Chengdu (CN); Yong Ge, Chengdu (CN); Yu Yang, Chengdu (CN); Huiping Chen, Chengdu (CN); Hongmei Song, Chengdu (CN); Jingyi Wang, Chengdu (CN)

(73) Assignee: Sichuan Kelun-Biotech Biopharmaceutical Co., Ltd. (CN)

( * ) Notice: Subject to any disclaimer, the term of this patent is extended or adjusted under 35 U.S.C. 154(b) by 833 days.

(21) Appl. No.: 17/926,763

(22) PCT Filed: Jun. 11, 2021

(86) PCT No.: PCT/CN2021/099561

§ 371 (c)(1),
(2) Date: Nov. 21, 2022

(87) PCT Pub. No.: WO2021/259077

PCT Pub. Date: Dec. 30, 2021

(65) Prior Publication Data

US 2023/0212180 A1 Jul. 6, 2023

(30) Foreign Application Priority Data

Jun. 22, 2020 (CN) ........................ 202010576572.X
Nov. 27, 2020 (CN) ........................ 202011359022.9

(51) Int. Cl.
*C07D 491/107* (2006.01)
*A61P 35/00* (2006.01)
(Continued)

(52) U.S. Cl.
CPC .......... *C07D 491/107* (2013.01); *A61P 35/00* (2018.01); *C07D 401/14* (2013.01); *C07D 471/10* (2013.01); *C07D 491/20* (2013.01)

(58) Field of Classification Search
CPC C07D 491/107; C07D 401/14; C07D 471/10; C07D 491/20; C07D 498/10; C07D 513/10; A61P 35/00
See application file for complete search history.

(56) References Cited

U.S. PATENT DOCUMENTS

2021/0355105 A1* 11/2021 Liu ..................... C07D 413/14

FOREIGN PATENT DOCUMENTS

CN 105899493 A 8/2016
CN 107922388 A 4/2018
(Continued)

OTHER PUBLICATIONS

Extended European Search Report in European Appln No. 21829137.5, dated Sep. 27, 2024, 14 pages.
(Continued)

*Primary Examiner* — Savitha M Rao
*Assistant Examiner* — Elena V Vishnyakova
(74) *Attorney, Agent, or Firm* — Fish & Richardson P.C.

(57) ABSTRACT

The present invention belongs to the field of pharmaceutical chemistry, and relates to a substituted pyrazine compound, a pharmaceutical composition comprising same, and the use thereof. In particular, the present invention relates to a compound with the structure of formula (I), which exhibits a good SHP2 inhibiting activity, and can act as an efficient SHP2 inhibitor for preventing and/or treating SHP2-related diseases.

(Continued)

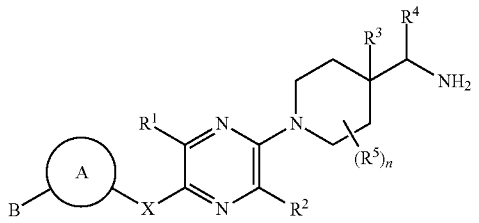

I

8 Claims, 1 Drawing Sheet

(51) Int. Cl.

| | |
|---|---|
| ***C07D 401/14*** | (2006.01) |
| ***C07D 471/10*** | (2006.01) |
| ***C07D 491/20*** | (2006.01) |

(56) References Cited

FOREIGN PATENT DOCUMENTS

| | | | | | |
|---|---|---|---|---|---|
| CN | 109415360 | A | | 3/2019 | |
| CN | 111212834 | A | | 5/2020 | |
| JP | 2017503000 | A | | 1/2017 | |
| JP | 2018517752 | A | | 7/2018 | |
| JP | 2019518033 | A | | 6/2019 | |
| JP | 2019521181 | A | | 7/2019 | |
| JP | 2020504136 | A | | 2/2020 | |
| WO | WO 2015107494 | A1 | | 7/2015 | |
| WO | WO 2015107495 | A1 | | 7/2015 | |
| WO | WO 2016203406 | A1 | | 12/2016 | |
| WO | WO 2017216706 | A1 | | 12/2017 | |
| WO | WO 2018013597 | A1 | | 1/2018 | |
| WO | WO2018218133 | A1 | | 11/2018 | |
| WO | WO 2019075265 | A1 | | 4/2019 | |
| WO | WO 2019182960 | A1 | | 9/2019 | |
| WO | WO-2020061101 | A1 | * | 3/2020 | ............. C07D 19/00 |
| WO | WO 2020073949 | A1 | | 4/2020 | |
| WO | WO 2020076723 | A1 | | 4/2020 | |
| WO | WO2020177653 | A1 | | 9/2020 | |

OTHER PUBLICATIONS

International Search Report and Written Opinion in International Appln. No. PCT/CN2021/099561, mailed on Sep. 8, 2021, 18 pages (with English translation).

Office Action in Japanese Appln. No. 2022-571308, dated Apr. 15, 2025, 11 pages (with English translation).

* cited by examiner

SUBSTITUTED PYRAZINE COMPOUND, PHARMACEUTICAL COMPOSITION COMPRISING SAME, AND USE THEREOF

CROSS-REFERENCE TO RELATED APPLICATION

The present disclosure claims the priority to and the benefits of Chinese patent application No. 202010576572.X, filed on Jun. 22, 2020, entitled "SUBSTITUTED PYRAZINE COMPOUND, PHARMACEUTICAL COMPOSITION COMPRISING SAME, AND USE THEREOF", and Chinese patent application No. 202011359022.9, filed on Nov. 27, 2020, entitled "SUBSTITUTED PYRAZINE COMPOUND, PHARMACEUTICAL COMPOSITION COMPRISING SAME, AND USE THEREOF", the disclosures of which are incorporated herein by reference in their entirety.

TECHNICAL FIELD

The present disclosure pertains to the field of medicinal chemistry, and relates to a substituted pyrazine compound used as an inhibitor of SHP2 (arc homology 2 domain-containing phosphotyrosine phosphatase 2), a pharmaceutical composition comprising the same, and medicinal use thereof for preventing and/or treating SHP2-associated diseases.

BACKGROUND

Among protein tyrosine phosphatases (PTPs), SHP2 encoded by the gene PTPN11 (protein tyrosine phosphatase nonreceptor 11) is a member of intracellular protein tyrosine phosphatases, non-receptor type, of the PTPs family. SHP2 catalyzes dephosphorylation of tyrosine in protein. SHP2 has two SH2 (src homology 2) domains (N-SH2 at N-terminal and C-SH2 at C-terminal), a catalytic phosphatase domain (PTP), and a C-terminal tail enriched with proline residues and tyrosine phosphorylation sites. These two SH2 domains control the subcellular localization and functional regulation of SHP2. In an inactive state, SHP2 adopts an autoinhibition station, and the N-SH2 and the PTP are bonded to each other, thereby inhibiting the activity of phosphatase. When stimulated by growth factors, cytokines, or inflammatory factors, e.g., PDGF (platelet-derived growth factor) and FGF (fibroblast growth factor), however, Tyr542 (Y542) and Tyr580 (Y580) as tyrosine residues are phosphorylated and bonded to N-SH2, and the catalytically active sites of the PTP domain are consequently exposed. Then the autoinhibition station is relieved and the SHP2 PTP activity is activated, thereby inducing a signaling cascade initiated by tyrosine phosphorylation.

SHP2 is widely expressed in the human body and is involved in multiple signaling pathways such as Ras-Erk, PI3K-Akt, Jak-Stat, Met, FGFR, EGFR, and NF-kB, thereby regulating cell proliferation, differentiation, migration, apoptosis, and other physiological functions. The activated mutants of SHP2 are associated with the occurrence of various diseases, such as Noonan syndrome, breast cancer, and melanoma, and the overexpression of SHP2 increases the risk of cancer such as chronic myelocytic leukemia, mastocytosis, malignant glioma, lung cancer, and breast cancer, suggesting that SHP2 acts extensively both in different types of cancer and in different stages of cancer development. There is thus a need to prevent and/or treat cancer and other associated diseases with SHP2 inhibitors.

At present, it has been found that compounds such as pyrimidones, pyrazines, carboxylic acids, quinones, quinolines, and indoles have a function of inhibiting SHP2 activity (see, e.g., WO2018013597A1). However, there still remains a need for novel SHP2 inhibitors, in particular an SHP2 inhibitor with high activity and other excellent properties.

SUMMARY

Technical Problem

After a large number of studies, it has been surprisingly found that a series of substituted pyrazine compounds of the present disclosure has a higher inhibitory activity against SHP2. As SHP2 inhibitors, the compounds can be used to prevent and/or treat SHP2-associated diseases, especially tumor diseases, showing good application prospects.

Solution to the Problem

In the first aspect, the present disclosure provides a compound having a structure of formula I or a pharmaceutically acceptable salt, ester, stereoisomer, tautomer, polymorph, solvate, isotope-labelled compound, metabolite, or prodrug thereof,

I

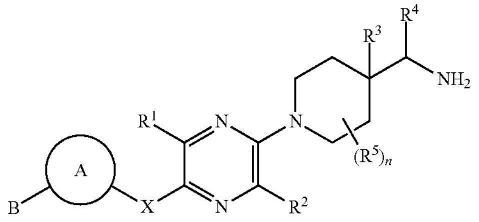

wherein

X is selected from the group consisting of a chemical bond, S, O, NH, and $CH_2$;

- $R^1$ is selected from the group consisting of hydrogen, hydroxyl, halogen, amino, $C_{1-6}$ alkyl, 3- to 6-membered heterocycloalkyl, and $C_{3-6}$ cycloalkyl, wherein the alkyl, heterocycloalkyl, and cycloalkyl are each optionally substituted by one or more substituents selected from the group consisting of halogen, hydroxyl, and amino;
- $R^2$ is selected from the group consisting of hydrogen, hydroxyl, amino, cyano, halogen, $C_{1-6}$ alkyl, 3- to 6-membered heterocycloalkyl, and $C_{3-6}$ cycloalkyl, wherein the alkyl, heterocycloalkyl, and cycloalkyl are each optionally substituted by one or more substituents selected from the group consisting of halogen, oxo, hydroxyl, and amino;
- A is selected from the group consisting of $C_{6-12}$ arylene, 5- to 12-membered heteroarylene, 3- to 12-membered heterocycloalkylene, and $C_{3-8}$ cycloalkylene, wherein the arylene, heteroarylene, heterocycloalkylene, and cycloalkylene are each optionally substituted by one or more $R^a$;
- each of the $R^a$, if present, is independently selected from the group consisting of hydrogen, halogen, hydroxyl, —O—($C_{1-6}$ alkyl), —O—($C_{3-6}$ cycloalkyl), cyano, $C_{1-6}$ alkyl, $C_{3-6}$ cycloalkyl, $C_{2-6}$ alkenyl, —S(=O)$_g$—($C_{1-6}$ alkyl), —S(=O)$_g$$NH_2$, amino, —NH($C_{1-6}$ alkyl), —N($C_{1-6}$ alkyl)$_2$, 3- to 12-membered heterocycloalkyl, $C_{6-10}$ aryl, and 5- to 12-membered heteroaryl, wherein the alkyl, cycloalkyl, alkenyl, heterocycloalkyl, aryl, and heteroaryl are each optionally substituted by one or more substituents selected from the group consisting of amino, —NH($C_{1-6}$ alkyl), —N($C_{1-6}$ alkyl)$_2$, halogen, cyano, oxo, hydroxyl, —O—($C_{1-6}$ alkyl), —S(=O)$_g$—($C_{1-6}$ alkyl), and $C_{1-6}$ alkyl; or when X is NH or $CH_2$, any one of $R^a$ together with X and the atoms to which they are linked form a 5- to 10-membered alicyclic ring, a 5- to 10-membered heteroalicyclic ring, a 5- to 6-membered heteroaromatic ring, or abenzene ring, wherein the alicyclic ring, heteroalicyclic ring, heteroaromatic ring, and benzene ring are each optionally substituted by one or more substituents selected from the group consisting of amino, —NH($C_{1-6}$ alkyl), —N($C_{1-6}$ alkyl)$_2$, halogen, cyano, oxo, hydroxyl, —O—($C_{1-6}$ alkyl), $C_{1-6}$ haloalkyl, and $C_{1-6}$ alkyl;

B is selected from the group consisting of —N($R^b$)—C(=O)-G-$R^d$, —N($R^b$)—S(=O)$_g$-G-$R^d$, —N($R^b$)—C(=O)—N($R^b$)-G-$R^d$, —N($R^b$)—S(=O)$_g$N($R^b$)-G-$R^d$, —C(=O)—N($R^b$)-G-$R^d$, —S(=O)$_g$N($R^b$)-G-$R^d$, —S(=O)$_g$-G-$R^d$, —O-G-(3- to 10-membered heterocycloalkyl), —O-G-($C_{3-6}$ cycloalkyl), —O—($C_{3-6}$ cycloalkylene)-G-H, —O-(3- to 10-membered heterocycloalkylene)-G-H, —O-G-$R^d$, —N($R^b$)-G-(3- to 10-membered heterocycloalkyl), —N($R^b$)-G-($C_{3-6}$ cycloalkyl), —N($R^b$)—($C_{3-6}$ cycloalkylene)-G-H, —N($R^b$)-(3- to 10-membered heterocycloalkylene)-G-H, -G-O—C(=O)—$R^b$, -G-N($R^b$)—C(=O)—$R^b$, -G-N($R^b$)—C(=O)—O$R^b$, and

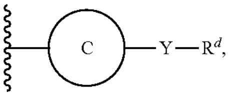

wherein the heterocycloalkyl, heterocycloalkylene, cycloalkyl, and cycloalkylene are each optionally substituted by one or more substituents selected from the group consisting of hydrogen, halogen, hydroxyl, amino, —NH($C_{1-6}$ alkyl), —N($C_{1-6}$ alkyl)$_2$, oxo, —O—($C_{1-6}$ alkyl), $C_{1-6}$ haloalkyl, and $C_{1-6}$ alkyl, and B is not —O—($C_{1-2}$ haloalkyl);

G is selected from the group consisting of $C_{1-6}$ alkylene, $C_{2-6}$ alkenylene, $C_{2-6}$ alkynylene, $C_{3-6}$ cycloalkylene, $C_{3-6}$ cycloalkenylene, 3- to 10-membered heterocycloalkenylene, and 3- to 10-membered heterocycloalkylene, wherein the alkylene, cycloalkylene, cycloalkenylene, heterocycloalkenylene, and heterocycloalkylene are each optionally substituted by one or more substituents selected from the group consisting of hydrogen, halogen, oxo, hydroxyl, cyano, amino, —O$R^b$, —NH$R^b$, —N($R^b$)$_2$, —N($R^b$)—C(=O)—$R^b$, —C(=O)—$NH_2$, —C(=O)—N($R^b$)$_2$, $C_{1-6}$ alkyl, $C_{1-6}$ haloalkyl, $C_{1-6}$ hydroxyalkyl, $C_{3-6}$ cycloalkyl, $C_{3-6}$ halocycloalkyl, $C_{3-6}$ hydroxycycloalkyl, 3- to 10-membered haloheterocycloalkyl, 3- to 10-membered hydroxyheterocycloalkyl, and 3- to 10-membered heterocycloalkyl;

$R^b$ is selected from the group consisting of hydrogen, halogen, amino, cyano, $C_{1-6}$ alkyl, $C_{3-6}$ cycloalkyl, $C_{3-6}$ cycloalkenyl, 3- to 10-membered heterocycloalkenyl, and 3- to 10-membered heterocycloalkyl, wherein the alkyl, cycloalkyl, cycloalkenyl, heterocycloalkenyl, and heterocycloalkyl are each optionally substituted by one or more substituents selected from the group consisting of hydrogen, halogen, oxo, hydroxyl, cyano, and amino;

C is selected from the group consisting of $C_{6-12}$ arylene, 5- to 12-membered heteroarylene, 3- to 12-membered heterocycloalkylene, $C_{3-12}$ cycloalkenylene, 3- to 12-membered heterocycloalkenylene, and $C_{3-8}$ cycloalkylene, wherein the arylene, heteroarylene, heterocycloalkylene, cycloalkenylene, heterocycloalkenylene, and cycloalkylene are each optionally substituted by one or more $R^c$;

each of the $R^c$, if present, is independently selected from the group consisting of hydrogen, halogen, hydroxyl, —O—($C_{1-6}$ alkyl), —O—($C_{3-6}$ cycloalkyl), cyano, $C_{1-6}$ alkyl, $C_{2-6}$ alkenyl, —S(=O)$_g$—($C_{1-6}$ alkyl), —S(=O)$_g$$NH_2$, amino, —NH($C_{1-6}$ alkyl), and —N($C_{1-6}$ alkyl)$_2$, wherein the alkyl and alkenyl are each optionally substituted by one or more substituents selected from the group consisting of amino, —NH($C_{1-6}$ alkyl), —N($C_{1-6}$ alkyl)$_2$, halogen, cyano, oxo, hydroxyl, —O—($C_{1-6}$ alkyl), —S(=O)$_g$—($C_{1-6}$ alkyl), and $C_{1-6}$ alkyl;

Y is selected from the group consisting of $C_{1-6}$ alkylene, $C_{3-6}$ cycloalkylene, 3- to 6-membered heterocycloalkylene, $C_{3-6}$ cycloalkenylene, 3- to 6-membered heterocycloalkenylene, $C_{6-10}$ arylene, 5- to 12-membered heteroarylene, $C_{2-6}$ alkenylene, —S(=O)$_g$—($C_{1-6}$ alkylene)-, —S(=O)$_g$—N($R^b$)—, —C(=O)—($C_{1-6}$ alkylene)-, —C(=O)—($C_{3-6}$ cycloalkylene)-, —C(=O)-(3- to 6-membered heterocycloalkylene)-, and —C(=O)—, wherein the alkylene, heterocycloalkylene, cycloalkenylene, heterocycloalkenylene, and cycloalkylene are each optionally substituted by one or more substituents selected from the group consisting of halogen, oxo, hydroxyl, and amino;

$R^d$ is selected from the group consisting of halogen, amino, hydroxyl, cyano, —S(=O)$_g$—($C_{1-6}$ alkyl), —O—($C_{1-6}$ alkyl), —O—($C_{3-6}$ cycloalkyl), —NH($C_{1-6}$ alkyl), —NH($C_{3-6}$ cycloalkyl), —N($C_{1-6}$ alkyl)$_2$, —NH—C(=O)—O—($C_{1-6}$ alkyl), —N($C_{1-6}$ alkyl)-C(=O)—O—($C_{1-6}$ alkyl), —O—C(=O)—$NH_2$, —O—C(=O)—NH($C_{1-6}$ alkyl), and —N($C_{1-6}$ alkyl)-C(=O)—($C_{1-6}$ alkyl), wherein the alkyl and cycloalkyl are each optionally substituted by one or more substituents selected from the group consisting of halogen, oxo, hydroxyl, amino, and —O—($C_{1-6}$ alkyl);

$R^3$ is selected from the group consisting of halogen, —O$R^z$, hydroxyl, cyano, —C(=O)—O$R^z$, —C(=O)—N($R^z$)$_2$, $C_{1-6}$ alkyl, —($C_{1-6}$ alkylene)-$R^z$, —($C_{1-6}$ alkylene)-O$R^z$, —($C_{1-6}$ alkylene)-OH, —($C_{1-6}$ alkylene)-N($R^z$)$_2$, $C_{3-6}$ cycloalkyl, 3- to 12-membered heterocycloalkyl, $C_{3-6}$ cycloalkenyl, 3- to 12-membered heterocycloalkenyl, $C_{2-6}$ alkenyl, $C_{2-6}$ alkynyl, $C_{6-12}$ aryl, 5- to 12-membered heteroaryl, —S(=O)$_g$—($C_{1-6}$ alkyl), amino, and —N($R^z$)$_2$, wherein the alkyl, alkylene, cycloalkyl, heterocycloalkyl, cycloalkenyl, heterocycloalkenyl, alkenyl, alkynyl, heteroaryl, and aryl are each optionally substituted by one or more substituents selected from the group consisting of halogen, cyano, oxo, —OW, hydroxyl, —N($R^z$)$_2$, —NH$R^z$, amino, $C_{1-6}$ alkyl, $C_{3-6}$ cycloalkyl, 3- to 12-membered heterocycloalkyl, $C_{6-10}$ aryl, 5- to 10-membered heteroaryl, —C(=O)—O$R^z$, —C(=O)—N($R^z$)$_2$, —C(=O)—$NH_2$, and nitro;

each of the $R^z$, if present, is independently selected from the group consisting of hydrogen, cyano, —C(=O)—($C_{1-6}$ alkyl), —C(=O)—($C_{3-8}$ cycloalkyl), —C(=O)-(3- to 8-membered heterocycloalkyl), $C_{1-6}$ alkyl, $C_{3-6}$ cycloalkyl, 3- to 12-membered heterocycloalkyl, $C_{2-6}$ alkenyl, $C_{2-6}$ alkynyl, $C_{6-12}$ aryl, and 5- to 12-membered heteroaryl, wherein the alkyl, cycloalkyl, heterocycloalkyl, alkenyl, alkynyl, aryl, and heteroaryl are each optionally substituted by one or more substituents selected from the group consisting of amino, halogen, cyano, oxo, nitro, hydroxyl, —O—($C_{1-6}$ alkyl), $C_{1-6}$ alkyl, $C_{1-6}$ haloalkyl, $C_{3-6}$ cycloalkyl, 3- to 12-membered heterocycloalkyl, $C_{6-10}$ aryl, and 5- to 10-membered heteroaryl;

$R^4$ is selected from the group consisting of halogen, $C_{1-6}$ alkyl, $C_{3-6}$ cycloalkyl, —C(═O)—$R^z$, 3- to 12-membered heterocycloalkyl, $C_{2-6}$ alkenyl, $C_{2-6}$ alkynyl, $C_{6-10}$ aryl, and 5- to 12-membered heteroaryl, wherein the alkyl, cycloalkyl, heterocycloalkyl, alkenyl, alkynyl, aryl, and heteroaryl are each optionally substituted by one or more substituents selected from the group consisting of amino, halogen, cyano, hydroxyl, oxo, —O—($C_{1-6}$ alkyl), $C_{1-6}$ alkyl, $C_{1-6}$ haloalkyl, $C_{3-6}$ cycloalkyl, 3- to 12-membered heterocycloalkyl, $C_{6-10}$ aryl, and 5- to 10-membered heteroaryl; or $R^3$ and $R^4$ together with the atoms to which they are linked form a 4- to 8-membered alicyclic ring or a 4- to 8-membered heteroalicyclic ring, wherein the alicyclic ring and heteroalicyclic ring are each optionally substituted by one or more $R^{4a}$, or the alicyclic ring and heteroalicyclic ring are each optionally fused with one or more $C_{6-10}$ aromatic rings or 5- to 12-membered heteroaromatic rings, and the aromatic rings and heteroaromatic rings are each optionally substituted by one or more $R^{4a}$;

each of the $R^{4a}$, if present, is independently selected from the group consisting of hydrogen, halogen, cyano, —C(═O)H, —C(═O)—($C_{1-6}$ alkyl), —C(═O)—($C_{3-8}$ cycloalkyl), —C(═O)-(3- to 8-membered heterocycloalkyl), —NH—C(═O)—($C_{1-6}$ alkyl), —NH—C(═O)—($C_{3-8}$ cycloalkyl), —NH—C(═O)-(3- to 8-membered heterocycloalkyl), oxo, $C_{1-6}$ alkyl, $C_{3-6}$ cycloalkyl, $C_{3-6}$ cycloalkenyl, 3- to 12-membered heterocycloalkenyl, 3- to 12-membered heterocycloalkyl, $C_{2-6}$ alkenyl, $C_{2-6}$ alkynyl, $C_{6-12}$ aryl, and 5- to 12-membered heteroaryl, wherein the alkyl, cycloalkyl, cycloalkenyl, heterocycloalkenyl, heterocycloalkyl, alkenyl, alkynyl, aryl, and heteroaryl are each optionally substituted by one or more substituents selected from the group consisting of halogen, cyano, hydroxyl, —O—($C_{1-6}$ alkyl), $C_{1-6}$ alkyl, $C_{3-6}$ cycloalkyl, 3- to 12-membered heterocycloalkyl, $C_{6-10}$ aryl, and 5- to 10-membered heteroaryl;

each of the $R^5$, if present, is independently selected from the group consisting of hydrogen, halogen, oxo, cyano, hydroxyl, carboxyl, —C(═O)—$NH_2$, —C(═O)—O—($C_{1-6}$ alkyl), $C_{1-6}$ alkyl, $C_{3-6}$ cycloalkyl, $C_{2-6}$ alkenyl, $C_{2-6}$ alkynyl, —S(═O)$_g$—($C_{1-6}$ alkyl), 3- to 6-membered heterocycloalkyl, $C_{6-10}$ aryl, and 5- to 10-membered heteroaryl, wherein the alkyl, cycloalkyl, heterocycloalkyl, alkenyl, alkynyl, aryl, and heteroaryl are each optionally substituted by one or more substituents selected from the group consisting of amino, hydroxyl, oxo, halogen, cyano, —O—($C_{1-6}$ alkyl), —NH($C_{1-6}$ alkyl), and —N($C_{1-6}$ alkyl)$_2$; or any two of $R^5$ together with the atoms to which they are linked form a $C_{3-10}$ alicyclic ring or a 4- to 12-membered heteroalicyclic ring;

g is 0, 1, or 2; and n is 0, 1, 2, 3, 4, or 5.

In the second aspect, the present disclosure provides specific examples of the compound of formula I, including:

(1) (3-((3S,4S)-4-amino-3-methyl-2-oxa-8-azaspiro[4.5]decan-8-yl)-6-(3-chloro-2-(2-(hydroxymethyl)pyrrolidin-1-yl)pyridin-4-ylthio)-5-methylpyrazin-2-yl)methanol;

(2) (3-((3S,4S)-4-amino-3-methyl-2-oxa-8-azaspiro[4.5]decan-8-yl)-6-(3-chloro-2-(2-(hydroxymethyl)pyrrolidin-1-yl)pyridin-4-ylthio)pyrazin-2-yl)methanol;

(3) (3-((3S,4S)-4-amino-3-methyl-2-oxa-8-azaspiro[4.5]decan-8-yl)-6-(3-chloro-2-(2-(fluoromethyl)pyrrolidin-1-yl)pyridin-4-ylthio)pyrazin-2-yl)methanol;

(4) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)pyrrolidin-2-yl)acetamide;

(5) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)pyrrolidin-2-yl)acetonitrile;

(6) (3-((3S,4S)-4-amino-3-methyl-2-oxa-8-azaspiro[4.5]decan-8-yl)-6-(3-chloro-2-(2-(hydroxymethyl)azetidin-1-yl)pyridin-4-ylthio)pyrazin-2-yl)methanol;

(7) (3-((3S,4S)-4-amino-3-methyl-2-oxa-8-azaspiro[4.5]decan-8-yl)-6-(3-chloro-2-(2-(methoxymethyl)azetidin-1-yl)pyridin-4-ylthio)pyrazin-2-yl)methanol;

(8) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-2-yl)acetonitrile;

(9) (3-((3S,4S)-4-amino-3-methyl-2-oxa-8-azaspiro[4.5]decan-8-yl)-6-(3-chloro-2-(2-(methylsulfonylmethyl)azetidin-1-yl)pyridin-4-ylthio)pyrazin-2-yl)methanol;

(10) (3-((3S,4S)-4-amino-3-methyl-2-oxa-8-azaspiro[4.5]decan-8-yl)-6-(3-chloro-2-(2-(methylsulfonylmethyl)pyrrolidin-1-yl)pyridin-4-ylthio)pyrazin-2-yl)methanol;

(11) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)acetonitrile;

(12) (3-((3S,4S)-4-amino-3-methyl-2-oxa-8-azaspiro[4.5]decan-8-yl)-6-(3-chloro-2-(3-(hydroxymethyl)azetidin-1-yl)pyridin-4-ylthio)pyrazin-2-yl)methanol;

(13) (3-((3S,4S)-4-amino-3-methyl-2-oxa-8-azaspiro[4.5]decan-8-yl)-6-(2-(3-(aminomethyl)azetidin-1-yl)-3-chloropyridin-4-ylthio)pyrazin-2-yl)methanol;

(14) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)pyrrolidin-3-yl)acetonitrile;

(15) N-(4-(5-((3S,4S)-4-amino-3-methyl-2-oxa-8-azaspiro[4.5]decan-8-yl)-6-(hydroxymethyl)-3-methylpyrazin-2-ylthio)-3-chloropyridin-2-yl)-2-cyanoacetamide;

(16) (1-(4-(5-((3S,4S)-4-amino-3-methyl-2-oxa-8-azaspiro[4.5]decan-8-yl)pyrazin-2-ylthio)-3-chloropyridin-2-yl)piperidin-4-yl)methanol;

(17) (3-(4-(1-aminoethyl)-4-methylpiperidin-1-yl)-6-(3-chloro-2-(2-(hydroxymethyl)pyrrolidin-1-yl)pyridin-4-ylthio)pyrazin-2-yl)methanol;

(18) (3-(4-(1-aminoethyl)-4-methylpiperidin-1-yl)-6-(3-chloro-2-(2-(fluoromethyl)pyrrolidin-1-yl)pyridin-4-ylthio)pyrazin-2-yl)methanol;

(19) 2-(1-(4-(5-(4-(1-aminoethyl)-4-methylpiperidin-1-yl)-6-(hydroxymethyl)pyrazin-2-ylthio)-3-chloropyridin-2-yl)azetidin-3-yl)acetonitrile;

(20) (3-(4-(1-aminoethyl)-4-methylpiperidin-1-yl)-6-(2-chloro-6-(2-(hydroxymethyl)azetidin-1-yl)pyrimidin-3-ylthio)pyrazin-2-yl)methanol;

(21) (3-((S)-4-amino-2-oxa-8-azaspiro[4.5]decan-8-yl)-6-(3-chloro-2-(2-(hydroxymethyl)pyrrolidin-1-yl)pyridin-4-ylthio)pyrazin-2-yl)methanol;

(22) (1-(4-(5-((3S,4S)-4-amino-3-methyl-2-oxa-8-azaspiro[4.5]decan-8-yl)-6-(fluoromethyl)pyrazin-2-ylthio)-3-chloropyridin-2-yl)pyrrolidin-2-yl)methanol;

(23) (1-(4-(5-(4-(1-aminoethyl)-4-methylpiperidin-1-yl)-3-fluoro-6-(hydroxymethyl)pyrazin-2-ylthio)-3-chloropyridin-2-yl)pyrrolidin-2-yl)methanol;

(24) (4S)-4-amino-8-(5-(3-chloro-2-(2-(hydroxymethyl)pyrrolidin-1-yl)pyridin-4-ylthio)-3-(hydroxymethyl)pyrazin-2-yl)-2-cyclopropyl-2,8-diazaspiro[4.5]decan-3-one;

(25) 1-((4S)-4-amino-8-(5-(3-chloro-2-(2-(hydroxymethyl)pyrrolidin-1-yl)pyridin-4-ylthio)-3-(hydroxymethyl)pyrazin-2-yl)-2,8-diazaspiro[4.5]decan-2-yl)ethan-1-one;

(26) (3-((3S,4S)-4-amino-3-methyl-2-oxa-8-azaspiro[4.5]decan-8-yl)-6-(3-chloro-2-(2-(hydroxymethyl)pyrrolidin-1-yl)pyrimidin-4-yl)-5-methylpyrazin-2-yl)methanol;

(27) (3-(4-(1-aminoethyl)-4-methylpiperidin-1-yl)-6-(2,3-dichloro-4-(3-(hydroxymethyl)azetidin-1-yl)phenyl)-5-methylpyrazin-2-yl)methanol;

(28) (1-(4-(5-((3S,4S)-4-amino-3-methyl-2-oxa-8-azaspiro[4.5]decan-8-yl)pyrazin-2-ylthio)-3-chloropyridin-2-yl)pyrrolidin-2-yl)methanol;

(29) 2-(1-(4-(5-(4-(1-aminoethyl)-4-methylpiperidin-1-yl)-6-(hydroxymethyl)pyrazin-2-ylthio)-3-chloropyridin-2-yl)pyrrolidin-2-yl)propan-2-ol;

(30) (3-(4-(1-aminoethyl)-4-methylpiperidin-1-yl)-6-(3-chloro-2-(3-(hydroxymethyl)azetidin-1-yl)pyridin-4-ylthio)pyrazin-2-yl)methanol;

(31) (3-(4-(1-aminoethyl)-4-methylpiperidin-1-yl)-6-(2-(3-(aminomethyl)azetidin-1-yl)-3-chloropyridin-4-ylthio)pyrazin-2-yl)methanol;

(32) 1-(4-(5-(4-(1-aminoethyl)-4-methylpiperidin-1-yl)-6-(hydroxymethyl)pyrazin-2-ylthio)-3-chloropyridin-2-yl)azetidine-3-carboxamide;

(33) (3-((3S,4S)-4-amino-3-methyl-2-oxa-8-azaspiro[4.5]decan-8-yl)-6-(3-chloro-2-((S)-2-(hydroxymethyl)azetidin-1-yl)pyridin-4-ylthio)pyrazin-2-yl)methanol;

(34) (3-((3S,4S)-4-amino-3-methyl-2-oxa-8-azaspiro[4.5]decan-8-yl)-6-(2-(2-(aminomethyl)pyrrolidin-1-yl)-3-chloropyridin-4-ylthio)pyrazin-2-yl)methanol;

(35) (3-(4-(1-aminoethyl)-4-methylpiperidin-1-yl)-6-(3-chloro-2-(3-(hydroxymethyl)pyrrolidin-1-yl)pyrimidin-4-yl)pyrazin-2-yl)methanol;

(36) (3-(4-(1-aminoethyl)-4-methylpiperidin-1-yl)-6-(3-chloro-2-(3-(hydroxymethyl)pyrrolidin-1-yl)pyrimidin-4-yl)-5-methylpyrazin-2-yl)methanol;

(37) (3-((3S,4S)-4-amino-3-methyl-2-oxa-8-azaspiro[4.5]decan-8-yl)-6-(3-chloro-2-(3-(hydroxymethyl)pyrrolidin-1-yl)pyridin-4-ylthio)pyrazin-2-yl)methanol;

(38) (1-(4-(5-(4-(1-amino-2-fluoroethyl)-4-methylpiperidin-1-yl)pyrazin-2-ylthio)-3-chloropyridin-2-yl)pyrrolidin-2-yl)methanol;

(39) (1-(4-(5-(4-(1-aminoethyl)-4-methylpiperidin-1-yl)-3-fluoro-6-(hydroxymethyl)pyrazin-2-yl)-3-chloropyridin-2-yl)pyrrolidin-2-yl)methanol;

(40) (3-(4-(1-aminoethyl)-4-methylpiperidin-1-yl)-6-(3-chloro-2-(4-(hydroxymethyl)piperidin-1-yl)pyridin-4-ylthio)pyrazin-2-yl)methanol;

(41) (3-(4-(1-aminoethyl)-4-methylpiperidin-1-yl)-6-(3-chloro-2-(4-(hydroxymethyl)piperidin-1-yl)pyrimidin-4-yl)-5-methylpyrazin-2-yl)methanol;

(42) N-(4-(5-(4-(1-aminoethyl)-4-methylpiperidin-1-yl)-6-(hydroxymethyl)pyrazin-2-ylthio)-3-chloropyridin-2-yl)-2-hydroxyl-N,2-dimethylpropanamide;

(43) (3-(4-(1-amino-2-methoxyethyl)-4-methylpiperidin-1-yl)-6-(3-chloro-2-(2-(hydroxymethyl)azetidin-1-yl)pyridin-4-ylthio)pyrazin-2-yl)methanol;

(44) (3-(4-(1-amino-2-methoxyethyl)-4-methylpiperidin-1-yl)-6-(3-chloro-2-(2-(hydroxymethyl)pyrrolidin-1-yl)pyridin-4-ylthio)pyrazin-2-yl)methanol;

(45) (3-(4-(1-amino-2-methoxyethyl)-4-methylpiperidin-1-yl)-6-(3-chloro-2-(3-(hydroxymethyl)azetidin-1-yl)pyridin-4-ylthio)pyrazin-2-yl)methanol;

(46) (3-(4-(1-aminoethyl)-4-fluoropiperidin-1-yl)-6-(3-chloro-2-(3-(hydroxymethyl)azetidin-1-yl)pyridin-4-ylthio)pyrazin-2-yl)methanol;

(47) 1-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-2-yl)cyclopropane-1-carbonitrile;

(48) 3-(4-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)piperazin-1-yl)-3-oxopropanenitrile;

(49) 1-((4-(5-((3S,4S)-4-amino-3-methyl-2-oxa-8-azaspiro[4.5]decan-8-yl)-6-(hydroxymethyl)pyrazin-2-ylthio)-3-chloropyridin-2-yloxy)methyl)cyclopropan-1-ol;

(50) (3-((3S,4S)-4-amino-3-methyl-2-oxa-8-azaspiro[4.5]decan-8-yl)-6-(3,6-dichloro-2-(2-(hydroxymethyl)pyrrolidin-1-yl)pyridin-4-ylthio)pyrazin-2-yl)methanol;

(51) (3-((3S,4S)-4-amino-3-methyl-2-oxa-8-azaspiro[4.5]decan-8-yl)-6-(2,3-dichloro-6-(2-(hydroxymethyl)pyrrolidin-1-yl)pyridin-4-ylthio)pyrazin-2-yl)methanol;

(52) (3-((3S,4S)-4-amino-3-methyl-2-oxa-8-azaspiro[4.5]decan-8-yl)-6-(5-chloro-2-(2-(hydroxymethyl)pyrrolidin-1-yl)pyridin-4-ylthio)pyrazin-2-yl)methanol;

(53) (3-(4-(1-aminoethyl)-4-methylpiperidin-1-yl)-6-(2,3-dichloro-6-(2-(hydroxymethyl)pyrrolidin-1-yl)pyridin-4-ylthio)pyrazin-2-yl)methanol;

(54) (3-(4-(1-aminoethyl)-4-methylpiperidin-1-yl)-6-(5-chloro-2-(2-(fluoromethyl)pyrrolidin-1-yl)pyridin-4-ylthio)pyrazin-2-yl)methanol;

(55) 2-(1-(4-(5-((3S,4S)-4-amino-3-methyl-2-oxa-8-azaspiro[4.5]decan-8-yl)-6-(hydroxymethyl)pyrazin-2-ylthio)pyridin-2-yl)pyrrolidin-2-yl)acetonitrile;

(56) (3-((3S,4S)-4-amino-3-methyl-2-oxa-8-azaspiro[4.5]decan-8-yl)-6-(2-(3-(fluoromethyl)azetidin-1-yl)pyrimidin-3-ylthio)pyrazin-2-yl)methanol;

(57) (3-(4-(1-aminoethyl)-4-methylpiperidin-1-yl)-6-(2-(3-(fluoromethyl)azetidin-1-yl)pyrimidin-3-ylthio)pyrazin-2-yl)methanol;

(58) 1-((4-(5-((3S,4S)-4-amino-3-methyl-2-oxa-8-azaspiro[4.5]decan-8-yl)-6-(hydroxymethyl)pyrazin-2-ylthio)-3-chloropyridin-2-ylamino)methyl)cyclopropan-1-ol;

(59) (3-((3S,4S)-4-amino-3-methyl-2-oxa-8-azaspiro[4.5]decan-8-yl)-6-(3-chloro-2-(oxetan-3-ylmethoxy)pyridin-4-ylthio)pyrazin-2-yl)methanol;

(60) (3-((S)-5-amino-5,7-dihydrospiro[cyclopenta[b]pyridin-6,4'-piperidin]-1'-yl)-6-(2-(2-(fluoromethyl)azetidin-1-yl)pyridin-3-ylthio)pyrazin-2-yl)methanol;

(61) (3-((3S,4S)-4-amino-3-methyl-2-oxa-8-azaspiro[4.5]decan-8-yl)-6-(3-fluoro-2-(2-(fluoromethyl)azetidin-1-yl)pyridin-4-ylthio)pyrazin-2-yl)methanol;

(62) (1-(3-(3-amino-5-((3S,4S)-4-amino-3-methyl-2-oxa-8-azaspiro[4.5]decan-8-yl)pyrazin-2-ylthio)pyridin-2-yl)pyrrolidin-2-yl)methanol;

(63) 2-(1-(3-(3-amino-5-((3S,4S)-4-amino-3-methyl-2-oxa-8-azaspiro[4.5]decan-8-yl)pyrazin-2-ylthio)pyridin-2-yl)pyrrolidin-3-yl)acetonitrile;

(64) (5-amino-3-((3S,4S)-4-amino-3-methyl-2-oxa-8-azaspiro[4.5]decan-8-yl)-6-(2-(2-(fluoromethyl)pyrrolidin-1-yl)pyridin-3-ylthio)pyrazin-2-yl)methanol;

(65) (1-(3-(5-((3S,4S)-4-amino-3-methyl-2-oxa-8-azaspiro[4.5]decan-8-yl)pyrazin-2-ylthio)pyridin-2-yl)pyrrolidin-3-yl)methanol;

(66) 1-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)cyclopropan-1-ol;

(67) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)propan-2-ol;

(68) (S)-2-(1-(4-(5-(4-amino-2-oxa-8-azaspiro[4.5]decan-8-yl)-6-(hydroxymethyl)pyrazin-2-ylthio)-3-chloropyridin-2-yl)azetidin-3-yl)propan-2-ol;

(69) (S)-2-(1-(4-(5-(4-(1-amino-2-methoxyethyl)-4-methylpiperidin-1-yl)-6-(hydroxymethyl)pyrazin-2-ylthio)-3-chloropyridin-2-yl)azetidin-3-yl)propan-2-ol;

(70) 1-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)ethan-1-ol;

(71) (3-((3S,4S)-4-amino-3-methyl-2-oxa-8-azaspiro[4.5]decan-8-yl)-6-(3-chloro-2-(3-(methoxymethyl)azetidin-1-yl)pyridin-4-ylthio)pyrazin-2-yl)methanol;

(72) (R)-2-(1-(4-(5-(3-amino-3H-spiro[benzofuran-2,4'-piperidin]-1'-yl)-6-(hydroxymethyl)pyrazin-2-ylthio)-3-chloropyridin-2-yl)azetidin-3-yl)propan-2-ol;

(73) (S)-2-(1-(4-(5-(1-amino-1,3-dihydrospiro[indene-2,4'-piperidin]-1'-yl)-6-(hydroxymethyl)pyrazin-2-ylthio)-3-chloropyridin-2-yl)azetidin-3-yl)propan-2-ol;

(74) 2-(1-(4-(5-(4-(1-aminoethyl)-4-methylpiperidin-1-yl)-6-(hydroxymethyl)pyrazin-2-ylthio)-3-chloropyridin-2-yl)azetidin-3-yl)propan-2-ol;

(75) (3-((3S,4S)-4-amino-3-methyl-2-oxa-8-azaspiro[4.5]decan-8-yl)-6-(3-chloro-2-(3-(methylsulfonylmethyl)azetidin-1-yl)pyridin-4-ylthio)-5-methylpyrazin-2-yl)methanol;

(76) (3-((3S,4S)-4-amino-3-methyl-2-oxa-8-azaspiro[4.5]decan-8-yl)-6-(3-chloro-2-(3-(methylsulfonylmethyl)azetidin-1-yl)pyridin-4-ylthio)pyrazin-2-yl)methanol;

(77) (3-((3S,4S)-4-amino-3-methyl-2-oxa-8-azaspiro[4.5]decan-8-yl)-6-(3-chloro-2-(3-(hydroxymethyl)-3-methylazetidin-1-yl)pyridin-4-ylthio)pyrazin-2-yl)methanol;

(78) 2-(1-(4-(5-((3S,4S)-4-amino-3-methyl-2-oxa-8-azaspiro[4.5]decan-8-yl)pyrazin-2-ylthio)-3-chloropyridin-2-yl)azetidin-3-yl)propan-2-ol;

(79) (3-((3S,4S)-4-amino-3-methyl-2-oxa-8-azaspiro[4.5]decan-8-yl)-6-(3-chloro-2-(3-methyl-3-(methylsulfonylmethyl)azetidin-1-yl)pyridin-4-ylthio)pyrazin-2-yl)methanol;

(80) 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)-2-methylpropanenitrile;

(81) 3-((4-(5-((3S,4S)-4-amino-3-methyl-2-oxa-8-azaspiro[4.5]decan-8-yl)-6-(hydroxymethyl)-3-methylpyrazin-2-ylthio)-3-chloropyridin-2-ylamino)methyl)oxetan-3-ol;

(82) 2-(1-(4-(5-((3S,4S)-4-amino-3-methyl-2-oxa-8-azaspiro[4.5]decan-8-yl)-6-(hydroxymethyl)-3-methylpyrazin-2-ylthio)-3-chloropyridin-2-yl)azetidin-3-yl)propan-2-ol;

(83) (3-((3S,4S)-4-amino-3-methyl-2-oxa-8-azaspiro[4.5]decan-8-yl)-6-(3-chloro-2-(3-(methoxymethyl)-3-methylazetidin-1-yl)pyridin-4-ylthio)pyrazin-2-yl)methanol;

(84) 2-(1-(4-(5-(4-(1-amino-2-fluoroethyl)-4-methylpiperidin-1-yl)-6-(hydroxymethyl)pyrazin-2-ylthio)-3-chloropyridin-2-yl)azetidin-3-yl)propan-2-ol;

(85) 2-(1-(4-(3-amino-5-((3S,4S)-4-amino-3-methyl-2-oxa-8-azaspiro[4.5]decan-8-yl)pyrazin-2-ylthio)-3-chloropyridin-2-yl)azetidin-3-yl)propan-2-ol;

(86) (1-(4-(3-amino-5-((3S,4S)-4-amino-3-methyl-2-oxa-8-azaspiro[4.5]decan-8-yl)pyrazin-2-ylthio)-3-chloropyridin-2-yl)pyrrolidin-2-yl)methanol;

(87) (3S,4S)-8-(6-amino-5-(3-chloro-2-(3-(methylsulfonylmethyl)azetidin-1-yl)pyridin-4-ylthio)pyrazin-2-yl)-3-methyl-2-oxa-8-azaspiro[4.5]decan-4-amine;

(88) (3-((3S,4S)-4-amino-3-methyl-2-oxa-8-azaspiro[4.5]decan-8-yl)-6-(3-chloro-2-(3-fluoro-3-(hydroxymethyl)azetidin-1-yl)pyridin-4-ylthio)pyrazin-2-yl)methanol;

(89) (S)-2-(1-(4-(5-(5-amino-5,7-dihydrospiro[cyclopenta[b]pyridine-6,4'-piperidin]-1'-yl)-6-(hydroxymethyl)pyrazin-2-ylthio)-3-chloropyridin-2-yl)azetidin-3-yl)propan-2-ol;

(90) 2-(1-(4-(5-((3S,4S)-4-amino-3-methyl-2-oxa-8-azaspiro[4.5]decan-8-yl)-6-(hydroxymethyl)pyrazin-2-ylthio)-3-fluoropyridin-2-yl)azetidin-3-yl)propan-2-ol;

(91) (S)-2-(1-(4-(5-(7-amino-5,7-dihydrospiro[cyclopenta[b]pyridine-6,4'-piperidin]-1'-yl)-6-(hydroxymethyl)pyrazin-2-ylthio)-3-chloropyridin-2-yl)azetidin-3-yl)propan-2-ol;

(92) (S)-2-(1-(4-(5-(5-amino-5,7-dihydrospiro[cyclopenta[c]pyridine-6,4'-piperidin]-1'-yl)-6-(hydroxymethyl)pyrazin-2-ylthio)-3-chloropyridin-2-yl)azetidin-3-yl)propan-2-ol;

(93) (S)-2-(1-(4-(5-(4-amino-2-chloro-4,6-dihydrospiro[cyclopenta[d]thiazole-5,4'-piperidin]-1'-yl)-6-(hydroxymethyl)pyrazin-2-ylthio)-3-chloropyridin-2-yl)azetidin-3-yl)propan-2-ol;

(94) (S)-2-(1-(4-(5-(4-amino-4,6-dihydrospiro[cyclopenta[d]thiazole-5,4'-piperidin]-1'-yl)-6-(hydroxymethyl)pyrazin-2-ylthio)-3-chloropyridin-2-yl)azetidin-3-yl)propan-2-ol;

(95) (S)-2-(1-(4-(5-(4-amino-4,6-dihydrospiro[cyclopenta[d]oxazole-5,4'-piperidin]-1'-yl)-6-(hydroxymethyl)pyrazin-2-ylthio)-3-chloropyridin-2-yl)azetidin-3-yl)propan-2-ol;

(96) (S)-2-(1-(4-(5-(6-amino-4,6-dihydrospiro[cyclopenta[d]oxazole-5,4'-piperidin]-1'-yl)-6-(hydroxymethyl)pyrazin-2-ylthio)-3-chloropyridin-2-yl)azetidin-3-yl)propan-2-ol;

(97) (R)-2-(1-(4-(5-(3-amino-5-fluoro-3H-spiro[benzofuran-2,4'-piperidin]-1'-yl)-6-(hydroxymethyl)pyrazin-2-ylthio)-3-chloropyridin-2-yl)azetidin-3-yl)propan-2-ol;

(98) (R)-2-(1-(4-(5-(3-amino-5-fluoro-3H-spiro[benzofuran-2,4'-piperidin]-1'-yl)-6-(hydroxymethyl)pyrazin-2-ylthio)-3-fluoropyridin-2-yl)azetidin-3-yl)propan-2-ol;

(99) (R)-2-(1-(4-(5-(3-amino-6-fluoro-3H-spiro[benzofuran-2,4'-piperidin]-1'-yl)-6-(hydroxymethyl)pyrazin-2-ylthio)-3-chloropyridin-2-yl)azetidin-3-yl)propan-2-ol;

(100) (R)-2-(1-(4-(5-(3-amino-6-fluoro-3H-spiro[benzofuran-2,4'-piperidin]-1'-yl)-6-(hydroxymethyl)pyrazin-2-ylthio)-3-fluoropyridin-2-yl)azetidin-3-yl)propan-2-ol;

(101) (R)-2-(1-(4-(5-(3-amino-3H-spiro[furo[2,3-b]pyridine-2,4'-piperidin]-1'-yl)-6-(hydroxymethyl)pyrazin-2-ylthio)-3-chloropyridin-2-yl)azetidin-3-yl)propan-2-ol;

(102) (S)-2-(1-(4-(5-(7-amino-5,7-dihydrospiro[cyclopenta[c]pyridine-6,4'-piperidin]-1'-yl)-6-(hydroxymethyl)pyrazin-2-ylthio)-3-chloropyridin-2-yl)azetidin-3-yl)propan-2-ol;

(103) (S)-2-(1-(4-(5-(5-amino-5,7-dihydrospiro[cyclopenta[b]pyridine-6,4'-piperidin]-1'-yl)pyrazin-2-ylthio)-3-chloropyridin-2-yl)azetidin-3-yl)propan-2-ol;

(104) (S)-2-(1-(4-(5-(5-amino-5,7-dihydrospiro[cyclopenta[c]pyridine-6,4'-piperidin]-1'-yl)pyrazin-2-ylthio)-3-chloropyridin-2-yl)azetidin-3-yl)propan-2-ol;

(105) (S)-2-(1-(4-(5-(7-amino-5,7-dihydrospiro[cyclopenta[b]pyridine-6,4'-piperidin]-1'-yl)pyrazin-2-ylthio)-3-chloropyridin-2-yl)azetidin-3-yl)propan-2-ol;

(106) (R)-2-(1-(4-(5-(3-amino-3H-spiro[furo[2,3-b]pyridine-2,4'-piperidin]-1'-yl)pyrazin-2-ylthio)-3-chloropyridin-2-yl)azetidin-3-yl)propan-2-ol;

(107) (R)-2-(1-(4-(5-(3-amino-5-fluoro-3H-spiro[benzofuran-2,4'-piperidin]-1'-yl)pyrazin-2-ylthio)-3-chloropyridin-2-yl)azetidin-3-yl)propan-2-ol;

(108) (R)-2-(1-(4-(5-(3-amino-6-fluoro-3H-spiro[benzofuran-2,4'-piperidin]-1'-yl)pyrazin-2-ylthio)-3-chloropyridin-2-yl)azetidin-3-yl)propan-2-ol;

(109) (S)-2-(1-(4-(5-(4-amino-2-chloro-4,6-dihydrospiro[cyclopenta[d]thiazole-5,4'-piperidin]-1'-yl)pyrazin-2-ylthio)-3-chloropyridin-2-yl)azetidin-3-yl)propan-2-ol;

(110) (S)-2-(1-(4-(5-(4-amino-4,6-dihydrospiro[cyclopenta[d]thiazole-5,4'-piperidin]-1'-yl)pyrazin-2-ylthio)-3-chloropyridin-2-yl)azetidin-3-yl)propan-2-ol;

(111) (S)-2-(1-(4-(5-(4-amino-4,6-dihydrospiro[cyclopenta[d]oxazole-5,4'-piperidin]-1'-yl)pyrazin-2-ylthio)-3-chloropyridin-2-yl)azetidin-3-yl)propan-2-ol;

(112) (S)-2-(1-(4-(5-(6-amino-4,6-dihydrospiro[cyclopenta[d]oxazole-5,4'-piperidin]-1'-yl)pyrazin-2-ylthio)-3-chloropyridin-2-yl)azetidin-3-yl)propan-2-ol;

(113) (S)-2-(1-(4-(3-amino-5-(7-amino-5,7-dihydrospiro[cyclopenta[c]pyridine-6,4'-piperidin]-1'-yl)pyrazin-2-ylthio)-3-chloropyridin-2-yl)azetidin-3-yl)propan-2-ol;

(114) (S)-2-(1-(4-(3-amino-5-(7-amino-5,7-dihydrospiro[cyclopenta[b]pyridine-6,4'-piperidin]-1'-yl)pyrazin-2-ylthio)-3-chloropyridin-2-yl)azetidin-3-yl)propan-2-ol;

(115) (S)-2-(1-(4-(3-amino-5-(5-amino-5,7-dihydrospiro[cyclopenta[b]pyridine-6,4'-piperidin]-1'-yl)pyrazin-2-ylthio)-3-chloropyridin-2-yl)azetidin-3-yl)propan-2-ol;

(116) (S)-2-(1-(4-(3-amino-5-(5-amino-5,7-dihydrospiro[cyclopenta[c]pyridine-6,4'-piperidin]-1'-yl)pyrazin-2-ylthio)-3-chloropyridin-2-yl)azetidin-3-yl)propan-2-ol;

(117) (S)-2-(1-(4-(3-amino-5-(4-amino-2-chloro-4,6-dihydrospiro[cyclopenta[d]thiazole-5,4'-piperidin]-1'-yl)pyrazin-2-ylthio)-3-chloropyridin-2-yl)azetidin-3-yl)propan-2-ol;

(118) (S)-2-(1-(4-(3-amino-5-(4-amino-4,6-dihydrospiro[cyclopenta[d]thiazole-5,4'-piperidin]-1'-yl)pyrazin-2-ylthio)-3-chloropyridin-2-yl)azetidin-3-yl)propan-2-ol;

(119) (R)-2-(1-(4-(3-amino-5-(3-amino-3H-spiro[benzofuran-2,4'-piperidin]-1'-yl)pyrazin-2-ylthio)-3-chloropyridin-2-yl)azetidin-3-yl)propan-2-ol;

(120) (R)-2-(1-(4-(3-amino-5-(3-amino-5-fluoro-3H-spiro[benzofuran-2,4'-piperidin]-1'-yl)pyrazin-2-ylthio)-3-chloropyridin-2-yl)azetidin-3-yl)propan-2-ol;

(121) (R)-2-(1-(4-(5-(4-amino-8-azadispiro[2.1.5.2]dodecan-8-yl)-6-(hydroxymethyl)pyrazin-2-ylthio)-3-chloropyridin-2-yl)azetidin-3-yl)propan-2-ol;

(122) (S)-2-(1-(4-(5-(1-amino-2,2-difluoro-8-azaspiro[4.5]decan-8-yl)-6-(hydroxymethyl)pyrazin-2-ylthio)-3-chloropyridin-2-yl)azetidin-3-yl)propan-2-ol;

(123) (S)-2-(1-(4-(5-(4-amino-8-aza-12-oxadispiro[2.1.5.2]dodecan-8-yl)-6-(hydroxymethyl)pyrazin-2-ylthio)-3-chloropyridin-2-yl)azetidin-3-yl)propan-2-ol;

(124) (3-((3S,4S)-4-amino-3-methyl-2-oxa-8-azaspiro[4.5]decan-8-yl)-6-(3-chloro-2-(3-(fluoromethyl)-3-(hydroxymethyl)azetidin-1-yl)pyridin-4-ylthio)pyrazin-2-yl)methanol;

(125) (3-((3S,4S)-4-amino-3-methyl-2-oxa-8-azaspiro[4.5]decan-8-yl)-6-(3-chloro-2-(3-(fluoromethyl)azetidin-1-yl)pyridin-4-ylthio)pyrazin-2-yl)methanol;

(126) 1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)-3-(hydroxymethyl)azetidine-3-carbonitrile;

(127) (3-((3S,4S)-4-amino-3-methyl-2-oxa-8-azaspiro[4.5]decan-8-yl)-6-(3-chloro-2-(3-ethyl-3-(hydroxymethyl)azetidin-1-yl)pyridin-4-ylthio)pyrazin-2-yl)methanol;

(128) 2-(1-(4-(5-((3S,4S)-4-amino-3-methyl-2-oxa-8-azaspiro[4.5]decan-8-yl)-6-(fluoromethyl)pyrazin-2-ylthio)-3-fluoropyridin-2-yl)azetidin-3-yl)propan-2-ol;

(129) 2-(1-(4-(5-((3S,4S)-4-amino-3-methyl-2-oxa-8-azaspiro[4.5]decan-8-yl)-6-(hydroxymethyl)pyrazin-2-ylthio)-5-chloropyridin-2-yl)azetidin-3-yl)propan-2-ol;

(130) 2-(1-(5-(5-((3S,4S)-4-amino-3-methyl-2-oxa-8-azaspiro[4.5]decan-8-yl)-6-(hydroxymethyl)pyrazin-2-ylthio)-6-chloropyridin-2-yl)azetidin-3-yl)propan-2-ol;

(131) 2-(1-(4-(5-((3S,4S)-4-amino-3-methyl-2-oxa-8-azaspiro[4.5]decan-8-yl)pyrazin-2-ylthio)-3-fluoropyridin-2-yl)azetidin-3-yl)propan-2-ol;

(132) (R)-2-(1-(4-(3-amino-5-(4-amino-8-azadispiro[2.1.5.2]dodecan-8-yl)pyrazin-2-ylthio)-3-chloropyridin-2-yl)azetidin-3-yl)propan-2-ol;

(133) (S)-2-(1-(4-(3-amino-5-(1-amino-2,2-difluoro-8-azaspiro[4.5]decan-8-yl)pyrazin-2-ylthio)-3-chloropyridin-2-yl)azetidin-3-yl)propan-2-ol;

(134) (S)-2-(1-(4-(3-amino-5-(4-amino-8-aza-12-oxadispiro[2.1.5.2]dodecan-8-yl)pyrazin-2-ylthio)-3-chloropyridin-2-yl)azetidin-3-yl)propan-2-ol;

(135) (1-(4-(3-amino-5-((3S,4S)-4-amino-3-methyl-2-oxa-8-azaspiro[4.5]decan-8-yl)pyrazin-2-ylthio)-3-chloropyridin-2-yl)-3-(fluoromethyl)azetidin-3-yl)methanol;

(136) (3-((3S,4S)-4-amino-3-methyl-2-oxa-8-azaspiro[4.5]decan-8-yl)-6-(3-chloro-2-(3-(fluoromethyl)-3-(hydroxymethyl)azetidin-1-yl)pyridin-4-ylthio)-5-methylpyrazin-2-yl)methanol;

(137) 2-(1-(4-(5-((3S,4S)-4-amino-3-methyl-2-oxa-8-azaspiro[4.5]decan-8-yl)-6-(hydroxymethyl)pyrazin-2-ylthio)pyrimidin-2-yl)azetidin-3-yl)propan-2-ol;

(138) (1-(4-(5-((3S,4S)-4-amino-3-methyl-2-oxa-8-azaspiro[4.5]decan-8-yl)pyrazin-2-ylthio)-3-chloropyridin-2-yl)-3-fluoroazetidin-3-yl)methanol;

(139) 2-(1-(4-(5-(4-amino-8-azadispiro[2.1.5.2]dodecan-8-yl)-6-(hydroxymethyl)pyrazin-2-ylthio)-3-chloropyridin-2-yl)azetidin-3-yl)propan-2-ol; and (140) (S)-2-(1-(4-(5-(5-amino-5,7-dihydrospiro[cyclopenta[b]pyridine-6,4'-piperidin]-1'-yl)-6-(hydroxymethyl)-3-methylpyrazin-2-ylthio)-3-chloropyridin-2-yl)azetidin-3-yl)propan-2-ol.

In the third aspect, the present disclosure provides a pharmaceutical composition, comprising at least one compound of formula I, formula IIa, formula IIb, formula IIIa, formula IIIb, formula IVa, formula IVb, formula IVc, formula IVd, formula Va, formula Vb, or formula Vc, or the pharmaceutically acceptable salt, ester, stereoisomer, tautomer, polymorph, solvate, isotope-labelled compound, metabolite, or prodrug thereof, and one or more pharmaceutically acceptable carriers and/or one or more additional active pharmaceutical ingredients.

In the fourth aspect, the present disclosure provides a drug, comprising:

a) a container;

b) at least one compound of formula I, formula IIa, formula IIb, formula IIIa, formula IIIb, formula IVa, formula IVb, formula IVc, formula IVd, formula Va, formula Vb, or formula Vc, or the pharmaceutically acceptable salt, ester, stereoisomer, tautomer, polymorph, solvate, isotope-labelled compound, metabolite, or prodrug thereof, or the pharmaceutical composition held in the container; and c) an optional packaging and/or instruction.

In the fifth aspect, the present disclosure provides the compound of formula I, formula IIa, formula IIb, formula IIIa, formula IIIb, formula IVa, formula IVb, formula IVc, formula IVd, formula Va, formula Vb, or formula Vc or the pharmaceutically acceptable salt, ester, stereoisomer, tautomer, polymorph, solvate, isotope-labelled compound, metabolite, or prodrug thereof, or the pharmaceutical composition, or the drug for use as an SHP2 inhibitor or for use in the prevention and/or treatment of a disease or condition that is at least partially mediated by SHP2 (in particular cancer).

In the sixth aspect, the present disclosure provides the compound of formula I, formula IIa, formula IIb, formula IIIa, formula IIIb, formula IVa, formula IVb, formula IVc, formula IVd, formula Va, formula Vb, or formula Vc or the pharmaceutically acceptable salt, ester, stereoisomer, tautomer, polymorph, solvate, isotope-labelled compound, metabolite, or prodrug thereof, or the pharmaceutical composition, or the drug for use as an SHP2 inhibitor.

In the seventh aspect, the present disclosure provides use of the compound of formula I, formula IIa, formula IIb, formula IIIa, formula IIIb, formula IVa, formula IVb, formula IVc, formula IVd, formula Va, formula Vb, or formula Vc or the pharmaceutically acceptable salt, ester, stereoisomer, tautomer, polymorph, solvate, isotope-labelled compound, metabolite, or prodrug thereof, or the pharmaceutical composition, or the drug in the preparation of a medication for preventing and/or treating a disease or condition that is at least partially mediated by SHP2 (in particular cancer).

In the eighth aspect, the present disclosure provides a method for preventing and/or treating a disease or condition that is at least partially mediated by SHP2 (in particular cancer), comprising the following step of administering to a subject in need thereof a prophylactically and/or therapeutically effective amount of the compound of formula I, formula IIa, formula IIb, formula IIIa, formula IIIb, formula IVa, formula IVb, formula IVc, formula IVd, formula Va, formula Vb, or formula Vc or the pharmaceutically acceptable salt, ester, stereoisomer, tautomer, polymorph, solvate, isotope-labelled compound, metabolite, or prodrug thereof, or the pharmaceutical composition, or the drug.

In the ninth aspect, the present disclosure provides a combined method for preventing and/or treating a disease or condition that is at least partially mediated by SHP2 (in particular cancer), comprising the steps of a) the method for preventing and/or treating a disease or condition that is at least partially mediated by SHP2 (in particular cancer); and b) an additional method.

Advantageous Effects

The present disclosure provides a substituted pyrazine compound with a novel structure, which can be used as a highly active SHP2 inhibitor, and is capable of achieving at least one of the following technical effects:

(1) a high inhibitory activity against SHP2;

(2) excellent pharmacokinetic properties (such as good bioavailability and suitable half-life and duration of action); and (3) excellent safety (lower toxic and side effects, wider therapeutic window).

DETAILED DESCRIPTION

General Terms and Definitions

Figure 1:
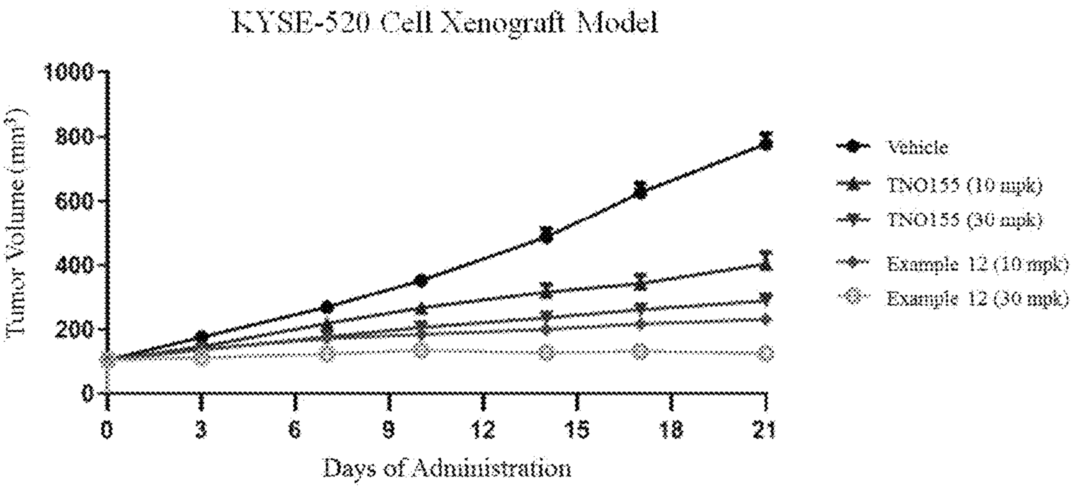
FIG. 1 shows the comparison of in vivo drug efficacy between positive control compound and compound of Example 12 in KYSE-520 cell xenograft model.

Unless otherwise defined, the terms used herein have the same meanings as commonly understood by those skilled in the art. The technologies used herein are intended to refer to those commonly understood in the art, including variations or equivalent replacements of the technologies that are apparent to those skilled in the art. The following terms, though accessible to those skilled in the art, are still set forth below in order to better explain the present disclosure.

The term "including", "comprising", "having", or "involving" and other variations thereof used herein refer to an all-inclusive or open-ended collective concept, without ruling out other unlisted elements or method steps. It should be appreciated by those skilled in the art that the above term such as "comprising" encompasses the meaning of "consisting of . . . ".

The term "one or more" or the similar expression "at least one" refers to, e.g., 1, 2, 3, 4, 5, 6, 7, 8, 9, 10, or more.

When the lower limit and the upper limit of a numerical range are disclosed, any value or sub-range within the range is intended to be specifically disclosed. In particular, each of the numerical ranges (e.g., in the form of "from about a to b", or equivalently "from approximately a to b", or equivalently "about a-b") of the parameters disclosed herein is to be understood to encompass each of the values and sub-ranges therein. For example, "$C_{1-6}$" should be understood to encompass any sub-range and each point value therein, e.g., $C_{2-5}$, $C_{3-4}$, $C_{1-2}$, $C_{1-3}$, $C_{1-4}$, $C_{1-5}$, etc., and $C_1$, $C_2$, $C_3$, $C_4$, $C_5$, $C_6$, etc. For another example, "3- to 10-membered" should be understood to encompass any sub-range and each point value therein, e.g., 3- to 4-membered, 3- to 5-membered, 3- to 6-membered, 3- to 7-membered, 3- to 8-membered, 3- to 9-membered, 4- to 5-membered, 4- to 6-membered, 4- to 7-membered, 4- to 8-membered, 5- to 7-membered, 5- to 8-membered, 6- to 7-membered, etc., and 3-, 4-, 5-, 6-, 7-, 8-, 9-, 10-membered, etc.

The term "pharmaceutically acceptable salt" refers to salts of the compounds of the present disclosure that are substantially non-toxic to an organism. Pharmaceutically acceptable salts generally include, but are not limited to, salts formed by reacting the compounds of the present disclosure with a pharmaceutically acceptable inorganic acid/organic acid/acidic amino acid or inorganic base/organic base/basic amino acid, and such salts are also referred to as acid addition salts or base addition salts. Examples of suitable acid addition salts include, but are not limited to, acetate. For a review of suitable salts, please see, for example, Jusiak, Soczewinski, et al., Remington's Pharmaceutical Sciences [M], Mack Publishing Company, 2005 and Stahl, Wermuth, Handbook of Pharmaceutical Salts: Properties, Selection, and Use [M], Wiley-VCH, 2002. Methods for preparing pharmaceutically acceptable salts of the compounds of the present disclosure are known to those skilled in the art.

The term "pharmaceutically acceptable ester" refers to esters substantially non-toxic to an organism and hydrolyzed in the organism into the compounds of the present disclosure or salts thereof. Pharmaceutically acceptable esters generally include, but are not limited to, esters formed of the compounds of the present disclosure and a pharmaceutically acceptable carboxylic acid or sulfonic acid, and such esters are also known as carboxylic acid esters or sulfonic acid esters. In addition, the compounds of the present disclosure per se may also be esters.

The term "isomer" refers to the compounds that have the same molecular weight because of the same number and type of atoms, but differ in the spatial arrangement or configuration of the atoms.

The term "stereoisomer" (or "optical isomer") refers to a stable isomer having a perpendicular and asymmetry-generated plane due to the presence of at least one chiral element (including a chiral center, a chiral axis, and a chiral plane), thereby enabling rotation of plane-polarized light. Since the compounds of the present disclosure have asymmetric centers and other chemical structures that may lead to stereoisomerism, the present disclosure also includes these stereoisomers and mixtures thereof. Since the compounds of the present disclosure (or the pharmaceutically acceptable salts thereof) include asymmetric carbon atoms, they can exist in the form of individual stereoisomers, in the form of racemates, or in the form of mixtures of enantiomers or diastereomers. Typically, these compounds can be prepared in the form of racemates. However, if desired, such compounds may be prepared or isolated to obtain pure stereoisomers, i.e., individual enantiomers or diastereoisomers, or individual stereoisomer-enriched mixtures (with a purity of ≥99%, ≥98%, ≥97%, ≥96%, ≥95%, ≥90%, ≥85%, ≥80%, ≥75%, ≥70%, ≥65%, or ≥60%). As described below, individual stereoisomers of compounds are prepared synthetically from optically active starting materials containing the desired chiral centers, or prepared by obtaining mixtures of enantiomeric products and then isolating or resolving the mixtures, for example, by converting into mixtures of diastereomers followed by isolation, recrystallization, chromatographic isolation, or use of chiral resolution reagents, or by isolating enantiomers directly on a chiral chromatographic column. Starting compounds with specific stereochemistry may be either commercially available or prepared according to the methods described below and resolved by the methods well known in the art. The term "enantiomer" refers to a pair of stereoisomers that are non-superimposable mirror images of each other. The term "diastereoisomer" or "diastereomer" refers to optical isomers that do not form mirror images of each other. The term "racemic mixture" or "racemate" refers to a mixture containing equal parts of individual enantiomers (i.e., an equimolar mixture of the two R- and S-enantiomers). The term "non-racemic mixture" refers to a mixture containing unequal parts of individual enantiomers. Unless otherwise indicated, all stereoisomeric forms of the compounds of the present disclosure are within the scope of the present disclosure.

Solid bonds (_), wedged bonds ( ), or hashed wedged bonds ( ) are used herein to depict the covalent bonds of the compounds of the present disclosure. When a solid bond is used to depict that a bond is linked to a chiral atom, it is meant to include all possible stereoisomers due to the chiral atom (e.g., specific enantiomers and racemic mixtures). When a wedged or hashed wedged bond is used herein to depict that a bond is linked to a chiral atom, this indicates the existence of the stereoisomer as shown. Unless otherwise indicated, the stereoisomers of the compounds of the present disclosure may encompass specific enantiomers, diastereoisomers, racemates, or mixtures thereof in any proportion.

The term "tautomer" (or "tautomeric form") refers to structural isomers of different energies that may be interconvertible over a low energy barrier. If tautomerism is possible (e.g., in a solution), a chemical equilibrium of tautomers can be achieved. For example, the causes of proton tautomers (or prototropic tautomers) include, but are not limited to, interconversion via proton migration, such as keto-enol tautomerism, imine-enamine tautomerism, amide-iminol tautomerism, and nitroso-oxime tautomerism. Unless otherwise indicated, all tautomeric forms of the compounds of the present disclosure are within the scope of the present disclosure.

The term "polymorph" (or "polymorphic form") refers to a solid crystal form of a compound or complex. Those skilled in the art may obtain a polymorph of a molecule by a number of known methods. These methods include, but are not limited to, melt recrystallization, melt cooling, solvent recrystallization, desolvation, rapid evaporation, rapid cooling, slow cooling, and vapor phase diffusion and sublimation. Furthermore, polymorphs may be detected, classified, and identified by well-known techniques including, but not limited to, differential scanning calorimetry (DSC), thermogravimetric analysis (TGA), X-ray powder diffraction (XRPD), single crystal X-ray diffraction (SCXRD), solid state nuclear magnetic resonance (NMR), infrared spectroscopy (IR), Raman spectroscopy, and scanning electron microscopy (SEM). The present disclosure covers all possible crystalline forms or polymorphs of the compounds of the present disclosure, which may be a single polymorph or a mixture of polymorphs mixed in any proportion.

The term "solvate" refers to a substance formed by the association of the compound of the present disclosure (or a pharmaceutically acceptable salt thereof) with at least one kind of solvent molecule through non-covalent intermolecular forces. The compounds of the present disclosure may exist in the form of solvates containing a polar solvent as a structural element of the crystal lattice. The polar solvent may be present at a stoichiometric ratio or non-stoichiometric ratio.

The term "isotope-labelled compound" refers to a derivative compound formed by replacing a particular atom in the compound of the present disclosure with its isotopic atom. Unless otherwise indicated, the compounds of the present disclosure include various isotopes of H, C, N, O, F, P, S, and Cl, for example, $^{2}$H (D), $^{3}$H (T), $^{13}$C, $^{14}$C, $^{13}$N, $^{15}$N, $^{17}$O, $^{18}$O, $^{18}$F, $^{31}$P, $^{32}$P, $^{34}$S $^{35}$S, $^{36}$S, $^{37}$Cl, and $^{125}$I. For example, $^{12}$C may be replaced with $^{13}$C or $^{14}$C; $^{1}$H may be replaced with $^{2}$H (D, deuterium) or $^{3}$H (T, tritium); and $^{16}$O may be replaced with $^{18}$O.

The term "metabolite" refers to a derivative compound formed after the compound of the present disclosure is metabolized, e.g., by reactions such as oxidation, reduction, hydrolysis, amidation, deamidation, esterification, and enzymolysis. For further information on metabolism, please see Goodman and Gilman's: The Pharmacological Basis of Therapeutics [M], McGraw-Hill International Editions, 1996. The present disclosure encompasses all possible metabolite forms of the compounds of the present disclosure, i.e., substances formed in the subject administered with the compound of the present disclosure. Metabolites of the compounds can be identified by techniques well known in the art, and their activities can be experimentally characterized.

The term "prodrug" refers to a derivative compound that, after administered to a subject, is capable of offering, directly or indirectly, the compound of the present disclosure. Particularly preferred derivative compounds or prodrugs are the compounds that, when administered to a subject, can increase the bioavailability of the compounds of the present disclosure (e.g., more readily absorbed into the blood), or the compounds that facilitate delivery of the parent compound to the site of action (e.g., the lymphatic system). Unless otherwise indicated, all prodrug forms of the compounds of the present disclosure are within the scope of the present disclosure, and various prodrug forms are known in the art, see, e.g., T. Higuchi, V. Stella, Prodrugs as Novel Drug Delivery Systems [J], American Chemical Society, Vol. 14, 1975. In addition, the present disclosure further encompasses the compounds of the present disclosure containing a protective group. In any process of preparing the compounds of the present disclosure it may be necessary and/or desirable to protect sensitive or reactive groups on any of the molecules concerned, thereby forming a chemically protected form of the compounds of the present disclosure. This may be realized by conventional protective groups, such as those described in T. W. Greene, P. G. M. Wuts, Protective Groups in Organic Synthesis [M], John Wiley & Sons, 2006. These protective groups may be removed at an appropriate subsequent stage by the methods known in the art.

The term "chemical bond" refers to a strong force between two or more adjacent atoms (or ions) in the molecule of a pure substance or in a crystal, which mainly includes covalent bond, ionic bond, metallic bond, coordinate bond, and the like. Unless otherwise indicated, the chemical bonds in the compounds of the present disclosure in the free form are mostly covalent bonds.

When used herein alone or in combination with an additional group, the term "alkyl" refers to a linear or branched, saturated aliphatic hydrocarbyl. For example, the term "$C_{1-6}$ alkyl" used herein refers to an alkyl (such as methyl, ethyl, n-propyl, isopropyl, n-butyl, sec-butyl, isobutyl, tert-butyl, n-pentyl, isopentyl, neopentyl, or n-hexyl) having 1 to 6 carbon atoms (such as 1, 2, 3, 4, 5, or 6 carbon atoms), which is optionally substituted by one or more (such as 1 to 3) substituents described herein (if substituted by a halogen, this group is "$C_{1-6}$ haloalkyl", such as $—CF_3$, $—C_2F_5$, $—CHF_2$, $—CH_2F$, $—CH_2CF_3$, $—CH_2Cl$, or $—CH_2CH_2CF_3$; if substituted by a hydroxyl, this group is "$C_{1-6}$ hydroxyalkyl", such as $—CH_2OH$, $—CH_2CH_2OH$, or $—CH(OH)CH_3$).

When used herein alone or in combination with an additional group, the term "alkylene" refers to a divalent, linear or branched, saturated aliphatic hydrocarbyl, and the two groups (or fragments) it links may be linked either to the same carbon atom or to different carbon atoms. For example, the term "$C_{1-6}$ alkylene" used herein refers to an alkylene (such as methylene, 1,1-ethylidene, 1,2-ethylidene, 1,2-propylidene, or 1,3-butylidene) having 1 to 6 carbon atoms, which is optionally substituted by one or more (such as 1 to 3) substituents described herein (if substituted by a halogen, this group is "$C_{1-6}$ haloalkylene", such as $—CF_2—$, $—C_2F_4—$, or $—CHF—$).

When used herein alone or in combination with an additional group, the term "cycloalkyl" refers to a monocyclic or polycyclic (such as bicyclic) alkyl (e.g., monocyclic cycloalkyl, such as cyclopropyl, cyclobutyl, cyclopentyl, cyclohexyl, cycloheptyl, cyclooctyl, or cyclononyl; or bicyclic cycloalkyl including fused rings, bridged rings, or spiro rings, such as decahydronaphthyl, bicyclo[2.2.1]heptyl, or spiro[4.5]decyl). For example, the term "$C_{3-6}$ cycloalkyl" used herein refers to a cycloalkyl having 3 to 6 ring carbon atoms, which is optionally substituted by one or more (such as 1 to 3) substituents described herein (if substituted by a halogen, this group is "$C_{1-6}$ halocycloalkyl", such as 2-fluorocyclopropyl, 3-chlorocyclobutyl, or 4-bromocyclohexyl; if substituted by a hydroxyl, this group is "$C_{1-6}$ hydroxycycloalkyl", such as 2-hydroxylcyclopropyl, 3-hydroxylcyclobutyl, or 4-hydroxylcyclohexyl).

When used herein alone or in combination with an additional group, the term "cycloalkylene" refers to a divalent, monocyclic or polycyclic (e.g., bicyclic) alkyl, and the two groups (or fragments) it links may be linked either to the same ring carbon atom or to different ring carbon atoms. For example, the term "$C_{3-6}$ cycloalkylene" used herein refers to a cycloalkylene having 3 to 6 ring carbon atoms, which is optionally substituted by one or more (such as 1 to 3) substituents described herein (e.g.,

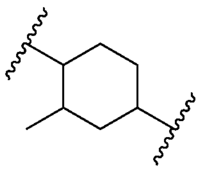 [SMILES: *C1CCC(*)C(C)C1]

group).

When used herein alone or in combination with an additional group, the term "heterocycloalkyl" refers to a saturated or unsaturated, monocyclic or polycyclic (e.g., bicyclic), non-aromatic group having, in its ring, one or more carbon atoms (such as 1, 2, 3, 4, 5, 6, 7, 8, or 9) and one or more (such as 1, 2, 3, or 4) heteroatoms each independently selected from the group consisting of N, O, P, and S, e.g., a total of 3 to 15 (preferably 3 to 8, more preferably 3 to 6) ring atoms. This term further covers the cases where the C atom, N atom and/or P atom in the ring may be substituted by an oxo group (═O) and/or the S atom in the ring may be substituted by one or two oxo groups (═O). The ring system of the heterocycloalkyl may be a fused, bridged, or spiro ring system. If the valency requirements are met, the heterocycloalkyl may be linked to an additional group (or fragment) via any one of the carbon atoms or heteroatoms in the ring. For example, the term "3- to 6-membered heterocycloalkyl" used herein refers to a heterocycloalkyl having 3 to 6 ring atoms (in which one or more heteroatoms are included), which is optionally substituted by one or more (such as 1 to 3) substituents described herein (such as oxiranyl, thiiranyl, aziranyl, azetidinyl, oxetanyl, thietanyl, tetrahydrofuranyl, dioxolanyl, tetrahydrothienyl, pyrrolidinyl, pyrrolidinonyl, imidazolidinyl, pyrazolidinyl, tetrahydropyranyl, tetrahydrothiopyranyl, piperidinyl, morpholinyl, thiomorpholinyl, 1,4-thioxanyl, 1,4-dioxanyl, 1,4-dithianyl, piperazinyl, trioxanyl, trithianyl, and thiazinanyl; if substituted by a halogen, this group is "3- to 6-membered haloheterocycloalkyl", such as 3-fluoropyrrolidin-1-yl; if substituted by a hydroxyl, this group is "3- to 6-membered hydroxyheterocycloalkyl", such as 4-hydroxytetrahydrofuran-2-yl).

When used herein alone or in combination with an additional group, the term "heterocycloalkylene" refers to a divalent, monocyclic or polycyclic (e.g., bicyclic) group having, in its ring, one or more carbon atoms (e.g., 1, 2, 3, 4, 5, 6, 7, 8, or 9) and one or more (e.g., 2, 3, or 4) heteroatoms each independently selected from the group consisting of N, O, P, and S, and the two groups (or fragments) it links may be linked either to the same ring carbon atom or to a ring carbon atom and a ring heteroatom (such as an N atom or a P atom) respectively. For example, the term "3- to 10-membered heterocycloalkylene" used herein refers to a heterocycloalkylene having 3 to 10 ring atoms (in which one or more heteroatoms are included), which is optionally substituted by one or more (such as 1 to 3) substituents described herein (e.g.,

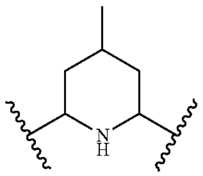 [SMILES: *C1CC(C)CC(*)N1]

group).

When used herein alone or in combination with an additional group, the term "heterocycloalkenyl" refers to a monocyclic or polycyclic (e.g., bicyclic) group having one or more carbon-carbon double bonds, which has, in its ring, one or more carbon atoms (such as 1, 2, 3, 4, 5, 6, 7, 8, or 9) and one or more (such as 1, 2, 3, or 4) heteroatoms each independently selected from the group consisting of N, O, P, and S, e.g., a total of 3 to 15 (preferably 3 to 8, more preferably 3 to 6) ring atoms. This term further covers the cases where the C atom, N atom and/or P atom in the ring may be substituted by an oxo group (═O) and/or the S atom in the ring may be substituted by one or two oxo groups (═O). The ring system of the heterocycloalkenyl may be a fused, bridged, or spiro ring system. If the valency requirements are met, the heterocycloalkenyl may be linked to an additional group (or fragment) via any one of the carbon atoms or heteroatoms in the ring. For example, the term "3- to 6-membered heterocycloalkenyl" used herein refers to a heterocycloalkyl having 3 to 6 ring atoms (in which one or more heteroatoms are included), which is optionally substituted by one or more (such as 1 to 3) substituents described herein.

When used herein alone or in combination with an additional group, the term "heterocycloalkenylene" refers to a divalent, monocyclic or polycyclic (e.g., bicyclic) group having one or more carbon-carbon double bonds, which has, in its ring, one or more carbon atoms (such as 1, 2, 3, 4, 5, 6, 7, 8, or 9) and one or more (such as 1, 2, 3, or 4) heteroatoms each independently selected from the group consisting of N, O, P, and S, e.g., a total of 3 to 15 (preferably 3 to 8, more preferably 3 to 6) ring atoms. This term further covers the cases where the C atom, N atom and/or P atom in the ring may be substituted by an oxo group (═O) and/or the S atom in the ring may be substituted by one or two oxo groups (═O).

When used herein alone or in combination with an additional group, the term "aryl" refers to a monocyclic or fused cyclic, aromatic hydrocarbonyl with a conjugated 71-electron system. For example, the term "$C_{6-12}$ aryl" used herein refers to an aryl (such as phenyl or naphthyl) having 6 to 12 carbon atoms, which is optionally substituted by one or more substituents described herein (such as $C_{1-6}$ alkyl-substituted tolyl and halogen-substituted chlorophenyl).

When used herein alone or in combination with an additional group, the term "arylene" refers to a divalent, monocyclic or fused cyclic, aromatic hydrocarbonyl with a conjugated n-electron system. For example, the term "$C_{6-10}$ arylene" used herein refers to an arylene having 6 to 10 carbon atoms, which is optionally substituted by one or more substituents described herein (such as $C_{1-6}$ alkyl-substituted tolylene and halogen-substituted chlorophenylene).

When used herein alone or in combination with an additional group, the term "heteroaryl" refers to a monocyclic or fused cyclic, aromatic group with a conjugated R-electron system, which has, in its ring, one or more carbon atoms (such as 1, 2, 3, 4, 5, 6, 9, or 10 carbon atoms) and one or more (such as 1, 2, 3, or 4) heteroatoms each independently selected from the group consisting of N, O, P, and S, e.g., a total of 5 to 12 (preferably 5 to 10, more preferably 5, 6, 9, or 10) ring atoms. If the valency requirements are met, the heterocycloalkyl may be linked to the parent molecular moiety via any one of the ring atoms. If the valency requirements are met, the heteroaryl may be linked to an additional group (or fragment) via any one of the carbon atoms or heteroatoms (such as an N atom) in the ring. Moreover, the heteroaryl may optionally be further fused with benzene. For example, the term "5- to 12-membered heteroaryl" used herein refers to a heteroaryl (such as furyl, thienyl, pyrrolyl, oxazolyl, thiazolyl, imidazolyl, isoxazolyl, isothiazolyl, pyrazolyl, oxadiazolyl, thiadiazolyl, triazolyl, pyridinyl, pyridazinyl, pyrimidinyl, pyrazinyl, triazinyl, quinolinyl, isoquinolinyl, benzofuranyl, isobenzofuranyl, benzothienyl, isobenzothienyl, indolyl, isoindolyl, or benzene-fused derivatives thereof) having 5 to 12 ring atoms, which is optionally substituted by one or more substituents described herein (such as $C_1$. 6 alkyl-substituted methylpyridinyl and halogen-substituted chloropyridinyl).

When used herein alone or in combination with an additional group, the term "heteroarylene" refers to a divalent, monocyclic or fused cyclic, aromatic group with a conjugated 2-electron system, which has, in its ring, one or more carbon atoms (such as 1, 2, 3, 4, 5, 6, 9, or 10 carbon atoms) and one or more (such as 1, 2, 3, or 4) heteroatoms each independently selected from the group consisting of N, O, P, and S, e.g., a total of 5 to 12 (preferably 5 to 10, more preferably 5, 6, 9, or 10) ring atoms. For example, the term "5- to 12-membered heteroarylene" used herein refers to a heteroarylene having 5 to 12 ring atoms, which is optionally substituted by one or more substituents described herein (e.g., $C_{1-6}$ alkyl-substituted

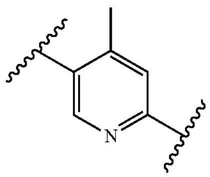 [SMILES: *c1cc(C)c(*)cn1]

group and halogen-substituted

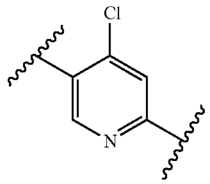 [SMILES: *c1cc(Cl)c(*)cn1]

group).

When used herein alone or in combination with an additional group, the term "alkenyl" refers to a linear or branched, aliphatic hydrocarbonyl having one or more carbon-carbon double bonds. For example, the term "$C_{2-6}$ alkenyl" used herein refers to an alkenyl (such as ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, or 4-methyl-3-pentenyl) having 2 to 6 carbon atoms and one, two, or three (preferably one) carbon-carbon double bonds, which is optionally substituted by one or more (such as 1 to 3) substituents described herein.

When used herein alone or in combination with an additional group, the term "alkenylene" refers to a divalent, linear or branched, aliphatic hydrocarbonyl having one or more carbon-carbon double bonds, and the two groups (or fragments) it links may be linked either to the same carbon atom or to different carbon atoms. For example, the term "$C_{2-6}$ alkenylene" used herein refers to an alkenylene (e.g.,

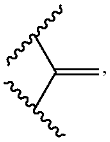,
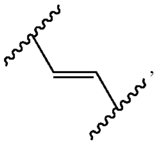,
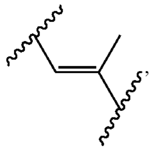, or

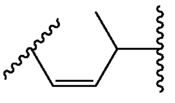

group) having 2 to 6 carbon atoms, which is optionally substituted by one or more (such as 1 to 3) substituents described herein.

When used herein alone or in combination with an additional group, the term "cycloalkenyl" refers to a monocyclic or polycyclic (e.g., bicyclic) alkenyl having one or more carbon-carbon double bonds (e.g., monocyclic cycloalkenyl such as cyclobutenyl, cyclopentenyl, cyclohexenyl, or cycloheptenyl). For example, the term "$C_{3-6}$ cycloalkenyl" used herein refers to a cycloalkenyl having 3 to 6 ring carbon atoms, which is optionally substituted by one or more (such as 1 to 3) substituents described herein (e.g.,

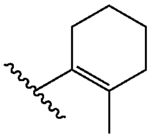 [SMILES: *C1=C(C)CCCC1]

group).

When used herein alone or in combination with an additional group, the term "cycloalkenylene" refers to a divalent, monocyclic or polycyclic (e.g., bicyclic) alkenyl having one or more carbon-carbon double bonds, and the two groups (or fragments) it links may be linked either to the same ring carbon atom or to different ring carbon atoms. For example, the term "$C_{3-6}$ cycloalkenylene" used herein refers to a cycloalkenylene having 3 to 6 ring carbon atoms, which is optionally substituted by one or more (such as 1 to 3) substituents described herein (e.g.,

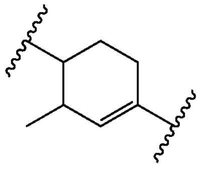 [SMILES: *C1=CC(C)C(*)CC1]

group).

When used herein alone or in combination with an additional group, the term "alkynyl" refers to a linear or branched, aliphatic hydrocarbonyl having one or more carbon-carbon triple bonds. For example, the term "$C_{2-6}$ alkynyl" as used herein refers to an alkynyl (such as ethynyl, 1-propynyl, 2-propynyl, 2-butynyl, 3-butynyl, 2-pentynyl, 3-pentynyl, 4-pentynyl, 2-hexynyl, 3-hexynyl, 4-hexynyl, or 5-hexynyl) having 2 to 6 carbon atoms and one, two, or three (preferably one) carbon-carbon triple bonds, which is optionally substituted by one or more (such as 1 to 3) substituents described herein.

When used herein alone or in combination with an additional group, the term "alkynylene" refers to a divalent, linear or branched, aliphatic hydrocarbonyl having one or more carbon-carbon triple bonds, and the two groups (or fragments) it links are linked to different carbon atoms respectively. For example, the term "$C_{2-6}$ alkynylene" used herein refers to an alkynylene (e.g.,

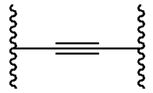 or 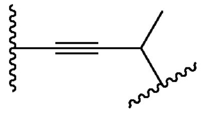

group) having 2 to 6 carbon atoms, which is optionally substituted by one or more (such as 1 to 3) substituents described herein.

When used herein alone or in combination with an additional group, the term "alicyclic ring" or "alicyclic hydrocarbon ring" refers to a monocyclic or polycyclic (including fused cyclic, bridged cyclic, and spirocyclic, such as bicyclic), aliphatic hydrocarbon ring system, including a cycloalkyl ring, a cycloalkenyl ring, and a cycloalkynyl ring.

When used herein alone or in combination with an additional group, the term "heteroalicyclic ring" or "heteroalicyclic hydrocarbon ring" refers to a monocyclic or polycyclic (including fused cyclic, bridged cyclic, and spirocyclic, such as bicyclic), aliphatic hydrocarbon ring system, which has, in its ring, one or more carbon atoms (such as 1, 2, 3, 4, 5, 6, 7, 8, or 9) and one or more (such as 1, 2, 3, or 4) heteroatoms each independently selected from the group consisting of N, O, P, and S, including a heterocycloalkyl ring, a heterocycloalkenyl ring, and a heterocycloalkynyl ring.

When used herein alone or in combination with an additional group, the term "aromatic ring" or "aromatic hydrocarbon ring" refers to a monocyclic or polycyclic (e.g., bicyclic), aromatic hydrocarbon ring system.

When used herein alone or in combination with an additional group, the term "heteroaromatic ring" or "heteroaromatic hydrocarbon ring" refers to a monocyclic or polycyclic (e.g., bicyclic), aromatic hydrocarbon ring system, which has, in its ring, one or more carbon atoms (such as 1, 2, 3, 4, 5, 6, 7, 8, or 9) and one or more (such as 1, 2, 3, or 4) heteroatoms each independently selected from the group consisting of N, O, P, and S.

When used herein alone or in combination with an additional group, the term "halogen" refers to fluorine (F), chlorine (Cl), bromine (Br), or iodine (I).

When used herein alone or in combination with an additional group, the term "hydroxyl" refers to —OH group.

When used herein alone or in combination with an additional group, the term "cyano" refers to —CN group.

When used herein alone or in combination with an additional group, the term "nitro" refers to $—NO_2$ group.

When used herein alone or in combination with an additional group, the term "amino" refers to $—NH_2$ group.

When used herein alone or in combination with an additional group, the term "oxo" refers to ═O group.

The term "each independently" used herein means that at least two groups (or fragments) with the same or similar definition of structure may have the same or different meanings under particular circumstances. For example, if the substituent X and the substituent Y are each independently hydrogen, halogen, hydroxyl, cyano, alkyl, or aryl, when the substituent X is hydrogen, the substituent Y may either be hydrogen or be halogen, hydroxyl, cyano, alkyl, or aryl; similarly, when the substituent Y is hydrogen, the substituent X may either be hydrogen or be halogen, hydroxyl, cyano, alkyl, or aryl.

The term "substitution" and other variations used herein mean that one or more (such as 1, 2, 3, or 4) atoms or atomic groups (such as a hydrogen atom) linked to the designated atom are replaced with additional equivalent(s), provided that the valence of the designated atom or atomic group in the current situation can be kept normal and that a stable compound can be formed. If an atom or atomic group is described as being "optionally substituted by . . . ", it may be either substituted or unsubstituted. Unless otherwise specified, a linking position of a substituent described herein may be at any appropriate position of the substituent. When a linking bond in a substituent is shown as a chemical bond across two interconnected atoms in a ring system, it means that the substituent may be linked to any of the ring atoms in the ring system.

Compound of General Formula

The present disclosure provides a compound of formula I or a pharmaceutically acceptable salt, ester, stereoisomer, tautomer, polymorph, solvate, isotope-labelled compound, metabolite, or prodrug thereof,

I

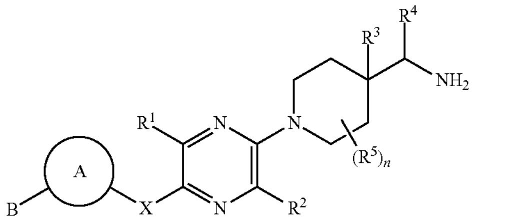

wherein

X is selected from the group consisting of a chemical bond, S, O, NH, and $CH_2$;

$R^1$ is selected from the group consisting of hydrogen, hydroxyl, halogen, amino, $C_{1-6}$ alkyl, 3- to 6-membered heterocycloalkyl, and $C_{3-6}$ cycloalkyl, wherein the alkyl, heterocycloalkyl, and cycloalkyl are each optionally substituted by one or more substituents selected from the group consisting of halogen, hydroxyl, and amino;

$R^2$ is selected from the group consisting of hydrogen, hydroxyl, amino, cyano, halogen, $C_{1-6}$ alkyl, 3- to 6-membered heterocycloalkyl, and $C_{3-6}$ cycloalkyl, wherein the alkyl, heterocycloalkyl, and cycloalkyl are each optionally substituted by one or more substituents selected from the group consisting of halogen, oxo, hydroxyl, and amino;

A is selected from the group consisting of $C_{6-12}$ arylene, 5- to 12-membered heteroarylene, 3- to 12-membered heterocycloalkylene, and $C_{3-8}$ cycloalkylene, wherein the arylene, heteroarylene, heterocycloalkylene, and cycloalkylene are each optionally substituted by one or more $R^a$;

each of the $R^a$, if present, is independently selected from the group consisting of hydrogen, halogen, hydroxyl, —O—($C_{1-6}$ alkyl), —O—($C_{3-6}$ cycloalkyl), cyano, $C_{1-6}$ alkyl, $C_{3-6}$ cycloalkyl, $C_{2-6}$ alkenyl, $—S(═O)_g—$($C_{1-6}$ alkyl), $—S(═O)_gNH_2$, amino, —NH($C_{1-6}$ alkyl), $—N(C_{1-6}\ alkyl)_2$, 3- to 12-membered heterocycloalkyl, $C_{6-10}$ aryl, and 5- to 12-membered heteroaryl, wherein the alkyl, cycloalkyl, alkenyl, heterocycloalkyl, aryl, and heteroaryl are each optionally substituted by one or more substituents selected from the group consisting of amino, —NH($C_{1-6}$ alkyl), $—N(C_{1-6}\ alkyl)_2$, halogen, cyano, oxo, hydroxyl, —O—($C_{1-6}$ alkyl), $—S(═O)_g—$($C_{1-6}$ alkyl), and $C_{1-6}$ alkyl; or when X is NH or $CH_2$, any one of $R^a$ together with X and the atoms to which they are linked form a 5- to 10-membered alicyclic ring, a 5- to 10-membered heteroalicyclic ring, a 5- to 6-membered heteroaromatic ring, or a benzene ring, wherein the alicyclic ring, heteroalicyclic ring, heteroaromatic ring, and benzene ring are each optionally substituted by one or more substituents selected from the group consisting of amino, —NH($C_{1-6}$ alkyl), $—N(C_{1-6}\ alkyl)_2$, halogen, cyano, oxo, hydroxyl, —O—($C_{1-6}$ alkyl), $C_{1-6}$ haloalkyl, and $C_{1-6}$ alkyl;

B is selected from the group consisting of $—N(R^b)—C(═O)-G-R^d$, $—N(R^b)—S(═O)_g-G-R^d$, $—N(R^b)—C(═O)—N(R^b)-G-R^d$, $—N(R^b)—S(═O)_g—N(R^b)-G-R^d$, $—C(═O)—N(R^b)-G-R^d$, $—S(═O)_g—N(R^b)-G-R^d$, $—S(═O)_g-G-R^d$, —O-G-(3- to 10-membered heterocycloalkyl), —O-G-($C_{3-6}$ cycloalkyl), —O—($C_{3-6}$ cycloalkylene)-G-H, —O-(3- to 10-membered heterocycloalkylene)-G-H, $—O-G-R^d$, $—N(R^b)$-G-(3- to 10-membered heterocycloalkyl), $—N(R^b)$-G-($C_{3-6}$ cycloalkyl), $—N(R^b)—$($C_{3-6}$ cycloalkylene)-G-H, $—N(R^b)$-(3- to 10-membered heterocycloalkylene)-G-H, $-G-O—C(═O)—R^b$, $-G-N(R^b)—C(═O)—R^b$, $G-N(R^b)C(═O)OR^b$, and

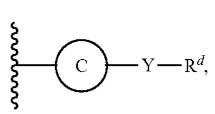

wherein the heterocycloalkyl, heterocycloalkylene, cycloalkyl, and cycloalkylene are each optionally substituted by one or more substituents selected from the group consisting of hydrogen, halogen, hydroxyl, amino, —NH($C_{1-6}$ alkyl), $—N(C_{1-6}\ alkyl)_2$, oxo, —O—($C_{1-6}$ alkyl), $C_{1-6}$ haloalkyl, and $C_{1-6}$ alkyl, and B is not —O—($C_{1-2}$ haloalkyl);

G is selected from the group consisting of $C_{1-6}$ alkylene, $C_{2-6}$ alkenylene, $C_{2-6}$ alkynylene, $C_{3-6}$ cycloalkylene, $C_{3-6}$ cycloalkenylene, 3- to 10-membered heterocycloalkenylene, and 3- to 10-membered heterocycloalkylene, wherein the alkylene, cycloalkylene, cycloalkenylene, heterocycloalkenylene, and heterocycloalkylene are each optionally substituted by one or more substituents selected from the group consisting of hydrogen, halogen, oxo, hydroxyl, cyano, amino, —$OR^b$, —$NHR^b$, —$N(R^b)_2$, —$N(R^b)$—C(═O)—$R^b$, —C(═O)—$NH_2$, —C(═O)—$N(R^b)_2$, $C_{1-6}$ alkyl, $C_{1-6}$ haloalkyl, $C_{1-6}$ hydroxyalkyl, $C_{3-6}$ cycloalkyl, $C_{3-6}$ halocycloalkyl, $C_{3-6}$ hydroxycycloalkyl, 3- to 10-membered haloheterocycloalkyl, 3- to 10-membered hydroxyheterocycloalkyl, and 3- to 10-membered heterocycloalkyl;

$R^b$ is selected from the group consisting of hydrogen, halogen, amino, cyano, $C_{1-6}$ alkyl, $C_{3-6}$ cycloalkyl, $C_{3-6}$ cycloalkenyl, 3- to 10-membered heterocycloalkenyl, and 3- to 10-membered heterocycloalkyl, wherein the alkyl, cycloalkyl, cycloalkenyl, heterocycloalkenyl, and heterocycloalkyl are each optionally substituted by one or more substituents selected from the group consisting of hydrogen, halogen, oxo, hydroxyl, cyano, and amino;

C is selected from the group consisting of $C_{6-12}$ arylene, 5- to 12-membered heteroarylene, 3- to 12-membered heterocycloalkylene, $C_{3-12}$ cycloalkenylene, 3- to 12-membered heterocycloalkenylene, and $C_{3-8}$ cycloalkylene, wherein the arylene, heteroarylene, heterocycloalkylene, cycloalkenylene, heterocycloalkenylene, and cycloalkylene are each optionally substituted by one or more $R^c$;

each of the $R^c$, if present, is independently selected from the group consisting of hydrogen, halogen, hydroxyl, —O—($C_{1-6}$ alkyl), —O—($C_{3-6}$ cycloalkyl), cyano, $C_{1-6}$ alkyl, $C_{2-6}$ alkenyl, —S(═O)$_g$—($C_{1-6}$ alkyl), —S(═O)$_g$$NH_2$, amino, —NH($C_{1-6}$ alkyl), and —N($C_{1-6}$ alkyl)$_2$, wherein the alkyl and alkenyl are each optionally substituted by one or more substituents selected from the group consisting of amino, —NH($C_{1-6}$ alkyl), —N($C_{1-6}$ alkyl)$_2$, halogen, cyano, oxo, hydroxyl, —O—($C_{1-6}$ alkyl), —S(═O)$_g$—($C_{1-6}$ alkyl), and $C_{1-6}$ alkyl;

Y is selected from the group consisting of $C_{1-6}$ alkylene, $C_{3-6}$ cycloalkylene, 3- to 6-membered heterocycloalkylene, $C_{3-6}$ cycloalkenylene, 3- to 6-membered heterocycloalkenylene, $C_{6-10}$ arylene, 5- to 12-membered heteroarylene, $C_{2-6}$ alkenylene, —S(═O)$_g$—($C_{1-6}$ alkylene)-, —S(═O)$_g$—N($R^b$)—, —C(═O)—($C_{1-6}$ alkylene)-, —C(═O)—($C_{3-6}$ cycloalkylene)-, —C(═O)-(3- to 6-membered heterocycloalkylene)-, and —C(═O)—, wherein the alkylene, heterocycloalkylene, cycloalkenylene, heterocycloalkenylene, and cycloalkylene are each optionally substituted by one or more substituents selected from the group consisting of halogen, oxo, hydroxyl, and amino;

$R^d$ is selected from the group consisting of halogen, amino, hydroxyl, cyano, —S(═O)$_g$—($C_{1-6}$ alkyl), —O—($C_{1-6}$ alkyl), —O—($C_{3-6}$ cycloalkyl), —NH—($C_{1-6}$ alkyl), —NH($C_{3-6}$ cycloalkyl), —N($C_{1-6}$ alkyl)$_2$, —NH—C(═O)—O—($C_{1-6}$ alkyl), —N($C_{1-6}$ alkyl)-C(═O)—O—($C_{1-6}$ alkyl), —O—C(═O)—$NH_2$, —O—C(═O)—NH($C_{1-6}$ alkyl), and —N($C_{1-6}$ alkyl)-C(═O)—($C_{1-6}$ alkyl), wherein the alkyl and cycloalkyl are each optionally substituted by one or more substituents selected from the group consisting of halogen, oxo, hydroxyl, amino, and —O—($C_{1-6}$ alkyl);

$R^3$ is selected from the group consisting of halogen, —$OR^z$, hydroxyl, cyano, —C(═O)—$OR^z$, —C(═O)—$N(R^z)_2$, $C_{1-6}$ alkyl, —($C_{1-6}$ alkylene)-$R^z$, —($C_{1-6}$ alkylene)-$OR^z$, —($C_{1-6}$ alkylene)-OH, —($C_{1-6}$ alkylene)-$N(R^z)_2$, $C_{3-6}$ cycloalkyl, 3- to 12-membered heterocycloalkyl, $C_{3-6}$ cycloalkenyl, 3- to 12-membered heterocycloalkenyl, $C_{2-6}$ alkenyl, $C_{2-6}$ alkynyl, $C_{6-12}$ aryl, 5- to 12-membered heteroaryl, —S(═O)$_g$—($C_{1-6}$ alkyl), amino, and —$N(R^z)_2$, wherein the alkyl, alkylene, cycloalkyl, heterocycloalkyl, cycloalkenyl, heterocycloalkenyl, alkenyl, alkynyl, aryl, and heteroaryl are each optionally substituted by one or more substituents selected from the group consisting of halogen, cyano, oxo, —OW, hydroxyl, —$N(R^z)_2$, —$NHR^z$, amino, $C_{1-6}$ alkyl, $C_{3-6}$ cycloalkyl, 3- to 12-membered heterocycloalkyl, $C_{6-10}$ aryl, 5- to 10-membered heteroaryl, —C(═O)—$OR^z$, —C(═O)—$N(R^z)_2$, —C(═O)—$NH_2$, and nitro;

each of the $R^z$, if present, is independently selected from the group consisting of hydrogen, cyano, —C(═O)—($C_{1-6}$ alkyl), —C(═O)—($C_{3-8}$ cycloalkyl), —C(═O)-(3- to 8-membered heterocycloalkyl), $C_{1-6}$ alkyl, $C_{3-6}$ cycloalkyl, 3- to 12-membered heterocycloalkyl, $C_{2-6}$ alkenyl, $C_{2-6}$ alkynyl, $C_{6-12}$ aryl, and 5- to 12-membered heteroaryl, wherein the alkyl, cycloalkyl, heterocycloalkyl, alkenyl, alkynyl, aryl, and heteroaryl are each optionally substituted by one or more substituents selected from the group consisting of amino, halogen, cyano, oxo, nitro, hydroxyl, —O—($C_{1-6}$ alkyl), $C_{1-6}$ alkyl, $C_{1-6}$ haloalkyl, $C_{3-6}$ cycloalkyl, 3- to 12-membered heterocycloalkyl, $C_{6-10}$ aryl, and 5- to 10-membered heteroaryl;

$R^4$ is selected from the group consisting of halogen, $C_{1-6}$ alkyl, $C_{3-6}$ cycloalkyl, —C(═O)—$R^z$, 3- to 12-membered heterocycloalkyl, $C_{2-6}$ alkenyl, $C_{2-6}$ alkynyl, $C_{6-10}$ aryl, and 5- to 12-membered heteroaryl, wherein the alkyl, cycloalkyl, heterocycloalkyl, alkenyl, alkynyl, aryl, and heteroaryl are each optionally substituted by one or more substituents selected from the group consisting of amino, halogen, cyano, hydroxyl, oxo, —O—($C_{1-6}$ alkyl), $C_{1-6}$ alkyl, $C_{1-6}$ haloalkyl, $C_{3-6}$ cycloalkyl, 3- to 12-membered heterocycloalkyl, $C_{6-10}$ aryl, and 5- to 10-membered heteroaryl; or $R^3$ and $R^4$ together with the atoms to which they are linked form a 4- to 8-membered alicyclic ring or a 4- to 8-membered heteroalicyclic ring, wherein the alicyclic ring and heteroalicyclic ring are each optionally substituted by one or more $R^{4a}$, or the alicyclic ring and heteroalicyclic ring are each optionally fused with one or more $C_{6-10}$ aromatic rings or 5- to 12-membered heteroaromatic rings, and the aromatic rings and heteroaromatic rings are each optionally substituted by one or more $R^{4a}$;

each of the $R^{4a}$, if present, is independently selected from the group consisting of hydrogen, halogen, cyano, —C(═O)H, —C(═O)—($C_{1-6}$ alkyl), —C(═O)—($C_{3-8}$ cycloalkyl), —C(═O)-(3- to 8-membered heterocycloalkyl), —NH—C(═O)—($C_{1-6}$ alkyl), —NH—C(═O)—($C_{3-8}$ cycloalkyl), —NH—C(═O)-(3- to 8-membered heterocycloalkyl), oxo, $C_{1-6}$ alkyl, $C_{3-6}$ cycloalkyl, $C_{3-6}$ cycloalkenyl, 3- to 12-membered heterocycloalkyl, 3- to 12-membered heterocycloalkyl, $C_{2-6}$ alkenyl, $C_{2-6}$ alkynyl, $C_{6-12}$ aryl, and 5- to 12-membered heteroaryl, wherein the alkyl, cycloalkyl, cycloalkenyl, heterocycloalkenyl, heterocycloalkyl, alkenyl, alkynyl, aryl, and heteroaryl are each optionally substituted by one or more substituents selected from the group consisting of halogen, cyano, hydroxyl, —O—($C_{1-6}$ alkyl), $C_{1-6}$ alkyl, $C_{3-6}$ cycloalkyl, 3- to 12-membered heterocycloalkyl, $C_{6-10}$ aryl, and 5- to 10-membered heteroaryl;

each of the $R^5$, if present, is independently selected from the group consisting of hydrogen, halogen, oxo, cyano, hydroxyl, carboxyl, —C(═O)—$NH_2$, —C(═O)—O—($C_{1-6}$ alkyl), $C_{1-6}$ alkyl, $C_{3-6}$ cycloalkyl, $C_{2-6}$ alkenyl, $C_{2-6}$ alkynyl, —S(═O)$_g$—($C_{1-6}$ alkyl), 3- to 6-membered heterocycloalkyl, $C_{6-10}$ aryl, and 5- to 10-membered heteroaryl, wherein the alkyl, cycloalkyl, heterocycloalkyl, alkenyl, alkynyl, aryl, and heteroaryl are each optionally substituted by one or more substituents selected from the group consisting of amino, hydroxyl, oxo, halogen, cyano, —O—($C_{1-6}$ alkyl), —NH($C_{1-6}$ alkyl), and —N($C_{1-6}$ alkyl)$_2$; or any two of $R^5$ together with the atoms to which they are linked form a $C_{3-10}$ alicyclic ring or a 4- to 12-membered heteroalicyclic ring;

g is 0, 1, or 2; and n is 0, 1, 2, 3, 4, or 5.

In some embodiments of the present disclosure, X in the compound of formula I as described above is selected from the group consisting of a chemical bond and S; preferably, X is S.

In some embodiments of the present disclosure, $R^1$ in the compound of formula I as described above is selected from the group consisting of hydrogen, hydroxyl, halogen, amino, $C_{1-6}$ alkyl, and $C_{3-6}$ cycloalkyl; preferably, $R^1$ is selected from the group consisting of hydrogen, halogen, amino, and $C_{1-6}$ alkyl (such as hydrogen, halogen, and $C_{1-6}$ alkyl); more preferably, $R^1$ is selected from the group consisting of hydrogen, fluorine, amino, and methyl; further preferably, $R^1$ is selected from the group consisting of hydrogen, fluorine, and methyl.

In some embodiments of the present disclosure, $R^2$ in the compound of formula I as described above is selected from the group consisting of hydrogen, hydroxyl, halogen, $C_{1-6}$ alkyl, and $C_{3-6}$ cycloalkyl, wherein the alkyl and cycloalkyl are each optionally substituted by one or more substituents selected from the group consisting of halogen and hydroxyl; preferably, $R^2$ is selected from the group consisting of hydrogen, hydroxyl, fluorine, hydroxymethyl (—$CH_2OH$), and fluoromethyl (—$CH_2F$); more preferably, $R^2$ is selected from the group consisting of hydrogen, hydroxymethyl, and fluoromethyl; further preferably, $R^2$ is hydroxymethyl.

In some embodiments of the present disclosure, A in the compound of formula I as described above is selected from the group consisting of $C_{6-12}$ arylene and 5- to 12-membered heteroarylene, wherein the arylene and heteroarylene are each optionally substituted by one or more $R^a$; preferably, A is selected from the group consisting of phenylene, pyridinylene, and pyrimidinylene, wherein the phenylene, pyridinylene, and pyrimidinylene are each optionally substituted by one or more $R^a$; more preferably, A is selected from the group consisting of phenylene and pyridinylene, wherein the phenylene and pyridinylene are each optionally substituted by one or more $R^a$.

In some embodiments of the present disclosure, in formula I, there is a plurality of $R^a$ at the same time, and each of $R^a$ is independently selected from the group consisting of hydrogen, halogen, hydroxyl, —O—($C_{1-3}$ alkyl), —O—($C_{3-6}$ cycloalkyl), cyano, $C_{1-3}$ alkyl, $C_{3-6}$ cycloalkyl, 3- to 6-membered heterocycloalkyl, amino, —NH($C_{1-3}$ alkyl), —N($C_{1-3}$ alkyl)$_2$, —S(═O)$_g$—($C_{1-3}$ alkyl), and —S(═O)$_g$$NH_2$; preferably, each of $R^a$ is independently selected from the group consisting of hydrogen, fluorine, chlorine, bromine, hydroxyl, methoxy, cyclopropoxy, cyano, methyl, ethyl, n-propyl, isopropyl, difluoromethoxy, trifluoromethoxy, trifluoromethyl, difluoromethyl, cyclopropyl, pyrrolidinyl, morpholinyl, amino, methylamino, dimethylamino, methylthio, methylsulfonyl, and sulfamoyl; more preferably, each of $R^a$ is independently selected from the group consisting of hydrogen, fluorine, chlorine, bromine, hydroxyl, cyano, methyl, ethyl, n-propyl, isopropyl, cyclopropyl, pyrrolidinyl, morpholinyl, amino, methylamino, and dimethylamino; further preferably, each of $R^a$ is independently selected from the group consisting of fluorine, chlorine, bromine, cyano, methyl, and amino.

In some embodiments of the present disclosure, when X in formula I is NH or $CH_2$ and there is a plurality of $R^a$ at the same time, any one of $R^a$ together with X and the atoms to which they are linked form a 5- to 7-membered alicyclic ring or a 5- to 7-membered heteroalicyclic ring, preferably a 5- to 6-membered alicyclic ring or a 5- to 6-membered heteroalicyclic ring, wherein the alicyclic ring and heteroalicyclic ring are each optionally substituted by one or more substituents selected from the group consisting of amino, fluorine, chlorine, cyano, oxo, hydroxyl, —O—($C_{1-3}$ alkyl), $C_{1-3}$ haloalkyl, and $C_{1-3}$ alkyl, preferably the alicyclic ring and heteroalicyclic ring are each optionally substituted by one or more substituents selected from the group consisting of amino, fluorine, chlorine, oxo, hydroxyl, methoxy, and methyl.

In some embodiments of the present disclosure, when X in formula I is NH and there is a plurality of $R^a$ at the same time, any one of $R^a$ together with X and the atoms to which they are linked form a morpholine ring.

In some embodiments of the present disclosure, B in the compound of formula I as described above is selected from the group consisting of —N($R^b$)—C(═O)-G-$R^d$, —N($R^b$)—S(═O)$_2$-G-$R^d$, —O-G-(3- to 10-membered heterocycloalkyl), —O-G-($C_{3-6}$ cycloalkyl), —O—($C_{3-6}$ cycloalkylene)-G-H, —O-(3- to 10-membered heterocycloalkylene)-G-H, —O-G-$R^d$, —N($R^b$)-G-(3- to 10-membered heterocycloalkyl), —N($R^b$)-G-($C_{3-6}$ cycloalkyl), —N($R^b$)—($C_{3-6}$ cycloalkylene)-G-H, —N($R^b$)-(3- to 10-membered heterocycloalkylene)-G-H, -G-O—C(═O)—$R^b$, -G-N($R^b$)—C(═O)—$R^b$, -G-N($R^b$)—C(═O)—O$R^b$, and

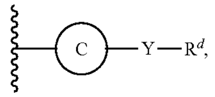

wherein the heterocycloalkyl, heterocycloalkylene, cycloalkyl, and cycloalkylene are each optionally substituted by one or more substituents selected from the group consisting of hydrogen, halogen, hydroxyl, amino, —NH($C_{1-6}$ alkyl), —N($C_{1-6}$ alkyl)$_2$, oxo, —O—($C_{1-6}$ alkyl), $C_{1-6}$ haloalkyl, and $C_{1-6}$ alkyl, and B is not —O—($C_{1-2}$ haloalkyl); preferably, B is selected from the group consisting of —N($R^b$)—C(═O)-G-$R^d$, —O-G-(3- to 10-membered heterocycloalkyl), —O-G-$R^d$, —N($R^b$)-G-(3- to 10-membered heterocycloalkyl), —N($R^b$)-G-($C_{3-6}$ cycloalkyl), —N($R^b$)—($C_{3-6}$ cycloalkylene)-G-H, —N($R^b$)-(3- to 10-membered heterocycloalkylene)-G-H, -G-O—C(═O)—$R^b$, and

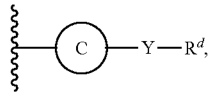

wherein the heterocycloalkyl, heterocycloalkylene, cycloalkyl, and cycloalkylene are each optionally substituted by one or more substituents selected from the group consisting of hydrogen, halogen, hydroxyl, amino, —NH($C_{1-6}$ alkyl), —N($C_{1-6}$ alkyl)$_2$, oxo, —O—($C_{1-6}$ alkyl), $C_{1-6}$ haloalkyl, and $C_{1-6}$ alkyl, and B is not —O—($C_{1-2}$ haloalkyl).

In some embodiments of the present disclosure, B in the compound of formula I as described above comprises G, and G is selected from the group consisting of $C_{1-6}$ alkylene, $C_{3-6}$ cycloalkylene, and 3- to 6-membered heterocycloalkylene, wherein the alkylene, cycloalkylene, and heterocycloalkylene are each optionally substituted by one or more substituents selected from the group consisting of hydrogen, fluorine, oxo, hydroxyl, cyano, —OR$^b$, $C_{1-6}$ alkyl, $C_{1-6}$ haloalkyl, and $C_{1-6}$ hydroxyalkyl, preferably the alkylene, cycloalkylene, and heterocycloalkylene are each optionally substituted by one or more substituents selected from the group consisting of hydrogen and fluorine; preferably, G is $C_{1-3}$ alkylene, and the alkylene is optionally substituted by one or more substituents selected from the group consisting of hydrogen, fluorine, oxo, hydroxyl, cyano, —OR$^b$, $C_{1-6}$ alkyl, $C_{1-6}$ haloalkyl, and $C_{1-6}$ hydroxyalkyl, preferably the alkylene is optionally substituted by one or more substituents selected from the group consisting of hydrogen and fluorine.

In some embodiments of the present disclosure, B in the compound of formula I as described above comprises R$^b$, and R$^b$ is selected from the group consisting of hydrogen, fluorine, chlorine, amino, $C_{1-3}$ alkyl, cyclopropyl, and 3- to 6-membered heterocycloalkyl, wherein the alkyl and heterocycloalkyl are each optionally substituted by one or more substituents selected from the group consisting of hydrogen, fluorine, oxo, hydroxyl, and cyano.

In some embodiments of the present disclosure, B in the compound of formula I as described above comprises C, and C is selected from the group consisting of 3- to 6-membered heterocycloalkylene and $C_{3-6}$ cycloalkylene, wherein the heterocycloalkylene and cycloalkylene are each optionally substituted by one or more R$^c$; preferably, C is selected from the group consisting of pyrrolidylidene, azetidinylene, piperidinylene, and piperazinylene, wherein the pyrrolidylidene, azetidinylene, piperidinylene, and piperazinylene are each optionally substituted by one or more R$^c$.

In some embodiments of the present disclosure, B in the compound of formula I as described above comprises a plurality of R$^c$, and each of R$^c$ is independently selected from the group consisting of hydrogen, fluorine, cyano, methyl, ethyl, fluoromethyl, hydroxymethyl, and hydroxyl; preferably, each of R$^c$ is independently selected from the group consisting of hydrogen, fluorine, and hydroxyl.

In some embodiments of the present disclosure, B in the compound of formula I as described above comprises Y, and Y is selected from the group consisting of $C_{1-3}$ alkylene, $C_{3-6}$ cycloalkylene, 3- to 6-membered heterocycloalkylene, $C_{2-6}$ alkenylene, —C(═O)—($C_{1-3}$ alkylene)-, —C(═O)—($C_{3-6}$ cycloalkylene)-, —C(═O)-(3- to 6-membered heterocycloalkylene)-, and —C(═O)—, wherein the alkylene, heterocycloalkylene, and cycloalkylene are each optionally substituted by one or more substituents selected from the group consisting of fluorine, hydroxyl, and amino; preferably, Y is selected from the group consisting of —$CH_2$—, —CH($CH_3$)—, —C($CH_3$)$_2$—, cyclopropylidene, and —C(═O)—$CH_2$—, wherein the —$CH_2$—, —CH($CH_3$)—, —C($CH_3$)$_2$—, cyclopropylidene, and —C(═O)—$CH_2$— are each optionally substituted by one or more substituents selected from the group consisting of fluorine, hydroxyl, and amino.

In some embodiments of the present disclosure, B in the compound of formula I as described above comprises R$^d$, and R$^d$ is selected from the group consisting of fluorine, amino, hydroxyl, cyano, —S(═O)$_2$—($C_{1-6}$ alkyl), —O—($C_{1-6}$ alkyl), —NH—C(═O)—O—($C_{1-6}$ alkyl), —O—C(═O)—$NH_2$, —O—C(═O)—NH($C_{1-6}$ alkyl), and —N($C_{1-6}$ alkyl)-C(═O)—($C_{1-6}$ alkyl), wherein the alkyl is optionally substituted by one or more substituents selected from the group consisting of fluorine, chlorine, oxo, hydroxyl, and —O—($C_{1-6}$ alkyl); preferably, R$^d$ is selected from the group consisting of fluorine, amino, hydroxyl, cyano, —S(═O)$_2$—$CH_3$, —O—$CH_3$, —NH—C(═O)—O—$CH_3$, and —O—C(═O)—$NH_2$, wherein the —S(═O)$_2$—$CH_3$, —O—$CH_3$, and —NH—C(═O)—O—$CH_3$ are each optionally substituted by one or more substituents selected from the group consisting of fluorine, chlorine, oxo, hydroxyl, and —O—($C_{1-6}$ alkyl).

In some embodiments of the present disclosure, B in the compound of formula I as described above is selected from the group consisting of

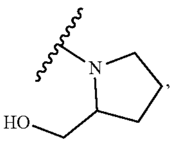, 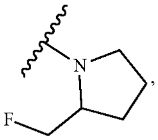, 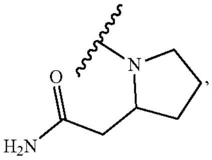,

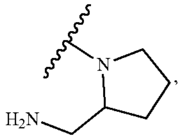, 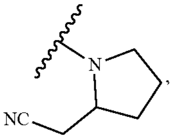, 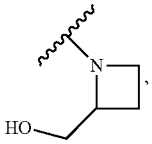,

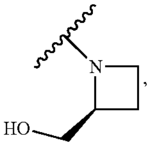, 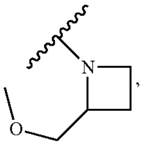, 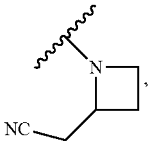,

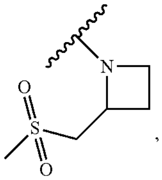, 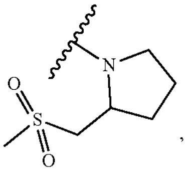, 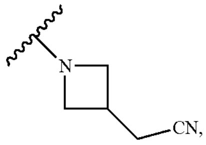,

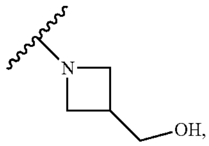, 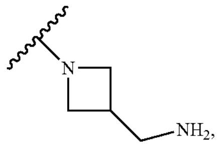,

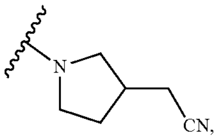, 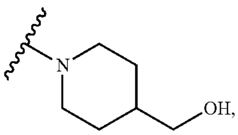,

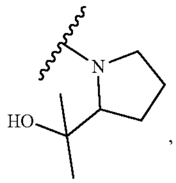, 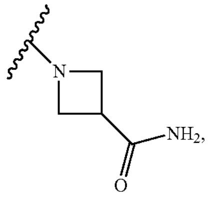,

-continued
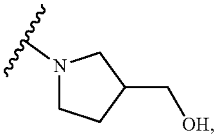
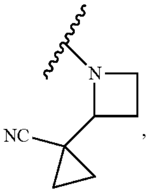
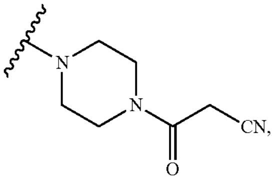
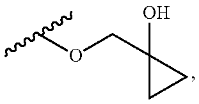
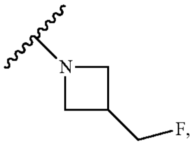
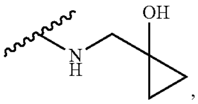
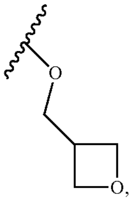
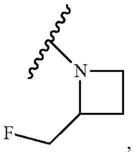
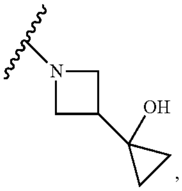
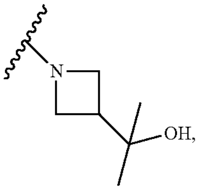
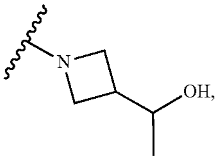
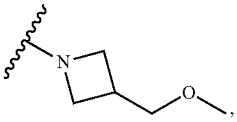
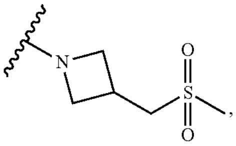
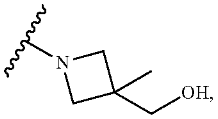
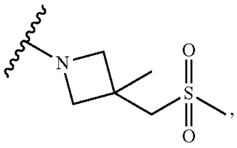
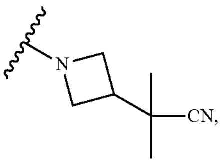
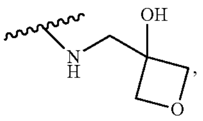
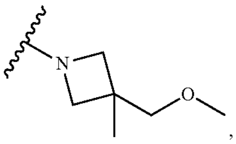
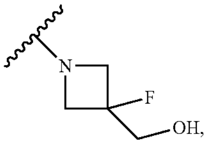
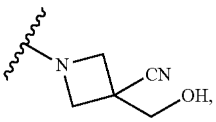
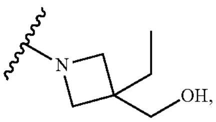
-continued
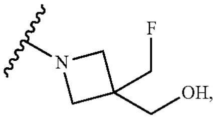
—NH—C(═O)—$CH_2$—CN, and —N($CH_3$)—C(═O)—C$(CH_3)_2$—OH; preferably, B is selected from the group consisting of
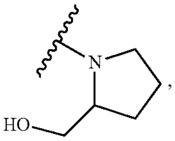
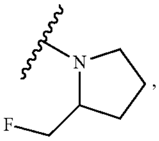
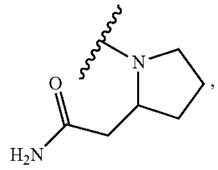
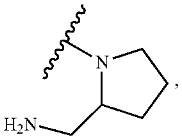
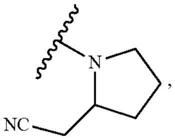
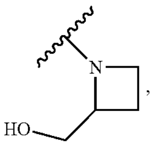
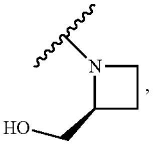
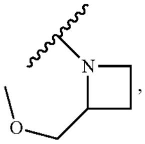
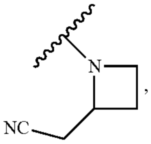
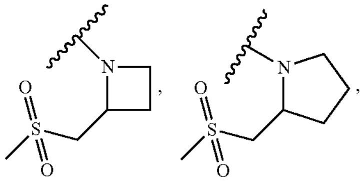
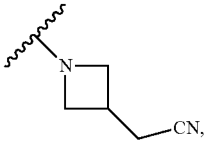
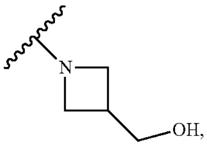
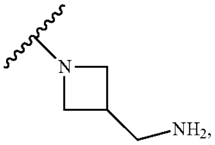
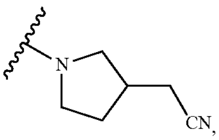
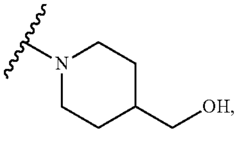
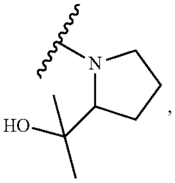
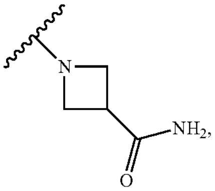
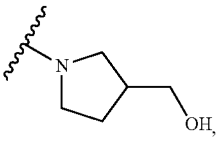

-continued

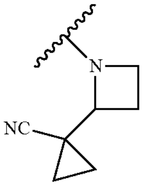,
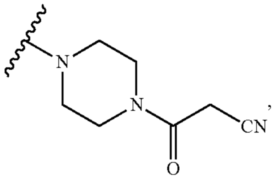,
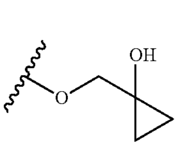,
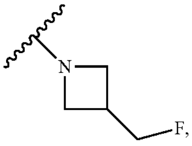
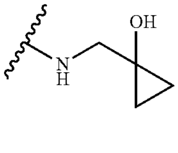,
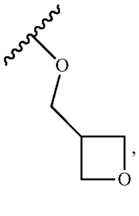,

—NH—C(═O)—$CH_2$—CN, and —N($CH_3$)—C(═O)—C($CH_3$)$_2$—OH.

In some embodiments of the present disclosure, $R^3$ and $R^4$ in the compound of formula I as described above are not linked to each other, and $R^3$ is selected from the group consisting of fluorine, chlorine, bromine, —$OR^z$, hydroxyl, cyano, $C_{1-6}$ alkyl, —($C_{1-4}$ alkylene)-$R^z$, —($C_{1-4}$ alkylene)-$OR^z$, $C_{3-6}$ cycloalkyl, 3- to 8-membered heterocycloalkyl (such as 3- to 6-membered heterocycloalkyl), $C_{2-4}$ alkenyl, $C_{2-4}$ alkynyl, phenyl, and 5- to 6-membered heteroaryl, wherein the alkyl, alkylene, cycloalkyl, heterocycloalkyl, alkenyl, alkynyl, phenyl, and heteroaryl are each optionally substituted by one or more substituents selected from the group consisting of fluorine, chlorine, cyano, oxo, —$OR^z$, hydroxyl, —N($R^z$)$_2$, —$NHR^z$, amino, $C_{1-4}$ alkyl, $C_{3-6}$ cycloalkyl, 3- to 6-membered heterocycloalkyl, phenyl, 5- to 6-membered heteroaryl; preferably, $R^3$ is selected from the group consisting of fluorine, chlorine, —$OR^z$, hydroxyl, cyano, methyl, ethyl, —$CH_2$—$R^z$, —$CH_2$—$OR^z$, cyclopropyl, oxetanyl, —$CH_2CH$═$CH_2$, —CH═$CH_2$, —$CH_2C$≡CH, —C≡CH, pyridinyl, pyrimidinyl, oxazolyl, thiazolyl, pyridazinyl, pyrazolyl, and thienyl, wherein the pyridinyl, pyrimidinyl, oxazolyl, thiazolyl, pyridazinyl, pyrazolyl, and thienyl are each optionally substituted by one or two substituents selected from the group consisting of fluorine, chlorine, cyano, —$OR^z$, hydroxyl, —N($R^z$)$_2$, —$NHR^z$, amino, and pyrazolyl; more preferably, $R^3$ is selected from the group consisting of fluorine, chlorine, hydroxyl, cyano, methyl, ethyl, cyclopropyl, oxetanyl, pyridinyl, pyrimidinyl, oxazolyl, thiazolyl, pyridazinyl, pyrazolyl, and thienyl; more preferably, $R^3$ is selected from the group consisting of fluorine, chlorine, methyl, ethyl, cyclopropyl, and oxetanyl; further preferably, $R^3$ is selected from the group consisting of fluorine and methyl.

In some embodiments of the present disclosure, $R^3$ in the compound of formula I as described above comprises a plurality of $R^z$, and each of $R^z$ is independently selected from the group consisting of cyano, $C_{1-4}$ alkyl, $C_{3-6}$ cycloalkyl, 3- to 6-membered heterocycloalkyl, phenyl, benzyl, and 5- to 6-membered heteroaryl, wherein the alkyl, cycloalkyl, heterocycloalkyl, phenyl, benzyl, and heteroaryl are each optionally substituted by one or more substituents selected from the group consisting of amino, fluorine, chlorine, cyano, oxo, hydroxyl, —O—($C_{1-3}$ alkyl), methyl, ethyl, difluoromethyl, trifluoromethyl, $C_{3-6}$ cycloalkyl, and phenyl; preferably, each of $R^z$ is independently selected from the group consisting of cyano, methyl, ethyl, isopropyl, cyclopropyl, cyclobutyl, cyclopentyl, cyclohexyl, morpholinyl, piperazinyl, oxetanyl, tetrahydrofuranyl, tetrahydropyranyl, pyrrolidinyl, azetidinyl, phenyl, benzyl, pyrrolyl, furanyl, thienyl, imidazolyl, pyrazolyl, oxazolyl, thiazolyl, triazazolyl, pyrazinyl, pyrimidinyl, and pyridinyl, wherein the piperazinyl, azetidinyl, phenyl, pyrrolyl, furanyl, thienyl, imidazolyl, pyrazolyl, oxazolyl, thiazolyl, triazazolyl, pyrazinyl, pyrimidinyl, and pyridinyl are each optionally substituted by one or two substituents selected from the group consisting of fluorine, chlorine, cyano, hydroxyl, methoxy, methyl, and ethyl.

In some embodiments of the present disclosure, $R^3$ and $R^4$ in the compound of formula I as described above are not linked to each other, and $R^4$ is selected from the group consisting of halogen, $C_{1-6}$ alkyl, $C_{3-6}$ cycloalkyl, —C(═O)—$R^z$, 3- to 12-membered heterocycloalkyl, $C_{2-6}$ alkenyl, $C_{2-6}$ alkynyl, $C_{6-12}$ aryl, and 5- to 12-membered heteroaryl, wherein the alkyl, cycloalkyl, heterocycloalkyl, aryl, and heteroaryl are each optionally substituted by one or more substituents selected from the group consisting of amino, fluorine, chlorine, cyano, hydroxyl, oxo, —O—($C_{1-3}$ alkyl), methyl, ethyl, difluoromethyl, trifluoromethyl, and $C_{3-6}$ cycloalkyl; preferably, $R^4$ is selected from the group consisting of fluorine, chlorine, methyl, ethyl, isopropyl, cyclopropyl, cyclobutyl, oxiranyl, oxetanyl, phenyl, pyrrolyl, furanyl, thienyl, imidazolyl, oxazolyl, thiazolyl, pyrazolyl, pyridinyl, pyridazinyl, and pyrimidinyl, wherein the phenyl, pyrrolyl, furanyl, thienyl, imidazolyl, oxazolyl, thiazolyl, pyrazolyl, pyridinyl, pyridazinyl, and pyrimidinyl are each optionally substituted by one or more substituents selected from the group consisting of amino, fluorine, chlorine, cyano, hydroxyl, methoxy, methyl, ethyl, difluoromethyl, and trifluoromethyl; more preferably, $R^4$ is selected from the group consisting of fluorine, chlorine, methyl, ethyl, isopropyl, cyclopropyl, methoxymethyl, hydroxymethyl, fluoromethyl, difluoromethyl, trifluoromethyl, fluoroethyl, cyanomethyl, hydroxymethyl, 2-methylfuryl, thiazolyl, pyridinyl, and pyrimidinyl; more preferably, $R^4$ is selected from the group consisting of methyl, fluoromethyl, difluoromethyl, trifluoromethyl, hydroxymethyl, methoxymethyl, fluoroethyl, cyanomethyl, and hydroxymethyl; further preferably, $R^4$ is selected from the group consisting of methyl, fluoromethyl, fluoroethyl, methoxymethyl, cyanomethyl, and hydroxymethyl.

In some embodiments of the present disclosure, $R^3$ and $R^4$ in the compound of formula I as described above are linked to each other, when $R^3$ and $R^4$ together with the atoms to which they are linked form a ring,

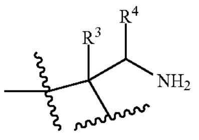

is any one selected from the group consisting of
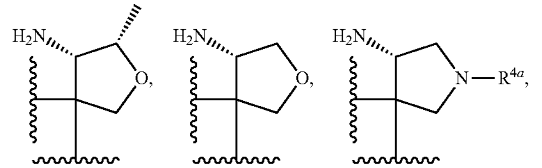
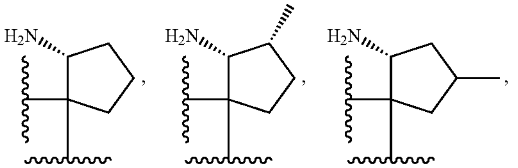
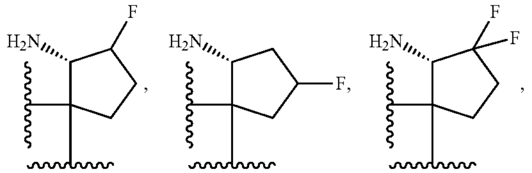
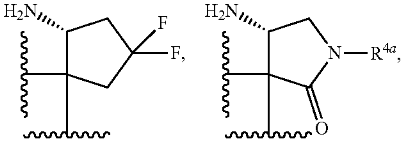
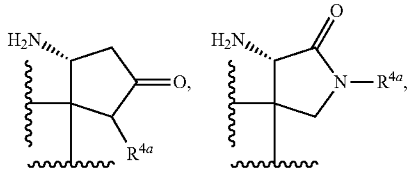
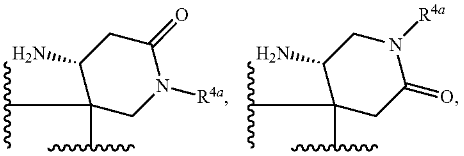
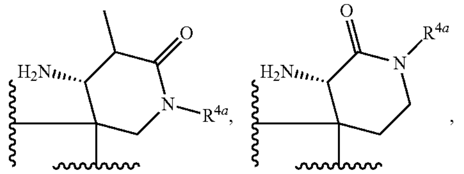
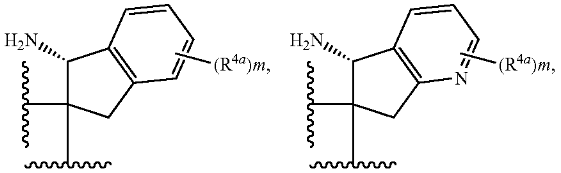
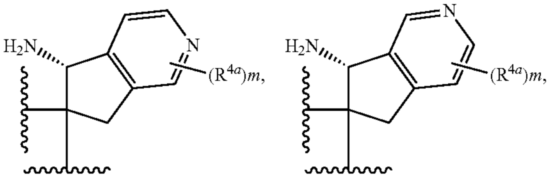
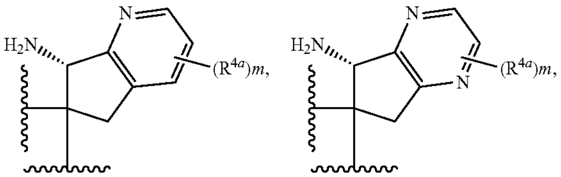
-continued
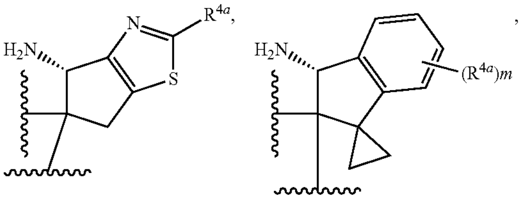
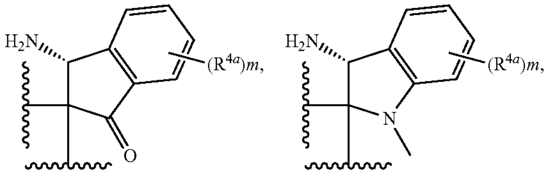
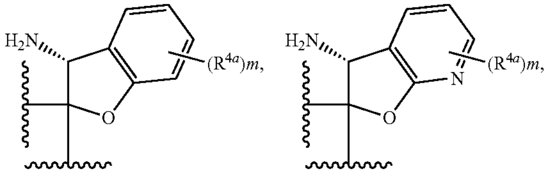
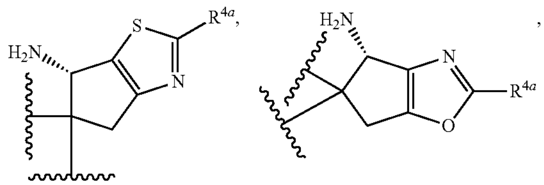
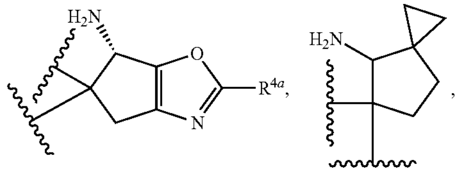
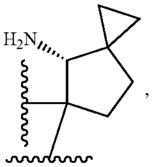
and
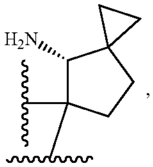
preferably any one selected from the group consisting of:
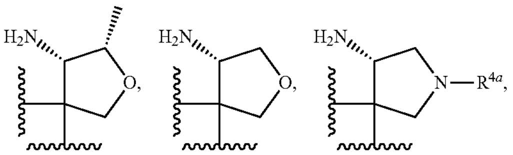
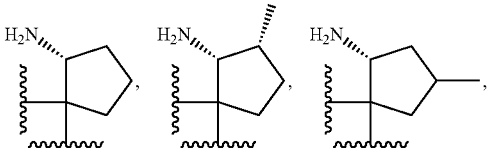
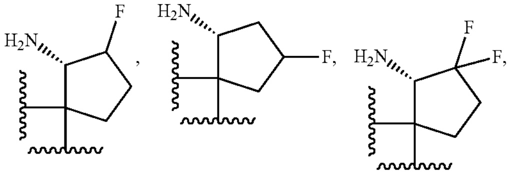

-continued
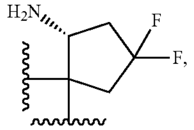
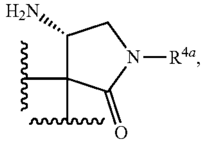
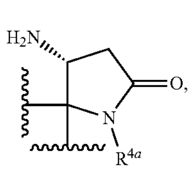
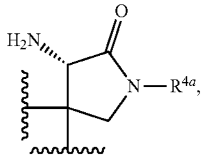
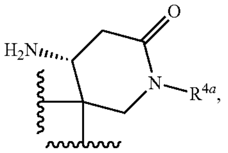
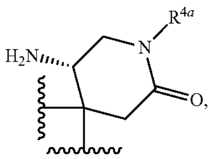
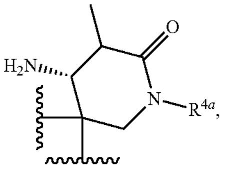
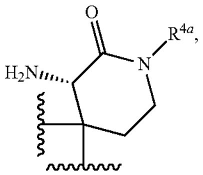
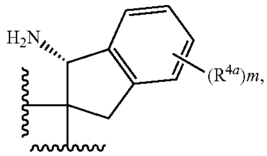
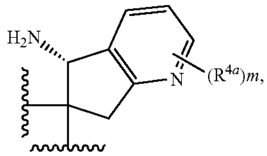
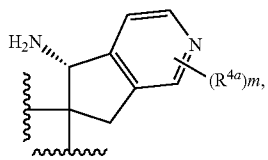
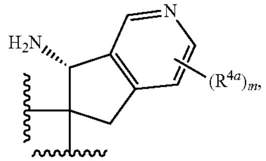
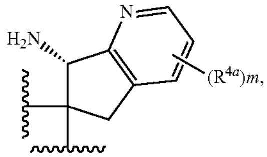
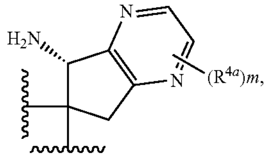
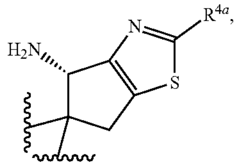
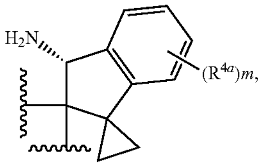
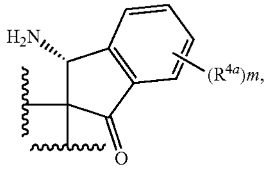
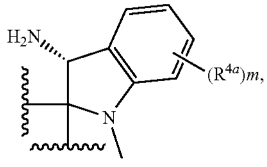
-continued
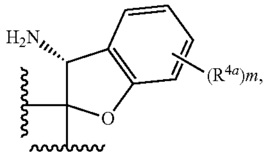
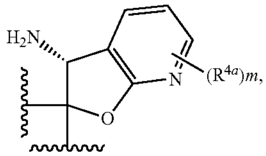
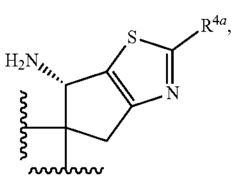
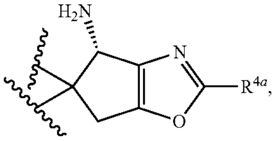
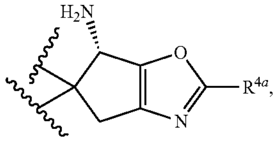
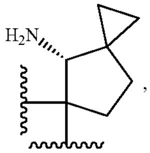
and
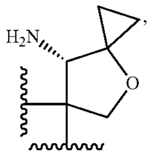
wherein m is 0, 1, or 2;
preferably, when $R^3$ and $R^4$ together with the atoms to which they are linked form a ring,
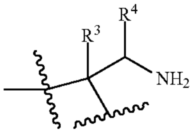
is any one selected from the group consisting of:
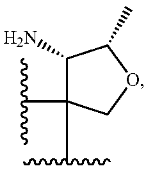
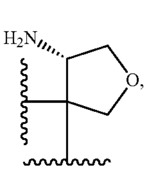
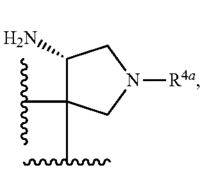
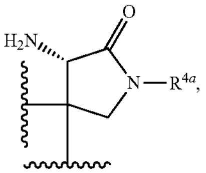
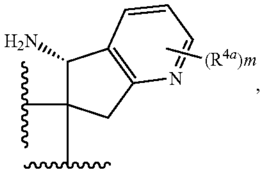
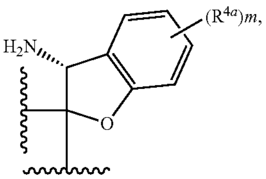
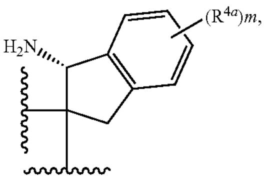

-continued
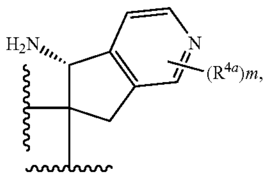
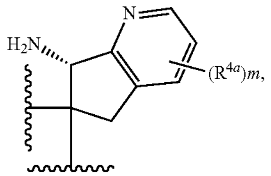
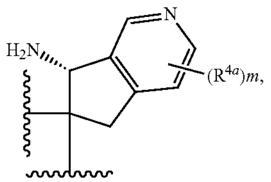
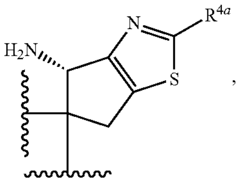
,
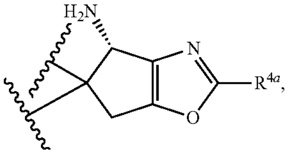
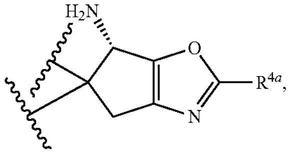
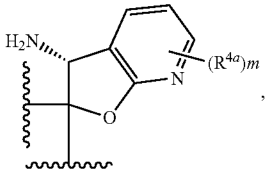
,
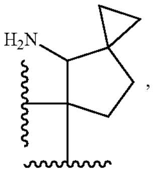
,
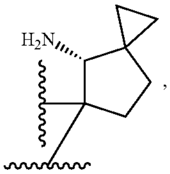
,
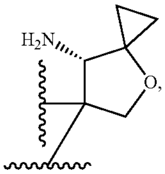
, and
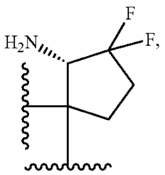
preferably any one selected from the group consisting of:
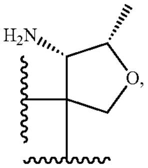
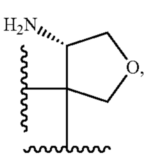
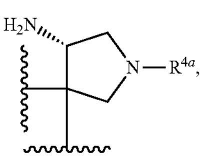
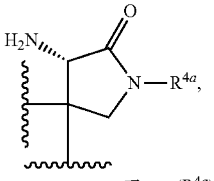
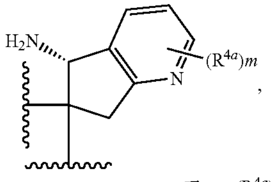
,
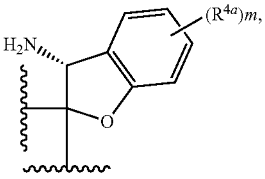
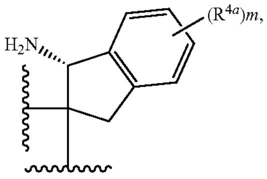
-continued
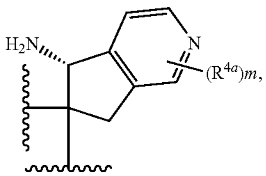
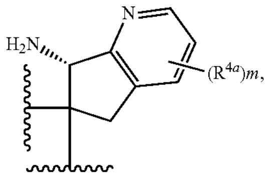
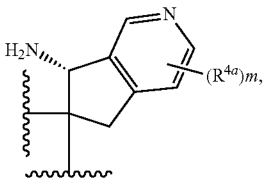
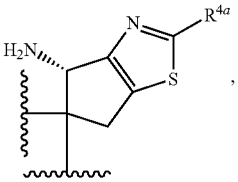
,
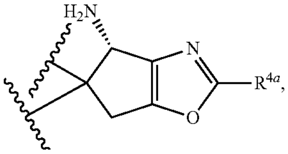
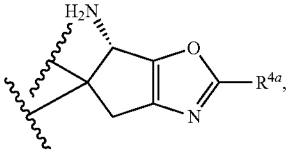
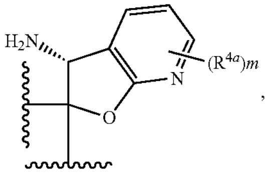
,
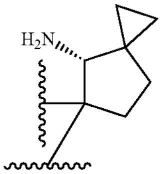
,
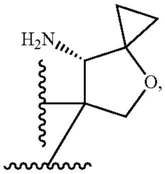
, and
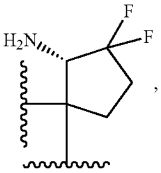
,
wherein m is 0, 1, or 2;
more preferably, when $R^3$ and $R^4$ together with the atoms to which they are linked form a ring,
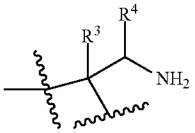
is any one selected from the group consisting of:
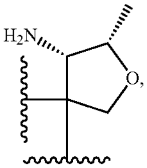
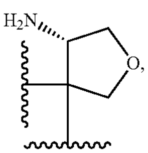
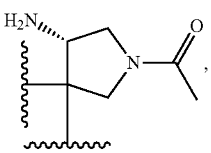
,
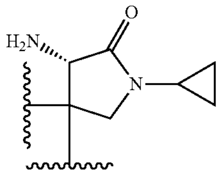
,
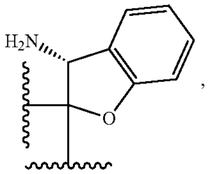
, -continued

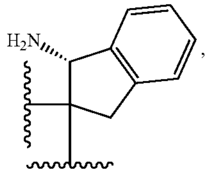,
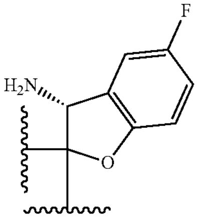,
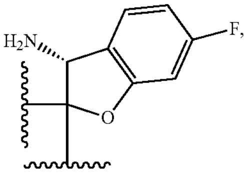,
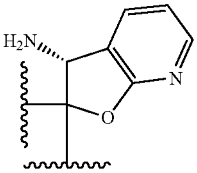,
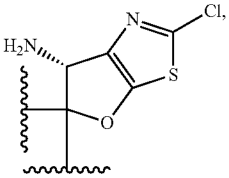,
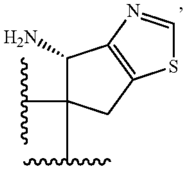,
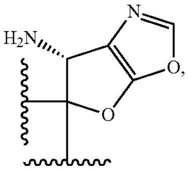,
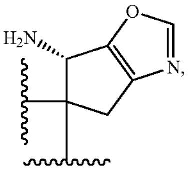,
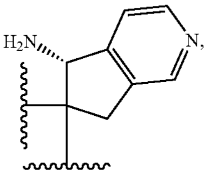,
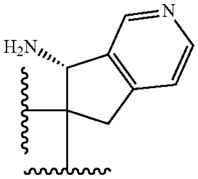,
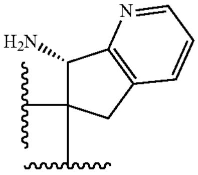,
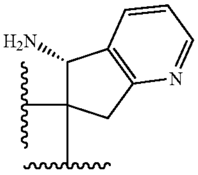,
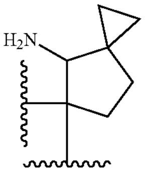 [SMILES: *C1(*)COC2(CC2)[C@H]1N],
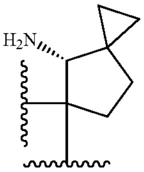,
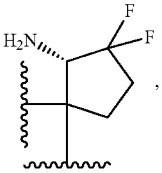, and
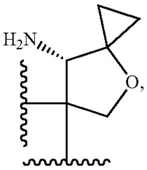, preferably any one selected from the group consisting of:

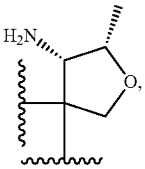,
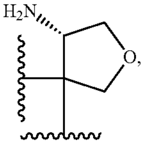,
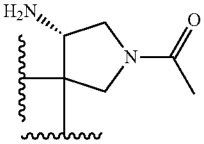,

-continued

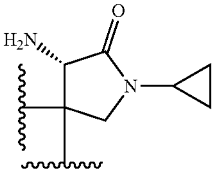,
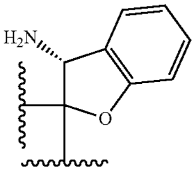,
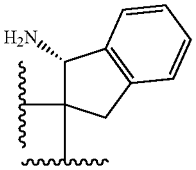,
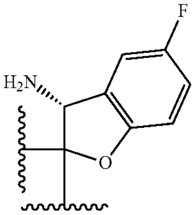,
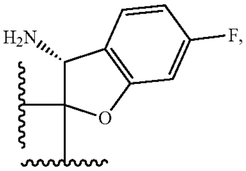,
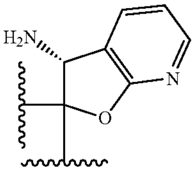,
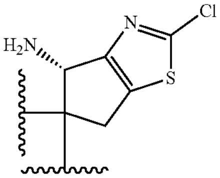,
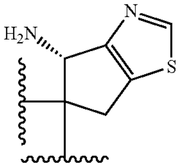,
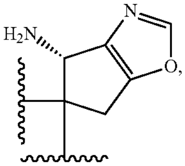,
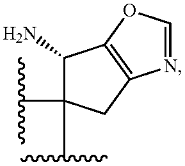,
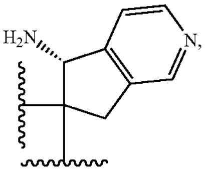,
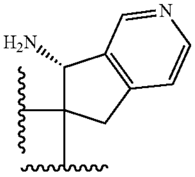,
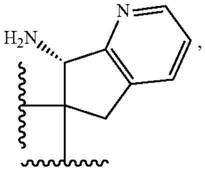,
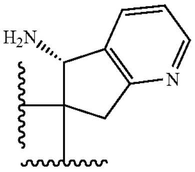,
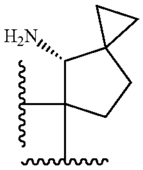,
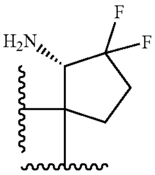, and
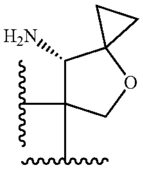.

In some embodiments of the present disclosure, $R^3$ and $R^4$ together with the atoms to which they are linked form a ring system comprising a plurality of $R^{4a}$ at the same time, and each of the $R^{4a}$ is independently selected from the group consisting of hydrogen, fluorine, chlorine, cyano, —C(═O)

H, —C(═O)—($C_{1-6}$ alkyl), —C(═O)—($C_{3-8}$ cycloalkyl), —C(═O)-(3- to 8-membered heterocycloalkyl), oxo, $C_{1-6}$ alkyl, $C_{3-6}$ cycloalkyl, 3- to 12-membered heterocycloalkyl, $C_{2-6}$ alkenyl, and $C_{2-6}$ alkynyl, wherein the alkyl, cycloalkyl, heterocycloalkyl, alkenyl, and alkynyl are each optionally substituted by one or more substituents selected from the group consisting of halogen, cyano, hydroxyl, —O—($C_{1-6}$ alkyl), and $C_{1-6}$ alkyl; preferably, each of the $R^{4a}$ is independently selected from the group consisting of hydrogen, fluorine, chlorine, oxo, methyl, acetyl, and cyclopropyl, wherein the methyl and cyclopropyl are each optionally substituted by one or more substituents selected from the group consisting of halogen, cyano, hydroxyl, —O—($C_{1-6}$ alkyl), and $C_{1-6}$ alkyl.

In some embodiments of the present disclosure, the compound of formula I as described above comprises a plurality of $R^5$ at the same time, and any two of the $R^5$ are not linked to each other and each of the $R^5$ is independently selected from the group consisting of hydrogen, fluorine, chlorine, oxo, cyano, —C(═O)—O—($C_{1-4}$ alkyl), and $C_{1-3}$ alkyl, wherein the alkyl is each optionally substituted by one or more substituents selected from the group consisting of amino, hydroxyl, oxo, and halogen; preferably, each of the $R^5$ is independently selected from the group consisting of hydrogen, fluorine, chlorine, cyano, methyl, and —C(═O)—O—$CH_3$; more preferably, each of the $R^5$ is independently selected from the group consisting of hydrogen, fluorine, and methyl; further preferably, each of the $R^5$ is hydrogen.

In some embodiments of the present disclosure, the compound of formula I as described above comprises a plurality of $R^5$ at the same time, and any two of the $R^5$ that are not linked to the same atom together with the atoms to which they are linked form a $C_{4-8}$ alicyclic ring or a 4- to 8-membered heteroalicyclic ring, preferably a $C_{4-6}$ alicyclic ring or a 4- to 6-membered nitrogen-containing heteroalicyclic ring, or any two of the $R^5$ that are linked to the same atom together with the atom to which they are linked form a $C_{3-6}$ alicyclic ring or a 3- to 6-membered heteroalicyclic ring, preferably a cyclopropane ring.

In some embodiments of the present disclosure, g is 0 or 2.

In some embodiments of the present disclosure, n is 0, 1, 2, or 3; preferably, n is 0, 1, or 2.

In some embodiments of the present disclosure, the compound of formula I as described above has a structure as represented by formula IIa or formula IIb, IIa

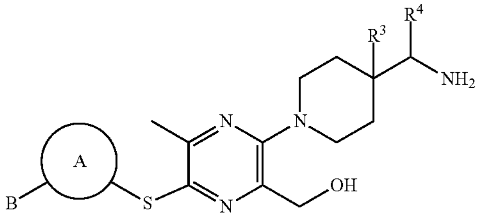

-continued

IIb

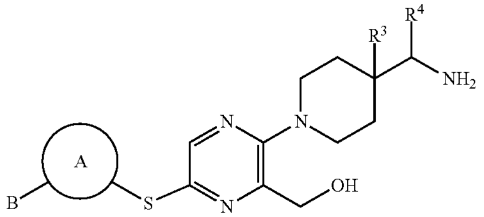

wherein

A, B, $R^3$, and $R^4$ are as defined above.

In some embodiments of the present disclosure, the compound of formula I as described above has a structure as represented by formula IIIa or formula IIIb, IIIa

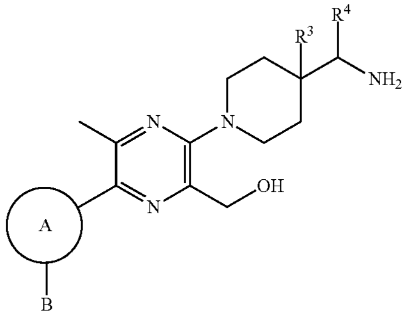

IIIb

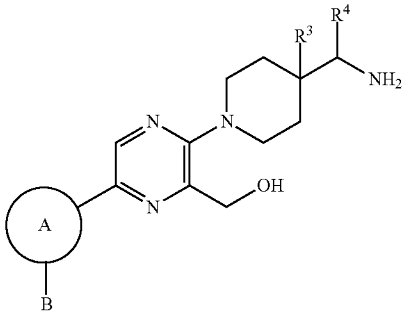

wherein

A, B, $R^3$, and $R^4$ are as defined above.

In some embodiments of the present disclosure, the compound of formula I as described above has a structure as represented by formula IVa, formula IVb, formula IVc, or formula IVd, IVa

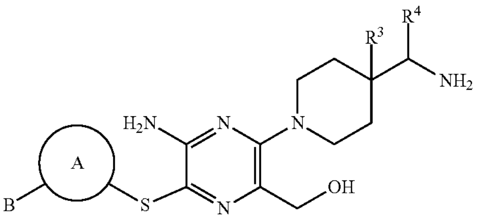

-continued

IVb

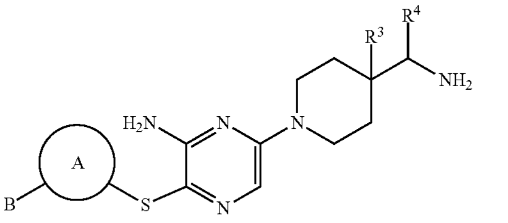

IVc

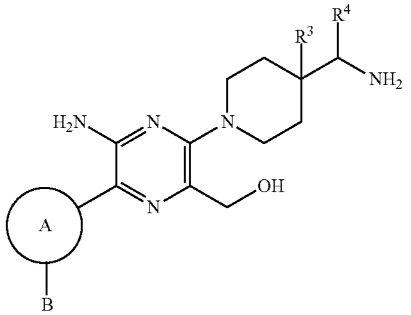

IVd

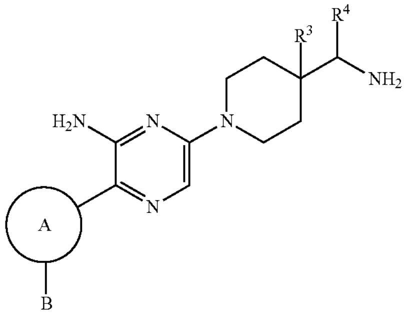

wherein

A, B, $R^3$, and $R^4$ are as defined above.

In some embodiments of the present disclosure, the compound of formula I as described above has a structure as represented by formula Va, formula Vb, or formula Vc, Va

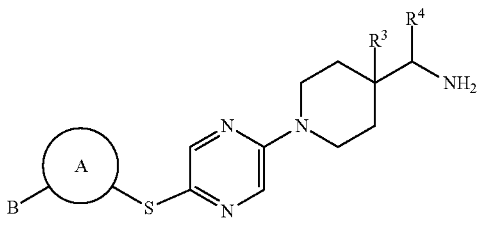

Vb

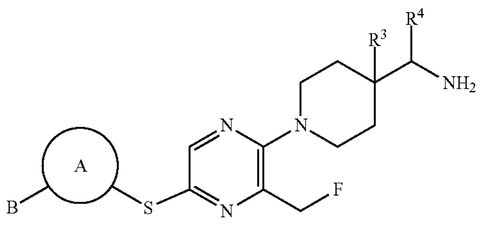

-continued

Vc

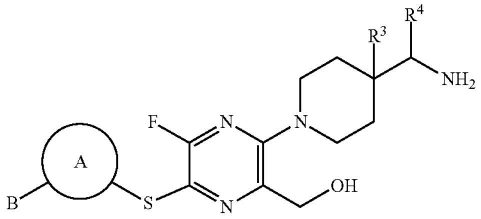

wherein

A, B, $R^3$, and $R^4$ are as defined above.

In some embodiments of the present disclosure, the compound of formula I as described above has a structure represented by any one of formulae IIa-IIb, IIIa-IIIb, IVa-IVd, and Va-Vc, wherein A is selected from the group consisting of $C_{6-12}$ arylene and 5- to 12-membered heteroarylene, wherein the arylene and heteroarylene are each optionally substituted by one or more $R^a$;

each of the $R^a$, if present, is independently selected from the group consisting of hydrogen, halogen, hydroxyl, —O—($C_{1-3}$ alkyl), —O—($C_{3-6}$ cycloalkyl), cyano, $C_{1-3}$ alkyl, $C_{3-6}$ cycloalkyl, 3- to 6-membered heterocycloalkyl, amino, —NH($C_{1-3}$ alkyl), —N($C_{1-3}$ alkyl)$_2$, —S(═O)$_g$—($C_{1-3}$ alkyl), and —S(═O)$_g$NH$_2$;

B is selected from the group consisting of —N($R^b$)—C(═O)-G-$R^d$, —N($R^b$)—S(═O)$_2$-G-$R^d$, —O-G-(3- to 10-membered heterocycloalkyl), —O-G-($C_{3-6}$ cycloalkyl), —O—($C_{3-6}$ cycloalkylene)-G-H, —O-(3- to 10-membered heterocycloalkylene)-G-H, —O-G-$R^d$, —N($R^b$)-G-(3- to 10-membered heterocycloalkyl), —N($R^b$)-G-($C_{3-6}$ cycloalkyl), —N($R^b$)—($C_{3-6}$ cycloalkylene)-G-H, —N($R^b$)-(3- to 10-membered heterocycloalkylene)-G-H, -G-O—C(═O)—$R^b$, -G-N($R^b$)—C(═O)—$R^b$, -G-N($R^b$)—C(═O)—O$R^b$, and

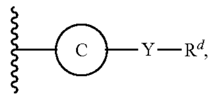

wherein the heterocycloalkyl, heterocycloalkylene, cycloalkyl, and cycloalkylene are each optionally substituted by one or more substituents selected from the group consisting of hydrogen, halogen, hydroxyl, amino, —NH($C_{1-6}$ alkyl), —N($C_{1-6}$ alkyl)$_2$, oxo, —O—($C_{1-6}$ alkyl), $C_{1-6}$ haloalkyl, and $C_{1-6}$ alkyl, and B is not —O—($C_{1-2}$ haloalkyl);

G is selected from the group consisting of $C_{1-6}$ alkylene, $C_{3-6}$ cycloalkylene, and 3- to 6-membered heterocycloalkylene, wherein the alkylene, cycloalkylene, and heterocycloalkylene are each optionally substituted by one or more substituents selected from the group consisting of hydrogen, fluorine, oxo, hydroxyl, cyano, —O$R^b$, $C_{1-6}$ alkyl, $C_{1-6}$ haloalkyl, and $C_{1-6}$ hydroxyalkyl, preferably the alkylene, cycloalkylene, and heterocycloalkylene are each optionally substituted by one or more substituents selected from the group consisting of hydrogen and fluorine;

$R^b$ is selected from the group consisting of hydrogen, fluorine, chlorine, amino, $C_{1-3}$ alkyl, cyclopropyl, and 3- to 6-membered heterocycloalkyl, wherein the alkyl and heterocycloalkyl are each optionally substituted by one or more substituents selected from the group consisting of hydrogen, fluorine, oxo, hydroxyl, and cyano;

C is selected from the group consisting of 3- to 6-membered heterocycloalkylene and $C_{3-6}$ cycloalkylene, wherein the heterocycloalkylene and cycloalkylene are each optionally substituted by one or more $R^c$;

each of the $R^c$, if present, is independently selected from the group consisting of hydrogen, fluorine, cyano, methyl, ethyl, fluoromethyl, hydroxymethyl, and hydroxyl;

Y is selected from the group consisting of $C_{1-3}$ alkylene, $C_{3-6}$ cycloalkylene, 3- to 6-membered heterocycloalkylene, $C_{2-6}$ alkenylene, —C(═O)—($C_{1-3}$ alkylene)-, —C(═O)—($C_{3-6}$ cycloalkylene)-, —C(═O)-(3- to 6-membered heterocycloalkylene)-, and —C(═O)—, wherein the alkylene, heterocycloalkylene, and cycloalkylene are each optionally substituted by one or more substituents selected from the group consisting of fluorine, hydroxyl, and amino;

$R^d$ is selected from the group consisting of fluorine, amino, hydroxyl, cyano, —S(═O)$_2$—($C_{1-6}$ alkyl), —O—($C_{1-6}$ alkyl), —NH—C(═O)—O—($C_{1-6}$ alkyl), —O—C(═O)—$NH_2$, —O—C(═O)—NH($C_{1-6}$ alkyl), and —N($C_{1-6}$ alkyl)-C(═O)—($C_{1-6}$ alkyl), wherein the alkyl is optionally substituted by one or more substituents selected from the group consisting of fluorine, chlorine, oxo, hydroxyl, and —O—($C_1$. 6 alkyl);

when $R^3$ and $R^4$ are not linked to each other, $R^3$ is selected from the group consisting of fluorine, chlorine, bromine, —$OR^z$, hydroxyl, cyano, $C_{1-6}$ alkyl, —($C_{1-4}$ alkylene)-$R^z$, —($C_{1-4}$ alkylene)-$OR^z$, $C_{3-6}$ cycloalkyl, 3- to 8-membered heterocycloalkyl (such as 3- to 6-membered heterocycloalkyl), $C_{2-4}$ alkenyl, $C_{2-4}$ alkynyl, phenyl, and 5- to 6-membered heteroaryl, wherein the alkyl, alkylene, cycloalkyl, heterocycloalkyl, alkenyl, alkynyl, phenyl, and heteroaryl are each optionally substituted by one or more substituents selected from the group consisting of fluorine, chlorine, cyano, oxo, —$OR^z$, hydroxyl, —N($R^z$)$_2$, —$NHR^z$, amino, $C_{1-4}$ alkyl, $C_{3-6}$ cycloalkyl, 3- to 6-membered heterocycloalkyl, phenyl, and 5- to 6-membered heteroaryl;

each of the $R^Z$, if present, is independently selected from the group consisting of cyano, $C_1$. 4 alkyl, $C_{3-6}$ cycloalkyl, 3- to 6-membered heterocycloalkyl, phenyl, benzyl, and 5- to 6-membered heteroaryl, wherein the alkyl, cycloalkyl, heterocycloalkyl, phenyl, benzyl, and heteroaryl are each optionally substituted by one or more substituents selected from the group consisting of amino, fluorine, chlorine, cyano, oxo, hydroxyl, —O—($C_{1-3}$ alkyl), methyl, ethyl, difluoromethyl, trifluoromethyl, $C_{3-6}$ cycloalkyl, and phenyl;

$R^4$ is selected from the group consisting of halogen, $C_{1-6}$ alkyl, $C_{3-6}$ cycloalkyl, —C(═O)—$R^z$, 3- to 12-membered heterocycloalkyl, $C_{2-6}$ alkenyl, $C_{2-6}$ alkynyl, $C_{6-12}$ aryl, and 5- to 12-membered heteroaryl, wherein the alkyl, cycloalkyl, heterocycloalkyl, aryl, and heteroaryl are each optionally substituted by one or more substituents selected from the group consisting of amino, fluorine, chlorine, cyano, hydroxyl, oxo, —O—($C_{1-3}$ alkyl), methyl, ethyl, difluoromethyl, trifluoromethyl, and $C_{3-6}$ cycloalkyl; or when $R^3$ and $R^4$ together with the atoms to which they are linked form a ring,

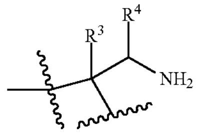

is any one selected from the group consisting of:

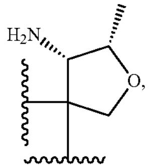 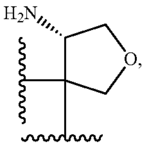 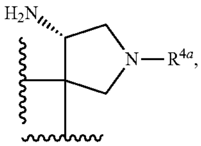

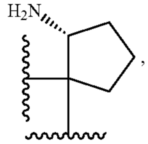, 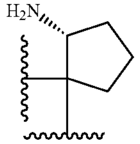, 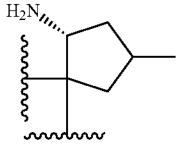,

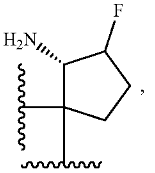, 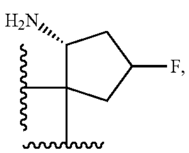 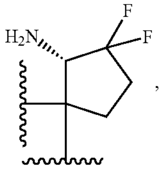,

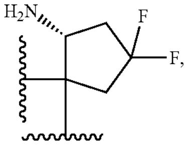 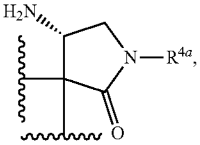

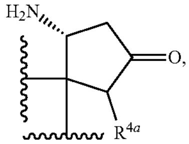 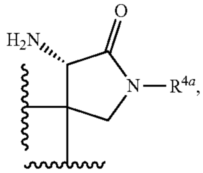

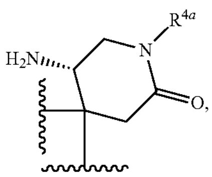 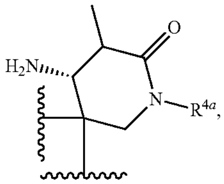,

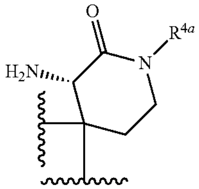, 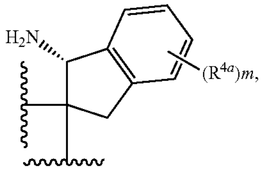

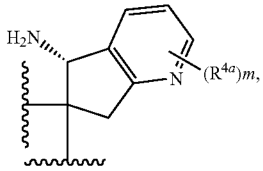 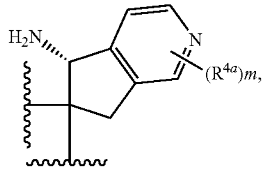

-continued
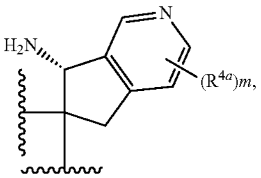
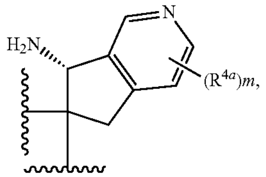
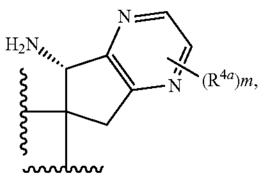
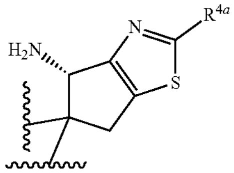
,
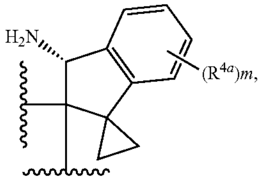
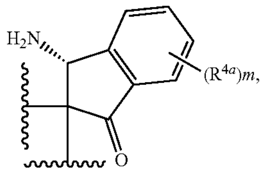
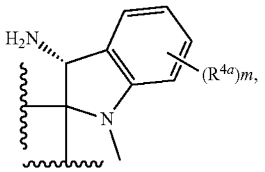
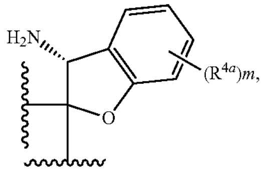
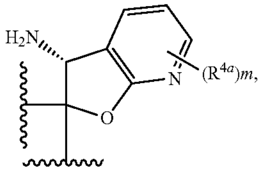
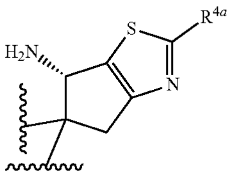
,
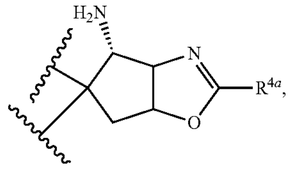
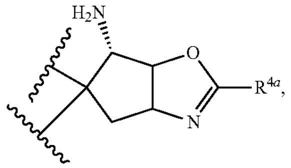
,
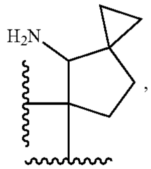
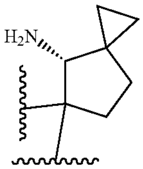
, and
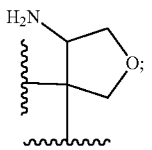
preferably any one selected from the group consisting of:
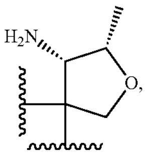
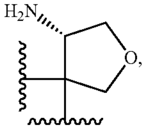
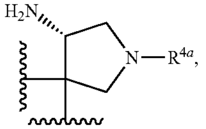
-continued
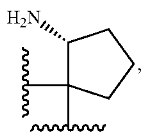
,
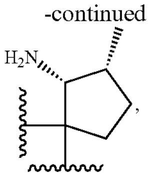
,
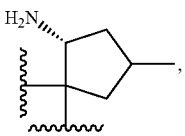
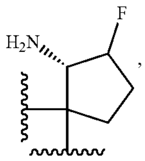
,
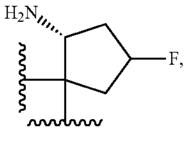
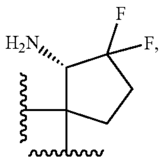
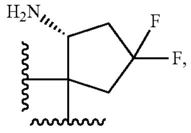
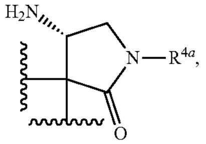
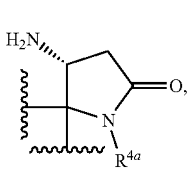
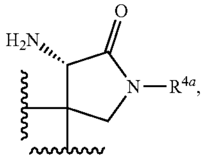
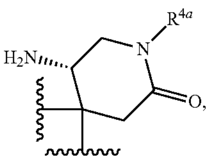
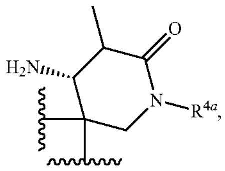
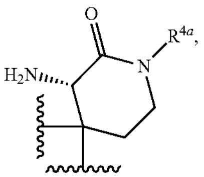
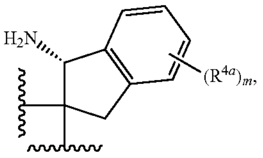
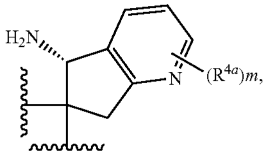
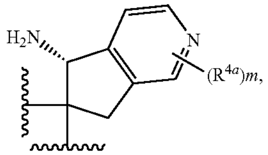
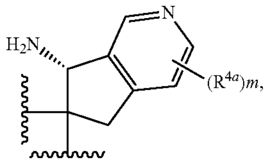
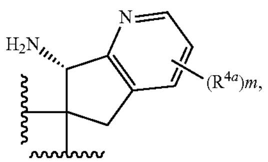
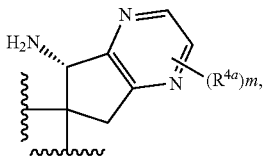
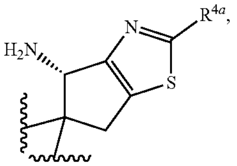
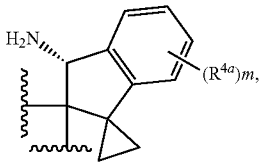

-continued

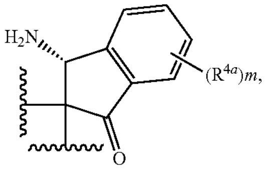,
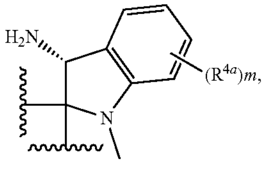,
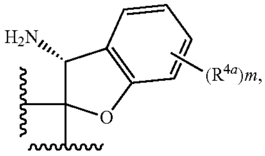,
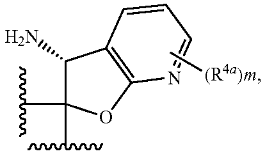,
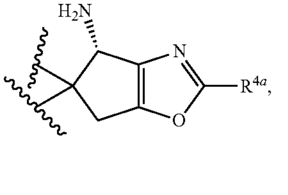,
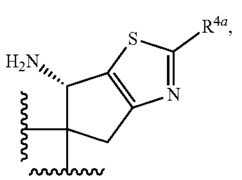,
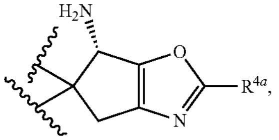,
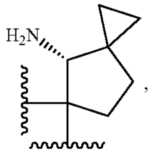, and
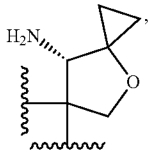, m is 0, 1, or 2; and each of the $R^{4a}$, if present, is independently selected from the group consisting of hydrogen, fluorine, chlorine, cyano, —C(═O)H, —C(═O)—($C_{1-6}$ alkyl), —C(═O)—($C_{3-8}$ cycloalkyl), —C(═O)-(3- to 8-membered heterocycloalkyl), oxo, $C_{1-6}$ alkyl, $C_{3-6}$ cycloalkyl, 3- to 12-membered heterocycloalkyl, $C_{2-6}$ alkenyl, and $C_{2-6}$ alkynyl, wherein the alkyl, cycloalkyl, heterocycloalkyl, alkenyl, and alkynyl are each optionally substituted by one or more substituents selected from the group consisting of halogen, cyano, hydroxyl, —O—($C_{1-6}$ alkyl), and $C_{1-6}$ alkyl.

In some embodiments of the present disclosure, the compound of formula I as described above has a structure represented by any one of formulae IIa-IIb, IIIa-IIIb, IVa-IVd, and Va-Vc, wherein A is selected from the group consisting of phenylene, pyridinylene, and pyrimidinylene, wherein the phenylene, pyridinylene, and pyrimidinylene are each optionally substituted by one or more $R^a$;

each of the $R^a$, if present, is independently selected from the group consisting of hydrogen, fluorine, chlorine, bromine, hydroxyl, methoxy, cyclopropoxy, cyano, methyl, ethyl, n-propyl, isopropyl, difluoromethoxy, trifluoromethoxy, trifluoromethyl, difluoromethyl, cyclopropyl, pyrrolidinyl, morpholinyl, amino, methylamino, dimethylamino, methylthio, methylsulfonyl, and sulfamoyl;

B is selected from the group consisting of —N($R^b$)—C(═O)-G-$R^d$, —O-G-(3- to 10-membered heterocycloalkyl), —O-G-$R^d$, —N($R^b$)-G-(3- to 10-membered heterocycloalkyl), —N($R^b$)-G-($C_{3-6}$ cycloalkyl), —N($R^b$)—($C_{3-6}$ cycloalkylene)-G-H, —N($R^b$)-(3- to 10-membered heterocycloalkylene)-G-H, -G-O—C(═O)—$R^b$, and

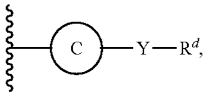, wherein the heterocycloalkyl, heterocycloalkylene, cycloalkyl, and cycloalkylene are each optionally substituted by one or more substituents selected from the group consisting of hydrogen, halogen, hydroxyl, amino, —NH($C_{1-6}$ alkyl), —N($C_{1-6}$ alkyl)$_2$, oxo, —O—($C_{1-6}$ alkyl), $C_{1-6}$ haloalkyl, and $C_{1-6}$ alkyl, and B is not —O—($C_{1-2}$ haloalkyl);

G is $C_{1-3}$ alkylene, and the alkylene is optionally substituted by one or more substituents selected from the group consisting of hydrogen, fluorine, oxo, hydroxyl, cyano, —$OR^b$, $C_{1-6}$ alkyl, $C_{1-6}$ haloalkyl, and $C_{1-6}$ hydroxyalkyl;

$R^b$ is selected from the group consisting of hydrogen, fluorine, chlorine, amino, $C_{1-3}$ alkyl, cyclopropyl, and 3- to 6-membered heterocycloalkyl, wherein the alkyl and heterocycloalkyl are each optionally substituted by one or more substituents selected from the group consisting of hydrogen, fluorine, oxo, hydroxyl, and cyano;

C is selected from the group consisting of pyrrolidylidene, azetidinylene, piperidinylene, and piperazinylene, wherein the pyrrolidylidene, azetidinylene, piperidinylene, and piperazinylene are each optionally substituted by one or more $R^c$.

each of the $R^c$, if present, is independently selected from the group consisting of hydrogen, fluorine, and hydroxyl;

Y is selected from the group consisting of —$CH_2$—, —CH($CH_3$)—, —C($CH_3$)$_2$—, cyclopropylidene, and —C(═O)—$CH_2$—, wherein the —$CH_2$—, —CH($CH_3$)—, —C($CH_3$)$_2$—, cyclopropylidene, and —C(═O)—$CH_2$— are each optionally substituted by one or more substituents selected from the group consisting of fluorine, hydroxyl, and amino;

$R^d$ is selected from the group consisting of fluorine, amino, hydroxyl, cyano, —S(═O)$_2$—$CH_3$, —O—$CH_3$, —NH—C(═O)—O—$CH_3$, and —O—C(═O)—$NH_2$, wherein the —S(═O)$_2$—$CH_3$, —O—$CH_3$, and —NH—C(═O)—O—$CH_3$ are each optionally substituted by one or more substituents selected from the group consisting of fluorine, chlorine, oxo, hydroxyl, and —O—($C_{1-6}$ alkyl);

when $R^3$ and $R^4$ are not linked to each other, $R^3$ is selected from the group consisting of fluorine, chlorine, —$OR^z$, hydroxyl, cyano, methyl, ethyl, —$CH_2$—$R^z$, —$CH_2$—$OR^z$, cyclopropyl, oxetanyl, —$CH_2CH$═$CH_2$, —CH═$CH_2$, —$CH_2C$≡CH, —C≡CH, pyridinyl, pyrimidinyl, oxazolyl, thiazolyl, pyridazinyl, pyrazolyl, and thienyl, wherein the pyridinyl, pyrimidinyl, oxazolyl, thiazolyl, pyridazinyl, pyrazolyl, and thienyl are each optionally substituted by one or two substituents selected from the group consisting of fluorine, chlorine, cyano, —$OR^z$, hydroxyl, —N($R^z$)$_2$, —$NHR^z$, amino, and pyrazolyl;

each of the $R^z$, if present, is independently selected from the group consisting of cyano, methyl, ethyl, isopropyl, cyclopropyl, cyclobutyl, cyclopentyl, cyclohexyl, morpholinyl, piperazinyl, oxetanyl, tetrahydrofuranyl, tetrahydropyranyl, pyrrolidinyl, azetidinyl, phenyl, benzyl, pyrrolyl, furanyl, thienyl, imidazolyl, pyrazolyl, oxazolyl, thiazolyl, triazazolyl, pyrazinyl, pyrimidinyl, and pyridinyl, wherein the piperazinyl, azetidinyl, phenyl, pyrrolyl, furanyl, thienyl, imidazolyl, pyrazolyl, oxazolyl, thiazolyl, triazazolyl, pyrazinyl, pyrimidinyl, and pyridinyl are each optionally substituted by one or two substituents selected from the group consisting of fluorine, chlorine, cyano, hydroxyl, methoxy, methyl, and ethyl;

$R^4$ is selected from the group consisting of fluorine, chlorine, methyl, ethyl, isopropyl, cyclopropyl, methoxymethyl, hydroxymethyl, fluoromethyl, difluoromethyl, trifluoromethyl, fluoroethyl, cyanomethyl, hydroxymethyl, 2-methylfuryl, thiazolyl, pyridinyl, and pyrimidinyl; or when $R^3$ and $R^4$ together with the atoms to which they are linked form a ring,

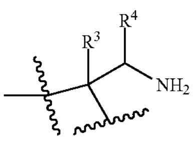

is any one selected from the group consisting of

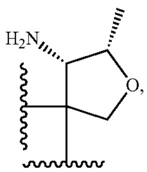
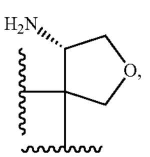
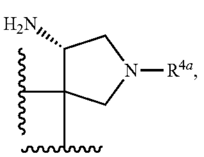
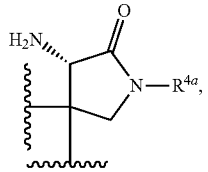
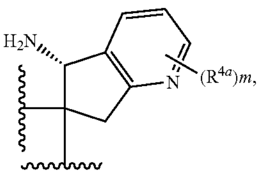
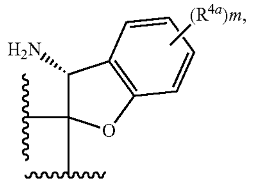
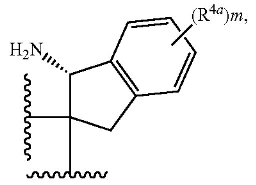
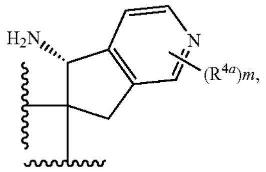
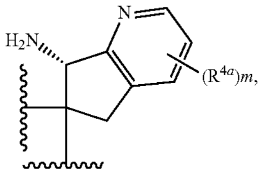
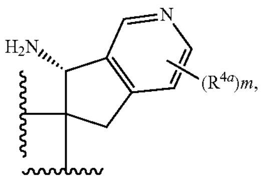
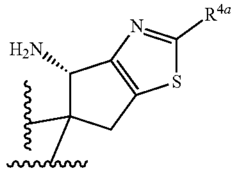
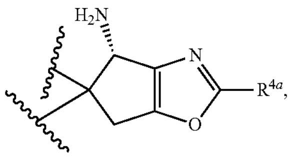

-continued

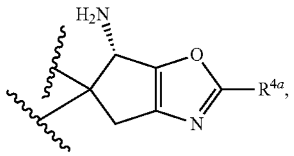
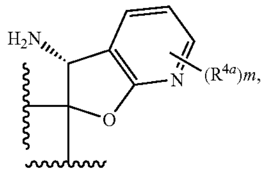
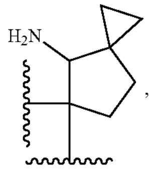
,
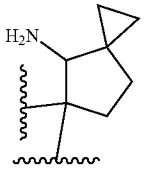
,
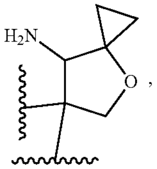
, and
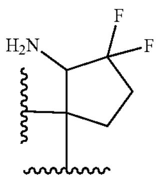
;

preferably any one selected from the group consisting of

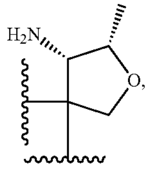
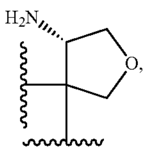
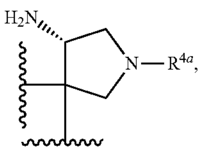
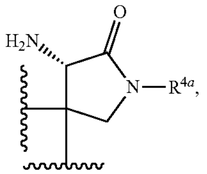
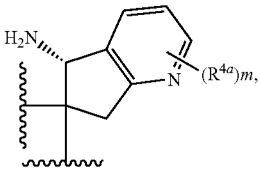
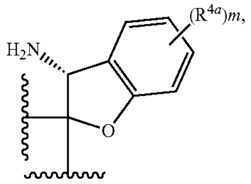
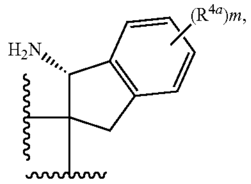
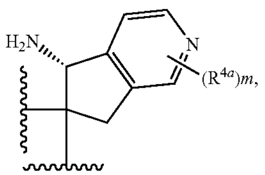
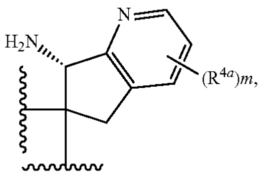
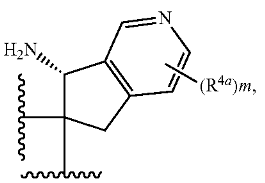
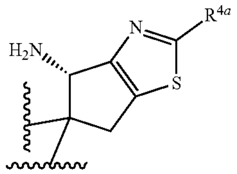
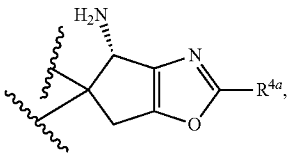

-continued

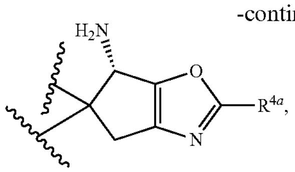

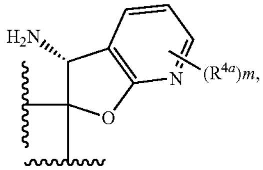

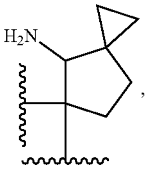
,
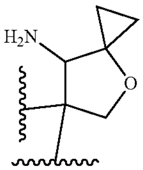
, and
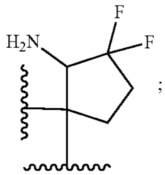
;

m is 0, 1, or 2; and each of the $R^{4a}$ if present, is independently selected from the group consisting of hydrogen, fluorine, chlorine, oxo, methyl, acetyl, and cyclopropyl, wherein the methyl and cyclopropyl are each optionally substituted by one or more substituents selected from the group consisting of halogen, cyano, hydroxyl, —O—($C_{1-6}$ alkyl), and $C_{1-6}$ alkyl.

In some embodiments of the present disclosure, the compound of formula I as described above has a structure represented by any one of formulae IIa-IIb, IIIa-IIIb, IVa-IVd, and Va-Vc, wherein A is selected from the group consisting of phenylene, pyridinylene, and pyrimidinylene, wherein the phenylene, pyridinylene, and pyrimidinylene are each optionally substituted by one or more $R^a$;

each of the $R^a$, if present, is independently selected from the group consisting of hydrogen, fluorine, chlorine, bromine, hydroxyl, cyano, methyl, ethyl, n-propyl, isopropyl, cyclopropyl, pyrrolidinyl, morpholinyl, amino, methylamino, and dimethylamino;

B is selected from the group consisting of

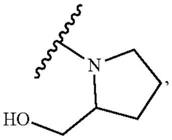

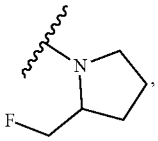

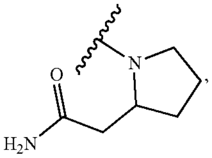

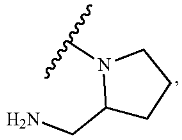

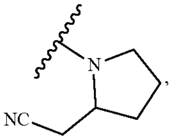

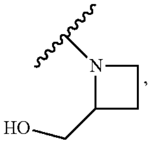

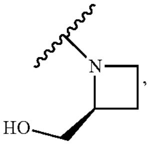

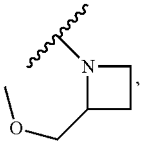

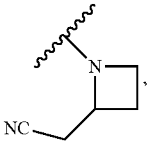

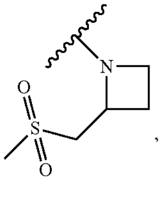
,
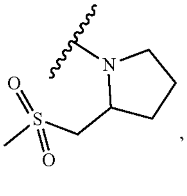
,
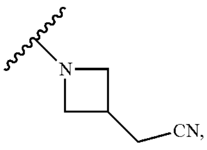

-continued

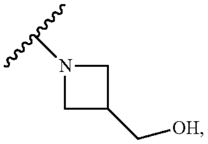

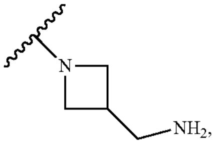

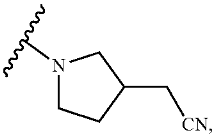

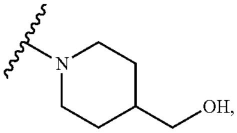

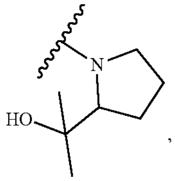
,
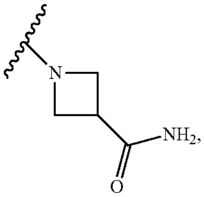

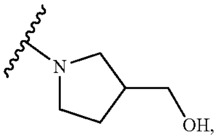

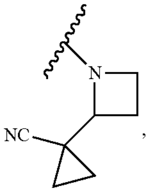

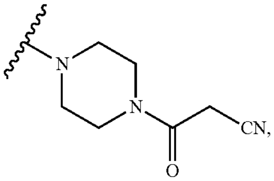

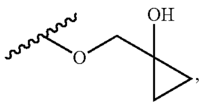

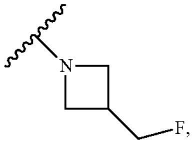

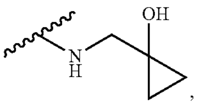

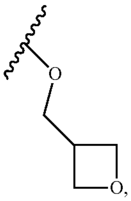

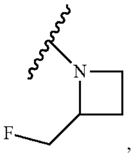

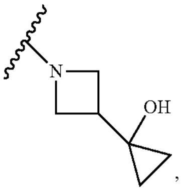

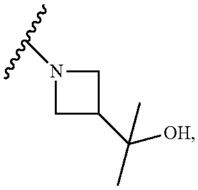

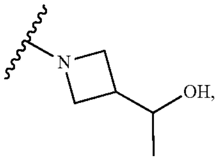

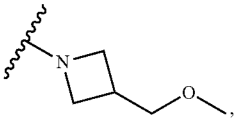

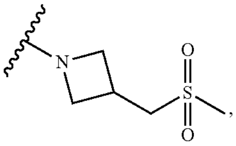

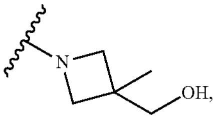

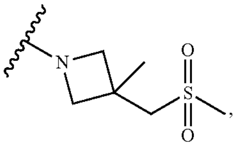

-continued

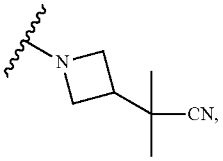 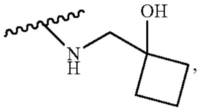,

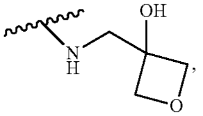, 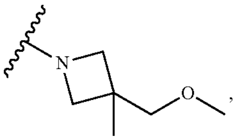,

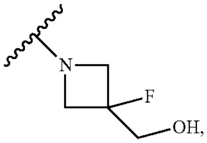 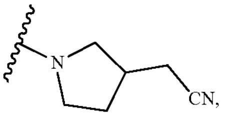

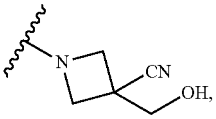 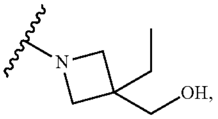

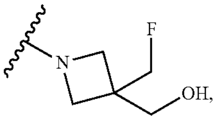

—NH—C(═O)—$CH_2$—CN, and —N($CH_3$)—C(═O)—C($CH_3$)$_2$—OH;

when $R^3$ and $R^4$ are not linked to each other, $R^3$ is selected from the group consisting of fluorine, chlorine, hydroxyl, cyano, methyl, ethyl, cyclopropyl, oxetanyl, pyridinyl, pyrimidinyl, oxazolyl, thiazolyl, pyridazinyl, pyrazolyl, and thienyl, preferably fluorine, chlorine, methyl, ethyl, cyclopropyl, and oxetanyl;

$R^4$ is selected from the group consisting of methyl, fluoromethyl, difluoromethyl, trifluoromethyl, hydroxymethyl, methoxymethyl, fluoroethyl, cyanomethyl, and hydroxymethyl; or when $R^3$ and $R^4$ together with the atoms to which they are linked form a ring,

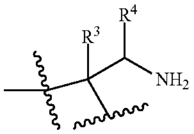

is any one selected from the group consisting of:

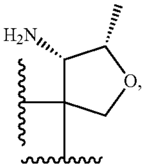 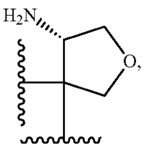 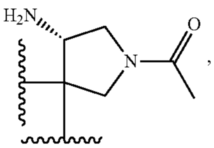,

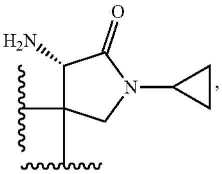, 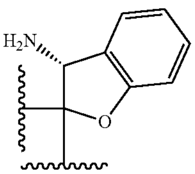,

-continued

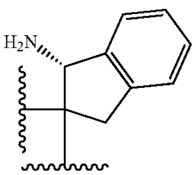, 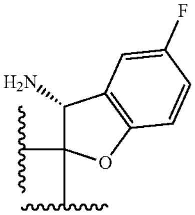,

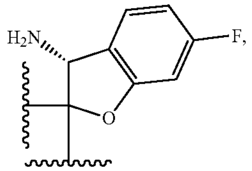 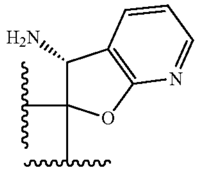,

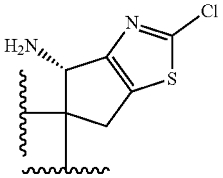, 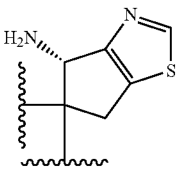,

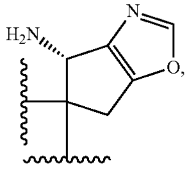 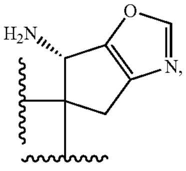

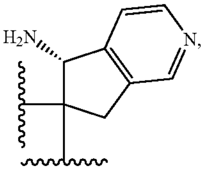 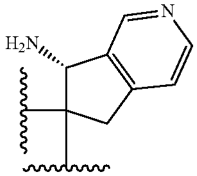,

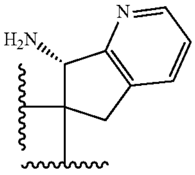, 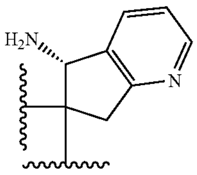,

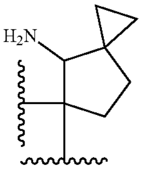, 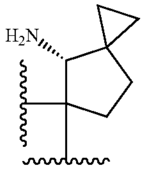,

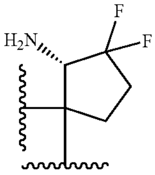, and 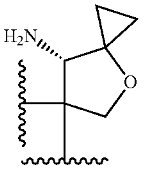;

preferably any one selected from the group consisting of

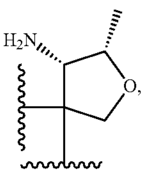 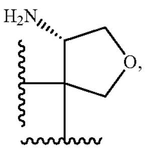 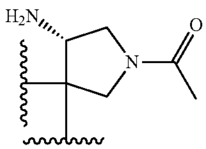,

-continued

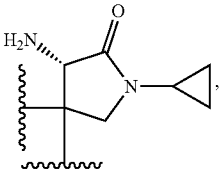, 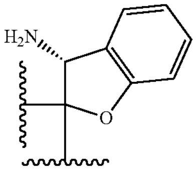,

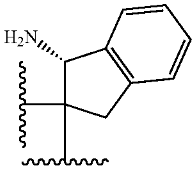, 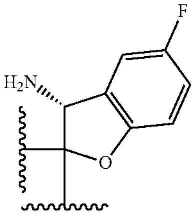,

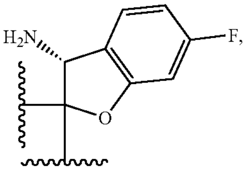, 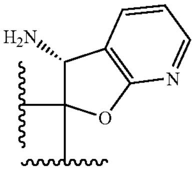,

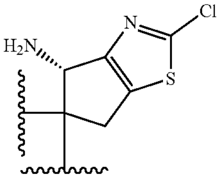, 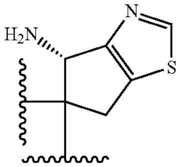,

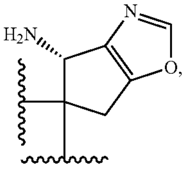 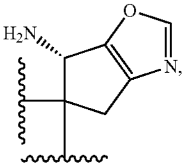

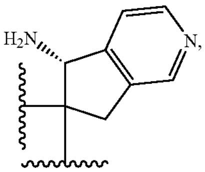 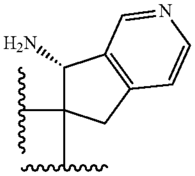,

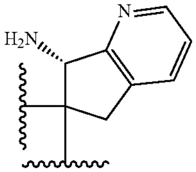, 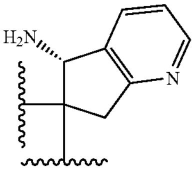,

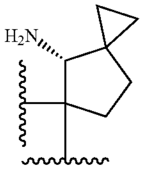, 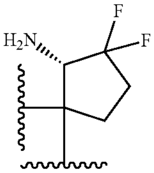, and

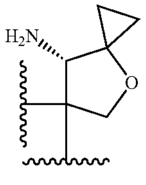.

In the other embodiments of the present disclosure, the compound of formula I as described above has a structure represented by any one of formulae IIa-IIb, IIIa-IIIb, IVa-IVd, and Va-Vc, wherein A is selected from the group consisting of phenylene, pyridinylene, and pyrimidinylene, wherein the phenylene, pyridinylene, and pyrimidinylene are each optionally substituted by one or more $R^a$;

each of the $R^a$, if present, is independently selected from the group consisting of fluorine, chlorine, bromine, cyano, methyl, and amino;

B is selected from the group consisting of

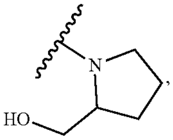, 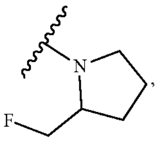, 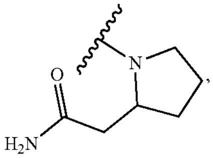,

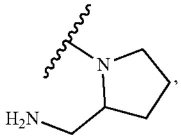, 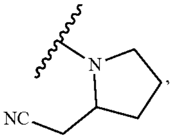, 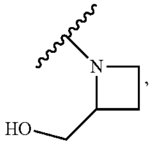,

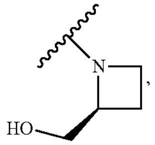, 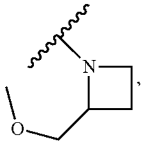, 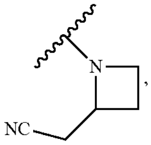,

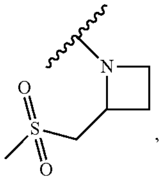, 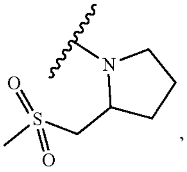, 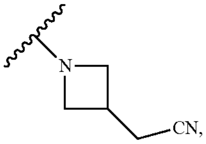

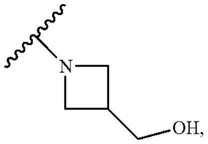 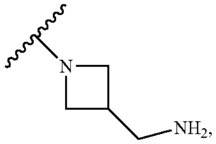

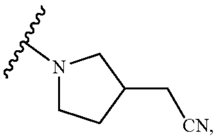 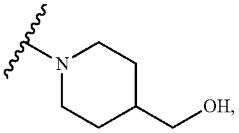

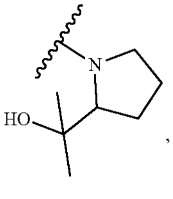, 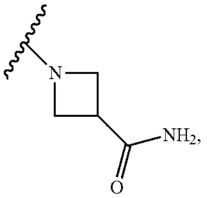

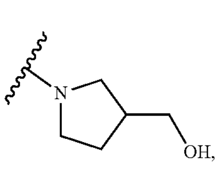 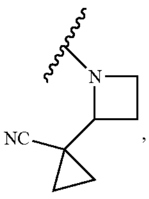,

-continued

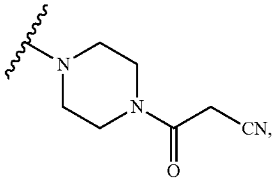 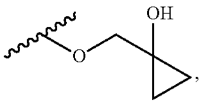

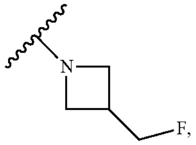 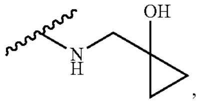

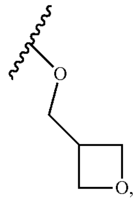 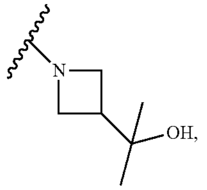

—NH—C(═O)—$CH_2$—CN, and —N($CH_3$)—C(═O)—C($CH_3$)$_2$—OH;

preferably any one selected from the group consisting of

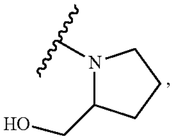 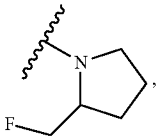

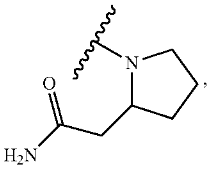 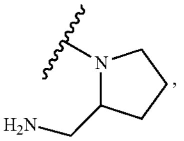

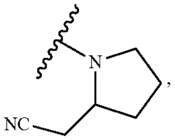 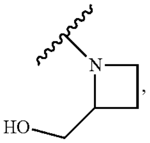 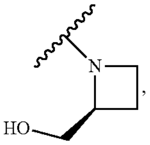

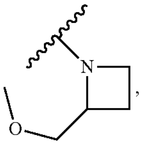 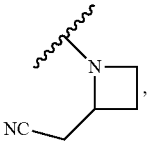 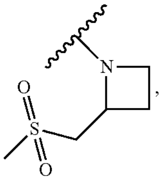

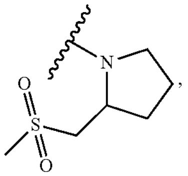 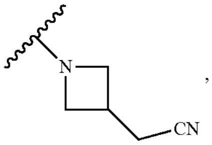

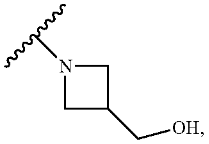 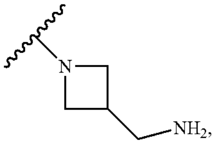

-continued

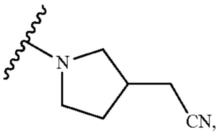 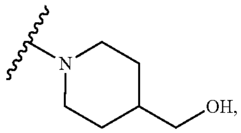

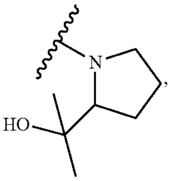 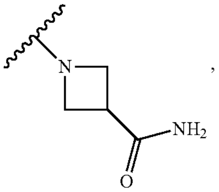

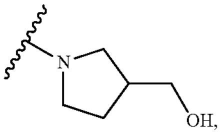 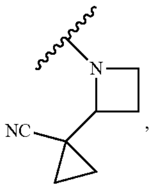

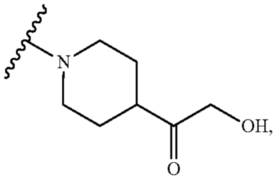 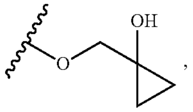

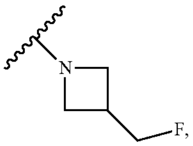 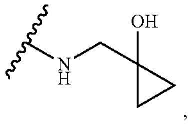

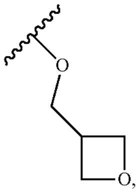

—NH—C(═O)—$CH_2$—CN, and —N($CH_3$)—C(═O)—C($CH_3$)$_2$—OH;

when $R^3$ and $R^4$ are not linked to each other, $R^3$ is selected from the group consisting of fluorine and methyl;

$R^4$ is selected from the group consisting of methyl, fluoromethyl, fluoroethyl, cyanomethyl, hydroxymethyl, and methoxymethyl; or when $R^3$ and $R^4$ together with the atoms to which they are linked form a ring,

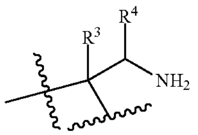

is any one selected from the group consisting of:
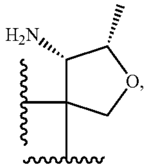
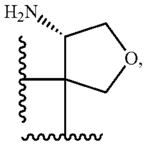
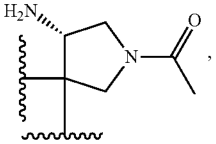
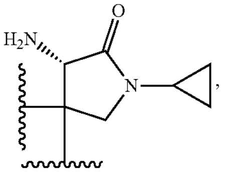
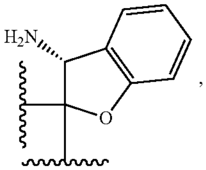
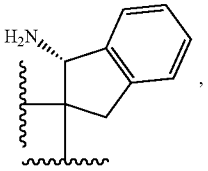
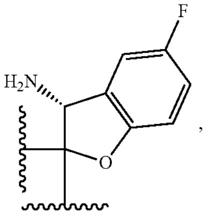
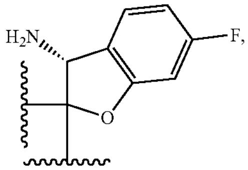
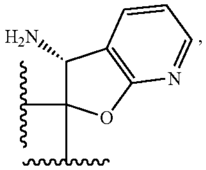
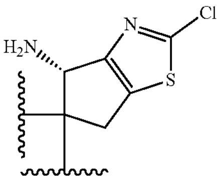
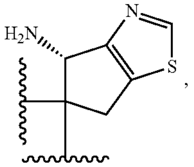
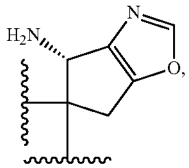
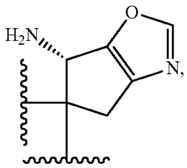
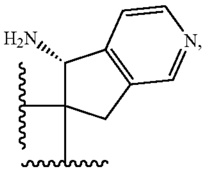
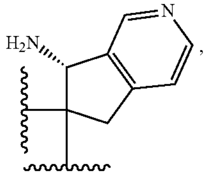
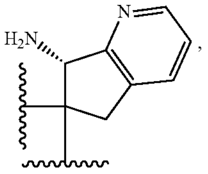
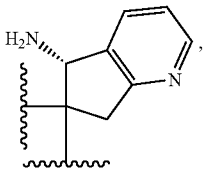
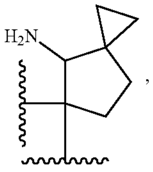
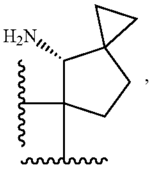
-continued
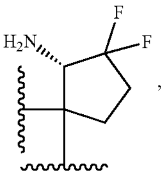
and
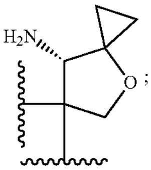
preferably any one selected from the group consisting of
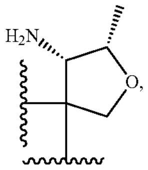
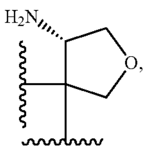
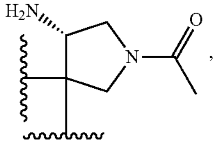
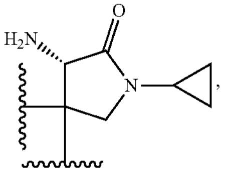
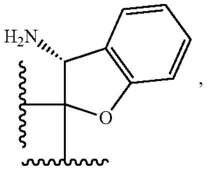
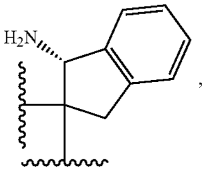
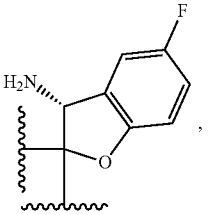
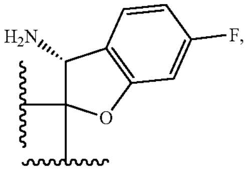
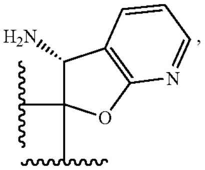
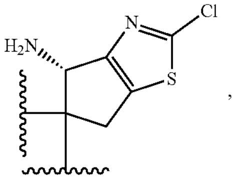
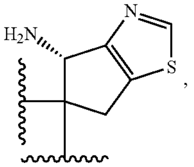
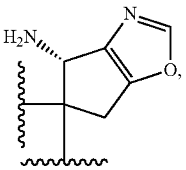
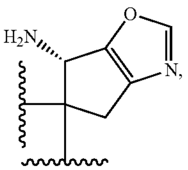
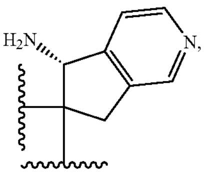
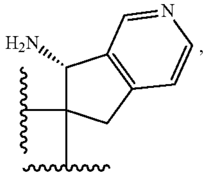
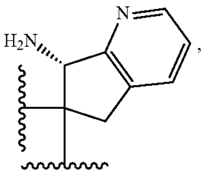
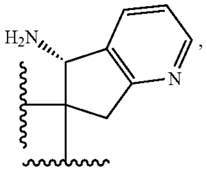

-continued

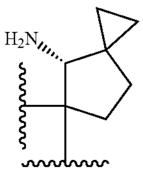, 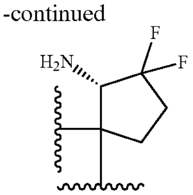, and

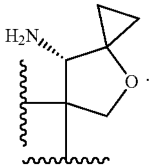

In some embodiments of the present disclosure, the compound of formula I as described above has a structure represented by any one of formulae IIa-IIb, IIIa-IIIb, IVa-IVd, and Va-Vc, wherein A is 5- to 12-membered heteroarylene, wherein the heteroarylene is optionally substituted by one or more halogen;

B is

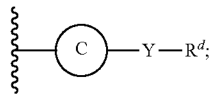

C is 3- to 6-membered heterocycloalkylene, and the heterocycloalkylene is optionally substituted by one or more substituents selected from the group consisting of fluorine, cyano, methyl, and fluoromethyl;

Y is selected from the group consisting of $C_{1-3}$ alkylene and —C(═O)—($C_{1-3}$ alkylene)-;

$R^d$ is selected from the group consisting of fluorine, amino, hydroxyl, cyano, —S(═O)$_2$—($C_{1-6}$ alkyl), and —O—($C_{1-6}$ alkyl);

when $R^3$ and $R^4$ are not linked to each other, $R^3$ is $C_{1-6}$ alkyl and $R^4$ is $C_{1-6}$ alkyl, wherein the alkyl is optionally substituted by —O—($C_{1-3}$ alkyl); or when $R^3$ and $R^4$ together with the atoms to which they are linked form a ring,

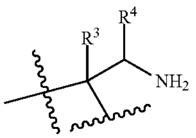

is selected from the group consisting of

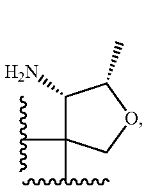 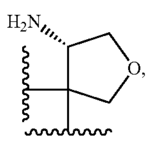

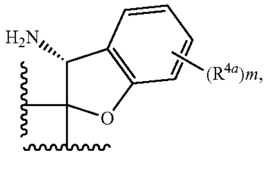 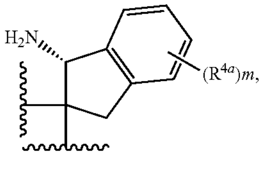

-continued

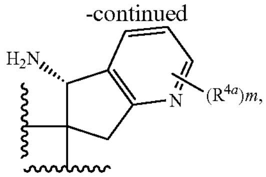

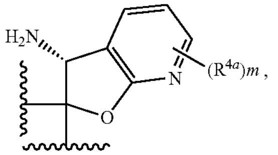 and 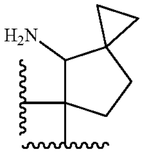 ;

m is 0, 1, or 2; and each of the $R^{4a}$, if present, is independently selected from the group consisting of hydrogen and fluorine.

In some embodiments of the present disclosure, the compound of formula I as described above has a structure represented by any one of formulae IIa-IIb, IIIa-IIIb, IVa-IVd, and Va-Vc, wherein A is pyridinylene, and the pyridinylene is optionally substituted by one or more chlorine;

B is

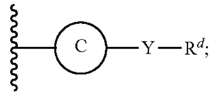

C is selected from the group consisting of azetidinylene and pyrrolidylidene, and the azetidinylene and pyrrolidylidene are each optionally substituted by one or more substituents selected from the group consisting of fluorine, cyano, methyl, and fluoromethyl;

Y is selected from the group consisting of —$CH_2$—, —CH($CH_3$)—, —C($CH_3$)$_2$—, and —C(═O)—$CH_2$—;

$R^d$ is selected from the group consisting of fluorine, amino, hydroxyl, cyano, S(═O)$_2$—$CH_3$, and —O—$CH_3$;

when $R^3$ and $R^4$ are not linked to each other, $R^3$ is methyl and $R^4$ is methyl, wherein the methyl is optionally substituted by methoxy; or when $R^3$ and $R^4$ together with the atoms to which they are linked form a ring,

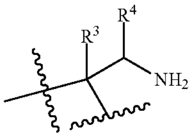

is selected from the group consisting of

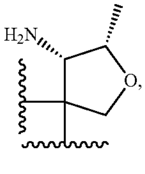 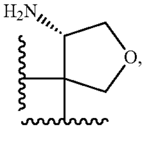

-continued

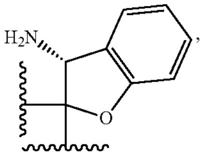
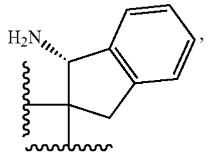
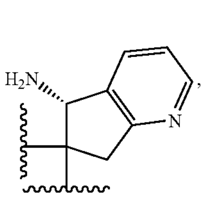
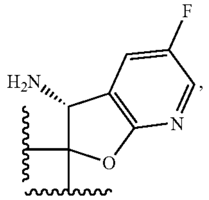
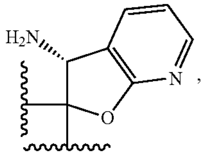
and
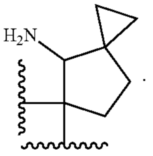

In some embodiments of the present disclosure, the compound of formula I as described above has a structure represented by any one of formulae IIa-IIb, IIIa-IIIb, IVa-IVd, and Va-Vc, wherein A is pyridinylene, and the pyridinylene is optionally substituted by one or more chlorine;

B is selected from the group consisting of

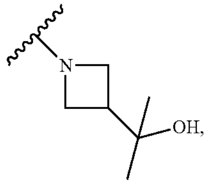
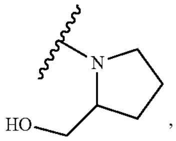
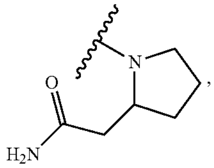
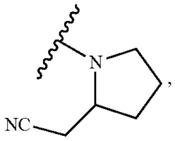
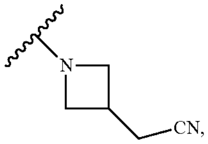
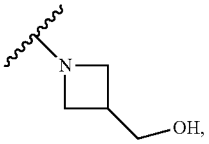
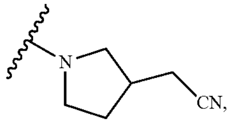
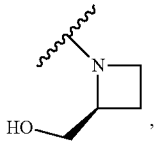
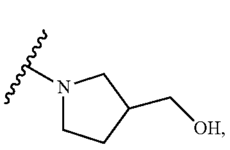
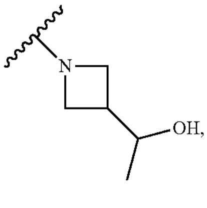

-continued

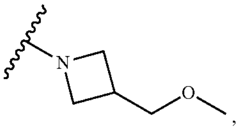
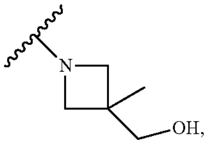
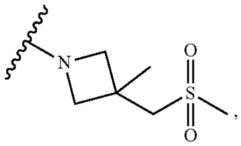
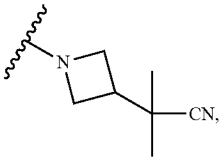
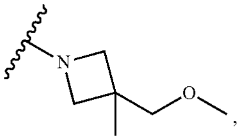
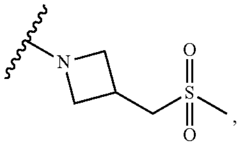
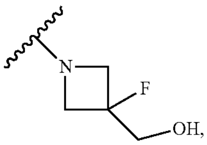
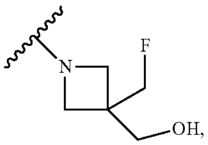
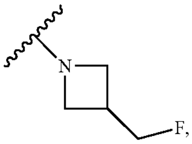
and
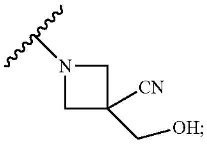

when $R^3$ and $R^4$ are not linked to each other, $R^3$ is methyl and $R^4$ is methyl, wherein the methyl is optionally substituted by methoxy; or when $R^3$ and $R^4$ together with the atoms to which they are linked form a ring,

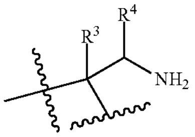

is selected from the group consisting of

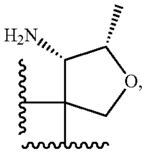
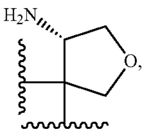
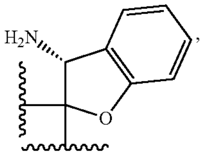
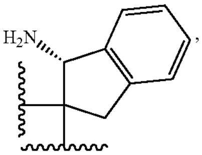
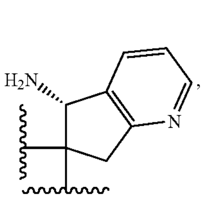
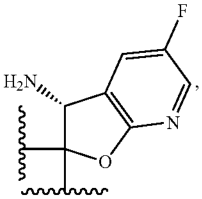

-continued

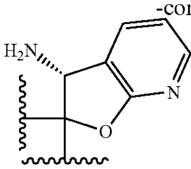

, or

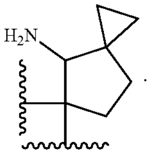

.

In some embodiments of the present disclosure, the compound of formula I as described above has a structure represented by formula IIb, wherein A is 5- to 12-membered heteroarylene, wherein the heteroarylene is optionally substituted by one or more halogen; preferably, A is pyridinylene, wherein the pyridinylene is optionally substituted by one or more chlorine;

B is

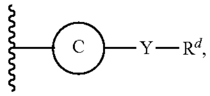

wherein C is 3- to 6-membered heterocycloalkylene, Y is $C_{1-3}$ alkylene, and $R^d$ is hydroxyl; preferably, B is

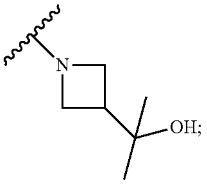 [SMILES: *N1CC(C(C)(C)O)C1]

$R^3$ and $R^4$ together with the atoms to which they are linked form a ring, and

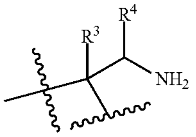

is

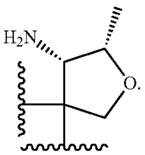

It will be appreciated by those skilled in the art that the present disclosure encompasses the compounds resulting from an arbitrary combination of various embodiments. An embodiment resulting from a combination of the technical features or preferred technical features in one embodiment with the technical features or preferred technical features in another embodiment is also within the scope of the present disclosure.

The present disclosure provides the following compounds included in the compounds of formula I, formula IIa, formula IIb, formula IIIa, formula IIIb, formula IVa, formula IVb, formula IVc, formula IVd, formula Va, formula Vb, and formula Vc:

1

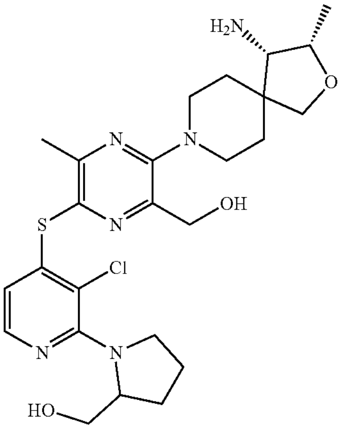

2

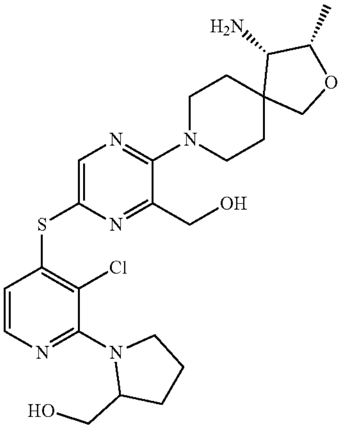

3

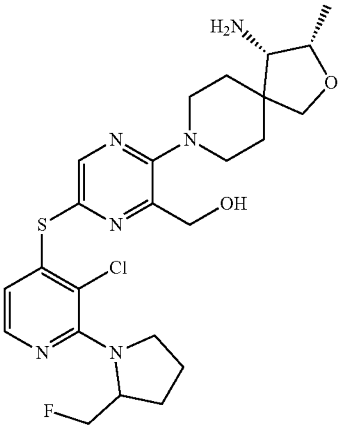

-continued
4
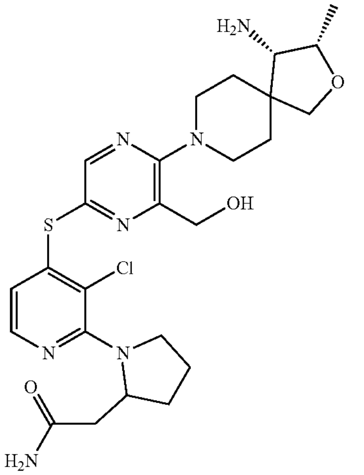
5
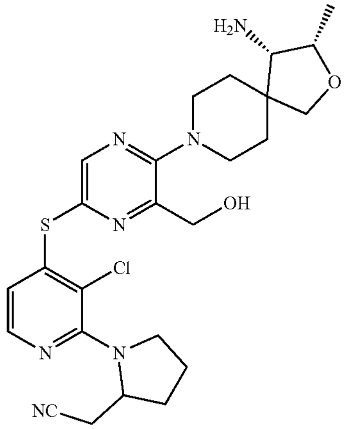
6
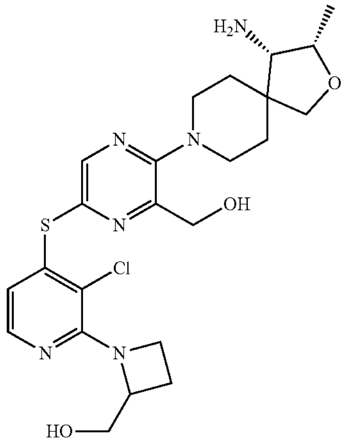
-continued
7
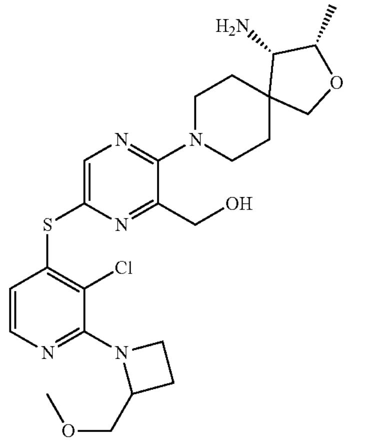
8
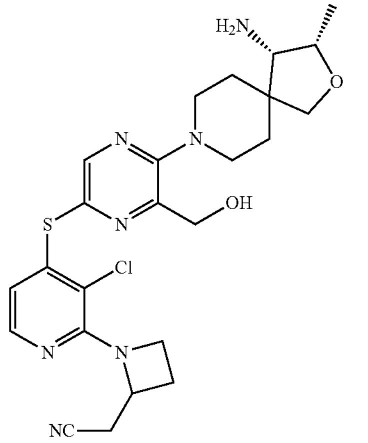
9
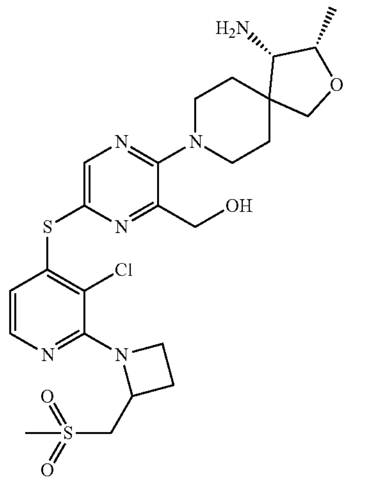

-continued
10
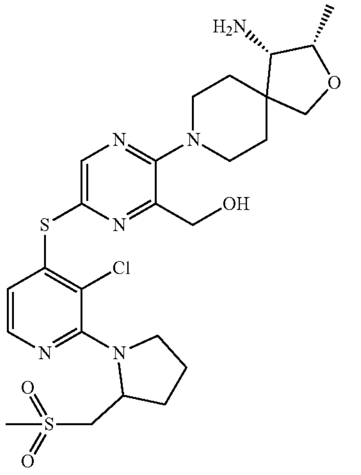
11
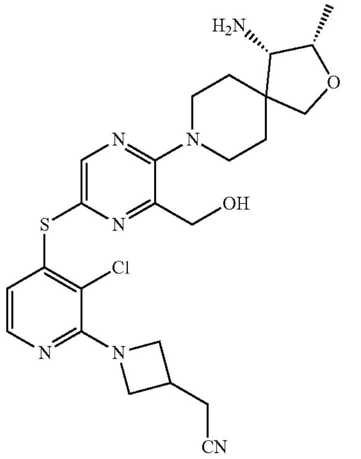
12
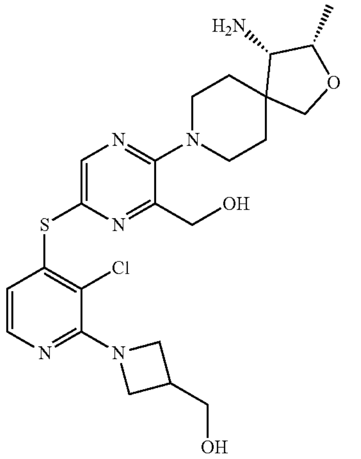
-continued
13
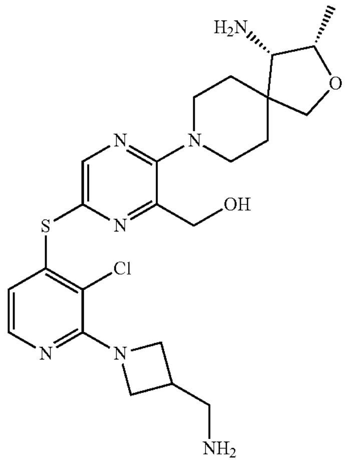
14
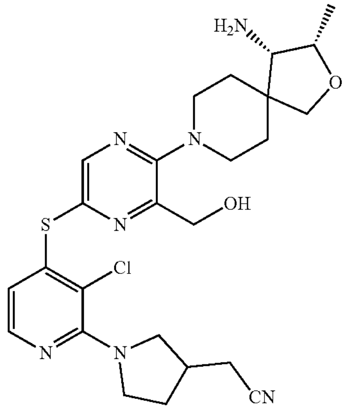
15
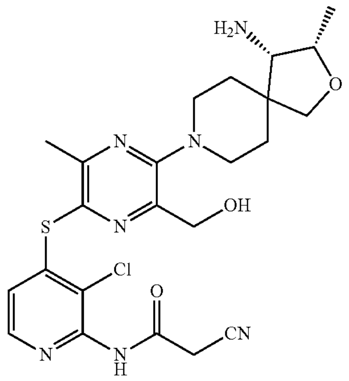

-continued
16
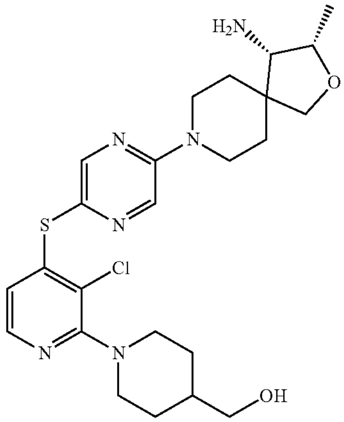
17
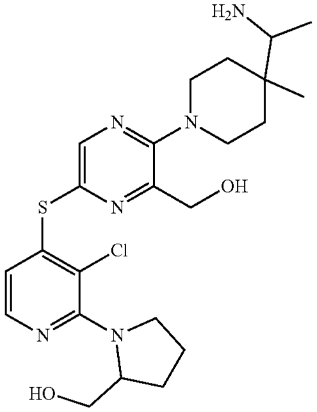
18
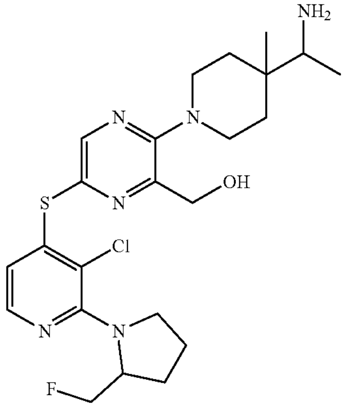
19
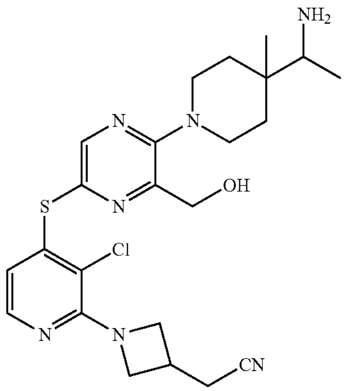
-continued
20
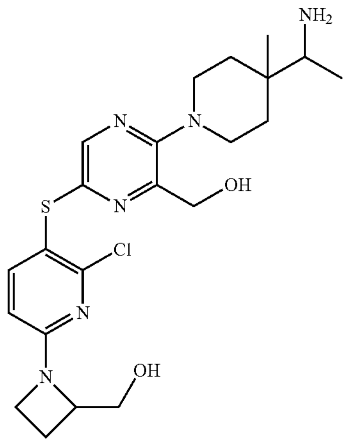
21
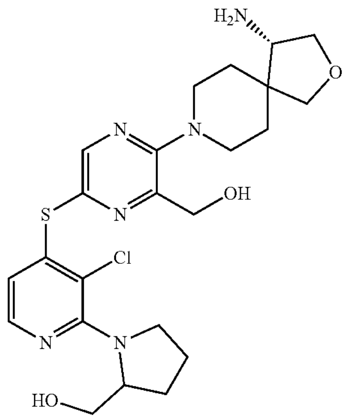
22
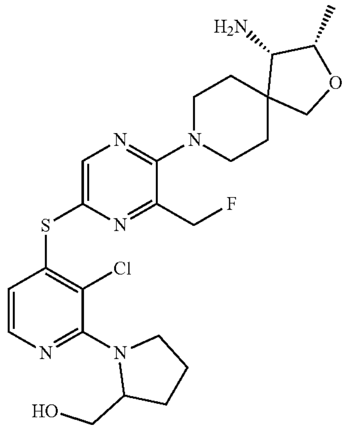

-continued
23
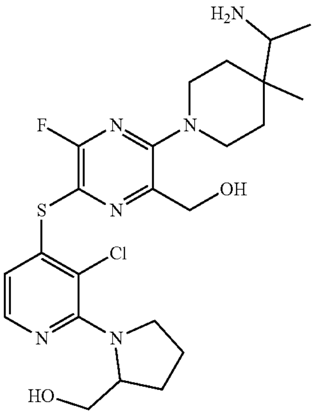
24
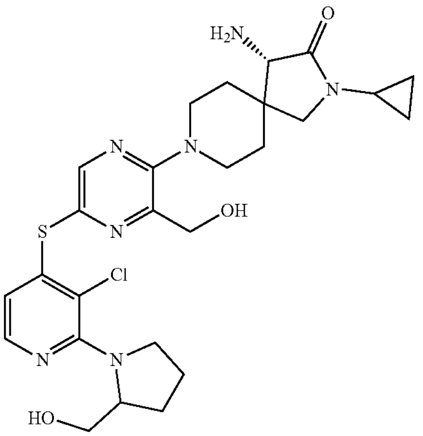
25
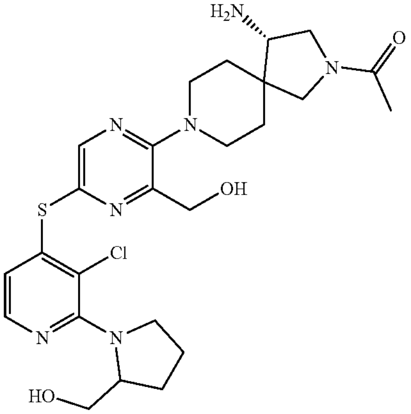
-continued
26
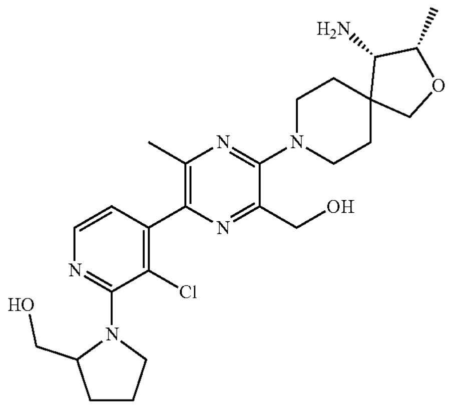
27
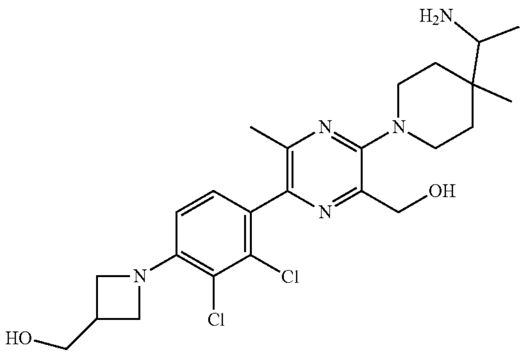
28
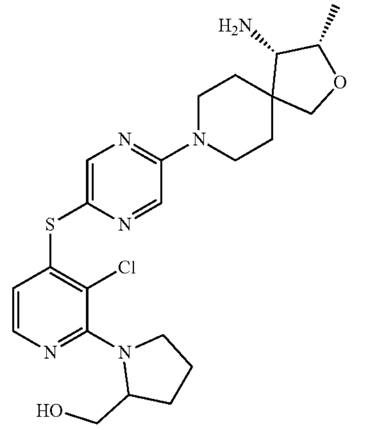
29
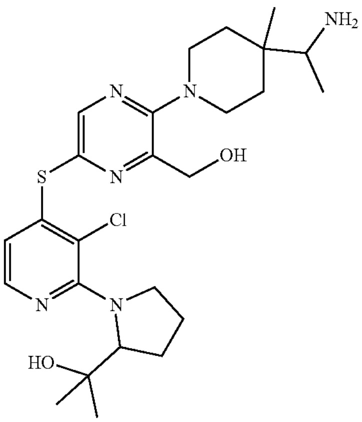

-continued
30
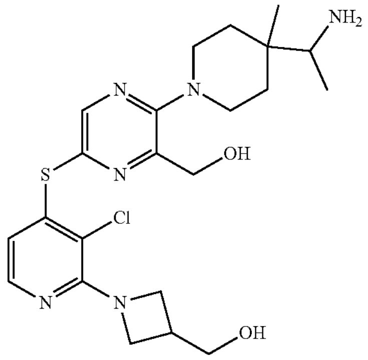
31
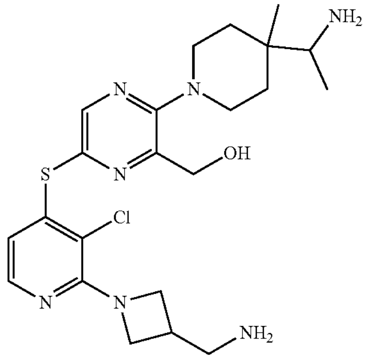
32
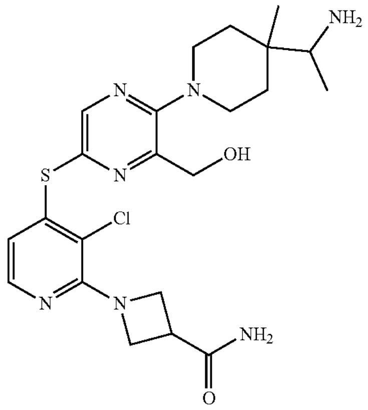
33
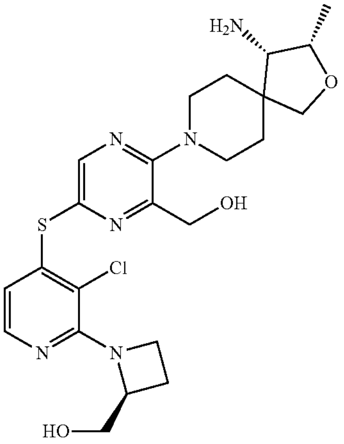
-continued
34
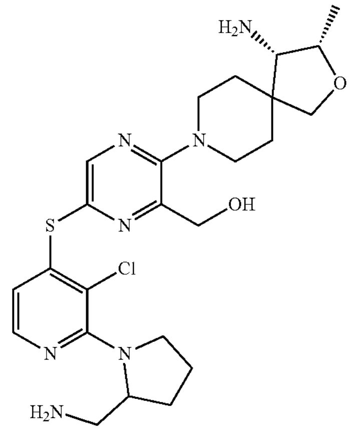
35
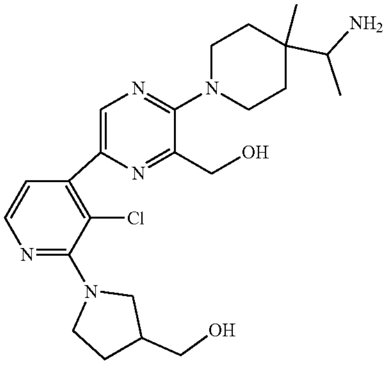
36
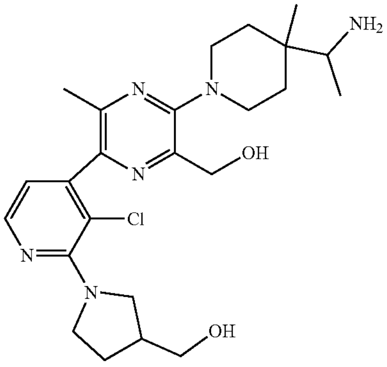
37
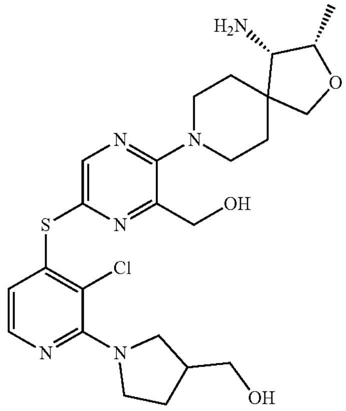

-continued
38
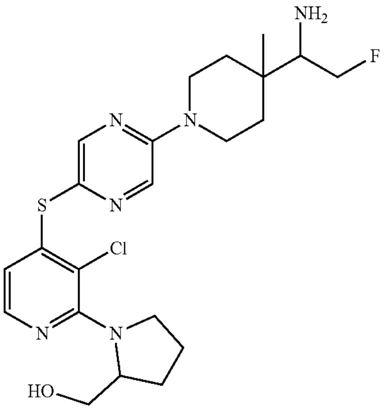
39
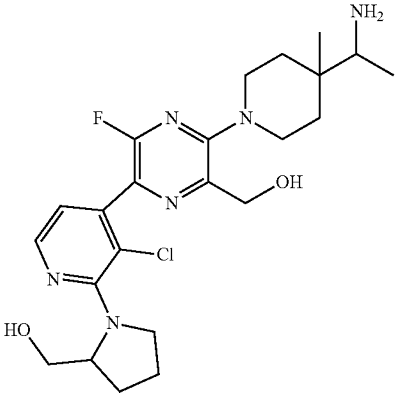
40
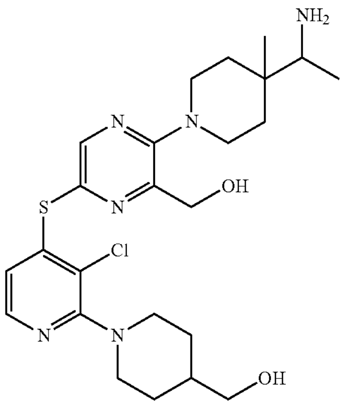
-continued
41
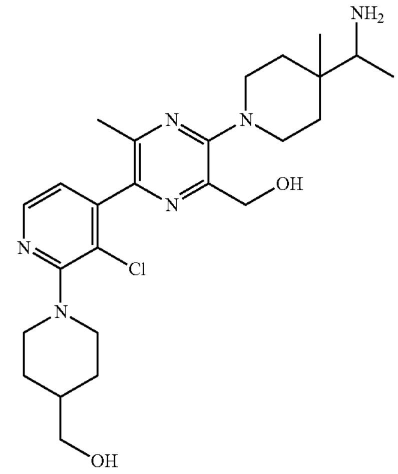
42
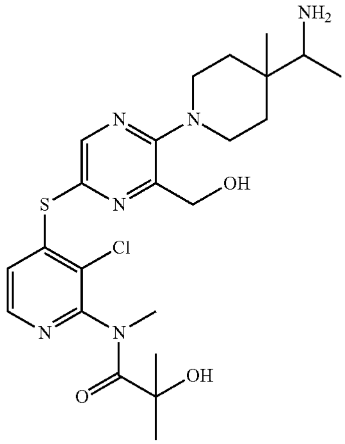
43
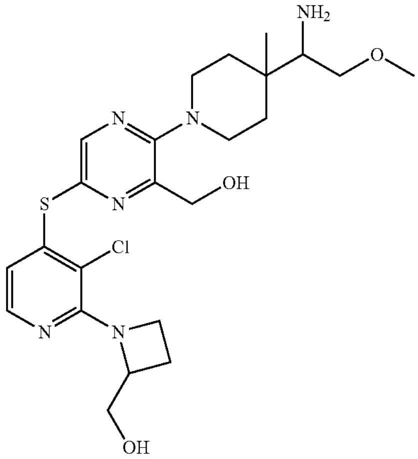

-continued
44
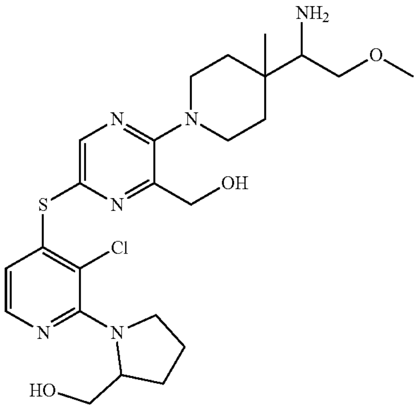
45
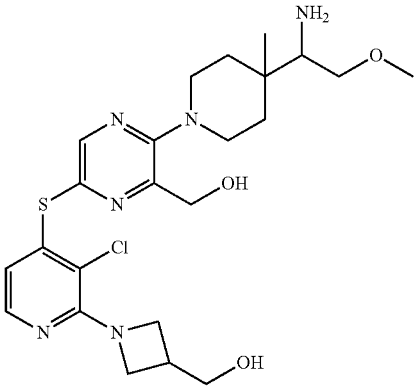
46
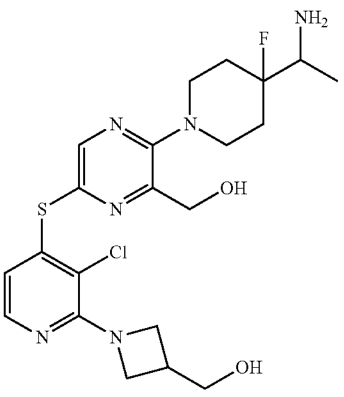
-continued
47
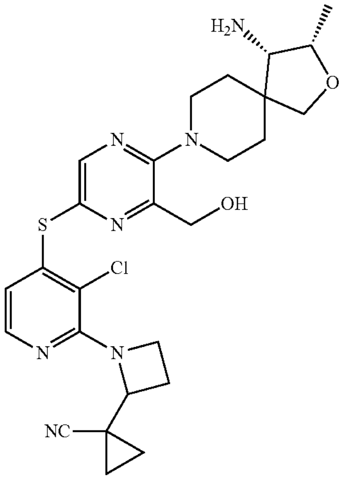
48
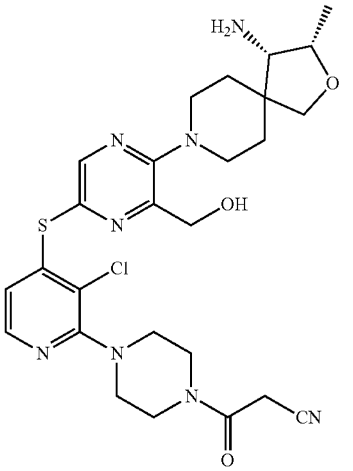
49
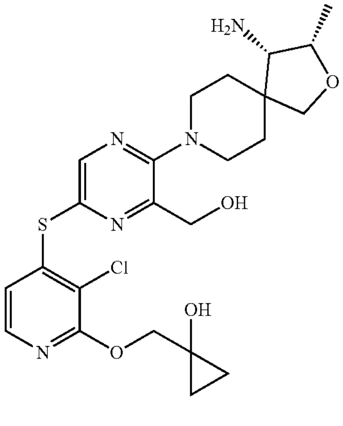

-continued
50
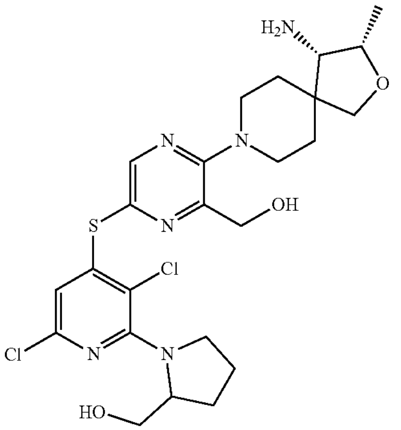
51
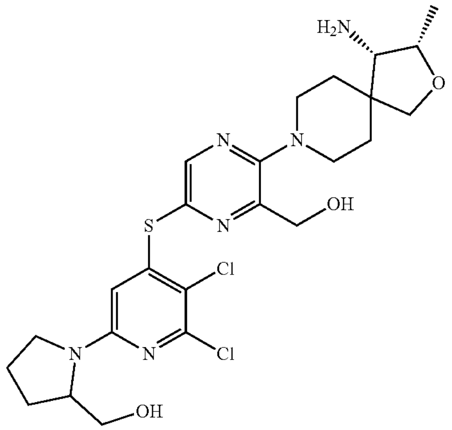
52
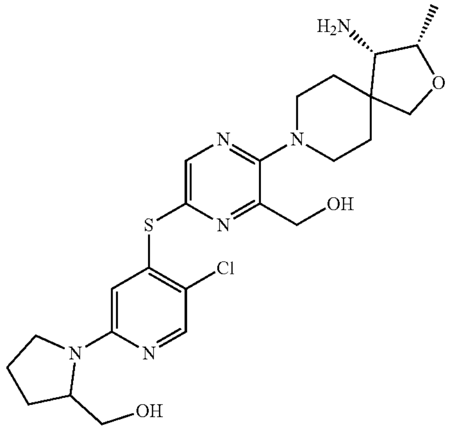
-continued
53
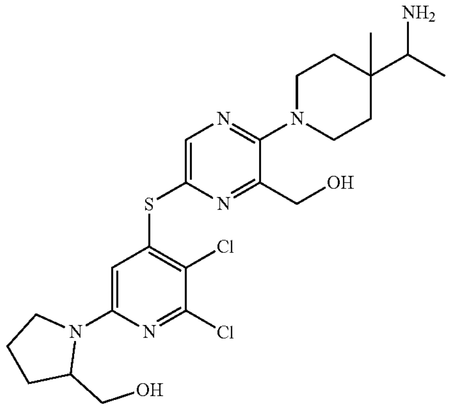
54
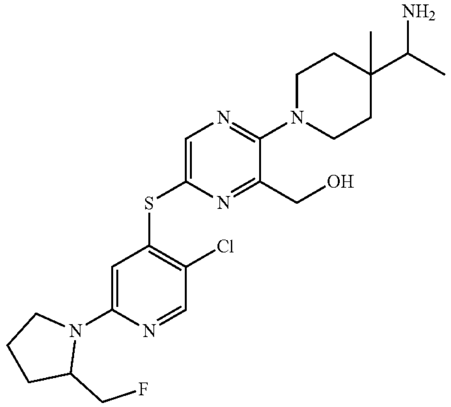
55
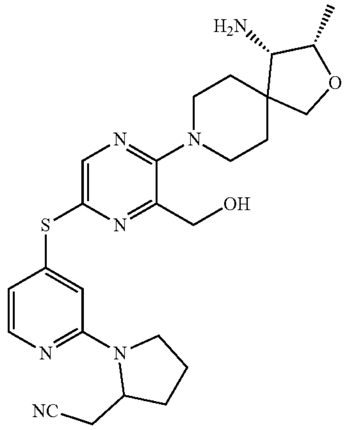

-continued
56
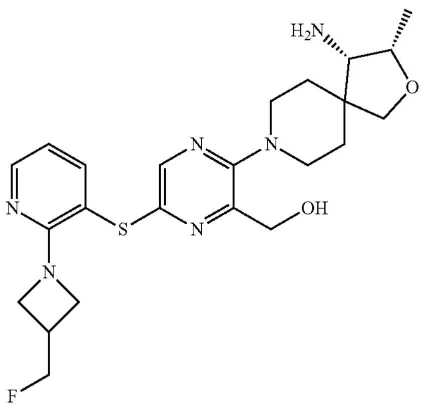
57
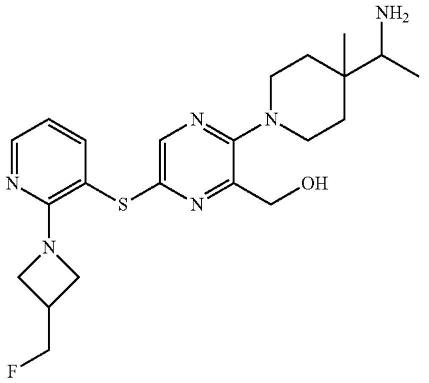
58
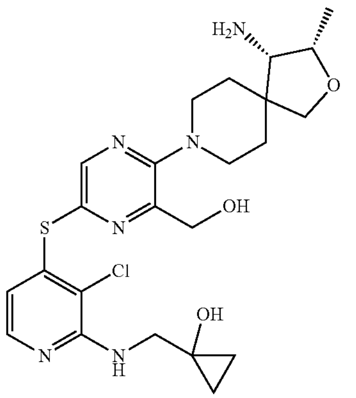
59
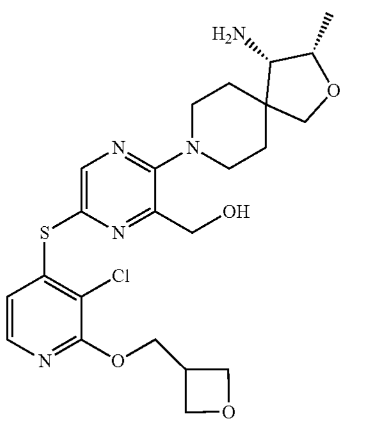
-continued
60
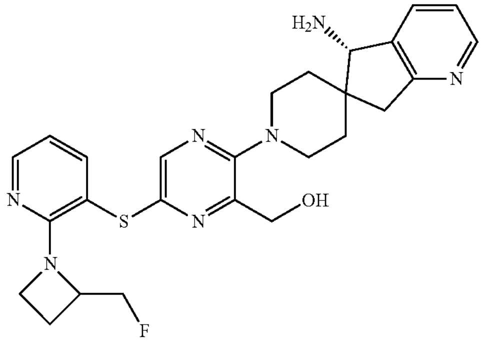
61
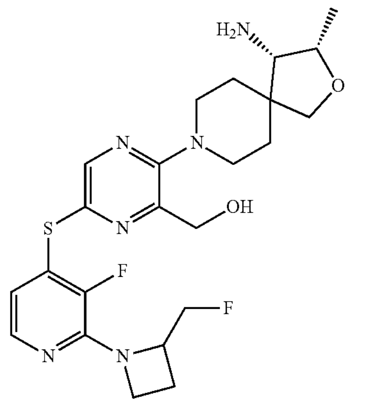
62
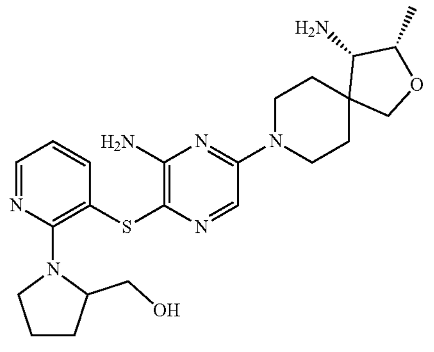
63
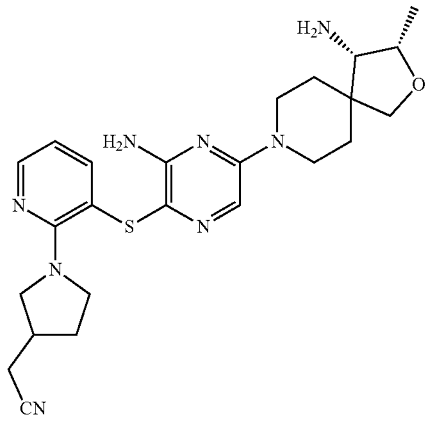

-continued
64
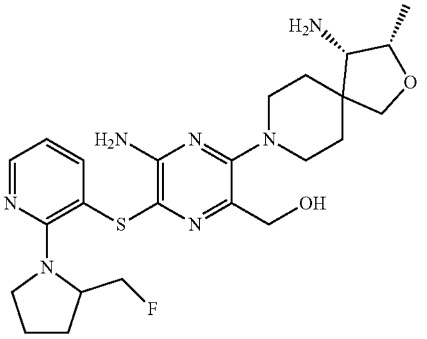
65
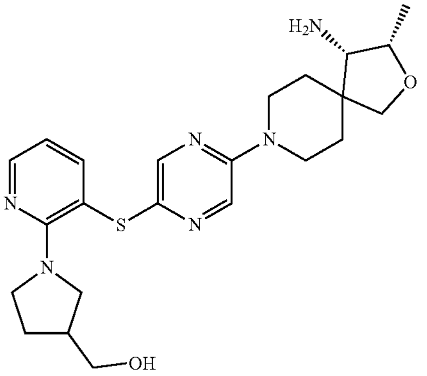
66
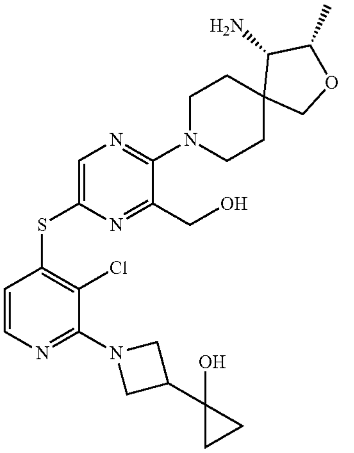
67
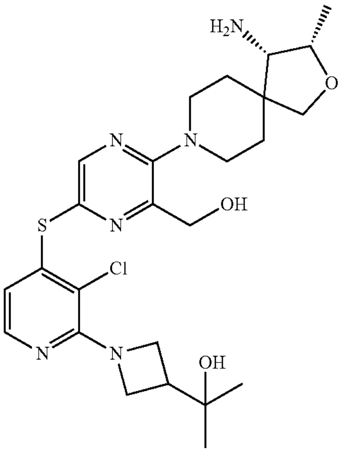
-continued
68
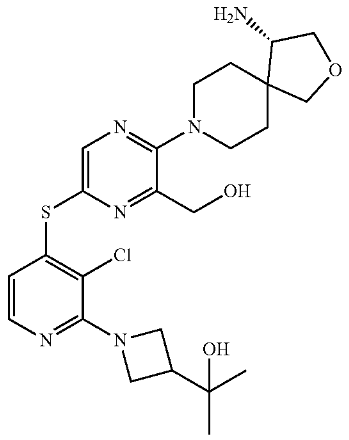
69
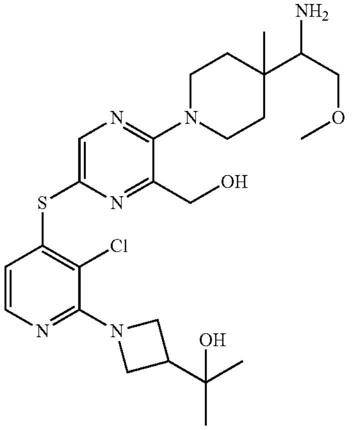
70
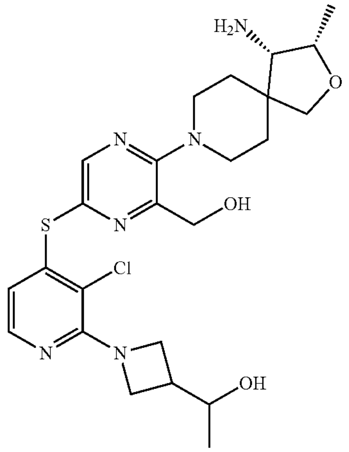

-continued
71
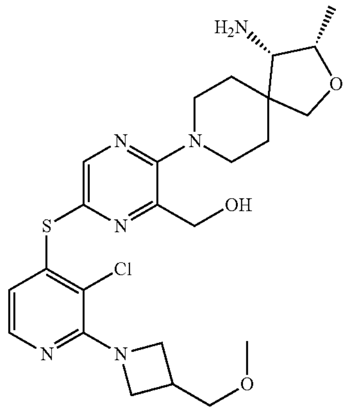
72
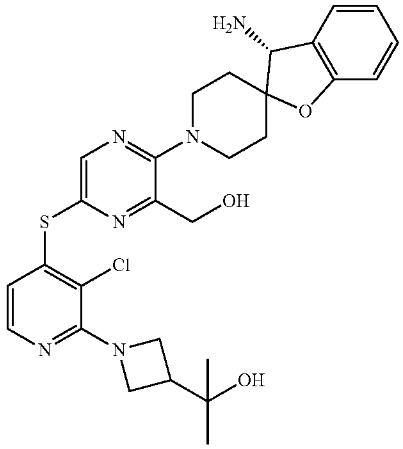
73
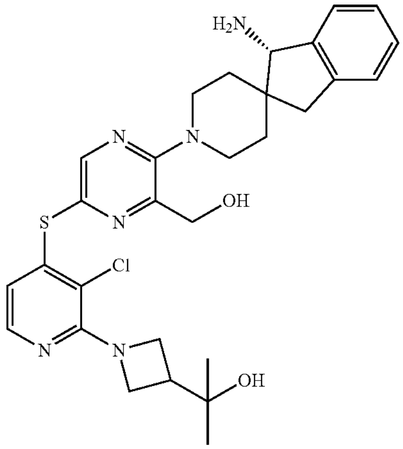
-continued
74
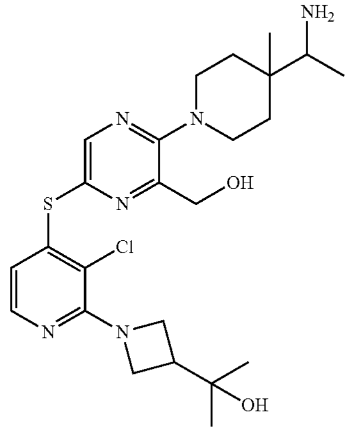
75
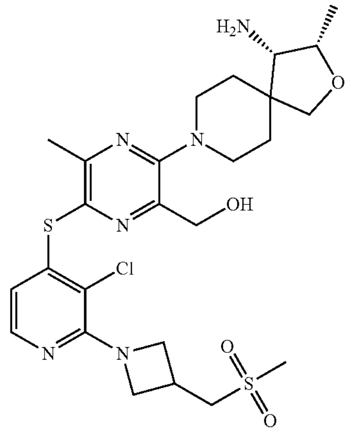
76
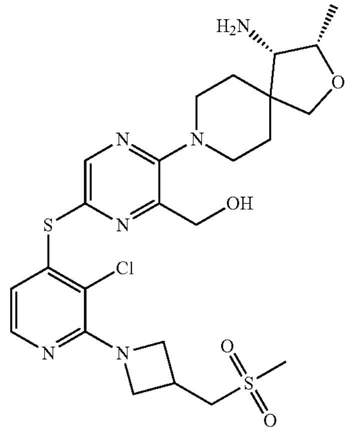

-continued
77
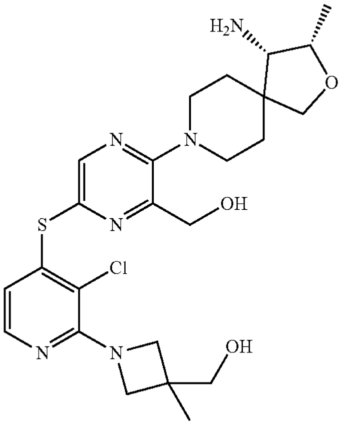
78
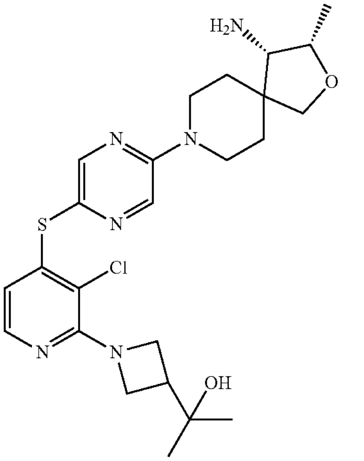
79
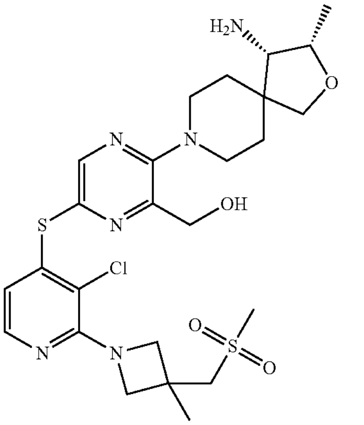
-continued
80
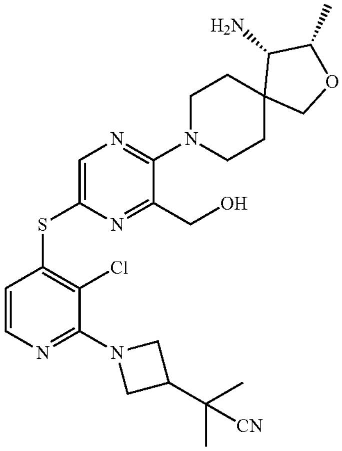
81
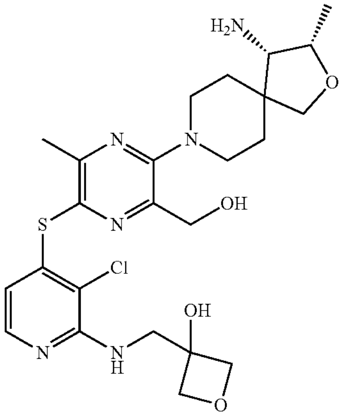
82
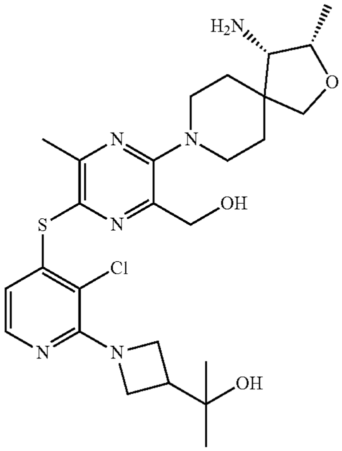

-continued
83
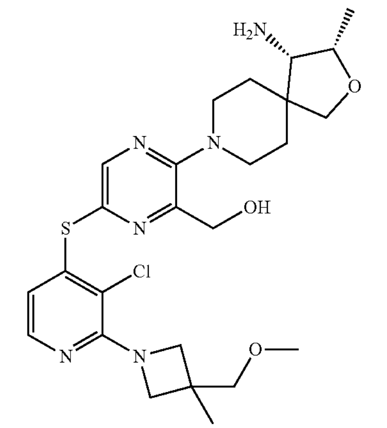
84
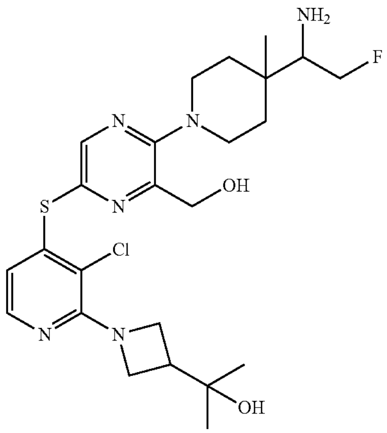
85
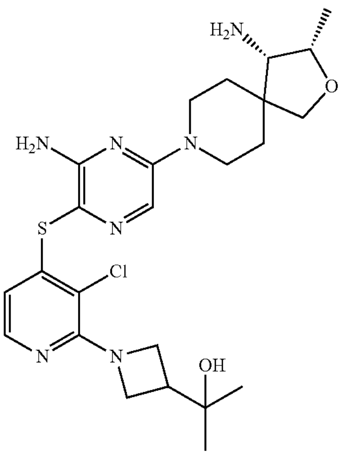
-continued
86
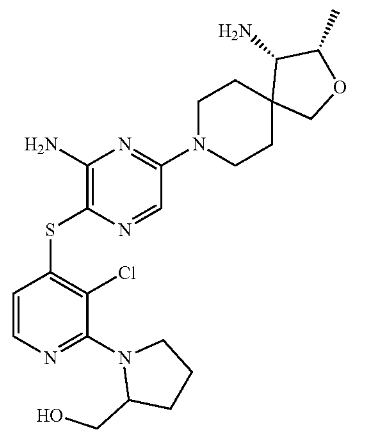
87
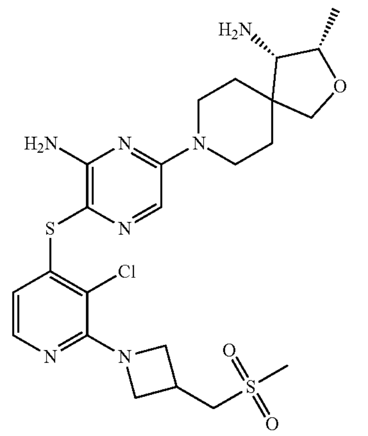
88
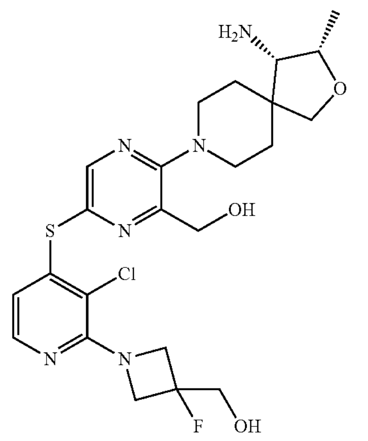

-continued
89
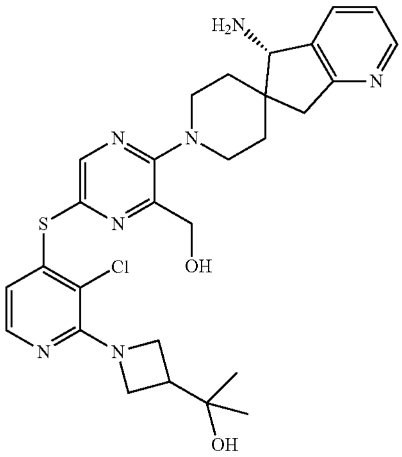
90
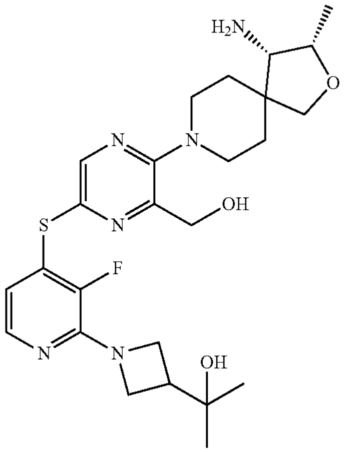
91
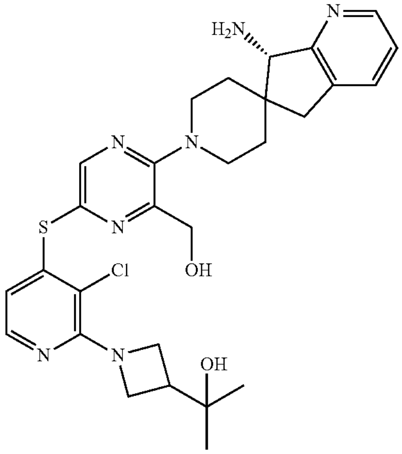
-continued
92
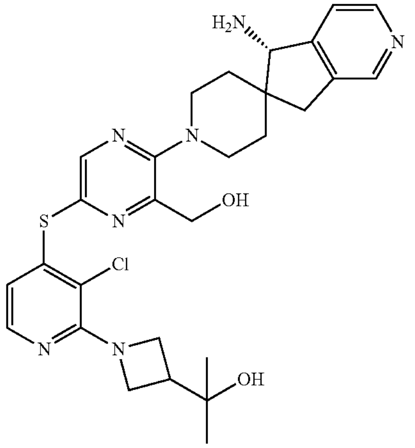
93
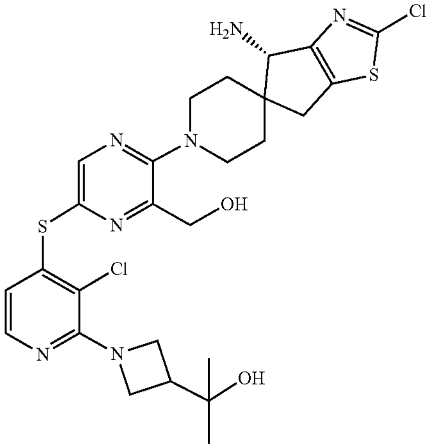
94
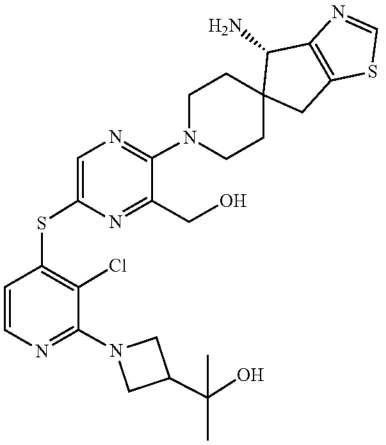

-continued
95
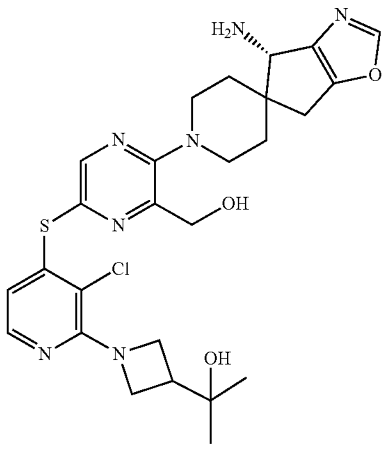
96
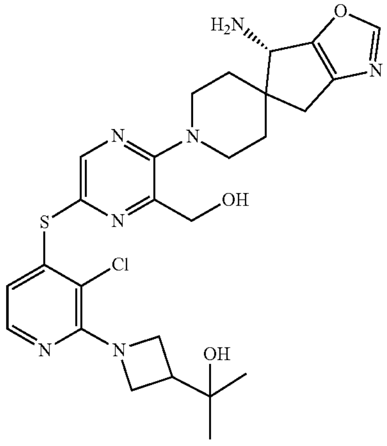
97
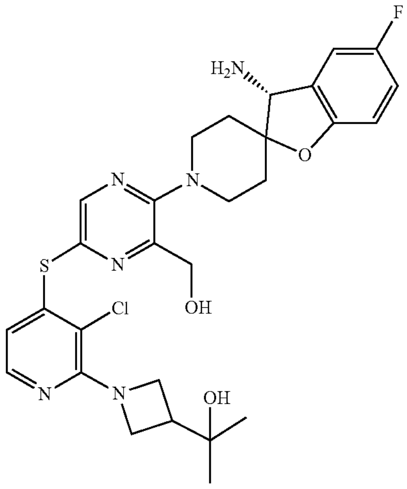
-continued
98
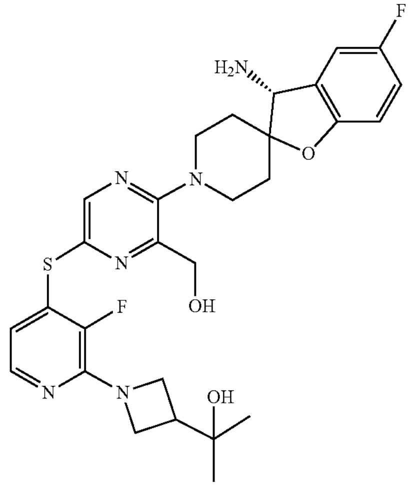
99
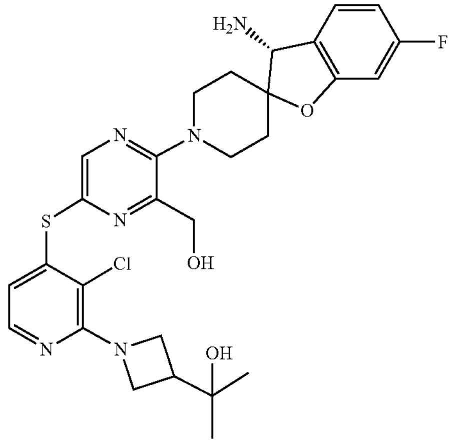
100
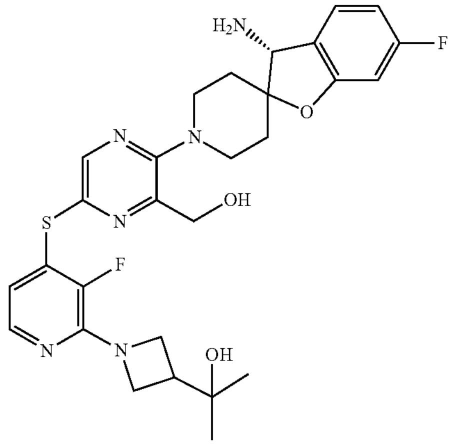

-continued
101
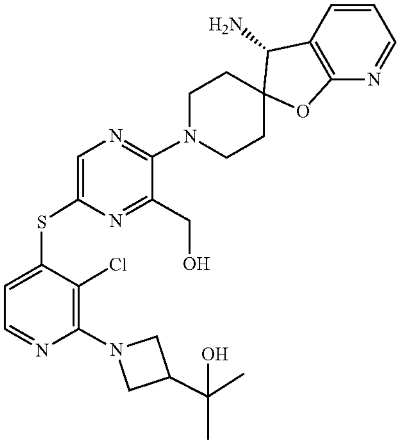
102
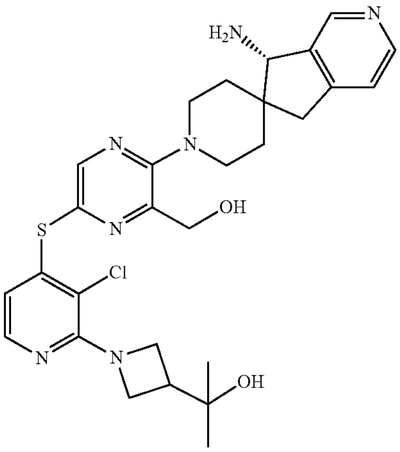
103
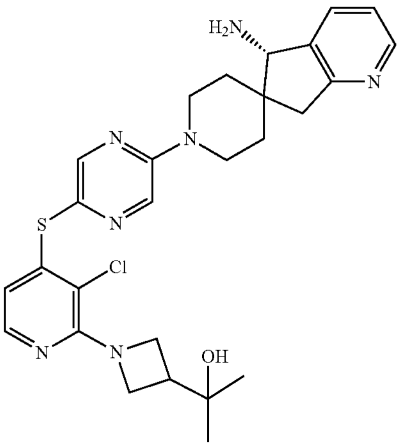
-continued
104
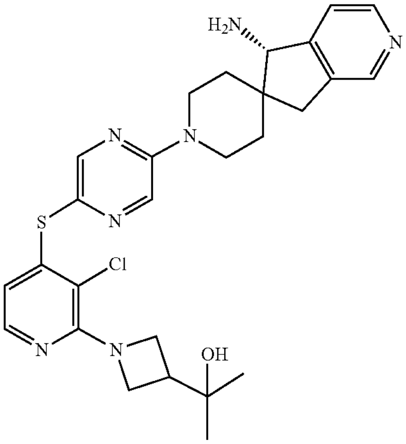
105
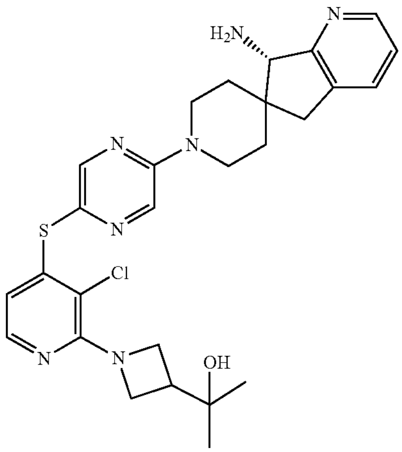
106
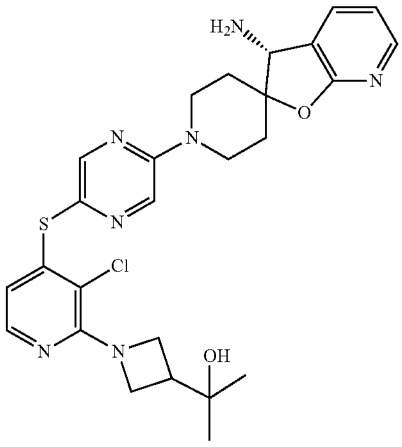

-continued
107
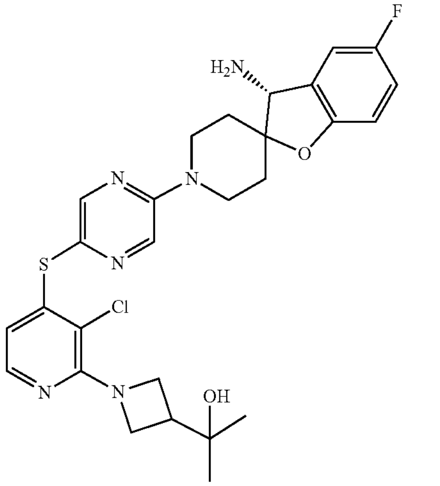
108
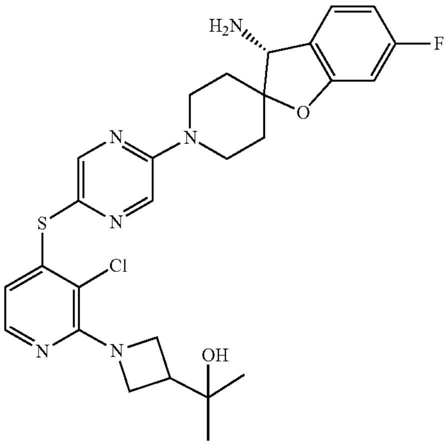
109
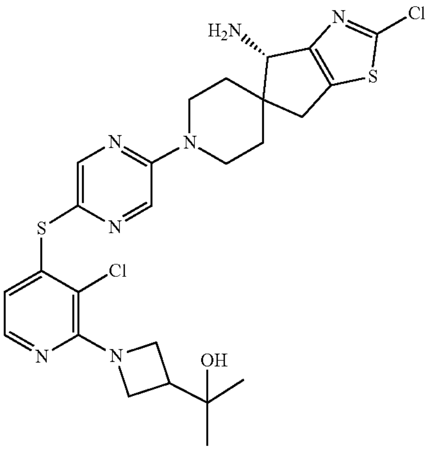
-continued
110
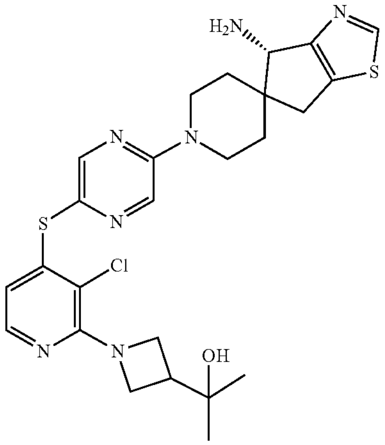
111
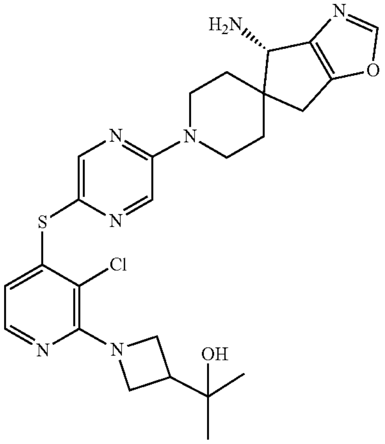
112
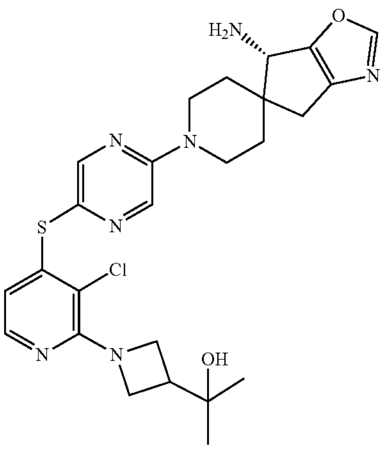

-continued
113
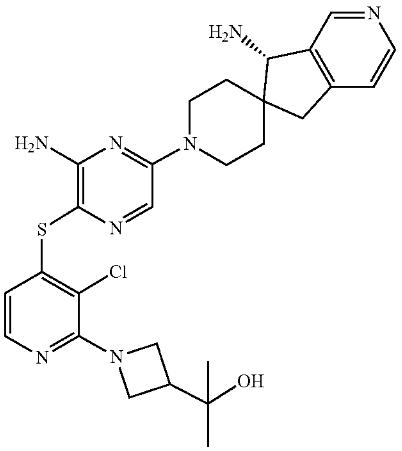
114
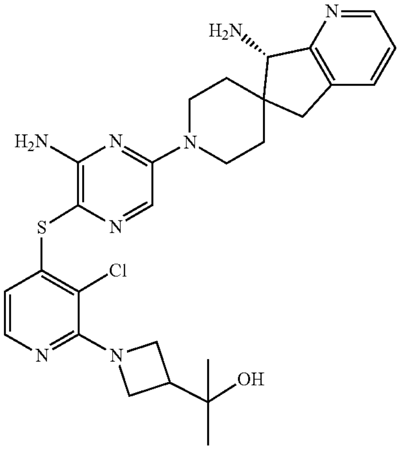
115
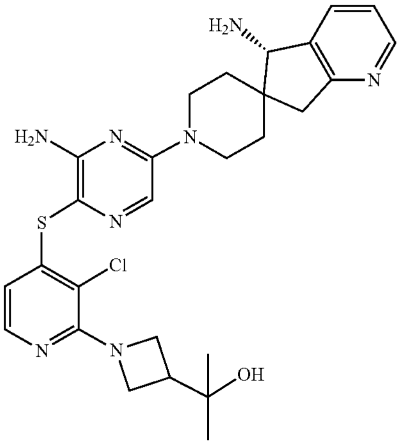
-continued
116
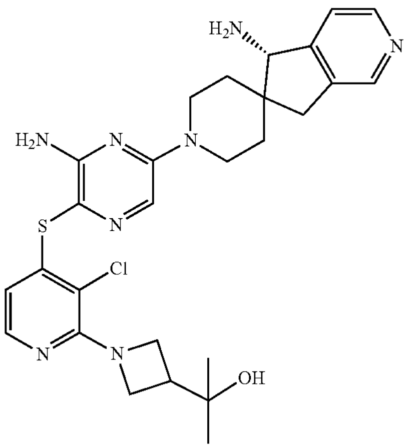
117
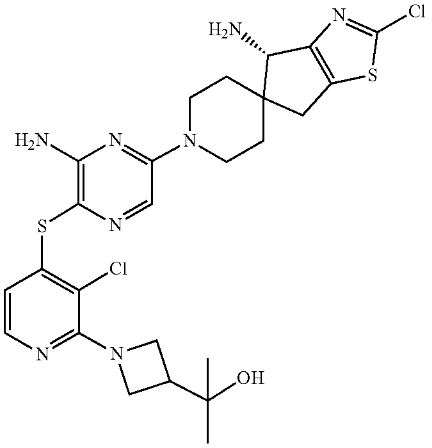
118
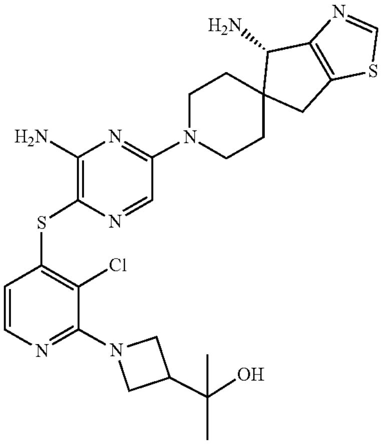

-continued
119
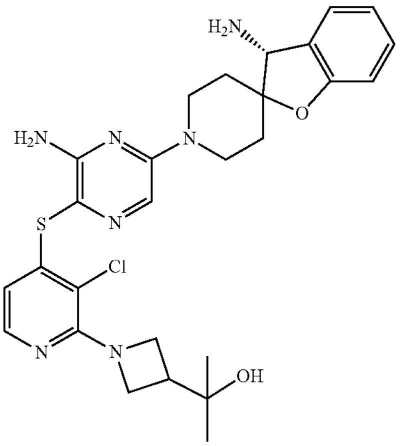
120
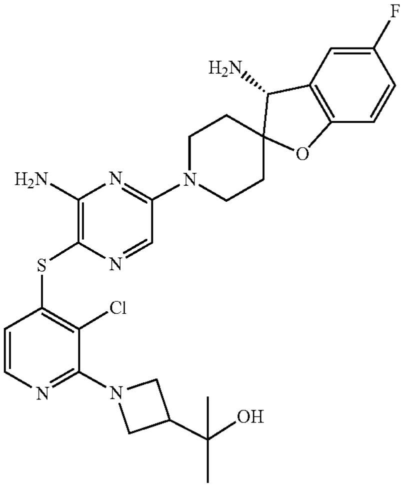
121
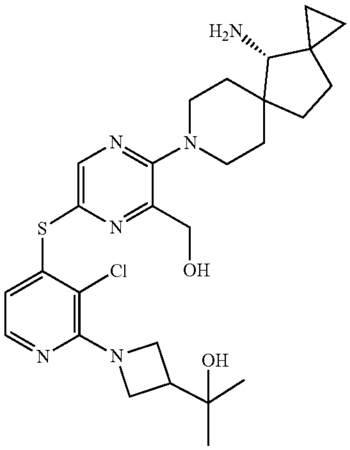
-continued
122
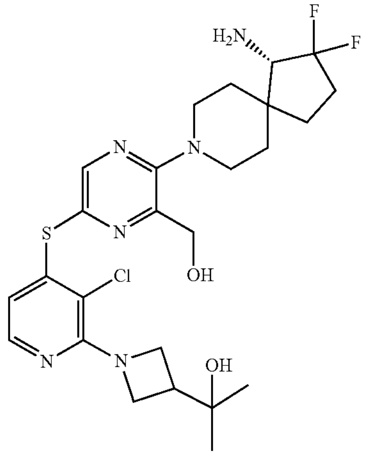
123
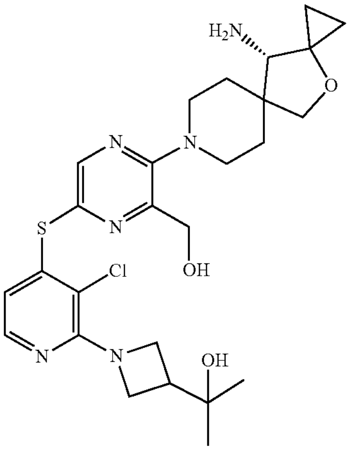
124
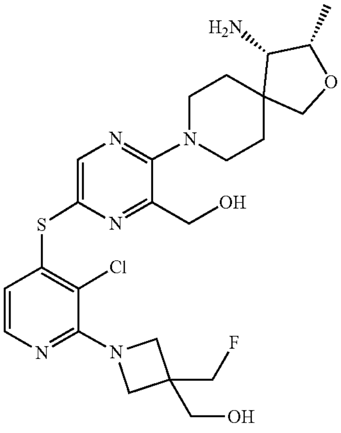

-continued
125
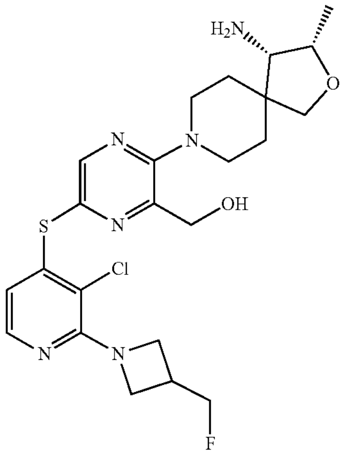
126
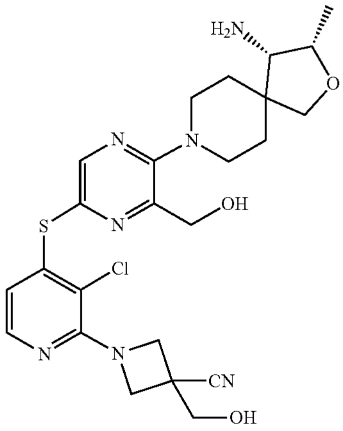
127
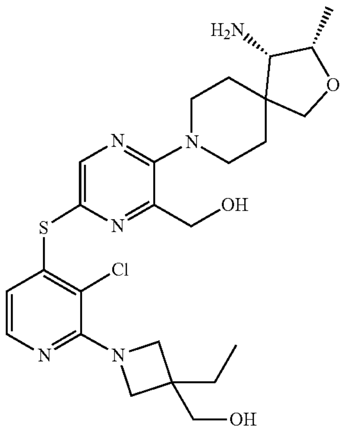
-continued
128
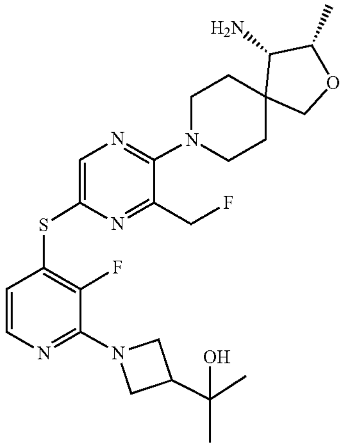
129
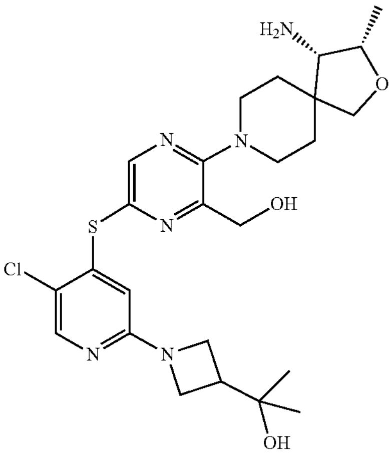
130
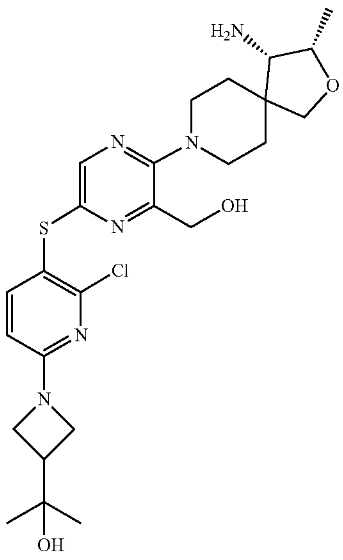

-continued
131
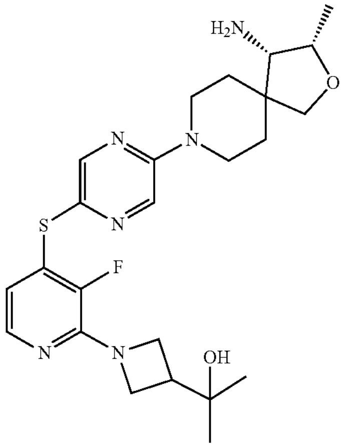
132
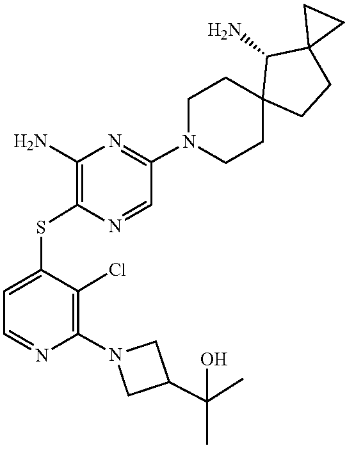
133
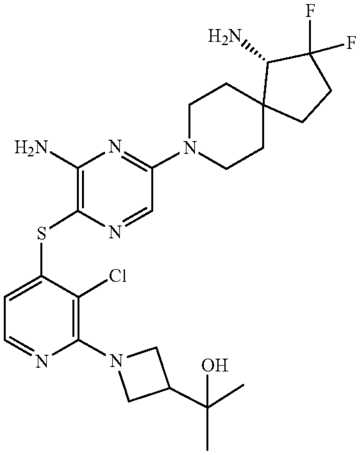
-continued
134
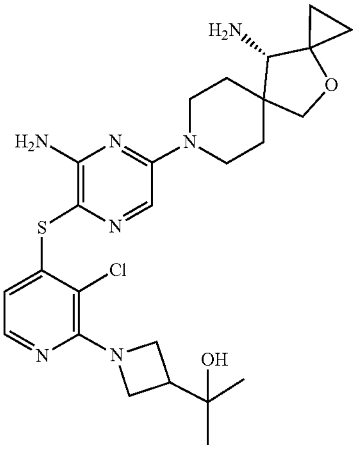
135
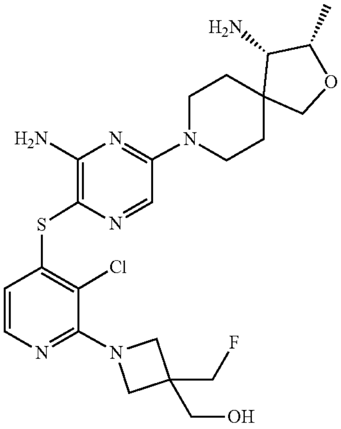
136
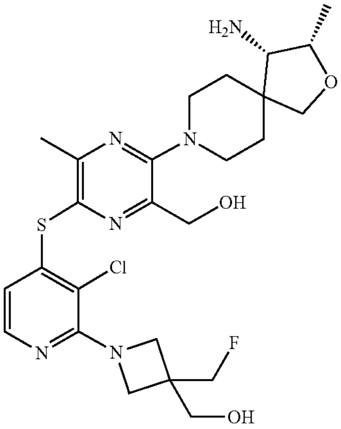

-continued

137

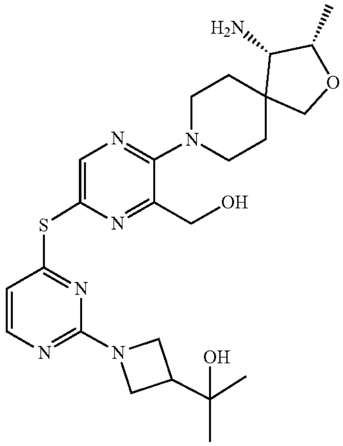

138

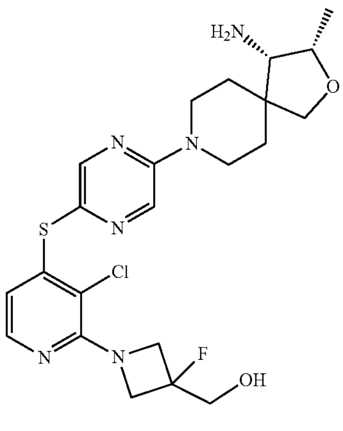

139

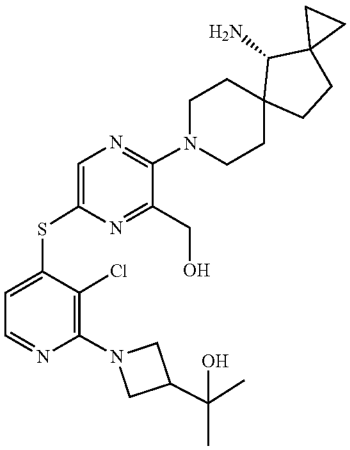

-continued

140

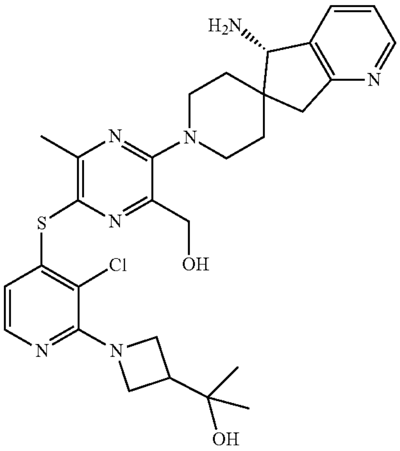

Preparation Methods for Compounds

The present disclosure provides two preparation methods for the compound of formula I.

Method 1 comprises the following steps:

(1) reacting the compound of formula S-1 with the compound of formula S-2 to afford the compound of formula M-1;

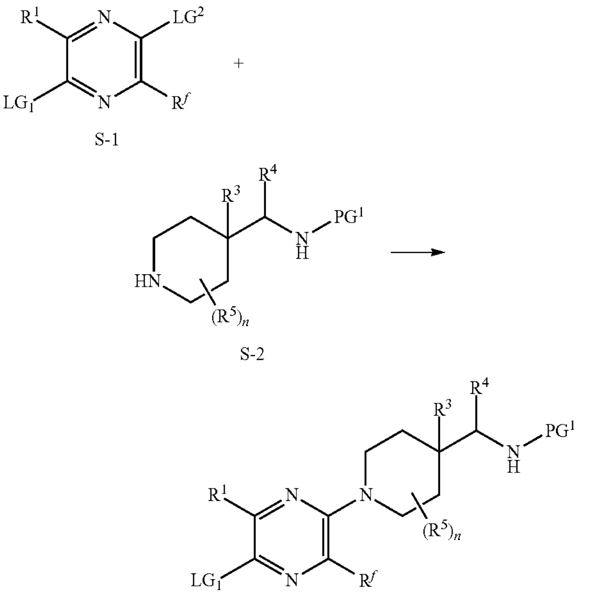

S-1

S-2

M-1

(2) reacting the compound of formula M-1 with the compound of formula S-3 to afford the compound of formula M-2; and

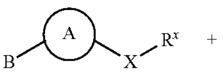

S-3

-continued

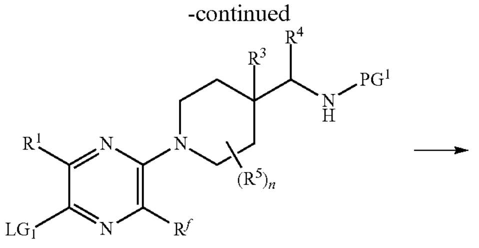

M-1

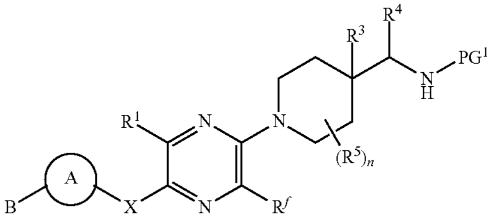

M-2

(3) subjecting the compound of formula M-2 to deprotection and functional group conversion to afford the compound of formula I;

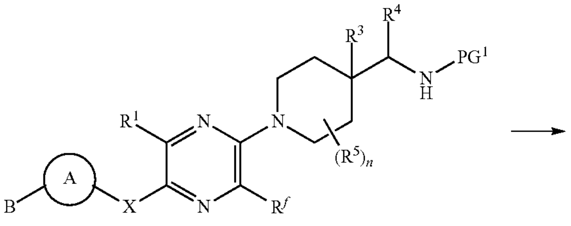

M-2

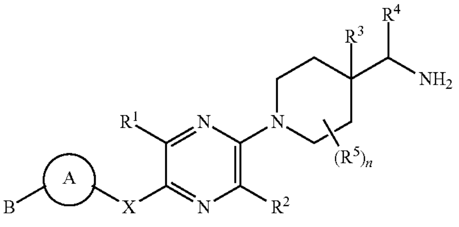

I method 2 comprises the following steps:

(1) reacting the compound of formula S-1 with the compound of formula S-3 to afford the compound of formula M-3; and

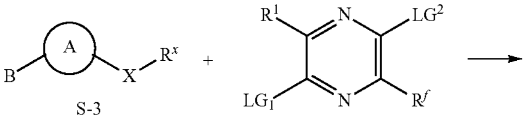

S-3

S-1

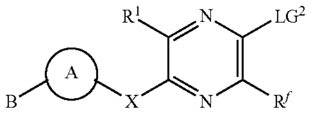

M-3

(2) reacting the compound of formula M-3 with the compound of formula S-2, and then subjecting the resultant to optional deprotection and functional group conversion to afford the compound of formula I;

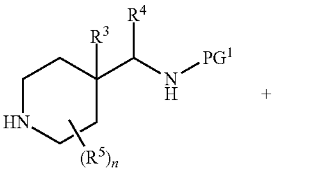

S-2

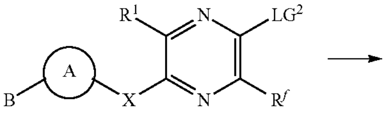

M-3

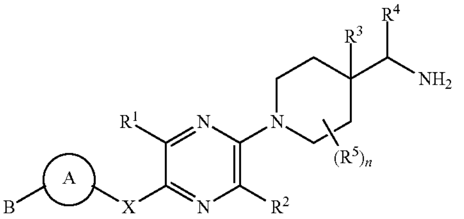

I wherein $LG^1$ and $LG^2$ are each independently a halogen leaving group or a $C_{1-6}$ alkylsulfonate leaving group optionally substituted by a halogen (such as a trifluoromethanesulfonate leaving group); besides, $LG^2$ may also be hydroxyl;

$R^x$ is hydrogen or a leaving group;

$R^f$ is hydrogen, hydroxymethyl, fluoromethyl, or a group converted to hydroxymethyl or fluoromethyl through a one-step or multiple-step reaction;

$PG^1$ is hydrogen or a protective group for amino (such as methyl, tert-butoxycarbonyl, tert-butyldimethylsilyl, triisopropylsilyl, benzyl, or methoxymethyl); and the remaining groups are as defined above.

In some embodiments of the present disclosure, $LG^1$ is a halogen leaving group (such as iodine or bromine).

In some embodiments of the present disclosure, $LG^2$ is a halogen leaving group (such as bromine or chlorine) or hydroxyl.

In some embodiments of the present disclosure, $R^x$ is hydrogen, halogen, a boronic acid group, a borate group, a substituted silyl, a substituted metallic group, or a $C_{1-6}$ alkylsulfonate group optionally substituted by a halogen, preferably a boronic acid group or a borate group.

In some embodiments of the present disclosure, $R^f$ is hydrogen, halogen (such as fluorine, chlorine, bromine, or iodine), fluoromethyl, or an ester group (such as $—C(=O)—OC_2H_5$).

In some embodiments of the present disclosure, the reaction in step (1) above is carried out in the presence of a base. In some preferred embodiments of the present disclosure, the base is an inorganic base, such as potassium phosphate.

In the other embodiments of the present disclosure, the reaction in step (1) above is carried out in the presence of a condensation reagent and a base. In some preferred embodiments of the present disclosure, the base is an organic base, such as DIPEA. In the other preferred embodiments of the present disclosure, the condensation reagent is BOP, HATU, or PyBOP, preferably BOP.

In some embodiments of the present disclosure, the reaction in step (2) above is carried out in the presence of a metal catalyst. In some preferred embodiments of the present disclosure, the metal catalyst is a palladium catalyst or a copper catalyst, such as tetrakis(triphenylphosphine)palladium, palladium acetate, tris(dibenzylideneacetone)dipalladium, [1,1'-bis(diphenylphosphino)ferrocene]dichloropalladium, 1,2-bis(diphenylphosphino)ethane dichloropalladium, and bis(triphenylphosphine)dichloropalladium, or copper iodide.

In some embodiments of the present disclosure, the functional group conversion in step (3) above includes, but is not limited to, the following reactions: 1) a reduction reaction (the reagent used is, e.g., $LiBH_4$ or DIBAL-H); 2) a metal-catalyzed coupling reaction; and 3) a hydrolysis reaction.

In some embodiments of the present disclosure, the deprotection in step (3) above is carried out under conditions of acid hydrolysis or of catalytic hydrogenolysis in the presence of a metal catalyst. In some preferred embodiments of the present disclosure, the acid used for the acid hydrolysis is an organic acid, preferably trifluoroformic acid. In the other preferred embodiments of the present disclosure, the metal catalyst used for the catalytic hydrogenation is palladium on carbon or palladium hydroxide on carbon.

It should be appreciated to those skilled in the art that depending upon the structure of the desired product, one or more steps in the above-mentioned preparation methods may be omitted, or it is also possible to properly adjust the order of the reaction steps as needed and add or omit the protection/deprotection step.

All of the other compounds of the general formulae of the present disclosure may be synthesized by similar methods.

Pharmaceutical Composition

The term "pharmaceutical composition" refers to a composition that can be used as a medication, comprising an active pharmaceutical ingredient (API) (or a therapeutic agent) and one or more optional pharmaceutically acceptable carriers for facilitating administration to an organism and helping absorption of the active ingredient, thereby exerting the bioactivity. The term "pharmaceutically acceptable carrier" refers to an excipient administered together with a therapeutic agent, which is suitable, within the scope of sound medical judgment, for contact with the tissues of human beings and/or other animals without undue toxicity, irritation, allergic response or other problems or complications commensurate with a reasonable benefit/risk ratio. Pharmaceutically acceptable carriers usable in the present disclosure include, but are not limited to, a) diluents; b) lubricants; c) binders; d) disintegrants; e) absorbents, colorants, flavoring agents, and sweetening agents; f) emulsifiers or dispersants; and/or g) reagents that enhance absorption of the compounds.

The present disclosure provides a pharmaceutical composition, comprising at least one compound of formula I, formula IIa, formula IIb, formula IIIa, formula IIIb, formula IVa, formula IVb, formula IVc, formula IVd, formula Va, formula Vb, or formula Vc of the present disclosure, or a pharmaceutically acceptable salt, ester, stereoisomer, tautomer, polymorph, solvate (such as a hydrate), isotope-labelled compound, metabolite, or prodrug thereof.

In some embodiments of the present disclosure, the above-mentioned pharmaceutical composition further comprises one or more pharmaceutically acceptable carriers.

In the other embodiments of the present disclosure, the above-mentioned pharmaceutical composition further comprises one or more additional active pharmaceutical ingredients (e.g., active pharmaceutical ingredients for preventing and/or treating SHP2-associated diseases).

In some preferred embodiments of the present disclosure, the above-mentioned pharmaceutical composition further comprises one or more pharmaceutically acceptable carriers and one or more additional active pharmaceutical ingredients (e.g., active pharmaceutical ingredients for preventing and/or treating SHP2-associated diseases) at the same time.

In some embodiments of the present disclosure, the above-mentioned pharmaceutical compositions may act systemically and/or topically. To this end, they may be administered by suitable routes, e.g., by parenteral, topical, intravenous, oral, subcutaneous, intra-arterial, intradermal, transdermal, rectal, intracranial, intraperitoneal, intranasal, intramuscular, or inhalation route, or by all means known to a person skilled in the art of medicine. The above-mentioned pharmaceutical compositions may be administered in combination with at least one additional therapeutic agent having a therapeutic effect on the disease or condition.

In some embodiments of the present disclosure, the routes of administration described above can be achieved by suitable dosage forms.

In some embodiments of the present disclosure, the above-mentioned pharmaceutical compositions may comprise 0.01 mg to 1000 mg of at least one compound of formula I, formula IIa, formula IIb, formula IIIa, formula IIIb, formula IVa, formula IVb, formula IVc, formula IVd, formula Va, formula Vb, or formula Vc of the present disclosure, or a pharmaceutically acceptable salt, ester, stereoisomer, tautomer, polymorph, solvate (such as a hydrate), isotope-labelled compound, metabolite, or prodrug thereof.

The present disclosure further provides a method for preparing the above-mentioned pharmaceutical composition or the corresponding dosage form thereof, comprising combining at least one compound of formula I, formula IIa, formula IIb, formula IIIa, formula IIIb, formula IVa, formula IVb, formula IVc, formula IVd, formula Va, formula Vb, or formula Vc of the present disclosure, or a pharmaceutically acceptable salt, ester, stereoisomer, tautomer, polymorph, solvate (such as a hydrate), isotope-labelled compound, metabolite, or prodrug thereof, with one or more pharmaceutically acceptable carriers and/or one or more additional active pharmaceutical ingredients (e.g., active pharmaceutical ingredients for preventing and/or treating SHP2-associated diseases).

Drug

The term "drug" refers to a combined product comprising a therapeutic agent, an optional additional therapeutic agent, and an optional packaging and/or instruction.

The term "active pharmaceutical ingredient", "active pharmaceutical substance", "active pharmaceutical agent", or "therapeutic agent" refers to a chemical entity effective in preventing and/or treating a target disease or one or more symptoms thereof.

The present disclosure provides a drug, comprising:

a) a container;

b) at least one compound of formula I, formula IIa, formula IIb, formula IIIa, formula IIIb, formula IVa, formula IVb, formula IVc, formula IVd, formula Va, formula Vb, or formula Vc of the present disclosure, or the pharmaceutically acceptable salt, ester, stereoisomer, tautomer, polymorph, solvate (such as a hydrate), isotope-labelled compound, metabolite, or prodrug thereof, or the pharmaceutical composition held in the container; and c) an optional packaging and/or instruction.

The instruction describes information about the active pharmaceutical ingredient or the pharmaceutical composition in the above-mentioned drug, preferably specifies the approved indications for the active pharmaceutical ingredient or the pharmaceutical composition. The instruction is a printable material (e.g., paper, plastics, metal foil, or adhesive paper) on which desired information can be formed (e.g., printed or coated).

In some embodiments of the present disclosure, the above-mentioned drug may comprise 0.01 mg to 1000 mg of at least one compound of formula I, formula IIa, formula IIb, formula IIIa, formula IIIb, formula IVa, formula IVb, formula IVc, formula IVd, formula Va, formula Vb, or formula Vc of the present disclosure, or the pharmaceutically acceptable salt, ester, stereoisomer, tautomer, polymorph, solvate (such as a hydrate), isotope-labelled compound, metabolite, or prodrug thereof.

The present disclosure further provides a method for preparing the above-mentioned drug, comprising combining at least one compound of formula I, formula IIa, formula IIb, formula IIIa, formula IIIb, formula IVa, formula IVb, formula IVc, formula IVd, formula Va, formula Vb, or formula Vc of the present disclosure, or the pharmaceutically acceptable salt, ester, stereoisomer, tautomer, polymorph, solvate (such as a hydrate), isotope-labelled compound, metabolite, or prodrug thereof, or the pharmaceutical composition with the container and the optional packaging and/or instruction.

Medical Use

The compounds of the present disclosure are capable of exhibiting a strong inhibitory effect on SHP2, and can be used as SHP2 inhibitors. In view of this, the present disclosure provides the compound of formula I, formula IIa, formula IIb, formula IIIa, formula IIIb, formula IVa, formula IVb, formula IVc, formula IVd, formula Va, formula Vb, or formula Vc of the present disclosure, or the pharmaceutically acceptable salt, ester, stereoisomer, tautomer, polymorph, solvate (such as a hydrate), isotope-labelled compound, metabolite, or prodrug thereof, or the pharmaceutical composition, or the drug for use as an SHP2 inhibitor.

Also, the present disclosure further provides use of the compound of formula I, formula IIa, formula IIb, formula IIIa, formula IIIb, formula IVa, formula IVb, formula IVc, formula IVd, formula Va, formula Vb, or formula Vc of the present disclosure, or the pharmaceutically acceptable salt, ester, stereoisomer, tautomer, polymorph, solvate (such as a hydrate), isotope-labelled compound, metabolite, or prodrug thereof, or the pharmaceutical composition, or the drug in the preparation of a medication for preventing and/or treating a disease or condition that is at least partially mediated by SHP2 (or referred to as an SHP2-associated disease, an SHP2 enzyme-associated disease, or an SHP2 phosphatase-associated disease, in particular cancer).

The term "a disease or condition that is at least partially mediated by SHP2 (or an SHP2-associated disease)" refers to a disease whose pathogenesis involves at least a part of SHP2-related factors, in particular a disease sensitive or responsive to inhibition of SHP2 phosphatase. These diseases include, but are not limited to, tumor diseases.

In some embodiments of the present disclosure, the tumor disorders described above include, but are not limited to, breast cancer, colorectal cancer, colon cancer, lung cancer (including small cell lung cancer, non-small cell lung cancer, and bronchioloalveolar cancer), prostate cancer, bile duct cancer, bone cancer, bladder cancer, head and neck cancer, kidney cancer, liver cancer, gastrointestinal tissue cancer, esophagus cancer, ovarian cancer, pancreatic cancer, skin cancer, testicular cancer, thyroid cancer, uterine cancer, cervical cancer, vulvar cancer, multiple myeloma, lymphoma, and leukemia, such as chronic lymphocytic leukemia (CLL), acute lymphocytic leukemia (ALL), and chronic myelogenous leukemia (CML).

Treatment Method

The present disclosure provides a method for preventing and/or treating a disease that is at least partially mediated by SHP2 (in particular cancer), comprising the following step of administering to a subject in need thereof a prophylactically and/or therapeutically effective amount of at least one compound of formula I, formula IIa, formula IIb, formula IIIa, formula IIIb, formula IVa, formula IVb, formula IVc, formula IVd, formula Va, formula Vb, or formula Vc of the present disclosure, or the pharmaceutically acceptable salt, ester, stereoisomer, tautomer, polymorph, solvate (such as a hydrate), isotope-labelled compound, metabolite, or prodrug thereof, or the pharmaceutical composition, or the drug.

The term "effective amount" refers to a dose that can induce a biological or medical response in a cell, tissue, organ, or organism (e.g., a subject) and is sufficient to achieve the desired prophylactic and/or therapeutic effect. The dosage regimen may be adjusted to provide an optimal response. For example, a single dose may be administered, divided doses may be administered over time, or the dose may be administered after it is proportionally reduced or increased as appropriate. It should be appreciated that for any specific subject, the specific dosage regimen should be adjusted according to the needs and the professional judgment of the administering practitioner. In addition, it is also necessary to distinguish whether the application is prophylactic or therapeutic. In prophylactic applications, a relatively low dose is typically administered chronically at a relatively long interval. In therapeutic applications, a relatively high dose is typically administered at a relatively short interval until progression of the disease is delayed or halted, preferably until the subject shows partial or complete amelioration of symptoms.

In the present disclosure, suitable in vitro or in vivo assays are carried out to determine the effects of the compounds, pharmaceutical compositions and/or drugs and determine whether the administration is appropriate for the treatment of a disease or condition suffered by the subject. Examples of such assays will be described in the non-limiting examples below. Generally, an effective amount of a compound sufficient to achieve a prophylactic and/or therapeutic effect is from about 0.001 mg/kg body weight per day to about 10,000 mg/kg body weight per day.

The term "prevention" encompasses suppression and delay of the onset of a disease, and includes not only the prevention prior to the development of the disease, but also the prevention of the recurrence of the disease after treatment.

The term "treatment" refers to reversion, alleviation, or elimination of a target disease or condition. If a testee receives a therapeutic dose of the compound of the present disclosure or a pharmaceutically acceptable form thereof or the pharmaceutical composition of the present disclosure and at least one index or symptom of the testee shows observable and/or detectable alleviation and/or amelioration, this indicates that the testee has been successfully "treated". It is to be appreciated that the treatment includes not only complete treatment but also achievement of some biologically or medically relevant outcomes while not yet completing treatment. Specifically, "treatment" means that the compound of the present disclosure or a pharmaceutically acceptable form thereof or the pharmaceutical composition of the present disclosure can achieve at least one of the following effects: (1) suppression of diseases (i.e., prevention of further development in pathology and/or symptomatology) in animals that are experiencing or showing pathological or symptomatological features of the diseases; and (2) amelioration of diseases (i.e., disease reversion in pathology and/or symptomatology) in animals that are experiencing or showing pathological or symptomatological features of the diseases.

The term "administration" refers to a process of applying an active pharmaceutical ingredient (e.g., the compound of the present disclosure) or a pharmaceutical composition comprising the active pharmaceutical ingredient (e.g., the pharmaceutical composition of the present disclosure) to a subject or the part thereof such as cells, tissues, organs, or biological fluids, so as to bring the active pharmaceutical ingredient or the pharmaceutical composition into contact with the subject or the part thereof such as cells, tissues, organs, or biological fluids.

The term "in need thereof" refers to a judgment made by a doctor or other paramedics on a subject who needs to or will benefit from the course of prevention and/or treatment, and the judgment is made based on various factors in the doctor or other paramedics' areas of expertise.

The term "subject" (or referred to as testee) refers to human beings or non-human animals. The subject of the present disclosure includes a subject (patient) with a disease and/or a condition and a normal subject. The non-human animals of the present disclosure include all vertebrates, e.g., non-mammals such as birds, amphibians, and reptiles, and mammals, e.g., non-human primates, livestock, and/or domesticated animals (such as sheep, dogs, cats, cows, and pigs).

The present disclosure further provides a combined method for preventing and/or treating a disease or condition that is at least partially mediated by SHP2 (in particular cancer), comprising: a) the method for preventing and/or treating a disease or condition that is at least partially mediated by SHP2 (in particular cancer) of the present disclosure; and b) an additional therapy.

In some embodiments of the present disclosure, the additional therapy in the combined method described above includes, but is not limited to, radiotherapy, chemotherapy, immunotherapy, or any combination thereof. The compound, pharmaceutical composition, or drug of the present disclosure may be administered before, during, or after the administration of the additional therapy. The performance of the additional therapy and the administration of the compound, pharmaceutical composition, or drug of the present disclosure may be carried out concurrently, or may be carried out one after another, or may be carried out at intervals, and the manner and sequence of administration may be selected and adapted to the specific situations of treatment.

In order to render the objective and technical solution of the present disclosure clearer, the embodiments of the present disclosure will be described in detail below with reference to the examples. Those skilled in the art will appreciate, however, that the following examples are intended only to illustrate the present disclosure, and should not be considered to limit the scope of the present disclosure.

The reagents or instruments used in the examples, where the manufacturers are not specified, are all commercially-available conventional products. Where no specific conditions are specified, conventional conditions or those recommended by the manufacturers are followed. The term "room temperature" used herein refers to 20° C.±5° C. When used to modify a value or a numerical range, the term "about" used herein is meant to include this value or numerical range and an error range of this value or numerical range acceptable to those skilled in the art, for example, the error range is ±10%, ±5%, ±4%, ±3%, ±2%, +1%, ±0.5%, etc. Unless otherwise stated, concentrations are determined on a weight basis and ratios (including percentages) are determined on a molar basis.

In the conventional synthesis methods as well as the examples and intermediate synthesis examples, the abbreviations have the meanings as shown in the table below.

| Abbrev. | Meaning | Abbrev. | Meaning |
|---|---|---|---|
| AcOH/HAc | Acetic acid | $LiBH_4$ | Lithium borohydride |
| DIPEA | Diisopropylethylamine | LC-MS | Liquid chromatography mass spectrometry |
| Prep-HPLC | Preparative high-performance liquid chromatography | TLC | Thin layer chromatography |
| Xantphos | 4,5-Bis(diphenylphosphino)-9,9-dimethylxanthene | NMP | N-Methylpyrrolidone |
| DMF | N,N-D imethylformamide | EtOH | Ethanol |
| dioxane/Diox | 1,4-Dioxane | MeOH | Methanol |
| DIBAL-H | Diisobutyl aluminium hydride | Raney Ni | Raney nickel |
| $H_2O$ | Water | $K_3PO_4$ | Potassium phosphate |
| HPLC | High-performance liquid chromatography | NaOH | Sodium hydroxide |
| NaH | Sodium hydride | $Na_2CO_3$ | Sodium carbonate |
| TMSCN | Trimethylsilyl cyanide | $CH_3SNa$ | Sodium thiomethoxide |
| BOP | (Benzotriazol-1-yloxy)tris(dimethylamino)phosphonium hexafluorophosphate (Castro's reagent) | $PdCl_2(PPh_3)_2$ | Bis(triphenylphosphine)dichloro palladium |
| HATU | O-(7-Azabenzotriazol-1-yl)-N,N,N',N'-tetramethyluronium hexafluorophosphate | PyBOP | (1H-Benzotriazol-1-yloxy)tris(pyrrolidin-1-yl)phosphonium hexafluorophosphate |
| LiHMDS | Lithium bis(trimethylsilyl)amide | Pd/C | Palladium on carbon |
| LDA | Lithium diisopropylamide | THF | Tetrahydrofuran |
| MsCl | Methanesulfonyl chloride | toluene/Tol | Toluene |
| $K_2CO_3$ | Potassium carbonate | TFA | Trifluoroacetic acid |
| $Boc_2O$ | Di-tert butyl dicarbonate | TEA | Triethylamine |
| CuI | Cuprous iodide | TFAA | Trifluoroacetic anhydride |

-continued

| Abbrev. | Meaning | Abbrev. | Meaning |
|---|---|---|---|
| MeCN/ACN | Acetonitrile | DCM | Dichloromethane |
| $Pd_2(dba)_3$ | Tris(dibenzylideneacetone)dipalladium | rt/r.t. | Room temperature |
| $PdCl_2(dppf)$• $CH_2Cl_2$ | [1,1'-Bis(diphenylphosphino)ferrocene] dichloropalladium-dichloromethane complex | $NaBH_4$ | Sodium borohydride |
| m-CPBA | m-Chloroperbenzoic acid | NaHMDS | Sodium bis(trimethylsilyl)amide |
| DAST | Diethylaminosulphur trifluoride | n-BuLi | n-Butyllithium |
| $NaN_3$ | Sodium azide | EtONa | Sodium ethoxide |
| NBS | N-Bromosuccinimide | | |

The structures of the compounds described in the examples below are determined by nuclear magnetic resonance ($^1$H-NMR) and/or mass spectrometry (MS).

The measuring instrument for the nuclear magnetic resonance ($^1$H-NMR) is a Bruker 400 MHz nuclear magnetic resonance instrument. Solvents for assay are deuterated methanol ($CD_3OD$), deuterated chloroform ($CDCl_3$), dimethyl sulfoxide-d6 (DMSO-$d_6$), or deuterated water ($D_2O$). The internal standard is tetramethylsilane (TMS).

The abbreviations used for the nuclear magnetic resonance (NMR) data in the following examples have meanings as follows:

s: singlet, d: doublet, t: triplet, q: quartet, dd: double doublet, qd: quartet doublet, ddd: double double doublet, ddt: double double triplet, dddd: double double double doublet, m: multiplet, br: broad, J: coupling constant, Hz: Hertz, δ: chemical shift.

All chemical shift (δ) values are given in parts per million (ppm).

Reactions are monitored using thin layer chromatography or liquid chromatography-mass spectrometry. The mobile phase system includes, but is not limited to, a dichloromethane-methanol system, an n-hexane-ethyl acetate system, and a petroleum ether-ethyl acetate system. The volume ratio of solvents may be adjusted depending on the chemical polarity of the compounds, or adjusted by adding a small amount of triethylamine or the like.

The thin layer chromatography uses GF 254 silica gel plates (0.4 nm to 0.5 nm, Yantai Jiangyou Silica Gel Development Co., Ltd.).

The measuring instrument for the preparative high-performance liquid chromatography is a Shimadzu LC-8A preparative liquid chromatograph (YMC, ODS, 250×20 mm×5 μm C18 chromatographic column).

The measuring instrument for mass spectrometry is an Agilent 6120B mass spectrometer with an ion source being an electrospray ion (ESI) source.

Column chromatography uses 200 to 300-mesh silica gel (Qingdao Haiyang Chemical Co., Ltd.) as a stationary phase. The mobile phase system includes, but is not limited to, a dichloromethane-methanol system and an n-hexane-ethyl acetate system. The volume ratio of solvents may be adjusted depending on the chemical polarity of the compounds, or adjusted by adding a small amount of trimethylamine or the like.

Unless otherwise specified, the reaction temperatures involved in the following examples are room temperature (20° C. to 30° C.).

Unless otherwise specified, the reagents used in the following examples are purchased from Acros Organics, Aldrich Chemical, PharmaBlock Sciences (Nanjing), Inc., Shanghai Shuya Pharmaceutical Technology Co., Ltd., etc.

Intermediate Preparation Example 1: Preparation of ethyl 6-bromo-3-((3S,4S)-4-(tert-butoxycarbonylamino)-3-methyl-2-oxa-8-azaspiro[4.5]decan-8-yl)-5-methylpyrazine-2-carboxylate (Compound IM-1) and tert-butyl (3S,4S)-8-(5-bromo-3-(hydroxymethyl)-6-methylpyrazin-2-yl)-3-methyl-2-oxa-8-azaspiro[4.5]decan-4-ylcarbamate (Compound IM-7)

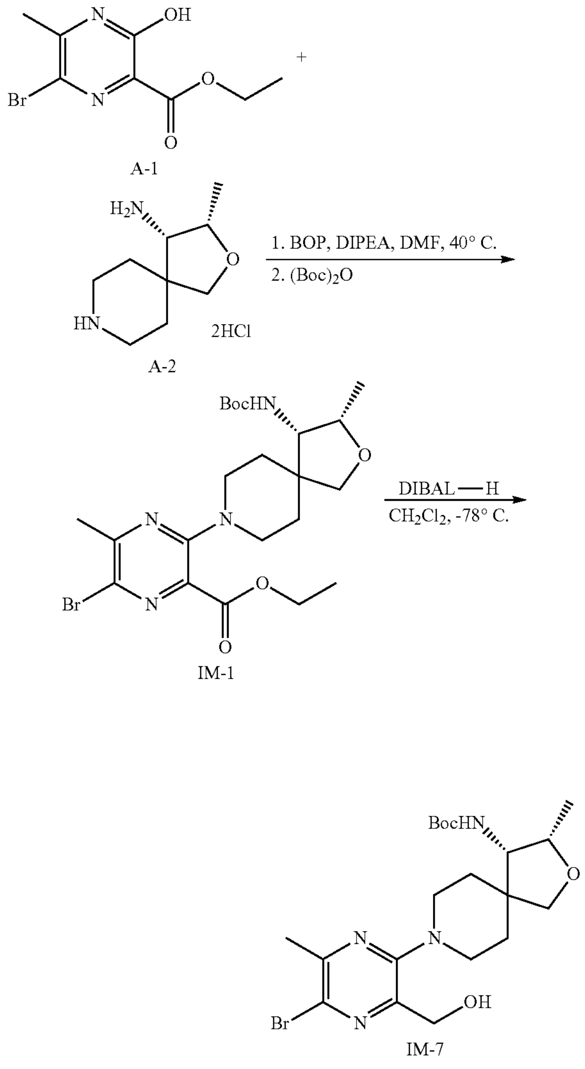

A-1 + A-2 → IM-1 → IM-7

Step 1: Preparation of ethyl 6-bromo-3-((3S,4S)-4-(tert-butoxycarbonylamino)-3-methyl-2-oxa-8-azaspiro[4.5]decan-8-yl)-5-methylpyrazine-2-carboxylate (Compound IM-1)

Compound A-1 (200 mg, 766.07 μmol), DMF (4 mL), Compound A-2 (195.60 mg, 804.37 μmol), BOP (312.74 mg, 1.53 mmol), and DIPEA (594.04 mg, 4.60 mmol) were mixed, and then warmed to 40° C. and reacted for 2 hours. After the reaction was complete, di-tert-butyl dicarbonate (250.79 mg, 1.15 mmol) was added, and the reaction was continued for 2 hours. The resultant was partitioned between water and ethyl acetate. The organic phase was washed with saturated saline, dried over anhydrous sodium sulfate, and concentrated to afford a crude product. The crude product was purified by thin layer chromatography to afford Compound IM-1 (290 mg, yield 73%).

Step 2: Preparation of tert-butyl (3S,4S)-8-(5-bromo-3-(hydroxymethyl)-6-methylpyrazin-2-yl)-3-methyl-2-oxa-8-azaspiro[4.5]decan-4-ylcarbamate (Compound IM-7)

Compound IM-1 (5.7 g, 11.74 mmol) was dissolved in $CH_2Cl_2$ (100 mL), and cooled to −78° C. DIBAL-H (35.23 mL, 35.23 mmol) was slowly added, and slowly warmed to 0° C. and reacted for 10 minutes. After the reaction was complete, the resultant was cooled to −78° C. A saturated aqueous solution of potassium sodium tartrate (200 mL) was added. After the reaction solution was warmed to room temperature and stirred for 2 hours, the resultant was subjected to liquid-liquid separation, and extracted with $CH_2Cl_2$. The combined organic phase was dried and concentrated to afford a crude product. The crude product was purified by silica gel column chromatography to afford Compound IM-7 (2.16 g, yield 39%).

Intermediate Preparation Example 2: Preparation of methyl (S)-6-bromo-3-(1-(tert-butoxycarbonylamino)-1,3-dihydrospiro[indene-2,4'-piperidin]-1'-yl)pyrazine-2-carboxylate (Compound IM-2)

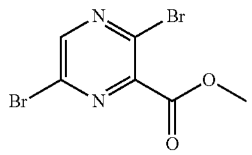

2-1

+

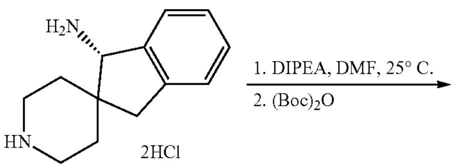

2HCl

A-3

-continued

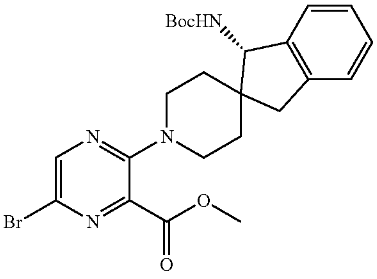

IM-2

Compound 2-1 (300 mg, 1.01 mmol) was added into NMP (5 mL), to which DIPEA (786.14 mg, 6.08 mmol) was then added, followed by adding Compound A-3 (215.34 mg, 1.06 mmol) in batches. The mixture was reacted at 25° C. for 6 hours. Thereafter, di-tert-butyl dicarbonate (442.52 mg, 2.03 mmol) was added and reacted at 40° C. for 2 hours. After the reaction was complete, water (15 mL) was added, and then the resultant was extracted with ethyl acetate. The organic phase was concentrated to afford a crude product. The crude product was purified by column chromatography to afford Compound IM-2 (310 mg, yield 56%).

Fragment Preparation Example 1: Preparation of 2-fluoro-1-(4-methylpiperidin-4-yl)ethylamine (Compound A-4)

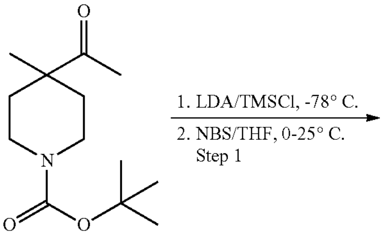

B1-1

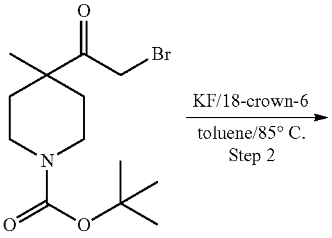

B1-2

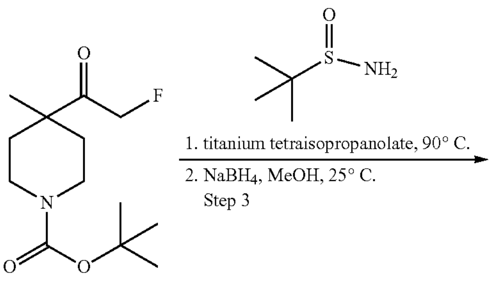

B1-3

-continued

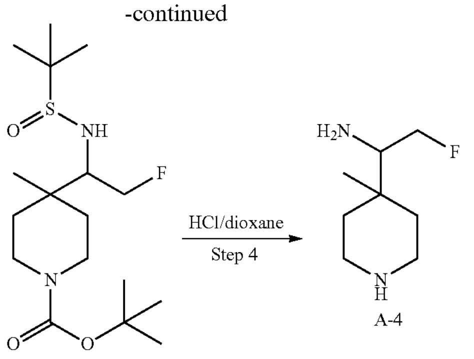

B1-4

A-4

Step 1: Preparation of tert-butyl 4-(2-bromoacetyl)-4-methylpiperidine-1-carboxylate (Compound B1-2)

Under the protection of nitrogen gas, Compound B1-1 (5.00 g, 20.72 mmol) was added into THF (50 mL) and cooled to −78° C., and LDA (2 M solution in tetrahydrofuran, 34.19 mL) was added dropwise. After the dropwise addition was complete, the reactants were stirred at the same temperature for 10 minutes. Thereafter, TMSCl (7.43 g, 68.37 mmol) was added dropwise into the system while controlling the temperature at −78° C. After the dropwise addition was complete, the reactants were stirred for 1 hour. The reaction solution was poured into a saturated aqueous solution of sodium bicarbonate and extracted twice with methyl tert-butyl ether. The combined organic phases was washed with saturated saline, dried over anhydrous sodium sulfate, and filtered. The filtrate was concentrated to dryness to afford an oily product. The oily product was dissolved into THF (25 mL), added with sodium carbonate (4.39 g, 41.44 mmol), and cooled to 0° C. NBS (4.06 g, 22.79 mmol) was added in batches, and then the reactants were warmed to 25° C. and reacted for 4 hours. After the reaction was complete, the reaction solution was subjected to liquid-liquid separation by adding methyl tert-butyl ether and a 10% aqueous solution of sodium carbonate and stirring. The organic phase was washed once with saline, dried over anhydrous sodium sulfate, and filtered. The filtrate was concentrated and then purified by column chromatography to afford Compound B1-2 (6.60 g, yield 99%).

Step 2: Preparation of tert-butyl 4-(2-fluoroacetyl)-4-methylpiperidine-1-carboxylate (Compound B1-3)

Compound B1-2 (6.60 g, 20.61 mmol), 18-crown-6 (6.86 g, 25.97 mmol), and anhydrous potassium fluoride (3.23 g, 55.65 mmol) were added into toluene (100 mL), warmed to 85° C., and reacted for 6 hours. After the reaction was complete, the resultant was cooled to room temperature. Water was added into the system to separate the organic phase. The organic phase was washed with saline, dried over anhydrous sodium sulfate, and filtered. The filtrate was concentrated to dryness to afford a crude product of Compound B1-3 (4.68 g). The crude product was used directly in the next reaction step without purification.

Step 3: Preparation of tert-butyl 4-(1-(tert-butylsulfinamido)-2-fluoroethyl)-4-methylpiperidine-1-carboxylate (Compound B1-4)

Compound B1-3 (4.68 g, 16.24 mmol) was dissolved into titanium tetraisopropanolate (50 mL), and tert-butylsulfinamide (2.95 g, 24.36 mmol) was added thereto. After purged with nitrogen gas, the system was warmed to 90° C. and reacted for 5 hours. After cooling to room temperature, a saturated solution of sodium chloride was added, and the resultant was extracted with ethyl acetate. The combined organic phase was dried, and then concentrated under reduced pressure. The residue was dissolved in methanol (50 mL), and sodium borohydride (1.69 g, 44.67 mmol) was slowly added under the condition of ice bath. The reactants were warmed to 25° C., and reacted for 2 hours. After the reaction was complete, the resultant was cooled to 0° C., quenched by adding saturated ammonium chloride, and extracted with ethyl acetate. The combined organic phase was dried, concentrated under reduced pressure, and then purified by column chromatography to afford Compound B1-4 (4.85 g, yield 80%).

Step 4: Preparation of 2-fluoro-1-(4-methylpiperidin-4-yl)ethylamine (Compound A-4)

Compound B1-4 (0.30 g, 0.82 mmol) was dissolved in a solution of hydrochloric acid in dioxane (4 M, 3 mL), and reacted at 25° C. for 2 hours. The resultant was concentrated to afford a hydrochloride salt of crude Compound A-4 (0.19 g), which was used directly in the next reaction step without purification.

Fragment Preparation Example 2: Preparation of 2-methoxy-1-(4-methylpiperidin-4-yl)ethylamine (Compound A-5)

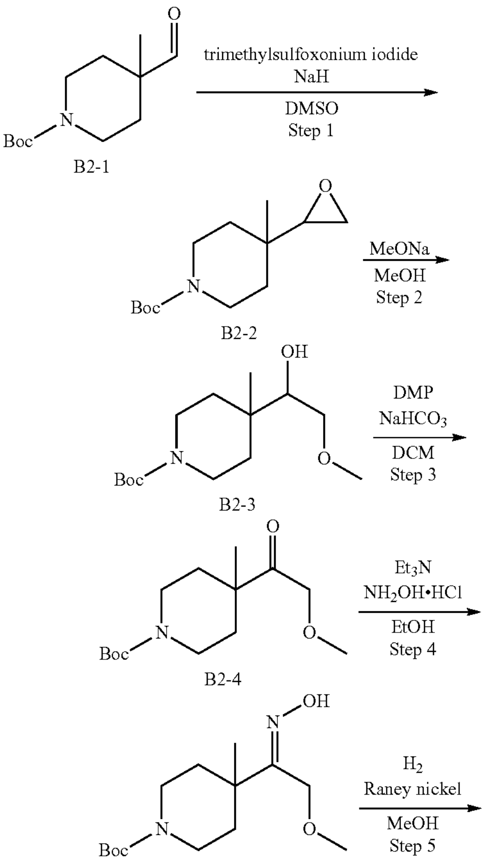

B2-1

B2-2

B2-3

B2-4

B2-5

-continued

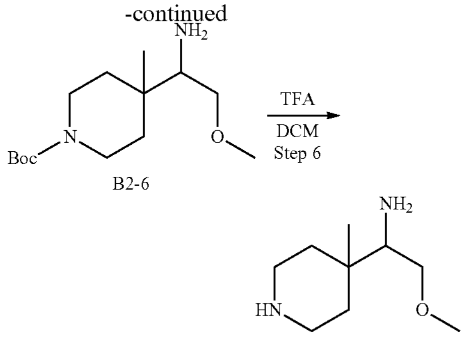

B2-6

A-5

Step 1: Preparation of tert-butyl 4-methyl-4-(oxiran-2-yl)piperidine-1-carboxylate (Compound B2-2)

Under the protection of nitrogen gas, trimethylsulfoxonium iodide (12.20 g, 55.4 mmol) was added to DMSO (50 mL), and cooled to 0° C. in an ice water bath. NaH (1.27 g, 55.4 mmol) was added in batches, and then the reactants were held at 10° C. to 20° C., and reacted for 0.5 hours. Tert-butyl 4-formyl-4-methylpiperidine-1-carboxylate (7.00 g, 30.8 mmol) was added at one time, and then the reactants were held at 10° C. to 20° C., and reacted for 4 hours. The resultant was cooled to 0° C. in an ice water bath. Water (150 ml) and ethyl acetate (200 ml) were added in sequence and stirred for 10 minutes to separate the organic phase. The organic phase was washed with saturated saline, dried over anhydrous sodium sulfate, and filtered. The filtrate was concentrated to dryness to afford a crude product of Compound B2-2 (5.37 g, crude product yield 72%). The crude product was used directly for the next step without further purification.

Step 2: Preparation of tert-butyl 4-(1-hydroxy-2-methoxyethyl)-4-methylpiperidine-1-carboxylate (Compound B2-3)

Compound B2-2 (1.40 g, 5.80 mmol) was dissolved in MeOH (60 mL), and NaOMe (10.44 g, 58.0 mmol, 30% solution in MeOH) was added and then stirred at 40° C. for 5 h. LCMS showed that the raw materials basically disappeared. The resultant was cooled to room temperature, quenched by adding 1N HCl, and extracted with ethyl acetate. The combined organic phase was dried over anhydrous sodium sulfate, subjected to suction filtration, and concentrated to afford a crude product of Compound B2-3 (1.4 g, crude product yield 88%). The crude product was used directly for the next step without further purification.

Step 3: Preparation of tert-butyl 4-(2-methoxyacetyl)-4-methylpiperidine-1-carboxylate (Compound B2-4)

Compound B2-3 (300 mg, 1.10 mmol) was dissolved in DCM (20 mL), and sodium bicarbonate (277 mg, 3.30 mmol) and Dess-Martin reagent (710 mg, 1.65 mmol) were added, and then the reactants were stirred at room temperature for 5 h. LCMS showed that the raw materials basically disappeared. The resultant was cooled to room temperature, quenched by adding a saturated sodium sulfite solution, and extracted with dichloromethane. The combined organic phase was dried over anhydrous sodium sulfate, subjected to suction filtration, and concentrated to afford a crude product of Compound B2-4 (250 mg, crude product yield 84%). The crude product was used directly for the next step without further purification.

Step 4: Preparation of tert-butyl (Z)-4-(1-(oximido)-2-methoxyethyl)-4-methylpiperidine-1-carboxylate (Compound B2-5)

Compound B2-4 (230 mg, 0.85 mmol) was dissolved in EtOH (10 mL), and hydroxylamine hydrochloride (118 mg, 1.70 mmol) and triethylamine (257 mg, 2.54 mmol) were added, and then the reactants were stirred at 60° C. for 2 h. LCMS showed that the raw materials basically disappeared. The resultant was cooled to room temperature, diluted with ethyl acetate, and washed with a 1N hydrochloric acid solution. The combined organic phase was dried over anhydrous sodium sulfate, subjected to suction filtration, and concentrated to afford a crude product of Compound B2-5 (230 mg, crude product yield 95%). The crude product was used directly for the next step without further purification.

Step 5: Preparation of tert-butyl 4-(1-amino-2-methoxyethyl)-4-methylpiperidine-1-carboxylate (Compound B2-6)

Compound B2-5 (230 mg, 0.85 mmol) was dissolved in MeOH (10 mL), and Raney nickel (94 mg, 1.61 mmol) was added. After purged three times with hydrogen gas in a balloon, the reactants were stirred at room temperature for 10 hours. LCMS showed that the raw materials basically disappeared. The resultant was subjected to suction filtration through diatomite, and concentrated to afford a crude product of Compound B2-6 (200 mg, crude product yield 91%). The crude product was used directly for the next step without further purification.

Step 6: Preparation of 2-methoxy-1-(4-methylpiperidin-4-yl)ethylamine (Compound A-5)

Compound B2-6 (200 mg, 0.73 mmol) was dissolved in DCM (10 mL), and trifluoroacetic acid (3 mL) was added and stirred at room temperature for 1 hour. LCMS showed that the raw materials basically disappeared. The resultant was concentrated to afford a trifluoroacetate salt of crude Compound A-5 (200 mg, crude product yield 95%), which was used directly for the next step without further purification.

With reference to the method described in Intermediate Preparation Example 2, appropriate starting materials were used to synthesize intermediate compounds IM-3, IM-4, IM-5, IM-6, IM-8, IM-9, IM-10, IM-11, IM-12, IM-13, and IM-14. With reference to the method described in Intermediate Preparation Example 1, appropriate starting materials were used to synthesize intermediate compound IM-15.

IM-3

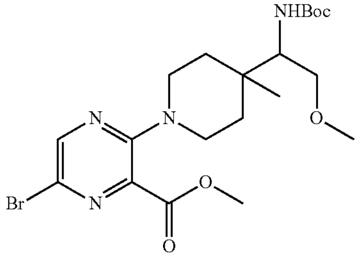

IM-4
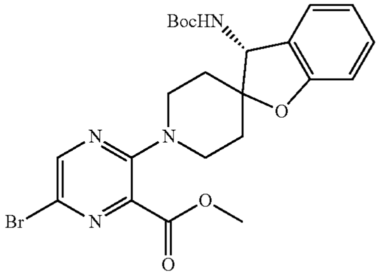
IM-5
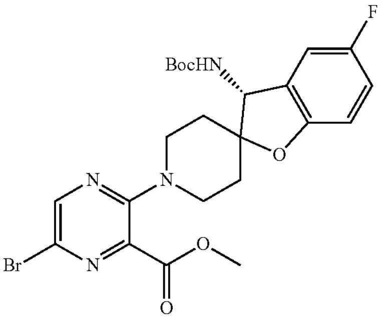
IM-6
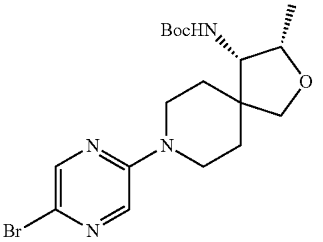
IM-8
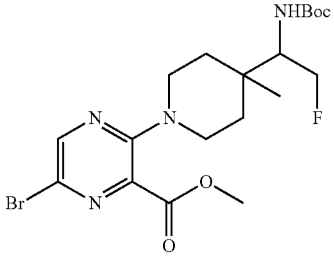
IM-9
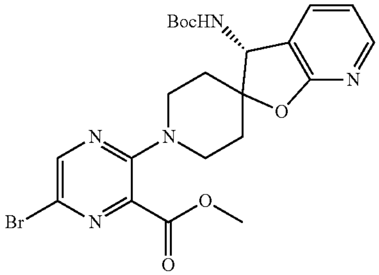
IM-10
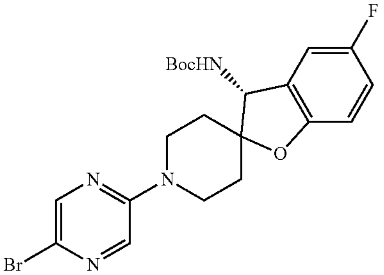
IM-11
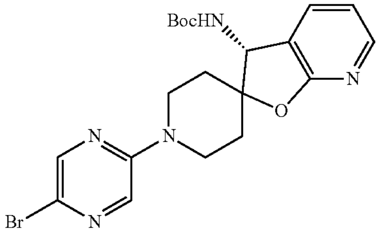
IM-12
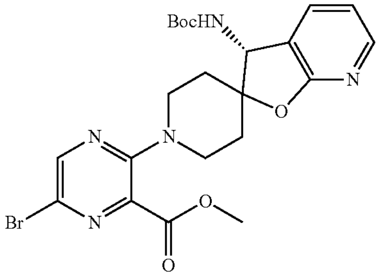
IM-13
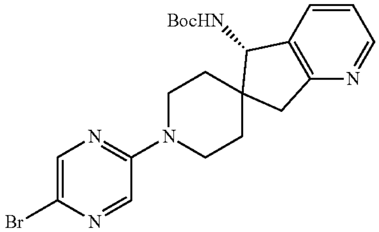
IM-14
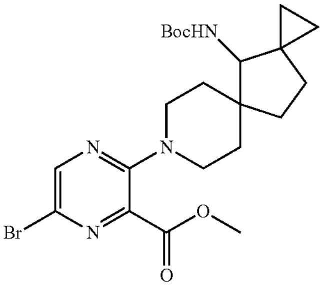
IM-15
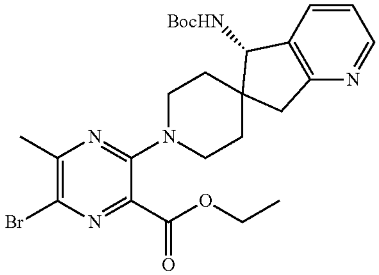

Example 1: Preparation of (3-((3S,4S)-4-amino-3-methyl-2-oxo-8-azaspiro[4.5]decan-8-yl)-6-(3-chloro-2-(2-hydroxymethyl)pyrrolidin-1-yl)pyridin-4-ylthio)-5-methylpyrazin-2-yl)methanol (Compound 1)

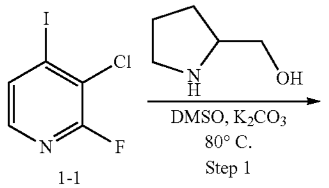

1-1

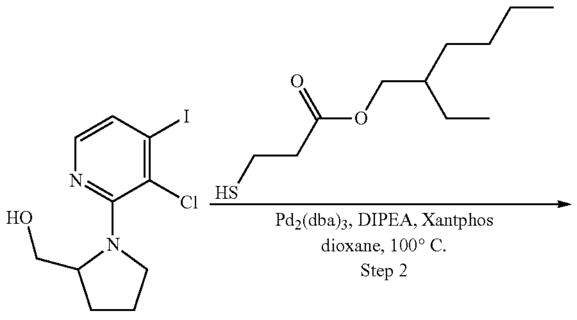

1-2

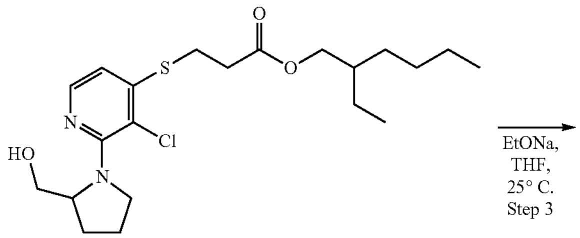

1-3

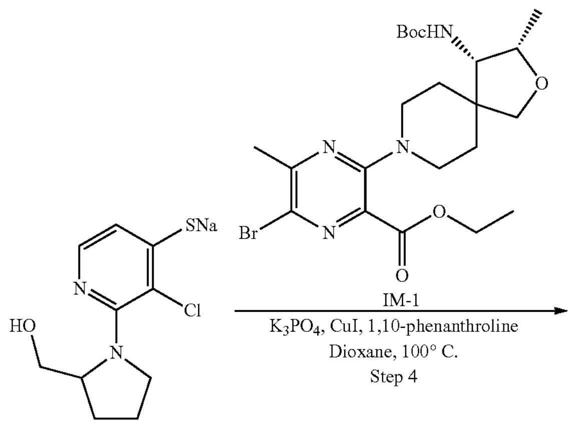

1-4

-continued

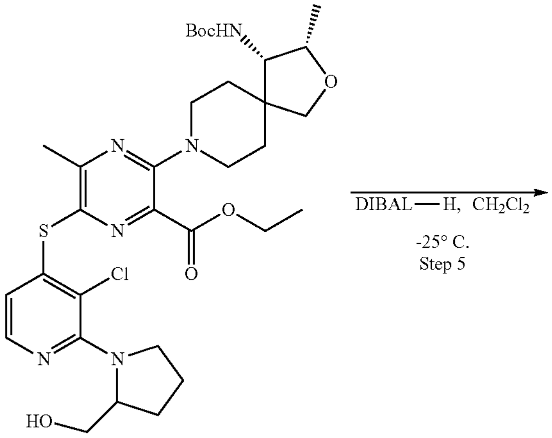

1-5

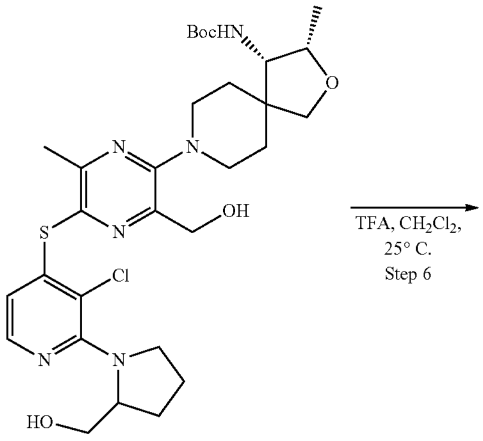

1-6

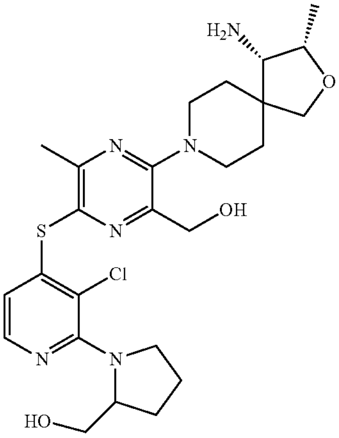

1

Step 1: Preparation of (1-(3-chloro-4-iodopyridin-2-yl)pyrrolidin-2-yl)methanol (Compound 1-2)

Compound 1-1 (1.00 g, 3.88 mmol), DMSO (12 mL), pyrrolidin-2-ylmethanol (432.20 mg, 4.28 mmol), and $K_2CO_3$ (1.61 g, 11.65 mmol) were mixed, then warmed to 80° C., and reacted for 4 hours. The resultant was cooled to room temperature, and partitioned between water and ethyl acetate. The organic phase was washed with saturated saline, dried over anhydrous sodium sulfate, and concentrated to afford a crude product of Compound 1-2 (1.29 g, yield 98%). The crude product was used directly in the next reaction step without purification.

Step 2: Preparation of 2-ethylhexyl 3-(3-chloro-2-(2-hydroxymethyl)pyrrolidin-1-yl)pyridin-4-ylthio) propanoate (Compound 1-3)

Compound 1-2 (0.50 g, 1.48 mmol), 2-ethylhexyl 3-mercaptopropanoate (370.83 mg, 1.70 mmol), DIPEA (381.72 mg, 2.95 mmol), Xantphos (85.45 mg, 147.68 μmol), and $Pd_2(dba)_3$ (67.62 mg, 73.84 μmol) were added into 1,4-dioxane (5 mL), evacuated, and purged three times with nitrogen gas. Thereafter, the reactants were warmed to 100° C. and reacted for 4 hours. The resultant was cooled to room temperature, and filtered to remove the solid. The filtrate was concentrated, and partitioned between water and ethyl acetate. The organic phase was washed with saturated saline, dried over anhydrous sodium sulfate, and concentrated to afford a crude product of Compound 1-3 (632.00 mg, yield 99%). The crude product was used directly in the next reaction step without purification.

Step 3: Preparation of sodium 3-chloro-2-(2-(hydroxymethyl)pyrrolidin-1-yl)pyridine-4-thiophenate (Compound 1-4)

Sodium ethoxide (20% solution in ethanol, 0.35 mL) was added into a solution of Compound 1-3 (300 mg, 559.42 μmol) in THF (5 mL), and reacted at 25° C. for 1 hour. The resultant was concentrated to remove most of the solvent therefrom. Dichloromethane (5 mL) was added, stirred for 10 minutes, and filtered. The filter cake was dried to afford a crude product of Compound 1-4 (149.77 mg, yield 100%). The crude product was used directly in the next reaction step without purification.

Step 4: Preparation of ethyl 3-((3S,4S)-4-(tert-butoxycarbonylamino)-3-methyl-2-oxa-8-azaspiro[4.5] decan-8-yl)-6-(3-chloro-2-(2-(hydroxymethyl)pyrrolidin-1-yl)pyridin-4-ylthio)-5-methylpyrazine-2-carboxylate (Compound 1-5)

Compound IM-1 (100.0 mg, 194.77 μmol), Compound 1-4 (143.40 mg, 428.50 μmol), CuI (37.09 mg, 194.77 μmol), 1,10-phenanthroline (35.10 mg, 194.77 μmol), and $K_3PO_4$ (124.03 mg, 584.31 μmol) were added into 1,4-dioxane (5 mL), warmed to 100° C. in a microwave reactor, and reacted for 1.5 hours. The resultant was cooled to room temperature, and filtered to remove the insoluble. The filtrate was concentrated to afford a crude product. The crude product was purified by thin layer chromatography to afford Compound 1-5 (65.00 mg, yield 49.28%).

Step 5: Preparation of tert-butyl (3S,4S)-8-(5-(3-chloro-2-(2-hydroxymethyl)pyrrolidin-1-yl)pyridin-4-ylthio)-3-(hydroxymethyl)-6-methylpyrazin-2-yl)-3-methyl-2-oxa-8-azaspiro[4.5]decan-4-ylcarbamate (Compound 1-6)

Compound 1-5 (65 mg, 95.98 μmol) was dissolved into dichloromethane (2 mL). At −25° C., DIBAL-H (1 M solution in hexane, 0.67 mL) was slowly added and reacted for 1 hour while the temperature was maintained. After the reaction was complete, dichloromethane (10 mL) and a saturated aqueous solution of potassium sodium tartrate (5 mL) were added into the reaction solution and stirred for 2 hours. The resultant was extracted. The organic phase was dried over anhydrous sodium sulfate and filtered. The filtrate was concentrated to afford a crude product. The crude product was purified by thin layer chromatography to afford Compound 1-6 (42 mg, yield 68.89%).

Step 6: Preparation of a trifluoroacetate salt of (3-((3S,4S)-4-amino-3-methyl-2-oxo-8-azaspiro[4.5] decan-8-yl)-6-(3-chloro-2-(2-(hydroxymethyl)pyrrolidin-1-yl)pyridin-4-ylthio)-5-methylpyrazin-2-yl) methanol (Compound 1)

Compound 1-6 (42 mg, 66.12 μmol) was dissolved into a mixture of dichloromethane (1 mL) and TFA (150.78 mg, 1.32 mmol) and reacted at 25° C. for 1 hour. The resultant was concentrated to remove the solvent therefrom, thereby obtaining a crude product. The crude product was purified by HPLC (mobile phase A: acetonitrile, mobile phase B: 0.05% aqueous solution of trifluoroacetic acid) to afford a trifluoroacetate salt of Compound 1 (27.10 mg, yield 61%).

MS (ESI): m/z 535.0 $[M+H]^+$.

$^1$H-NMR (400 MHz, DMSO-$d_6$): δ 7.92 (s, 3H), 7.80 (d, J=5.2 Hz, 1H), 5.90 (d, J=5.2 Hz, 1H), 4.48 (s, 2H), 4.43-4.40 (m, 1H), 4.23-4.19 (m, 1H), 3.92 (m, 1H), 3.82 (m, 2H), 3.70 (d, J=8.8 Hz, 1H), 3.52 (dd, J=10.4, 3.6 Hz, 1H), 3.46-3.36 (m, 2H), 3.23 (m, 1H), 3.08 (m, 2H), 2.42 (s, 3H), 2.07-1.98 (m, 1H), 1.96-1.67 (m, 6H), 1.61 (m, 1H), 1.22 (d, J=6.4 Hz, 3H).

Example 2: Preparation of (3-((3S,4S)-4-amino-3-methyl-2-oxa-8-azaspiro[4.5]decan-8-yl)-6-(3-chloro-2-(2-hydroxymethyl)pyrrolidin-1-yl)pyridin-4-ylthio)pyrazin-2-yl)methanol (Compound 2)

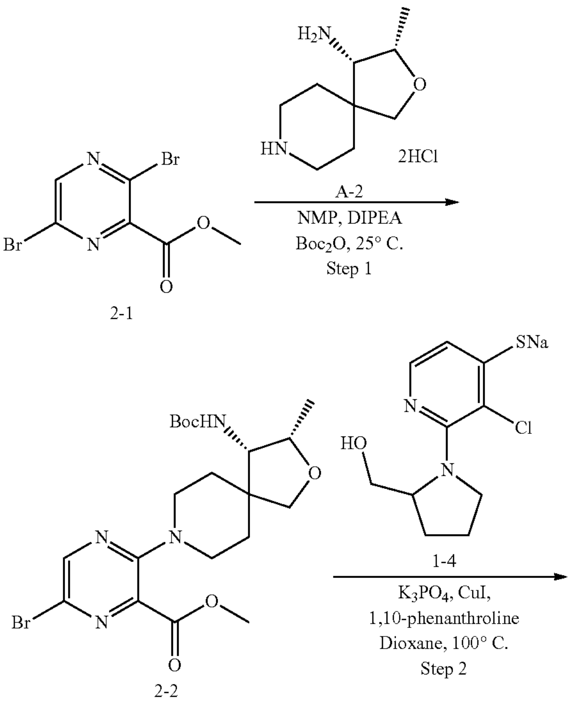

-continued

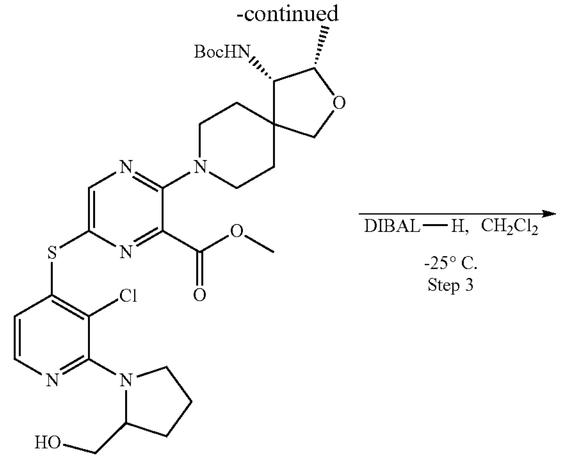

2-3

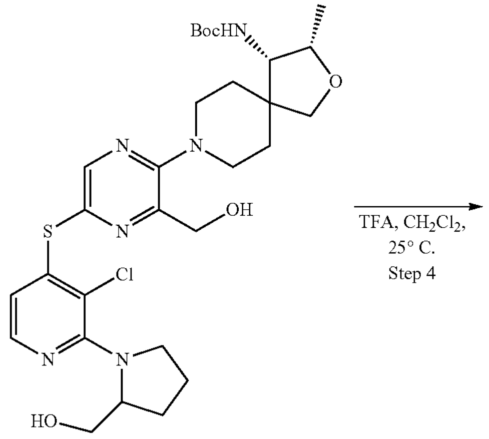

2-4

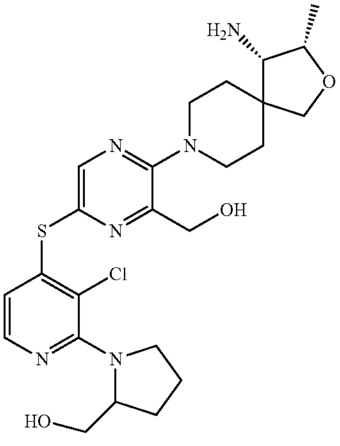

2

Step 1: Preparation of methyl 6-bromo-3-((3S,4S)-4-(tert-butoxycarbonylamino)-3-methyl-2-oxa-8-azaspiro[4.5]decan-8-yl)pyrazine-2-carboxylate (Compound 2-2)

Compound 2-1 (120.0 mg, 0.41 mmol), Compound A-2 (103.54 mg, 0.43 mmol), and DIPEA (314.46 mg, 2.43 mmol) were added into NMP (3 mL) and reacted at 25° C. for 12 hours. Thereafter, di-tert-butyl dicarbonate (177.01 mg, 811.04 μmol) was added into the reaction solution. The reaction was continued at 25° C. for 2 hours. Water and ethyl acetate were added to extract the product. The organic phase was washed with saturated saline, dried over anhydrous sodium sulfate, and concentrated to afford a crude product. The crude product was purified by thin layer chromatography to afford Compound 2-2 (162 mg, yield 82%).

Step 2 to Step 4: Preparation of (3-((3S,4S)-4-amino-3-methyl-2-oxa-8-azaspiro[4.5]decan-8-yl)-6-(3-chloro-2-(2-hydroxymethyl)pyrrolidin-1-yl)pyridin-4-ylthio)pyrazin-2-yl)methanol (Compound 2)

A crude product of Compound 2 was synthesized by similar methods described in Step 4 to Step 6 of Example 1, except that Compound 2-2 was used in Step 2 to replace Compound IM-1 in Step 4 of Example 1. The crude product was purified by HPLC (mobile phase A: acetonitrile, mobile phase B: 0.05% aqueous solution of trifluoroacetic acid) to afford a trifluoroacetate salt of Compound 2.

MS (ESI): m/z 521.3 $[M+H]^+$.

$^1$H-NMR (400 MHz, DMSO-$d_6$): δ 8.36 (s, 1H), 7.94 (s, 3H), 7.82 (d, J=5.2 Hz, 1H), 6.07 (d, J=5.2 Hz, 1H), 4.52 (s, 2H), 4.44-4.39 (m, 1H), 4.23-4.20 (m, 1H), 3.89-3.81 (m, 3H), 3.70 (d, J=8.8 Hz, 1H), 3.51 (dd, J=10.4, 3.6 Hz, 1H), 3.46-3.34 (m, 2H), 3.22 (m, 1H), 3.09 (m, 2H), 2.07-1.99 (m, 1H), 1.96-1.79 (m, 4H), 1.78-1.67 (m, 2H), 1.60 (m, 1H), 1.22 (d, J=6.4 Hz, 3H).

Example 3: Preparation of (3-(4-(1-aminoethyl)-4-methylpiperidin-1-yl)-6-(3-chloro-2-(2-hydroxymethyl)pyrrolidin-1-yl)pyridin-4-ylthio)pyrazin-2-yl) methanol (Compound 17)

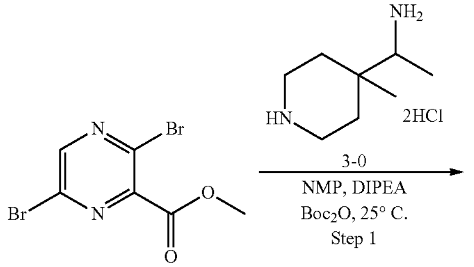

2-1

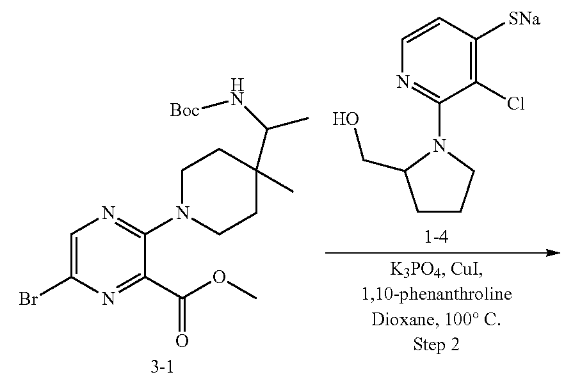

3-1

-continued

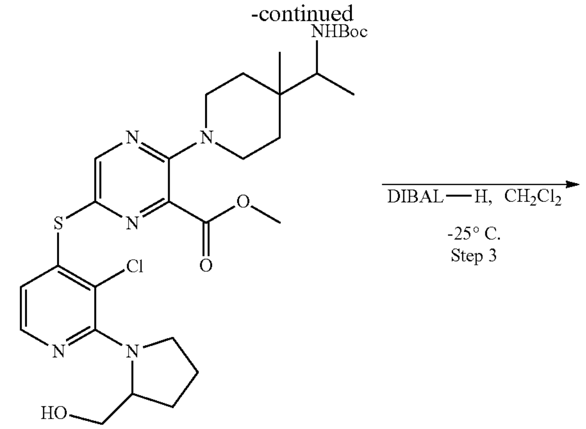

3-2

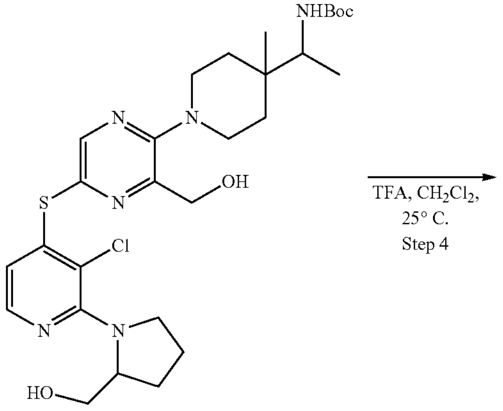

3-3

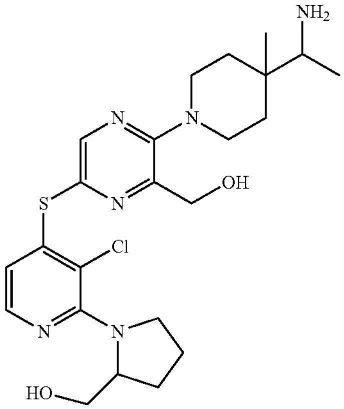

17

A crude product of Compound 17 was synthesized by similar methods described in Step 1 to Step 4 of Example 2, except that 1-(4-methylpiperidin-4-yl)ethylamine dihydrochloride (Compound 3-0) was used in Step 1 to replace Compound A-2 in Step 1 of Example 2. The crude product was purified by HPLC (mobile phase A: acetonitrile, mobile phase B: 0.05% aqueous solution of trifluoroacetic acid) to afford a trifluoroacetate salt of Compound 17.

MS (ESI): m/z 493.2 $[M+H]^+$.

$^1$H-NMR (400 MHz, DMSO-$d_6$): δ 8.35 (s, 1H), 7.83 (d, J=5.2 Hz, 1H), 7.71 (s, 3H), 6.08 (d, J=5.2 Hz, 1H), 4.53 (s, 2H), 4.46-4.40 (m, 2H), 3.84 (m, 3H), 3.53 (dd, J=10.4, 3.6 Hz, 1H), 3.41-3.35 (m, 1H), 3.25-3.19 (m, 2H), 3.18-3.13 (m, 1H), 2.07-2.00 (m, 1H), 1.97-1.88 (m, 1H), 1.86-1.78 (m, 1H), 1.76-1.68 (m, 1H), 1.65-1.53 (m, 3H), 1.44 (m, 1H), 1.16 (d, J=6.4 Hz, 3H), 1.03 (s, 3H).

Example 4: Preparation of (1-(4-(5-((3S,4S)-4-amino-3-methyl-2-oxa-8-azaspiro[4.5]decan-8-yl)-6-(fluoromethyl)pyrazin-2-ylthio)-3-chloropyridin-2-yl)pyrrolidin-2-yl)methanol (Compound 22)

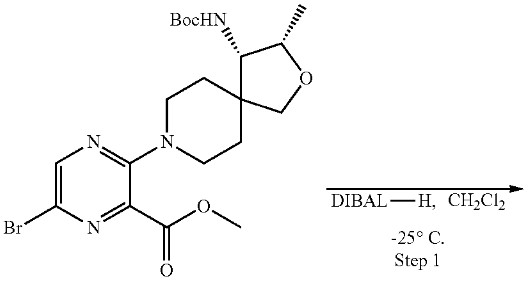

2-2

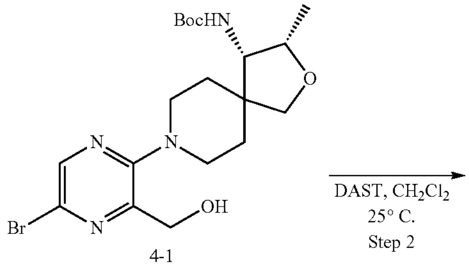

4-1

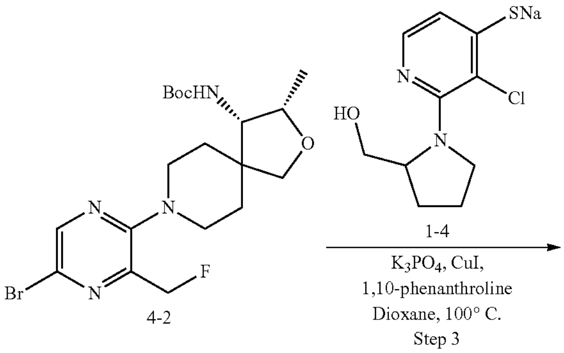

1-4

4-2

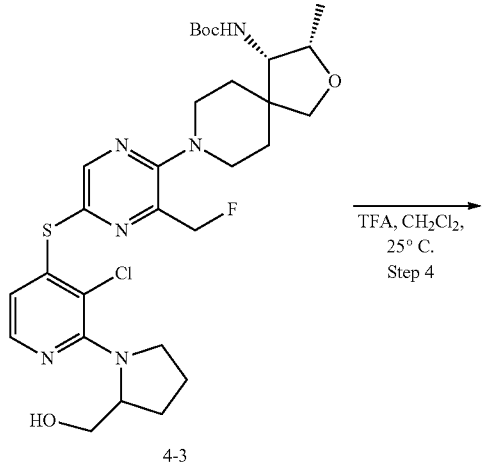

4-3

-continued

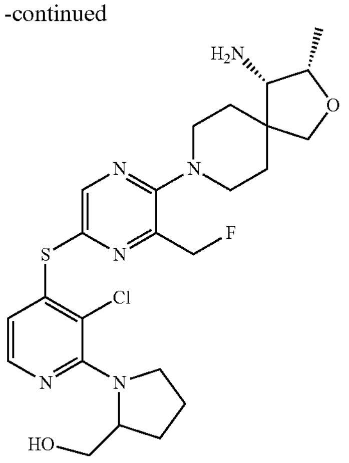

22

Step 1: Preparation of tert-butyl (3S,4S)-8-(5-bromo-3-(hydroxymethyl)pyrazin-2-yl)-3-methyl-2-oxa-8-azaspiro[4.5]decan-4-ylcarbamate (Compound 4-1)

Compound 2-2 (60 mg, 0.12 mmol) was dissolved into dichloromethane (2 mL). At −25° C., DIBAL-H (1 M solution in hexane, 0.84 mL) was slowly added and reacted for 1 hour while the temperature was maintained. After the reaction was complete, dichloromethane (10 mL) and a saturated aqueous solution of potassium sodium tartrate (5 mL) were added into the reaction solution and stirred for 2 hours to extract the product. The organic phase was dried over anhydrous sodium sulfate and filtered. The filtrate was concentrated to afford a crude product. The crude product was purified by thin layer chromatography to afford Compound 4-1 (40 mg, yield 71%).

Step 2: Preparation of tert-butyl (3S,4S)-8-(5-bromo-3-(fluoromethyl)pyrazin-2-yl)-3-methyl-2-oxa-8-azaspiro[4.5]decan-4-ylcarbamate (Compound 4-2)

Compound 4-1 (40 mg, 87.46 μmol) was added into dichloromethane (4 mL), and DAST (28.19 mg, 174.92 μmol) was slowly added and reacted at room temperature for 2 hours. The reaction solution was slowly poured into a mixed solution of a saturated aqueous solution of sodium bicarbonate (5 ml) and dichloromethane (5 ml) to extract the product. The organic phase was washed with saturated saline (2 ml), dried over anhydrous sodium sulfate, and filtered. The filtrate was concentrated to afford a crude product. The crude product was purified by thin layer chromatography to afford Compound 4-2 (32 mg, yield 80%).

Step 3: Preparation of tert-butyl (3S,4S)-8-(5-(3-chloro-2-(2-hydroxymethyl)pyrrolidin-1-yl)pyridin-4-ylthio)-3-(fluoromethyl)pyrazin-2-yl)-3-methyl-2-oxa-8-azaspiro[4.5]decan-4-ylcarbamate (Compound 4-3)

Compound 4-3 was synthesized by a similar method described in Step 4 of Example 1, except that Compound 4-2 was used in this step to replace Compound IM-1 in Step 4 of Example 1.

Step 4: Preparation of (1-(4-(5-((3S,4S)-4-amino-3-methyl-2-oxa-8-azaspiro[4.5]decan-8-yl)-6-(fluoromethyl)pyrazin-2-ylthio)-3-chloropyridin-2-yl)pyrrolidin-2-yl)methanol (Compound 22)

Compound 4-3 (20 mg, 0.03 mmol) was dissolved into a mixture of dichloromethane (1 mL) and TFA (1 mL) and reacted at 25° C. for 1 hour. The resultant was concentrated to remove the solvent therefrom, thereby affording a crude product. The crude product was purified by HPLC (mobile phase A: acetonitrile, mobile phase B: 0.05% aqueous solution of trifluoroacetic acid) to afford a trifluoroacetate salt of Compound 22 (5 mg, yield 24%).

MS (ESI): m/z 523.2 $[M+H]^+$.

$^1$H-NMR (400 MHz, $CD_3OD$): δ 8.41 (d, J=1.6 Hz, 1H), 7.74 (d, J=6.0 Hz, 1H), 6.28 (dd, J=6.0, 1.6 Hz, 1H), 5.47 (d, J=47.6 Hz, 2H), 4.68-4.53 (m, 1H), 4.33-4.27 (m, 1H), 3.99-3.86 (m, 4H), 3.67-3.61 (m, 2H), 3.56 (dd, J=11.2, 5.2 Hz, 1H), 3.46 (d, J=4.0 Hz, 1H), 3.27-3.14 (m, 3H), 2.22-2.16 (m, 1H), 2.08-2.02 (m, 1H), 1.98-1.84 (m, 5H), 1.76-1.72 (m, 1H), 1.32 (d, J=6.4 Hz, 3H).

Example 5: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)acetonitrile (Compound 11)

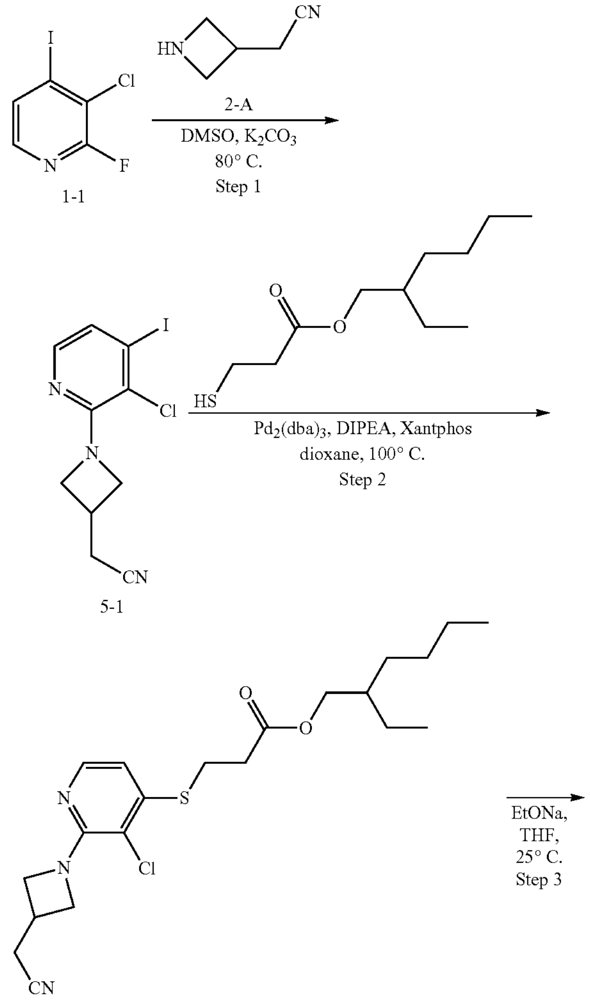

-continued

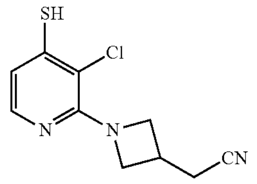

5-3

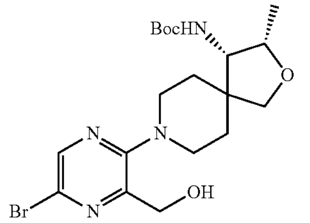

4-1

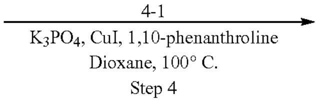

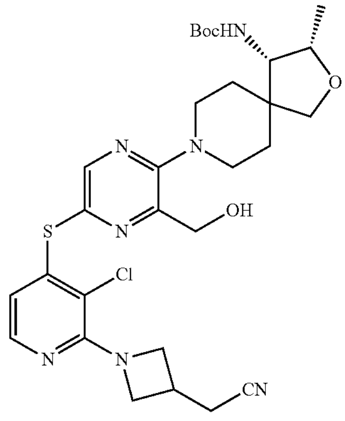

5-4

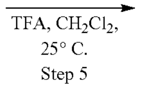

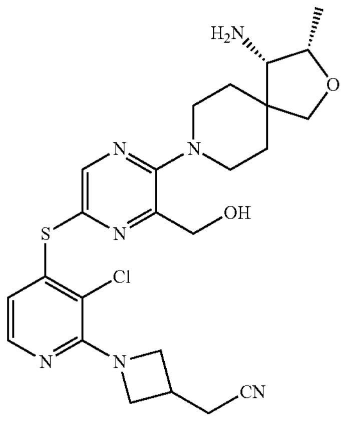

11

A crude product of Compound 11 was synthesized by similar methods described in Step 1 to Step 4 and Step 6 of Example 1, except that 3-cyanomethylazetidine was used in Step 1 to replace 2-hydroxymethylpyrrolidine in Step 1 of Example 1 and that Compound 4-1 was used in Step 4 to replace Compound IM-1 in Step 4 of Example 1. The crude product was purified by HPLC (mobile phase A: acetonitrile, mobile phase B: 0.05% aqueous solution of formic acid) to afford a formate salt of Compound 11.

MS (ESI): m/z 516.2 $[M+H]^+$.

$^1$H-NMR (400 MHz, $CD_3OD$): δ 8.53 (brs, 1H), 8.30 (s, 1H), 7.73 (d, J=5.6 Hz, 1H), 6.14 (d, J=5.6 Hz, 1H), 4.67 (s, 2H), 4.41 (t, J=8.8 Hz, 2H), 4.32-4.26 (m, 1H), 4.03-4.00 (m, 2H), 3.96-3.94 (m, 1H), 3.89-3.80 (m, 3H), 3.39 (d, J=4.0 Hz, 1H), 3.20-3.08 (m, 2H), 3.02-2.94 (m, 1H), 2.83 (d, J=6.8 Hz, 2H), 1.98-1.86 (m, 3H), 1.74-1.71 (m, 1H), 1.30 (d, J=6.4 Hz, 3H).

Example 6: Preparation of (3-((3S,4S)-4-amino-3-methyl-2-oxa-8-azaspiro[4.5]decan-8-yl)-6-(3-chloro-2-(3-(hydroxymethyl)azetidin-1-yl)pyridin-4-ylthio)pyrazin-2-yl)methanol (Compound 12)

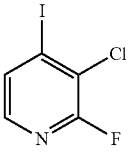

1-1

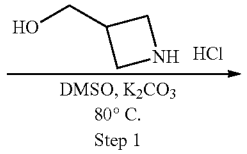

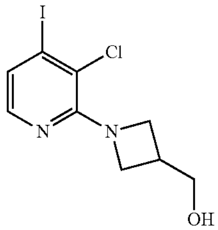

6-1

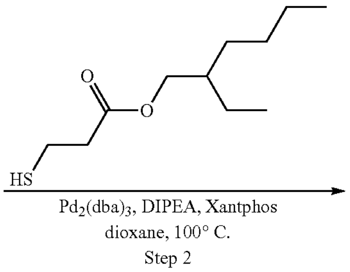

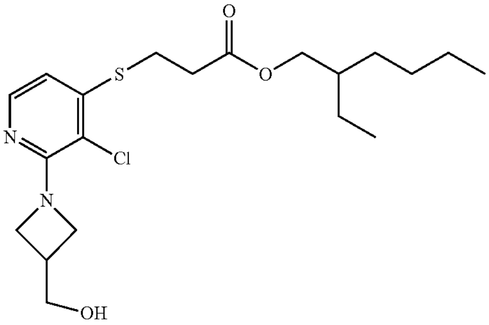

6-2

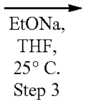

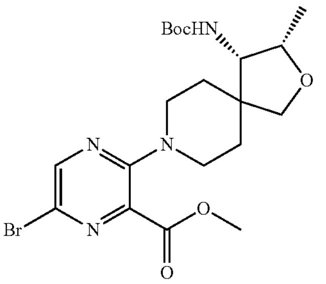

2-2

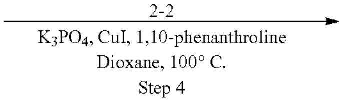

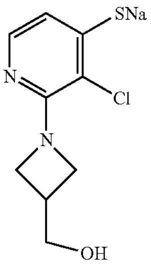

6-3

-continued

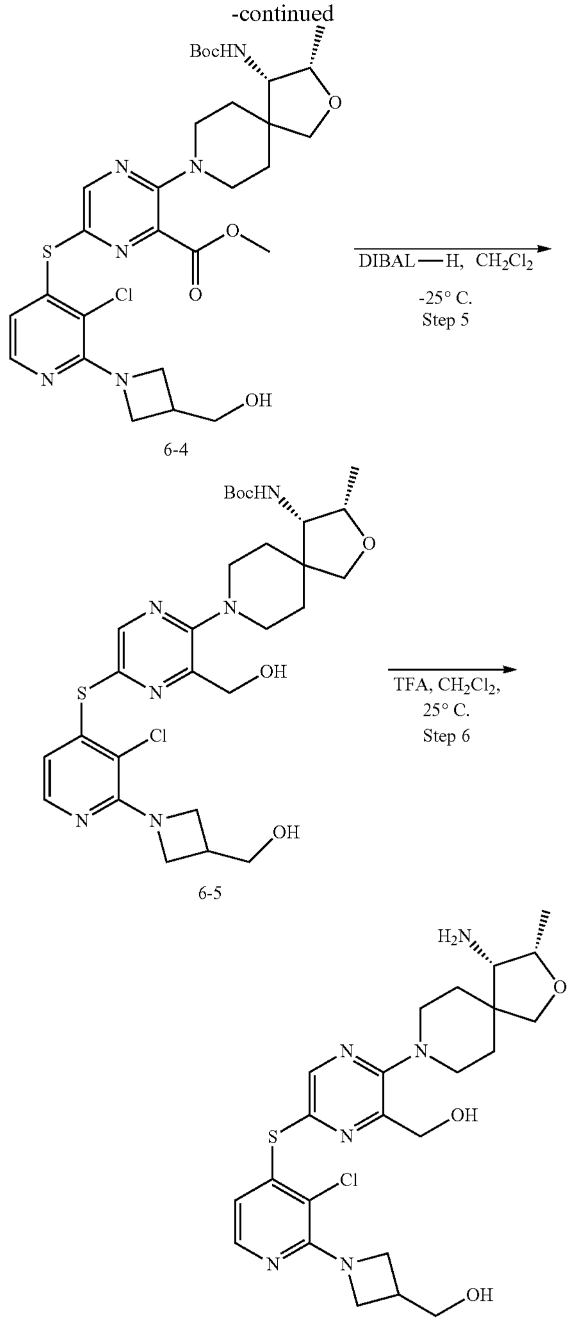

6-4

6-5

12

A crude product of Compound 12 was synthesized by similar methods described in Step 1 to Step 6 of Example 1, except that 3-hydroxymethylazetidine hydrochloride was used in Step 1 to replace 2-hydroxymethylpyrrolidine in Step 1 of Example 1 and that Compound 2-2 was used in Step 4 to replace Compound IM-1 in Step 4 of Example 1. The crude product was purified by HPLC (mobile phase A: acetonitrile, mobile phase B: 0.05% aqueous solution of trifluoroacetic acid) to afford a trifluoroacetate salt of Compound 12.

MS (ESI): m/z 507.2 $[M+H]^+$.

$^1$H-NMR (400 MHz, DMSO-$d_6$): δ 8.35 (s, 1H), 7.97 (s, 3H), 7.80 (d, J=5.2 Hz, 1H), 6.04 (d, J=5.2 Hz, 1H), 4.52 (s, 2H), 4.25-4.12 (m, 3H), 3.98-3.65 (m, 8H), 3.56 (d, J=6.0 Hz, 1H), 3.47-3.40 (m, 1H), 3.20-3.01 (m, 2H), 2.76-2.62 (m, 1H), 1.90-1.50 (m, 4H), 1.17 (d, J=6.4 Hz, 3H).

Example 7: Preparation of (3-((S)-4-amino-2-oxa-8-azaspiro[4.5]decan-8-yl)-6-(3-chloro-2-(2-(hydroxymethyl)pyrrolidin-1-yl)pyridin-4-ylthio)pyrazin-2-yl)methanol (Compound 21)

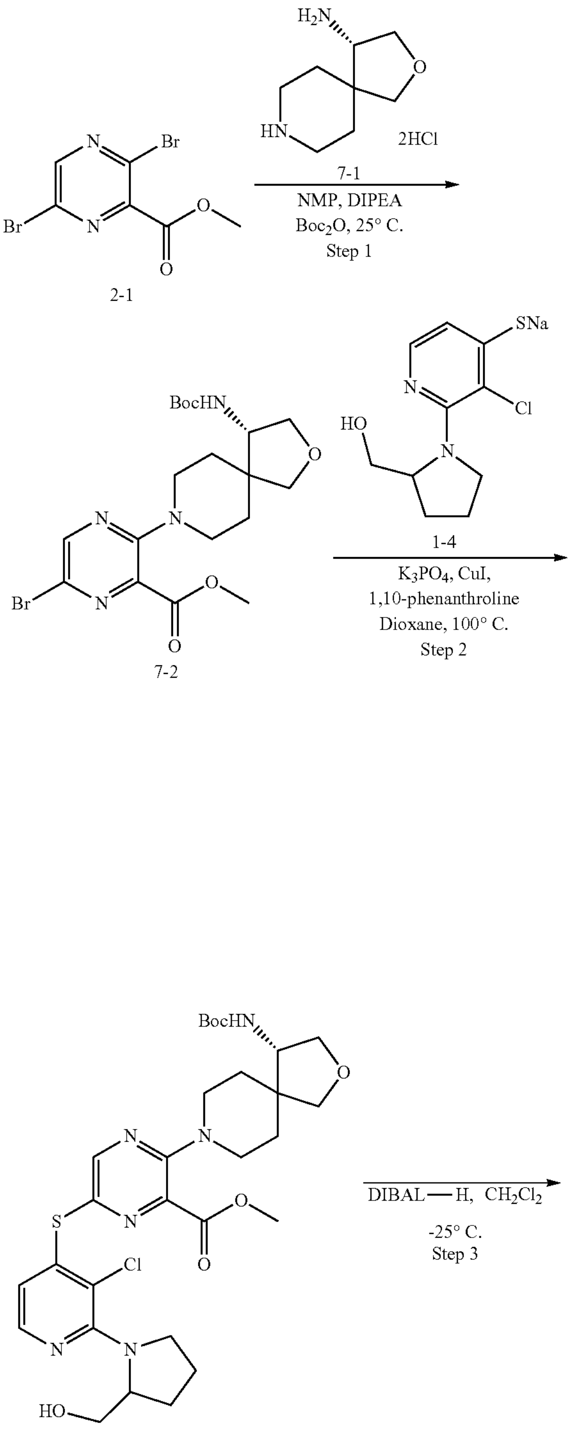

2-1

7-1

7-2

1-4

7-3

-continued

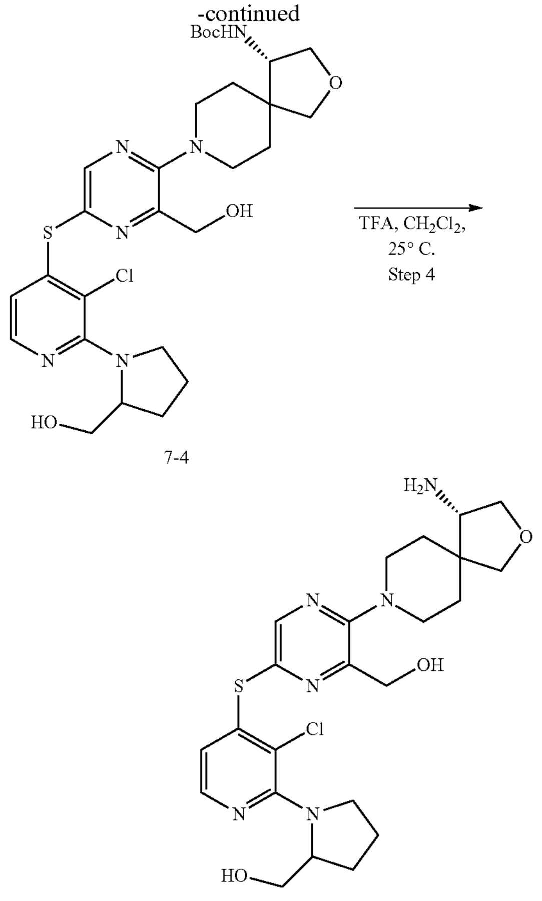

7-4

21

A crude product of Compound 21 was synthesized by similar methods described in Step 1 to Step 4 of Example 2, except that Compound 7-1 was used in Step 1 to replace Compound A-2 in Step 1 of Example 2. The crude product was purified by HPLC (mobile phase A: acetonitrile, mobile phase B: 0.05% aqueous solution of trifluoroacetic acid) to afford a trifluoroacetate salt of Compound 21.

MS (ESI): m/z 507.2 $[M+H]^+$.

$^1$H-NMR (400 MHz, $CD_3OD$): δ 8.33 (s, 1H), 7.72 (d, J=6.0 Hz, 1H), 6.28 (d, J=6.0 Hz, 1H), 4.68 (s, 2H), 4.63-4.53 (m, 1H), 4.17 (dd, J=10.8, 5.6 Hz, 1H), 4.02-3.81 (m, 6H), 3.71-3.50 (m, 4H), 3.27-3.19 (m, 1H), 3.18-3.10 (m, 1H), 2.22-2.15 (m, 1H), 2.07-1.99 (m, 1H), 1.99-1.73 (m, 6H).

Example 8: Preparation of (3-((3S,4S)-4-amino-3-methyl-2-oxa-8-azaspiro[4.5]decan-8-yl)-6-(3-chloro-2-(3-(hydroxymethyl)pyrrolidin-1-yl)pyridin-4-ylthio)pyrazin-2-yl)methanol (Compound 37)

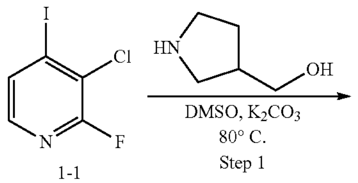

1-1

-continued

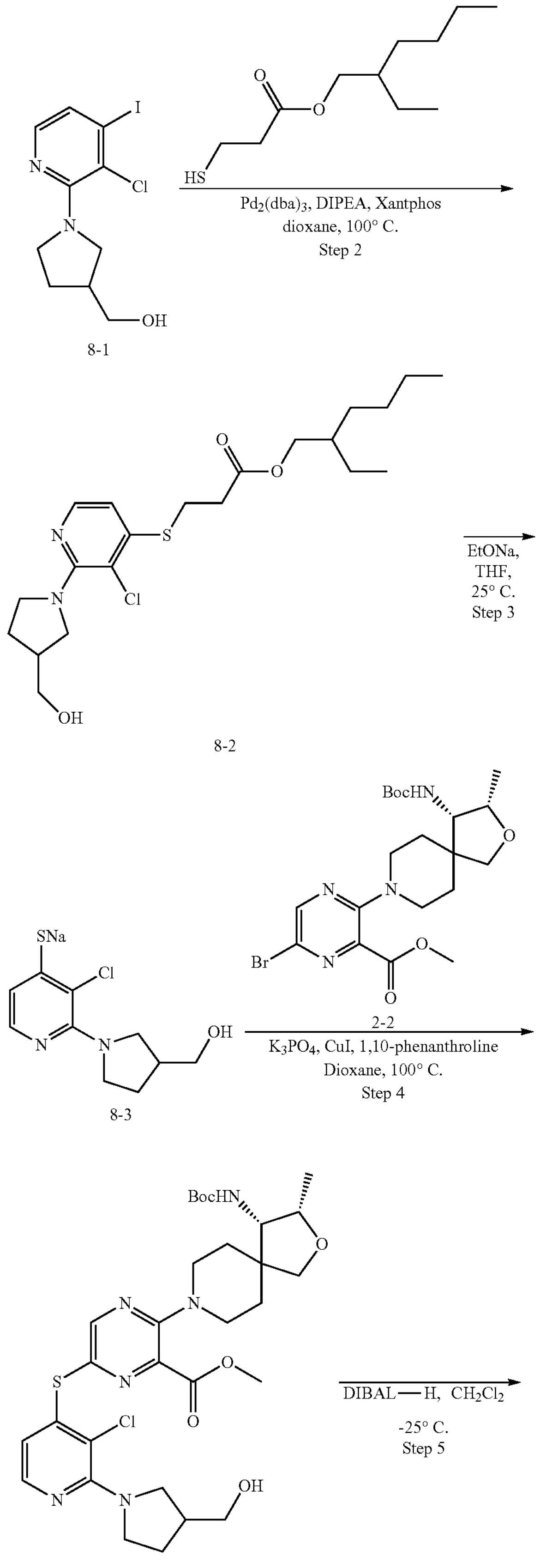

8-1

8-2

8-3

2-2

8-4

-continued

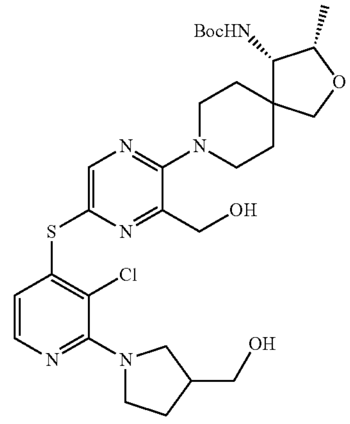

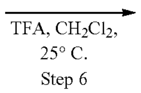

8-5

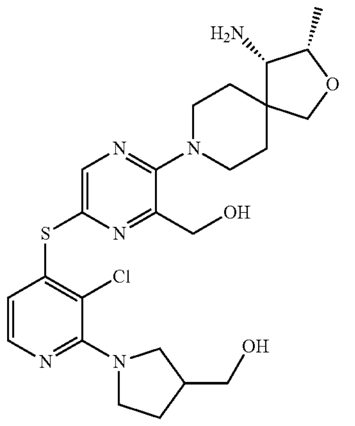

37

A crude product of Compound 37 was synthesized by similar methods described in Step 1 to Step 6 of Example 1, except that 3-hydroxymethylpyrrolidine was used in Step 1 to replace 2-hydroxymethylpyrrolidine in Step 1 of Example 1 and that Compound 2-2 was used in Step 4 to replace Compound IM-1 in Step 4 of Example 1. The crude product was purified by HPLC (mobile phase A: acetonitrile, mobile phase B: 0.05% aqueous solution of formic acid) to afford a formate salt of Compound 37.

MS (ESI): m/z 521.2 $[M+H]^+$.

$^1$H-NMR (400 MHz, $CD_3OD$): δ 8.48 (brs, 1H), 8.30 (s, 1H), 7.72 (d, J=4.0 Hz, 1H), 6.10 (d, J=4 Hz, 1H), 4.67 (s, 2H), 4.32-4.21 (m, 1H), 3.97-3.94 (m, 1H), 3.92-3.78 (m, 3H), 3.74-3.65 (m, 3H), 3.62-3.50 (m, 3H), 3.42 (d, J=4 Hz, 1H), 3.20-3.06 (m, 2H), 2.48-2.37 (m, 1H), 2.09-2.01 (m, 1H), 1.98-1.81 (m, 3H), 1.77-1.68 (m, 2H), 1.31 (d, J=8 Hz, 3H).

Example 9: Preparation of (3-((3S,4S)-4-amino-3-methyl-2-oxa-8-azaspiro[4.5]decan-8-yl)-6-(3-chloro-2-((S)-2-(hydroxymethyl)azetidin-1-yl)pyridin-4-ylthio)pyrazin-2-yl)methanol (Compound 33)

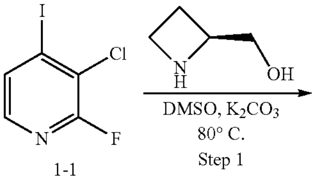

1-1

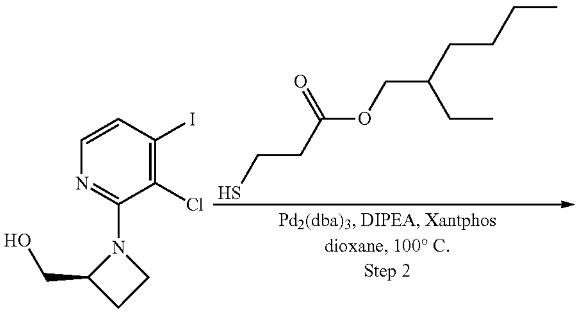

9-1

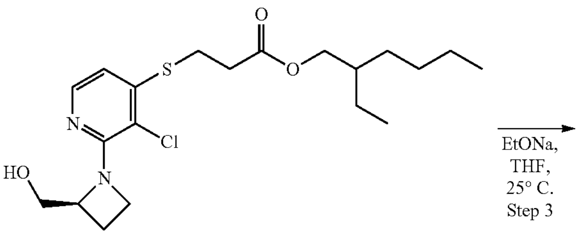

9-2

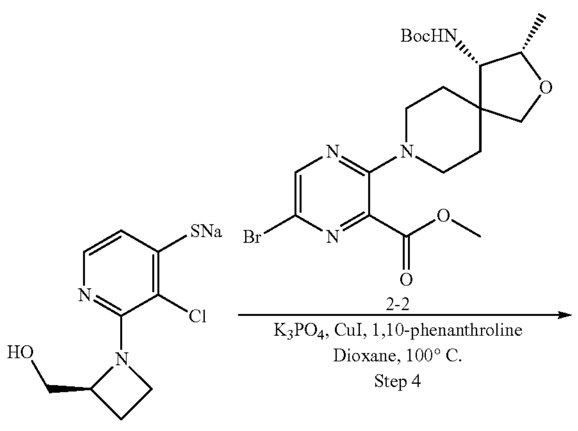

9-3

-continued

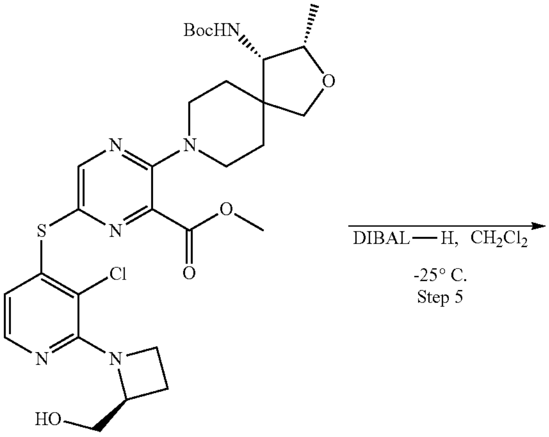

9-4

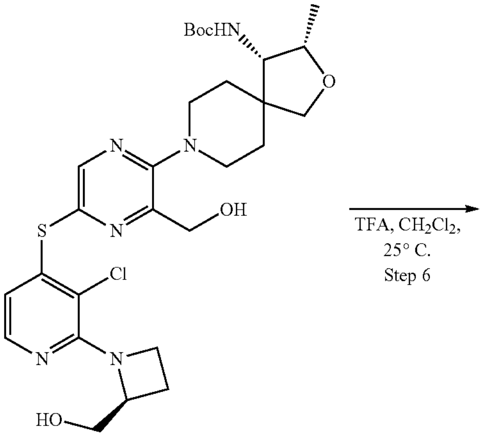

9-5

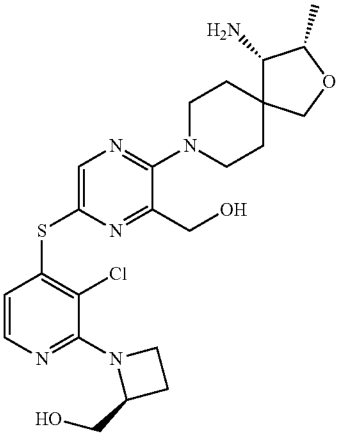

33

A crude product of Compound 33 was synthesized by similar methods described in Step 1 to Step 6 of Example 1, except that (S)-2-hydroxymethylazetidine was used in Step 1 to replace 2-hydroxymethylpyrrolidine in Step 1 of Example 1 and that Compound 2-2 was used in Step 4 to replace Compound IM-1 in Step 4 of Example 1. The crude product was purified by HPLC (mobile phase A: acetonitrile, mobile phase B: 0.05% aqueous solution of trifluoroacetic acid) to afford a trifluoroacetate salt of Compound 33.

MS (ESI): m/z 507.1 $[M+H]^+$.

$^1$H-NMR (400 MHz, $CD_3OD$): δ 8.35 (s, 1H), 7.67 (d, J=6.4 Hz, 1H), 6.31 (d, J=6.4 Hz, 1H), 4.89-4.82 (m, 1H), 4.68 (s, 2H), 4.67-4.52 m, 2H), 4.36-4.25 (m, 1H), 4.02-3.79 (m, 6H), 3.46 (d, J=4.0 Hz, 1H), 3.25-3.07 (m, 2H), 2.54-2.43 (m, 1H), 2.33-2.20 (m, 1H), 2.04-1.67 (m, 4H), 1.32 (d, J=6.4 Hz, 3H).

Example 10: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)pyrrolidin-3-yl)acetonitrile (Compound 14)

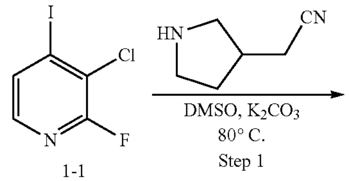

1-1

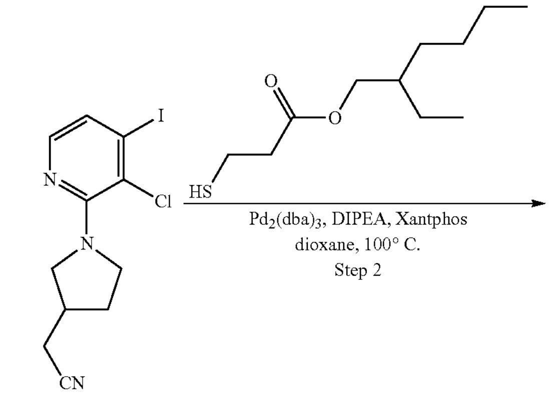

10-1

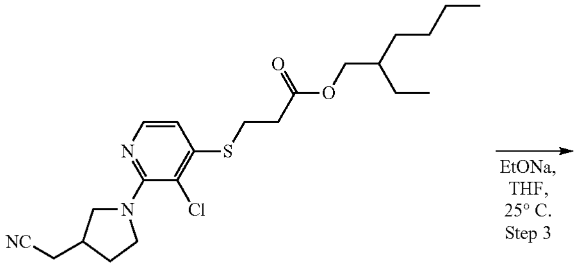

10-2

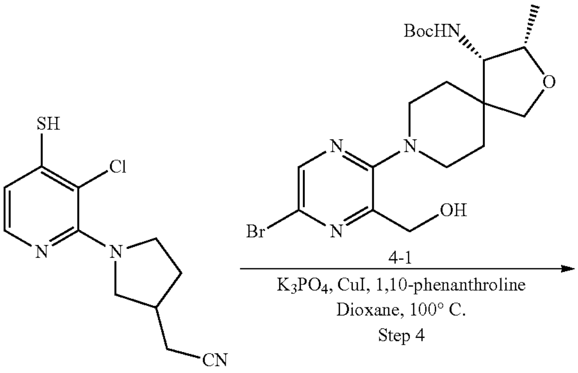

10-3

-continued

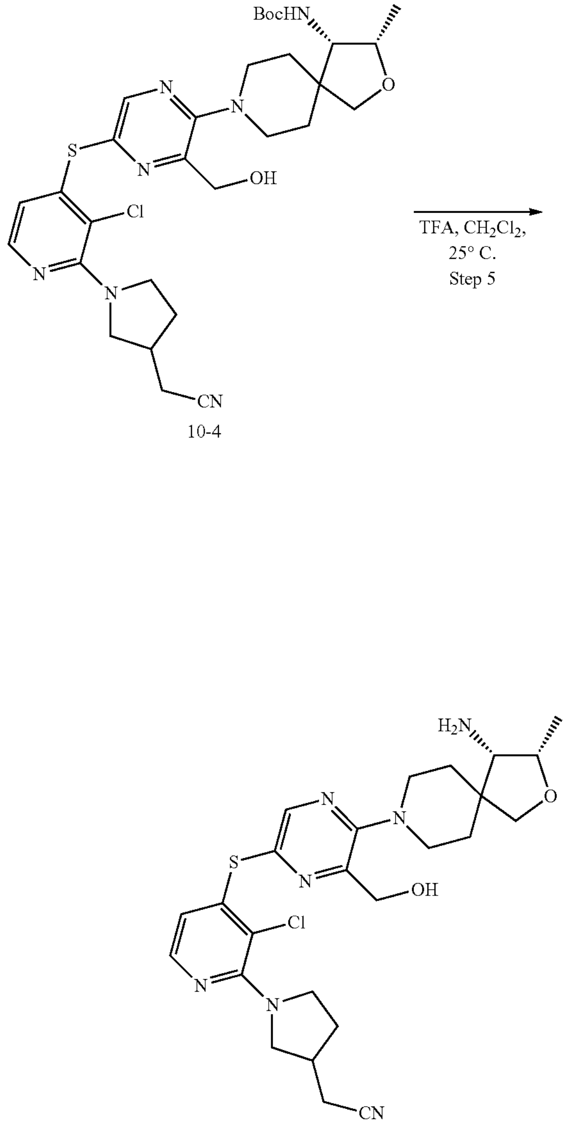

10-4

14

A crude product of Compound 14 was synthesized by similar methods described in Step 1 to Step 4 and Step 6 of Example 1, except that 2-(pyrrolidin-3-yl)acetonitrile was used in Step 1 to replace 2-hydroxymethylpyrrolidine in Step 1 of Example 1 and that Compound 4-1 was used in Step 4 to replace Compound IM-1 of Example 1. The crude product was purified by HPLC (mobile phase A: acetonitrile, mobile phase B: 0.05% aqueous solution of trifluoroacetic acid) to afford a trifluoroacetate salt of Compound 14.

MS (ESI): m/z 530.2 $[M+H]^+$.

$^1$H-NMR (400 MHz, DMSO-d6): δ 8.35 (s, 1H), 7.95 (s, 3H), 7.82 (d, J=5.2 Hz, 1H), 6.07 (d, J=5.2 Hz, 1H), 4.52 (s, 2H), 4.23-4.18 (m, 1H), 3.91-3.82 (m, 3H), 3.72-3.64 (m, 4H), 3.44-3.39 (m, 2H), 3.14-3.04 (m, 2H), 2.78-2.69 (m, 2H), 2.14-2.06 (m, 1H), 1.85-1.59 (m, 6H), 1.22 (d, J=6.4 Hz, 3H).

Example 11: Preparation of 2-(1-(5-(5-((3S,4S)-4-amino-3-methyl-2-oxa-8-azaspiro[4.5]decan-8-yl)-6-(hydroxymethyl)pyrazin-2-ylthio)-6-chloropyridin-2-yl)azetidin-3-yl)propan-2-ol (Compound 130)

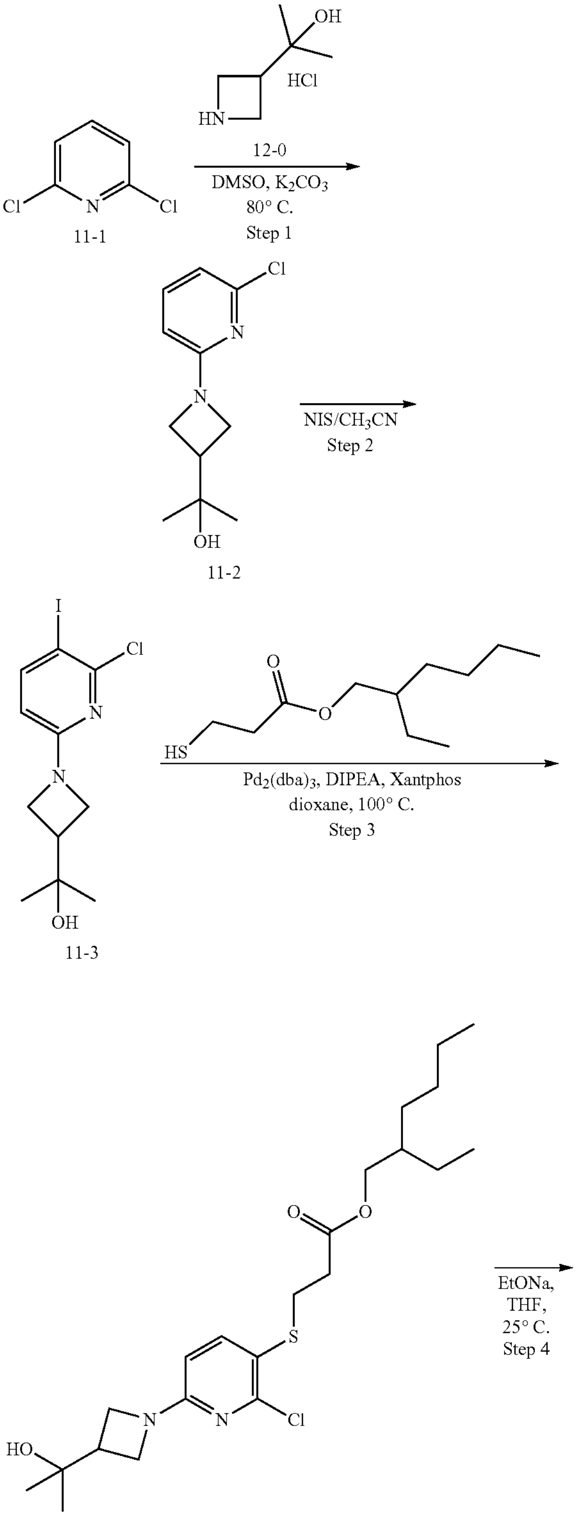

12-0

11-1

11-2

11-3

11-4

-continued

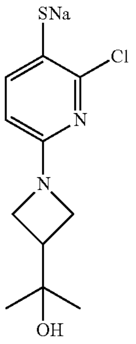

11-5

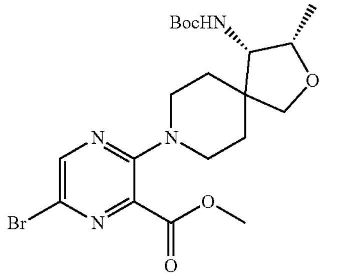

2-2

$K_3PO_4$, CuI, 1,10-phenanthroline
Dioxane, 100° C.
Step 5

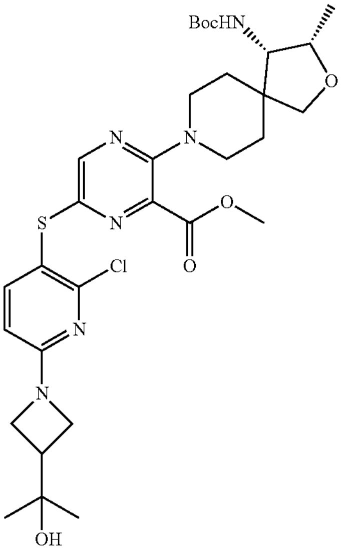

11-6

DIBAL—H,
$CH_2Cl_2$
-25° C.
Step 6

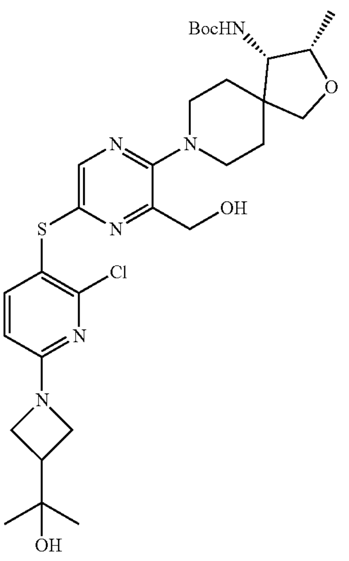

11-7

TFA, $CH_2Cl_2$,
25° C.
Step 7

-continued

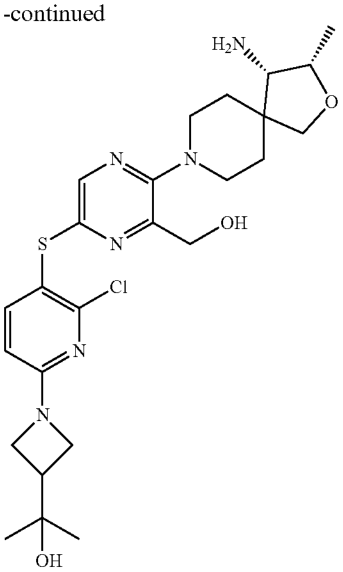

130

Step 1: Preparation of 2-(1-(6-chloropyridin-2-yl) azetidin-3-yl)propan-2-ol (Compound 11-2)

2,6-Dichloropyridine (800 mg, 5.41 mmol) was dissolved into DMSO (10 mL), and Compound 12-0 (983.64 mg, 6.49 mmol) and potassium carbonate (2.24 g, 16.22 mmol) were added, heated to 80° C., and reacted for 4 hours. After the completion of the reaction was detected by LCMS, water was added into the reaction solution and the resultant was extracted with ethyl acetate. The combined organic phase was dried, and concentrated to afford a crude product of Compound 11-2 (1.06 g). The crude product was used directly in the next reaction step without purification.

Step 2: Preparation of 2-(1-(6-chloro-5-iodopyridin-2-yl)azetidin-3-yl)propan-2-ol (Compound 11-3)

Compound 11-2 (1.06 g, 4.68 mmol) was dissolved into acetonitrile (20 mL), and NIS (1.16 g, 5.14 mmol) was added and reacted at 25° C. for 16 hours. After the completion of the reaction was detected by LCMS, the resultant was concentrated. The crude product was purified by preparative thin layer chromatography to afford Compound 11-3 (700 mg, yield 42%).

Step 3 to Step 7: Preparation of 2-(1-(5-(5-((3S, 4S)-4-amino-3-methyl-2-oxa-8-azaspiro[4.5]decan-8-yl)-6-(hydroxymethyl)pyrazin-2-ylthio)-6-chloropyridin-2-yl)azetidin-3-yl)propan-2-ol (Compound 130)

A crude product of Compound 130 was synthesized by similar methods described in Step 2 to Step 6 of Example 6. The crude product was purified by HPLC (mobile phase A: acetonitrile, mobile phase B: 0.05% aqueous solution of trifluoroacetic acid) to afford a trifluoroacetate salt of Compound 130.

MS (ESI): m/z 535.0 $[M+H]^+$.

$^1$H-NMR (400 MHz, DMSO-d6): δ 7.94 (s, 3H), 7.72 (s, 1H), 7.71 (d, J=8.4 Hz, 1H), 6.38 (d, J=8.4 Hz, 1H), 4.46 (s, 2H), 4.29-4.11 (m, 1H), 3.97-3.86 (m, 4H), 3.82 (d, J=8.8

Hz, 1H), 3.65 (d, J=8.8 Hz, 1H), 3.63-3.56 (m, 3H), 2.97-2.81 (m, 2H), 2.72 (dt, J=14.8, 7.6 Hz, 1H), 1.91-1.65 (m, 3H), 1.62-1.51 (m, 1H), 1.20 (d, J=7.2 Hz, 3H), 1.07 (s, 6H).

Example 12: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)propan-2-ol (Compound 67)

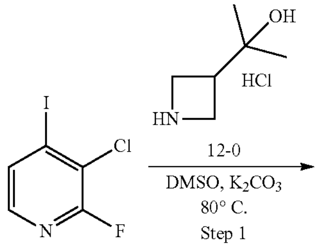

1-1

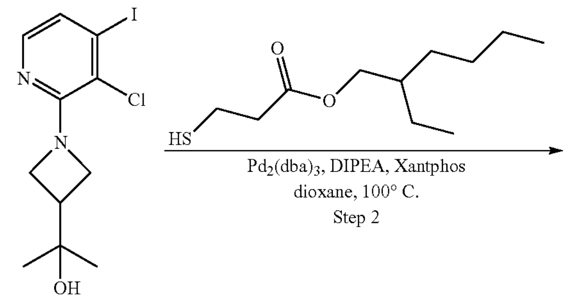

12-1

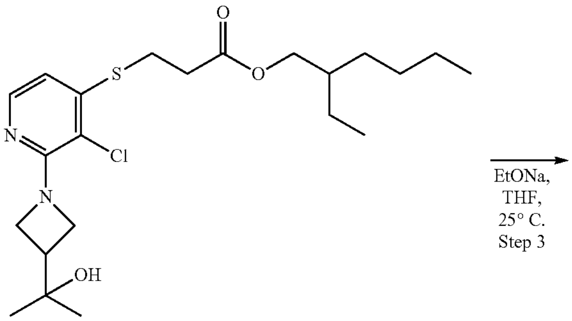

12-2

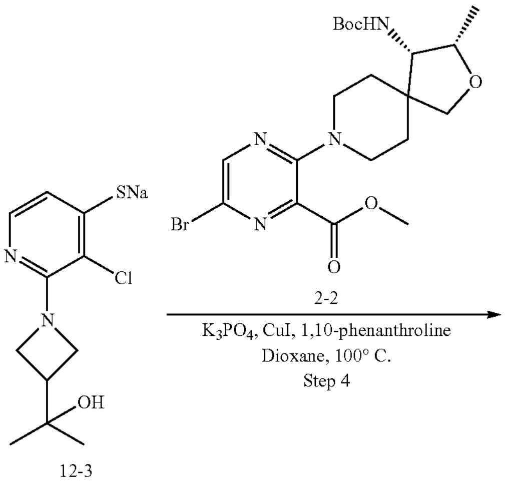

12-3

-continued

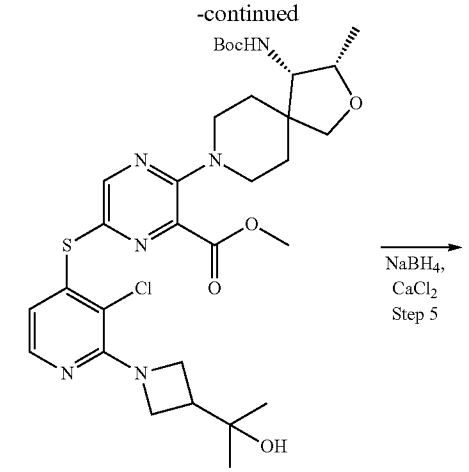

12-4

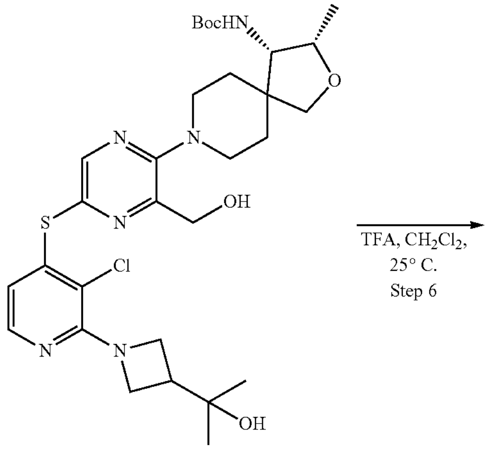

12-5

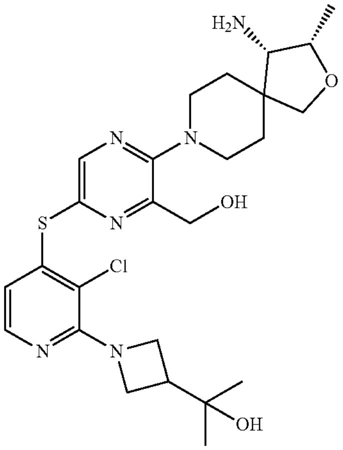

67

Step 1: Preparation of 2-(1-(3-chloro-4-iodopyridin-2-yl)azetidin-3-yl)propan-2-ol (Compound 12-1)

Compound 1-1 (25.0 g, 97.1 mmol), DMSO (200 mL), Compound 12-0 (18.8 g, 111.7 mmol), and $K_2CO_3$ (40.3 g, 291.3 mmol) were mixed, and then warmed to 80° C. and reacted for 4 hours. The resultant was cooled to room temperature, and partitioned between water and ethyl acetate. The organic phase was washed with saturated saline, dried over anhydrous sodium sulfate, and concentrated to afford a crude product of Compound 12-1 (36.7 g). The crude product was used directly in the next reaction step without purification.

Step 2: Preparation of 2-ethylhexyl 3-(3-chloro-2-(3-(2-hydroxylprop-2-yl)azetidin-1-yl)pyridin-4-ylthio)propanoate (Compound 12-2)

Compound 12-1 (36.7 g, 93.68 mmol), 2-ethylhexyl 3-mercaptopropanoate (24.6 g, 112.40 mmol), DIPEA (24.2 g, 187.4 mmol), Xantphos (542.0 mg, 0.94 mmol), and $Pd_2(dba)_3$ (428.9 mg, 0.47 mmol) were added into 1,4-dioxane (300 mL), evacuated, and purged three times with nitrogen gas. Thereafter, the reactants were warmed to 100° C. and reacted for 4 hours. The resultant was cooled to room temperature, and filtered to remove the solid. The filtrate was concentrated to afford a crude product. The crude product was purified by column chromatography to afford Compound 12-2 (37.8 g, yield 86%).

Step 3: Preparation of sodium 3-chloro-2-(3-(2-hydroxylprop-2-yl)azetidin-1-yl)pyridine-4-thiophenate (Compound 12-3)

Sodium ethoxide (5.85 g, 30% solution in methanol) was added into a solution of Compound 12-2 (12.00 g, 27.1 mmol) in THF (120 mL), and reacted at 25° C. for 1 hour. The reaction solution was concentrated to remove most of the solvent therefrom. Dichloromethane (100 mL) and petroleum ether (50 mL) were added, stirred for 20 minutes, and filtered. The filter cake was dried in vacuum to afford a crude product of Compound 12-3 (7.85 g). The crude product was used directly in the next reaction step without purification.

Step 4: Preparation of methyl 3-((3S,4S)-4-(tert-butoxycarbonylamino)-3-methyl-2-oxa-8-azaspiro[4.5]decan-8-yl)-6-(3-chloro-2-(3-(2-hydroxylprop-2-yl)azetidin-1-yl)pyridin-4-ylthio)pyrazine-2-carboxylate (Compound 12-4)

Compound 2-2 (5.00 g, 10.30 mmol), Compound 12-3 (5.80 g, 20.60 mmol), CuI (0.98 g, 5.15 mmol), 1,10-phenanthroline (1.02 g, 5.15 mmol), and $K_3PO_4$ (4.37 g, 20.6 mmol) were added into 1,4-dioxane (100 mL), warmed to 100° C., and reacted for 3 hours. The resultant was cooled to room temperature and filtered to remove the insoluble. The filtrate was concentrated to afford a crude product. The crude product was purified by column chromatography to afford Compound 12-4 (5.15 g, yield 71%).

Step 5: Preparation of tert-butyl (3S,4S)-8-(5-(3-(2-hydroxylprop-2-yl)azetidin-1-yl)pyridin-4-ylthio)-3-(hydroxymethyl)pyrazin-2-yl)-3-methyl-2-oxa-8-azaspiro[4.5]decan-4-ylcarbamate (Compound 12-5)

Compound 12-4 (5.15 g, 7.77 mmol) was dissolved into ethanol (80 mL), calcium chloride (3.45 g, 31.10 mmol) was added, and sodium borohydride (1.18 g, 31.10 mmol) was added in batches, slowly heated up to 35° C. and reacted for 3 hours. Water (50 mL) was slowly added. The resultant was adjusted to PH 7-8 with an aqueous solution of citric acid, concentrated to remove most of ethanol, and extracted with ethyl acetate (150 ml). The organic phase was concentrated to dryness to afford a crude product. The crude product was purified by column chromatography to afford Compound 12-5 (2.67 g, yield 51%).

Step 6: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)propan-2-ol (Compound 67)

Compound 12-5 (40 mg, 0.06 mmol) was dissolved into dichloromethane (2 mL), and TFA (4 mL) was slowly added, warmed to 30° C., and reacted for 1 hour. The resultant was concentrated to remove the solvent therefrom, thereby affording a crude product. The crude product was purified by HPLC (mobile phase A: acetonitrile, mobile phase B: 0.05% aqueous solution of formic acid) to afford Compound 67.

MS (ESI): m/z 535.2$[M+H]^+$.

$^1$H-NMR (400 MHz, DMSO-$d_6$) δ 8.31 (s, 1H), 7.79 (d, J=5.6 Hz, 1H), 6.01 (d, J=5.2 Hz, 1H), 4.51 (s, 2H), 4.14-4.02 (m, 5H), 3.75-3.62 (m, 3H), 3.53 (d, J=8.4 Hz, 1H), 3.30-3.15 (m, 2H), 3.00 (d, J=5.2 Hz, 1H), 2.62 (p, J=7.6 Hz, 1H), 1.90-1.79 (m, 1H), 1.79-1.68 (m, 1H), 1.67-1.50 (m, 2H), 1.10 (d, J=6.4 Hz, 3H), 1.05 (s, 6H).

Example 13: Preparation of (S)-2-(1-(4-(5-(4-amino-2-oxa-8-azaspiro[4.5]decan-8-yl)-6-(hydroxymethyl)pyrazin-2-ylthio)-3-chloropyridin-2-yl)azetidin-3-yl)propan-2-ol (Compound 68)

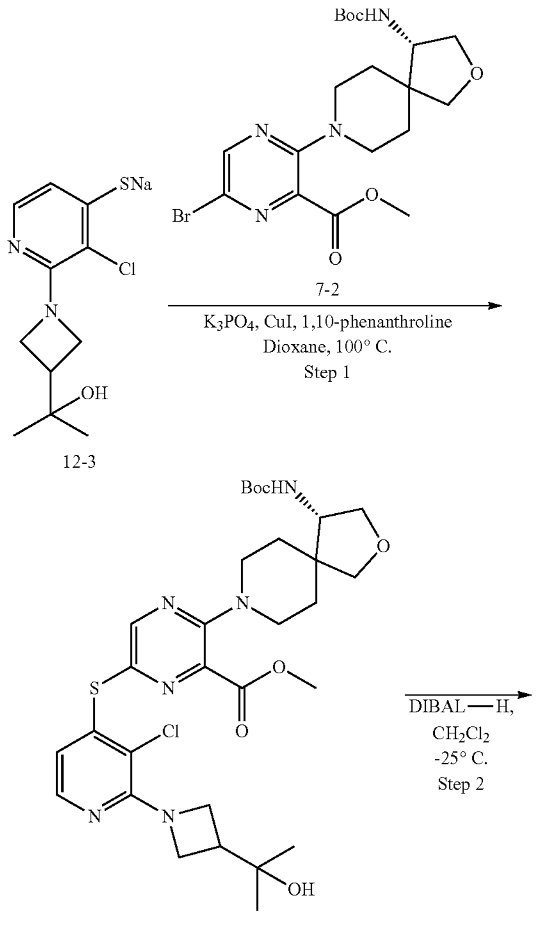

7-2

12-3

13-1

-continued

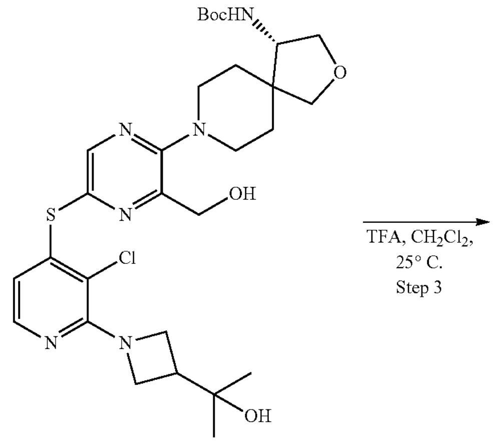

13-2

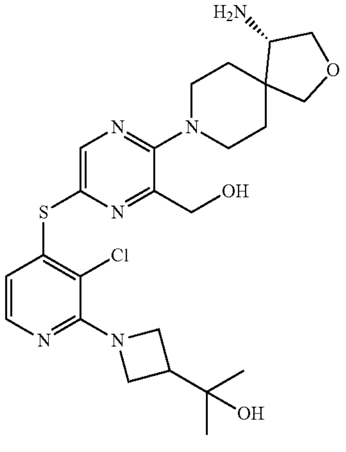

68

A crude product of Compound 68 was synthesized by similar methods described in Step 2 to Step 4 of Example 7, except that Compound 12-3 was used in Step 1 to replace Compound 1-4 in Step 2 of Example 7. The crude product was purified by Pre-TLC (MeOH/DCM=1:5, V/V) to afford Compound 68.

MS (ESI): m/z 521.2 $[M+H]^+$.

$^1$H-NMR (400 MHz, DMSO) δ 8.33 (s, 1H), 7.79 (d, J=5.2 Hz, 1H), 6.01 (d, J=5.2 Hz, 1H), 5.51 (t, J=6.0 Hz, 1H), 4.51 (d, J=5.2 Hz, 2H), 4.45 (s, 1H), 4.12-4.02 (m, 4H), 3.95 (dd, J=8.4, 6.4 Hz, 1H), 3.83-3.66 (m, 3H), 3.59 (d, J=8.4 Hz, 1H), 3.30-3.28 (m, 1H), 3.21-3.10 (m, 2H), 3.06 (t, J=6.0 Hz, 1H), 2.66-2.56 (m, 1H), 1.81-1.74 (m, 1H), 1.73-1.63 (m, 1H), 1.52-1.42 (m, 2H), 1.05 (s, 6H).

Example 14: Preparation of (S)-2-(1-(4-(5-(4-(1-amino-2-methoxyethyl)-4-methylpiperidin-1-yl)-6-(hydroxymethyl)pyrazin-2-ylthio)-3-chloropyridin-2-yl)azetidin-3-yl)propan-2-ol (Compound 69)

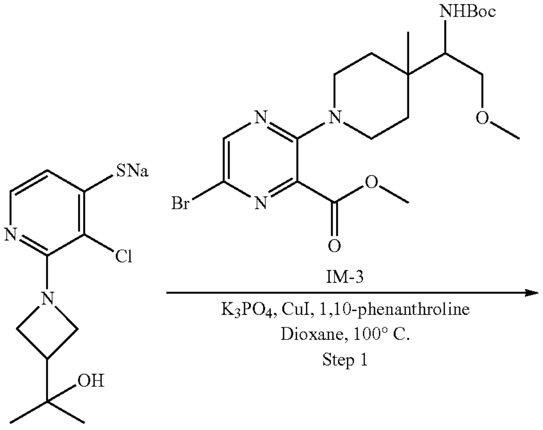

12-3

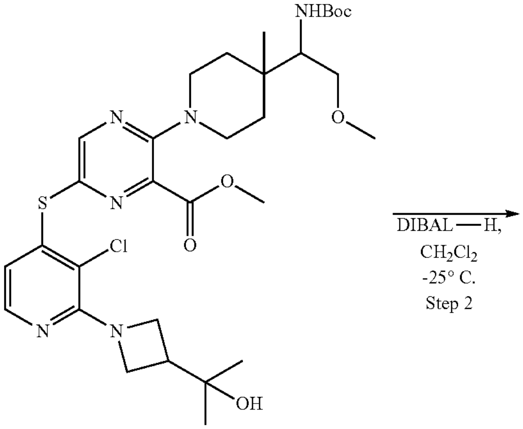

14-1

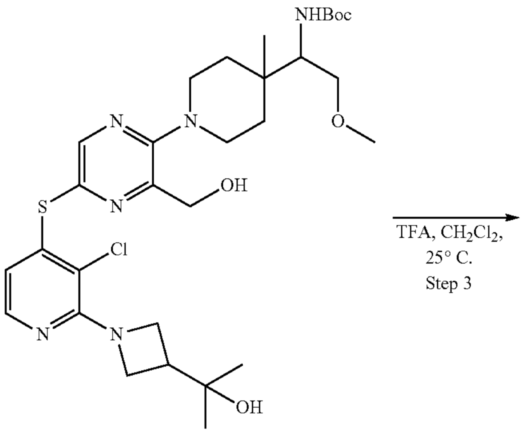

14-2

-continued

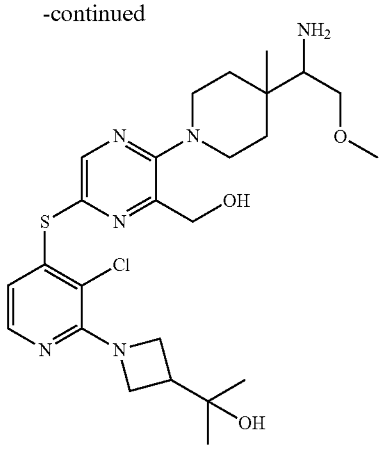

69

A crude product of Compound 69 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 69.

MS (ESI): m/z 537.2 $[M+H]^+$.

$^1$H-NMR (400 MHz, DMSO) δ 8.33 (s, 1H), 7.85 (br, 3H), 7.79 (d, J=5.6 Hz, 1H), 6.01 (d, J=5.2 Hz, 1H), 4.51 (s, 2H), 4.12-4.05 (m, 4H), 3.82-3.77 (m, 2H), 3.63 (dd, J=10.8, 3.2 Hz, 1H), 3.54-3.43 (m, 1H), 3.33 (s, 3H), 3.26-3.13 (m, 3H), 2.62 (p, J=7.6 Hz, 1H), 1.76-1.62 (m, 2H), 1.62-1.53 (m, 1H), 1.53-1.41 (m, 1H), 1.13-0.99 (m, 9H).

Example 15: Preparation of 1-((4-(5-((3S,4S)-4-amino-3-methyl-2-oxa-8-azaspiro[4.5]decan-8-yl)-6-(hydroxymethyl)pyrazin-2-ylthio)-3-chloropyridin-2-ylamino)methyl)cyclopropan-1-ol (Compound 58)

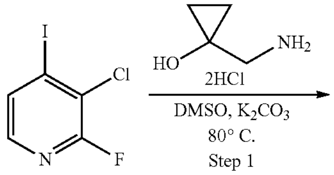

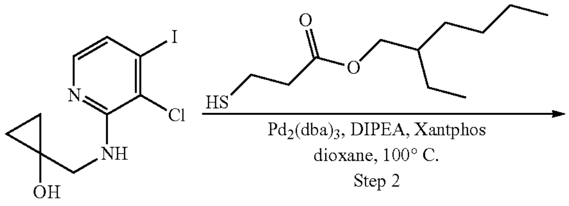

15-1

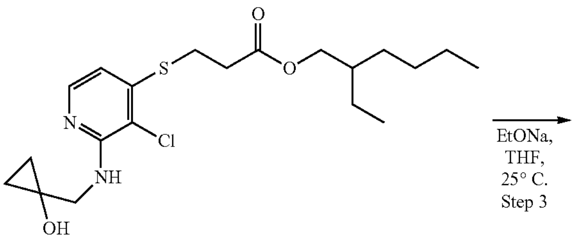

15-2

-continued

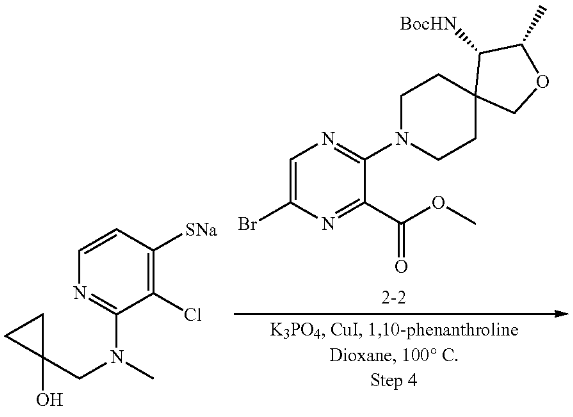

15-3

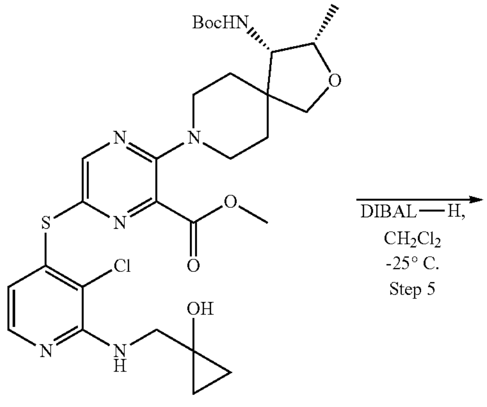

15-4

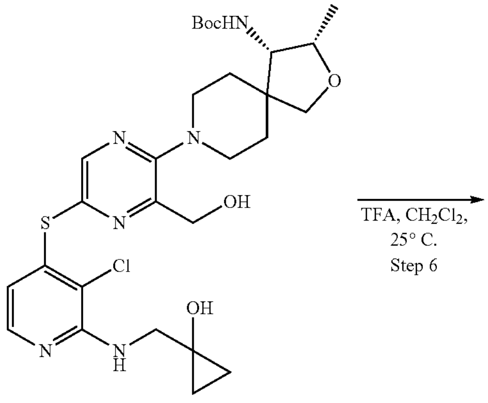

15-5

-continued

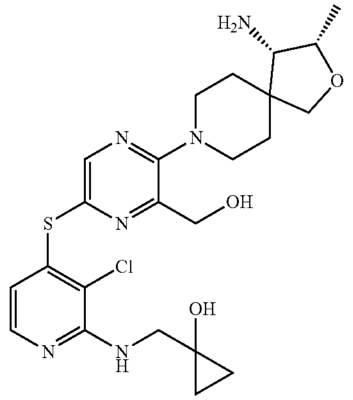

58

A crude product of Compound 58 was synthesized by similar methods described in Example 6. The crude product was purified by HPLC (mobile phase A: acetonitrile, mobile phase B: 0.05% aqueous solution of trifluoroacetic acid) to afford a trifluoroacetate salt of Compound 58.

MS (ESI): m/z 507.2 $[M+H]^+$.

$^1$H-NMR (400 MHz, $CD_3OD$): δ 8.35 (s, 1H), 7.63 (d, J=6.4 Hz, 1H), 6.24 (d, J=6.4 Hz, 1H), 4.68 (s, 2H), 4.33-4.26 (m, 1H), 4.00-3.82 (m, 4H), 3.60 (s, 2H), 3.46 (d, J=4.4 Hz, 1H), 3.27-3.14 (m, 2H), 2.01-1.67 (m, 4H), 1.32 (d, J=6.4 Hz, 3H), 0.81-0.75 (m, 2H), 0.74-0.67 (m, 2H).

Example 16: Preparation of (3-((3S,4S)-4-amino-3-methyl-2-oxa-8-azaspiro[4.5]decan-8-yl)-6-(3-chloro-2-(3-(fluoromethyl)azetidin-1-yl)pyridin-4-ylthio)pyrazin-2-yl)methanol (Compound 125)

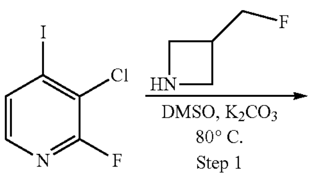

1-1

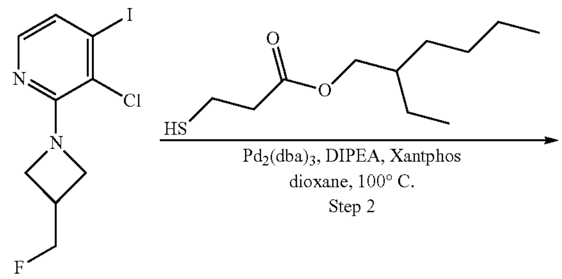

16-1

-continued

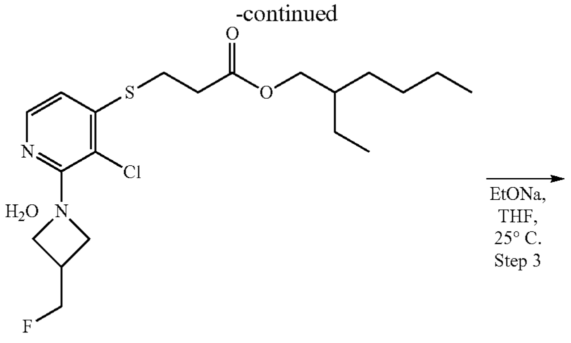

16-2

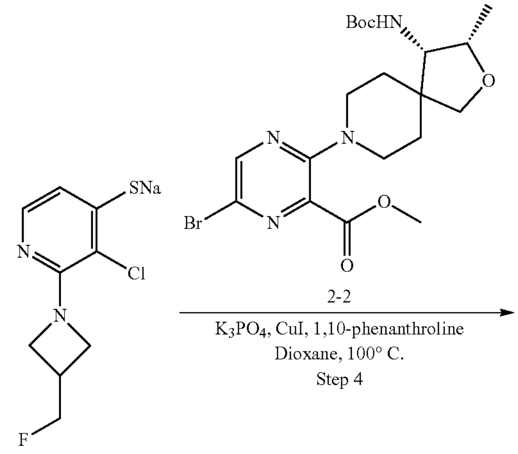

2-2

16-3

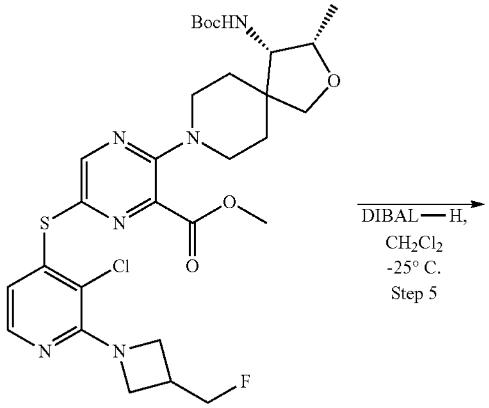

16-4

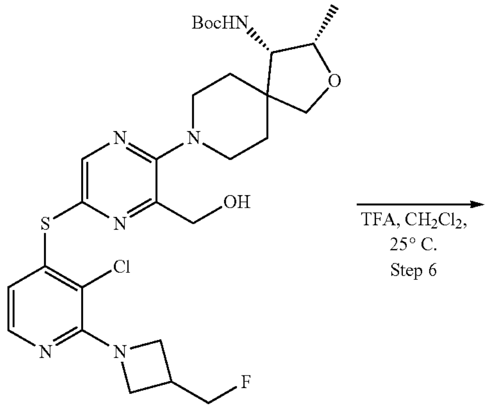

16-5

-continued

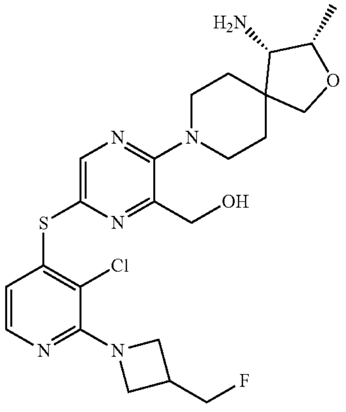

125

A crude product of Compound 125 was synthesized by similar methods described in Example 6. The crude product was purified by HPLC (mobile phase A: acetonitrile, mobile phase B: 0.05% aqueous solution of trifluoroacetic acid) to afford a trifluoroacetate salt of Compound 125.

MS (ESI): m/z 509.2 $[M+H]^+$.

$^1$H-NMR (400 MHz, DMSO-$d_6$): δ 8.35 (s, 1H), 8.02 (s, 3H), 7.82 (d, J=5.2 Hz, 1H), 6.08 (d, J=5.2 Hz, 1H), 4.68 (d, J=5.6 Hz, 1H), 4.56 (d, J=5.6 Hz, 1H), 4.52 (s, 2H), 4.30-4.17 (m, 4H), 4.00-3.78 (m, 4H), 3.70 (d, J=9.2 Hz, 1H), 3.48-3.40 (m, 1H), 3.15-2.90 (m, 3H), 1.93-1.55 (m, 4H), 1.22 (d, J=6.4 Hz, 3H).

Example 17: Preparation of 1-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)ethan-1-ol (Compound 70)

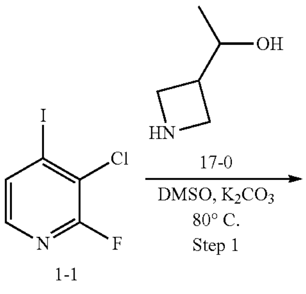

1-1

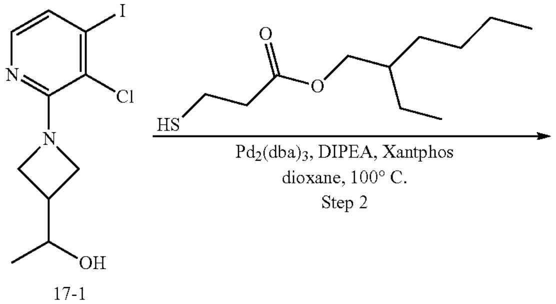

17-1

-continued

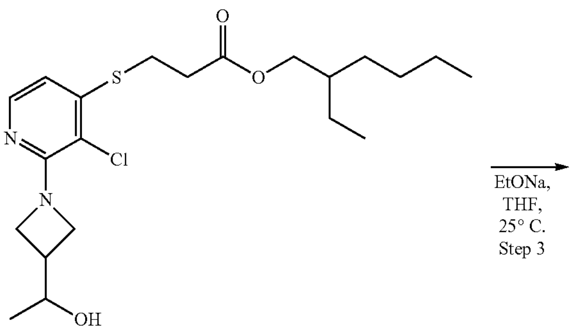

17-2

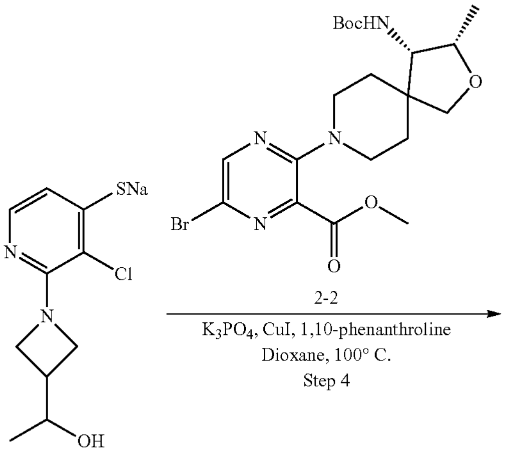

17-3

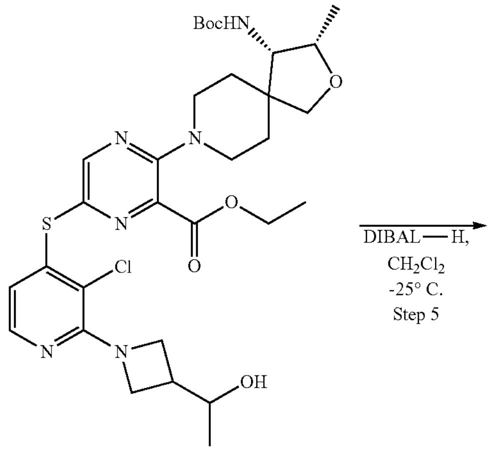

17-4

-continued

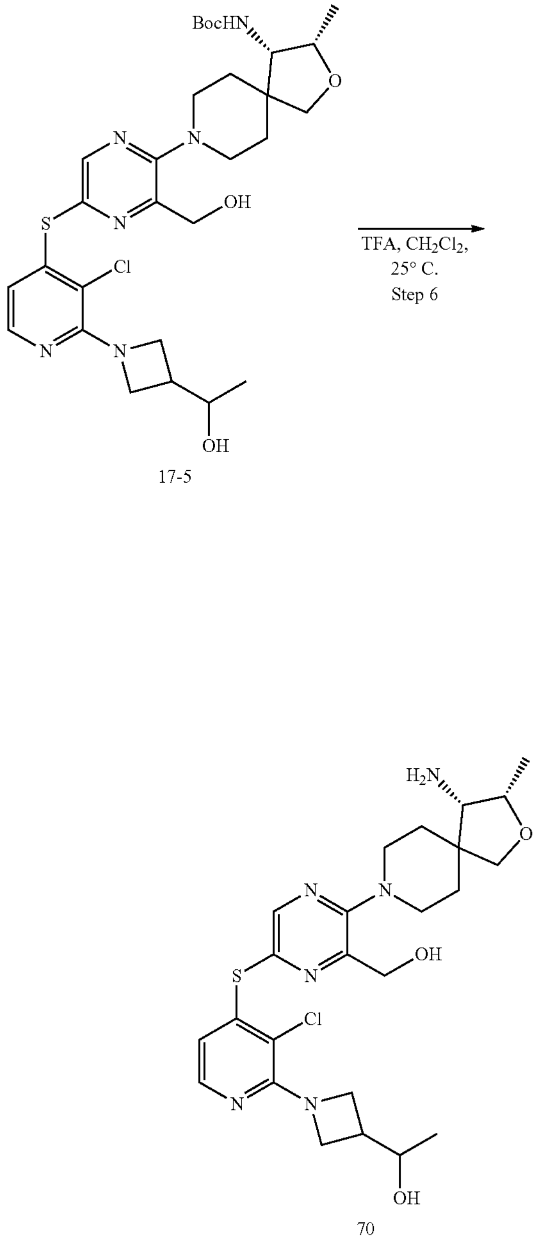

17-5

70

A crude product of Compound 70 was synthesized by similar methods described in Example 6. The crude product was purified by HPLC (mobile phase A: acetonitrile, mobile phase B: 0.05% aqueous solution of trifluoroacetic acid) to afford a trifluoroacetate salt of Compound 70.

MS (ESI): m/z 521.3 $[M+H]^+$.

$^1$H-NMR (400 MHz, DMSO-$d_6$): δ 8.34 (s, 1H), 7.95 (s, 3H), 7.80 (d, J=5.6 Hz, 1H), 6.03 (d, J=5.6 Hz, 1H), 4.52 (s, 2H), 4.25-4.18 (m, 1H), 4.17-4.10 (m, 2H), 4.08-4.01 (m, 1H), 3.90-3.45 (m, 7H), 3.15-3.01 (m, 2H), 2.57-2.52 (m, 1H), 1.92-1.55 (m, 4H), 1.22 (d, J=6.4 Hz, 3H), 1.02 (d, J=6.4 Hz, 3H).

Example 18: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)pyrrolidin-2-yl)acetonitrile (Compound 5)

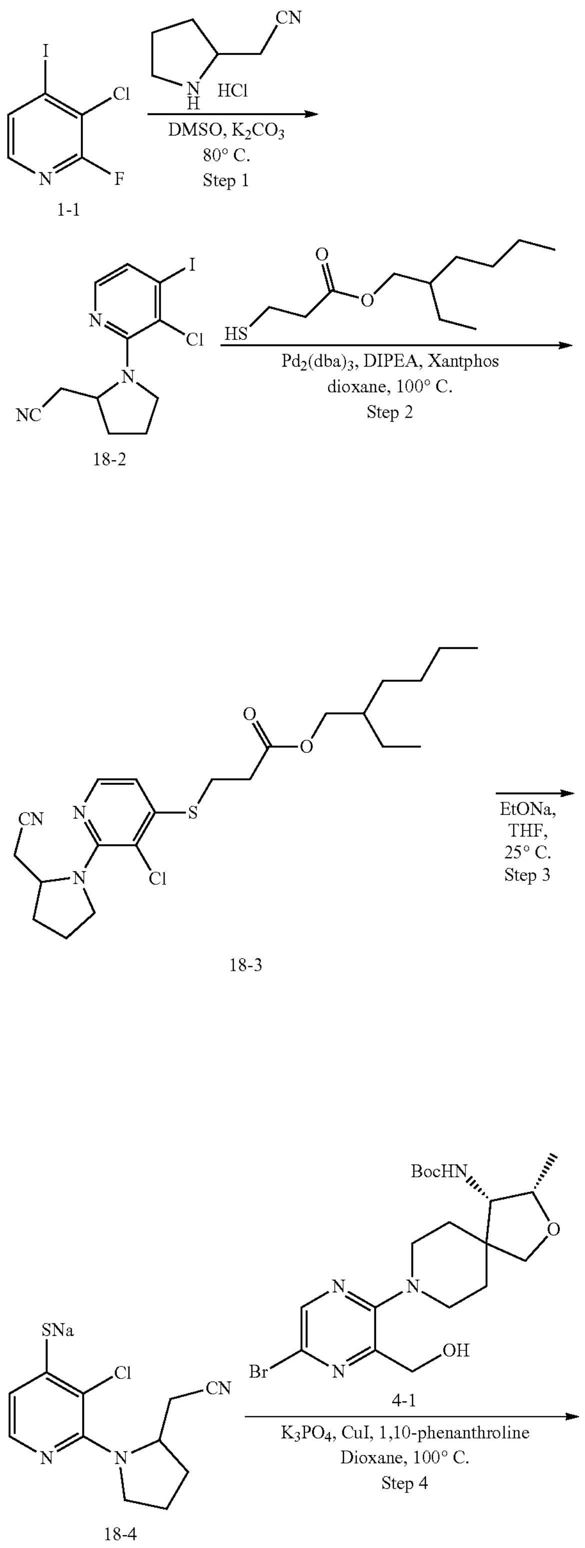

1-1

18-2

18-3

18-4

4-1

-continued

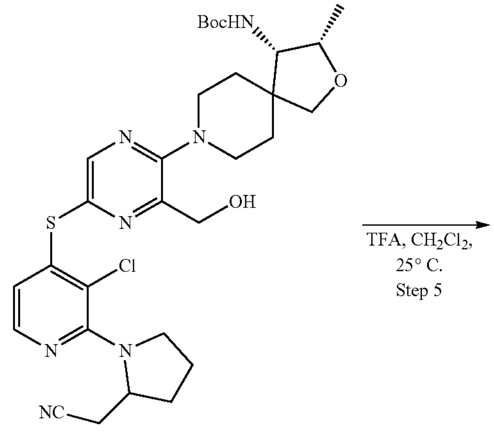

18-5

Example 19: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)pyrrolidin-2-yl)acetamide (Compound 4)

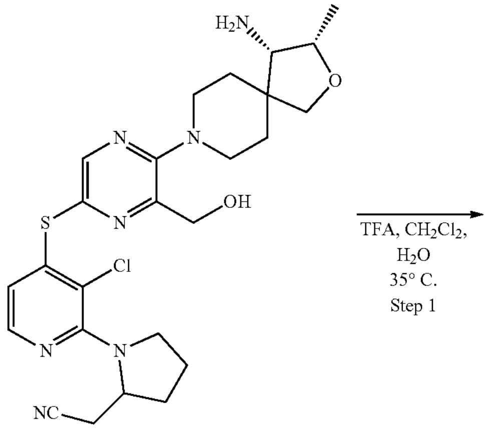

5

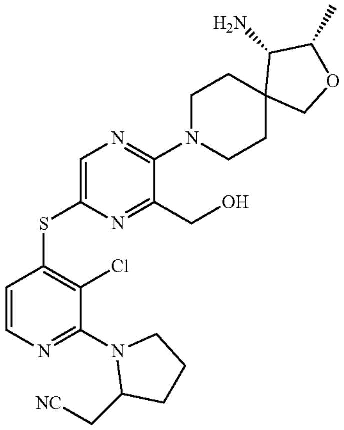

5

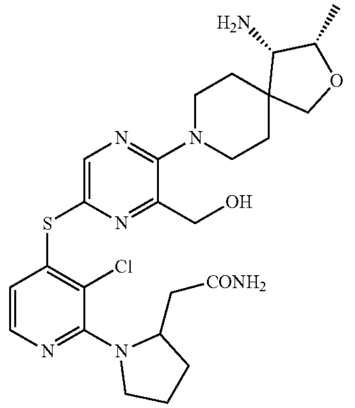

4

A crude product of Compound 5 was synthesized by similar methods described in Example 5. The crude product was purified by HPLC (mobile phase A: acetonitrile, mobile phase B: 0.05% aqueous solution of trifluoroacetic acid) to afford a trifluoroacetate salt of Compound 5.

MS (ESI): m/z 530.2 $[M+H]^+$.

$^1$H-NMR (400 MHz, DMSO-$d_6$): δ 8.37 (s, 1H), 7.98 (s, 3H), 7.88 (d, J=5.2 Hz, 1H), 6.18 (d, J=5.2 Hz, 1H), 4.52 (s, 2H), 4.45-4.44 (m, 1H), 4.24-4.18 (m, 1H), 3.97-3.81 (m, 4H), 3.70 (d, J=9.2 Hz, 1H), 3.43-3.37 (m, 2H), 3.14-3.04 (m, 2H), 2.89-2.78 (m, 2H), 2.22-2.16 (m, 1H), 2.06-1.95 (m, 1H), 1.89-1.74 (m, 5H), 1.63-1.59 (m, 1H), 1.20 (t, J=6.4 Hz, 3H).

Compound 5 (20 mg, 37.73 μmol) was dissolved into a mixture of dichloromethane (1 mL), water (0.5 mL), and TFA (80 mg, 0.69 mmol) and reacted at 35° C. for 2 hours. The reaction solution was concentrated to remove the solvent therefrom, thereby affording a crude product. The crude product was purified by HPLC (mobile phase A: acetonitrile, mobile phase B: 0.05% aqueous solution of trifluoroacetic acid) to afford a trifluoroacetate salt of Compound 4 (7.20 mg, yield 30%).

MS (ESI): m/z 548.1 $[M+H]^+$.

$^1$H-NMR (400 MHz, DMSO-$d_6$): δ 8.36 (s, 1H), 7.94 (s, 3H), 7.86 (d, J=5.2 Hz, 1H), 7.23 (s, 1H), 6.79 (s, 1H), 6.10 (d, J=5.2 Hz, 1H), 4.59-4.49 (m, 3H), 4.25-4.18 (m, 1H), 3.90-3.79 (m, 3H), 3.76-3.69 (m, 3H), 3.46-3.44 (m, 1H), 3.36-3.32 (m, 1H), 3.14-3.04 (m, 2H), 2.55 (dd, J=14.0, 3.6 Hz, 1H), 2.13-2.09 (m, 1H), 1.95-1.81 (m, 3H), 1.67-1.59 (m, 4H), 1.22 (d, J=6.4 Hz, 3H).

Example 20: Preparation of (R)-2-(1-(4-(5-(3-amino-5-fluoro-3H-spiro[benzofuran-2,4'-piperidin]-1'-yl)-6-(hydroxymethyl)pyrazin-2-ylthio)-3-chloropyridin-2-yl)azetidin-3-yl)propan-2-ol (Compound 97)

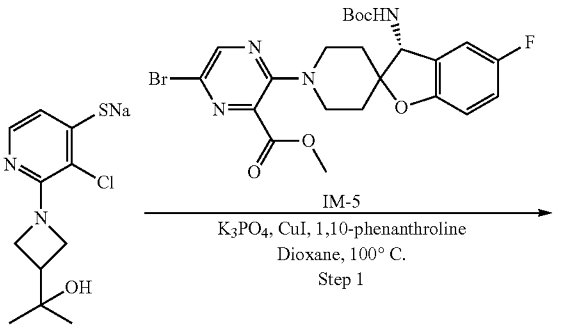

12-3

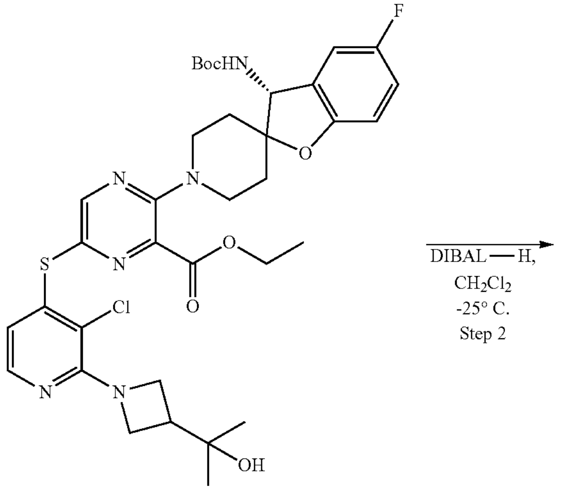

20-1

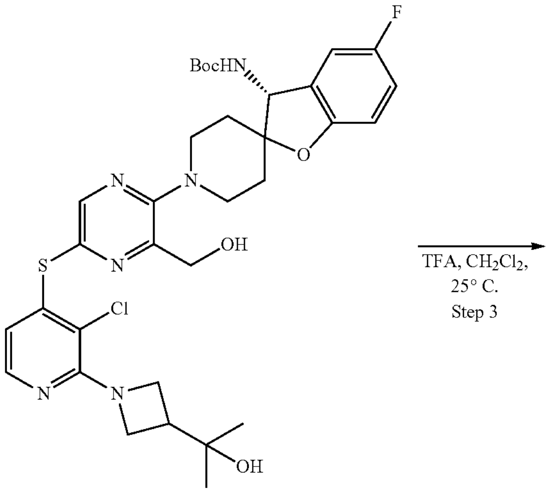

20-2

-continued

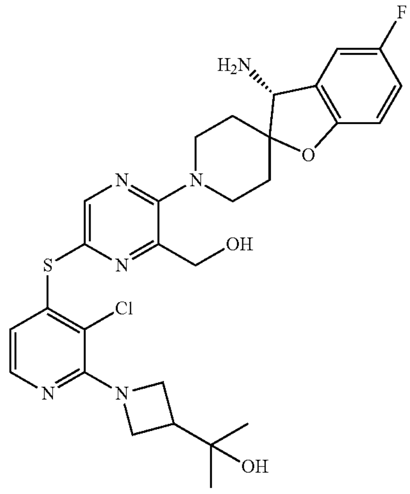

97

A crude product of Compound 97 was synthesized by similar methods described in Example 13. The crude product was purified by HPLC (mobile phase A: acetonitrile, mobile phase B: 0.050% aqueous solution of trifluoroacetic acid) to afford a trifluoroacetate salt of Compound 97.

MS (ESI): m/z 586.9 $[M+H]^+$.

$^1$H-NMR (400 MHz, DMSO-$d_6$): δ 8.54 (s, 3H), 8.38 (s, 1H), 7.80 (d, J=5.6 Hz, 1H), 7.38 (dd, J=8.0, 2.8 Hz, 1H), 7.23 (td, J=8.8, 4.4 Hz, 1H), 7.01 (dd, J=8.8, 4.4 Hz, 1H), 6.05 (d, J=5.6 Hz, 1H), 4.77-4.69 (m, 1H), 4.56 (s, 2H), 4.20-4.02 (m, 5H), 3.98-3.85 (m, 2H), 3.41-3.27 (m, 2H), 2.70-2.57 (m, 1H), 2.16 (t, J=13.2, 4.4 Hz, 1H), 2.07-1.76 (m, 3H), 1.05 (s, 6H).

Example 21: Preparation of (3-((3S,4S)-4-amino-3-methyl-2-oxa-8-azaspiro[4.5]decan-8-yl)-6-(3-chloro-2-(3-(methoxymethyl)azetidin-1-yl)pyridin-4-ylthio)pyrazin-2-yl)methanol (Compound 71)

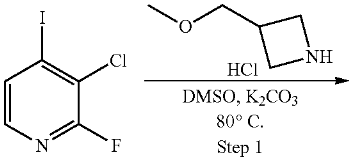

1-1

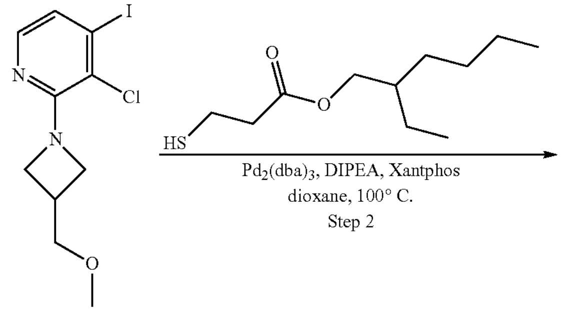

21-1

-continued

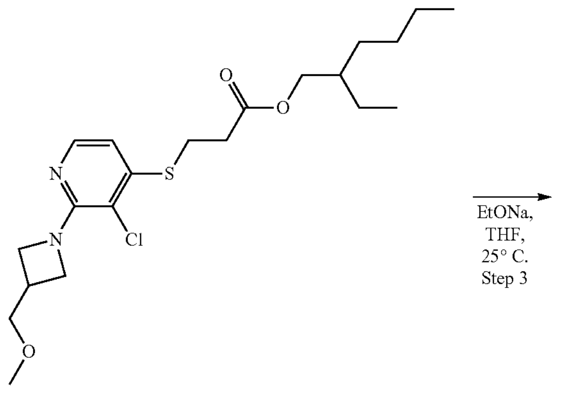

21-2

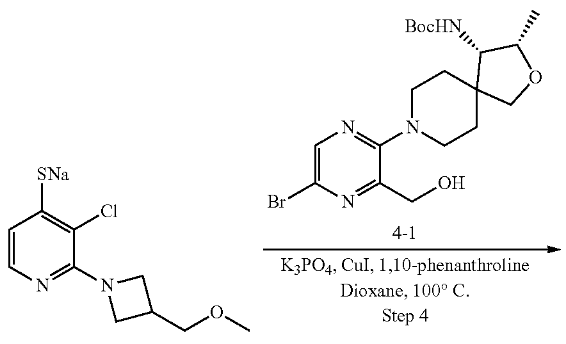

4-1

21-3

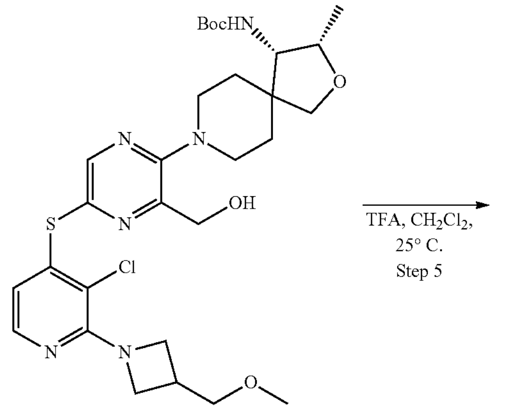

21-4

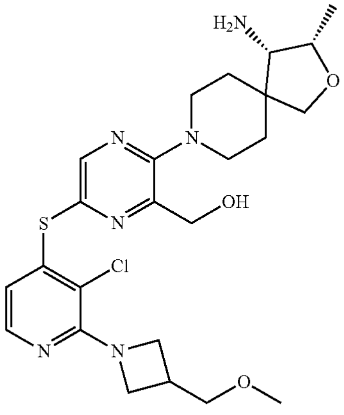

71

A crude product of Compound 71 was synthesized by similar methods described in Example 5. The crude product was purified by HPLC (mobile phase A: acetonitrile, mobile phase B: 0.05% aqueous solution of trifluoroacetic acid) to afford a trifluoroacetate salt of Compound 71.

MS (ESI): m/z 521.2 $[M+H]^+$.

$^1$H-NMR (400 MHz, DMSO-d$_6$): δ 8.33 (s, 1H), 7.99 (s, 3H), 7.80 (d, J=5.6 Hz, 1H), 6.06 (d, J=5.2 Hz, 1H), 4.52 (s, 2H), 4.24-4.20 (m, 3H), 3.92-3.85 (m, 4H), 3.71-3.69 (s, 2H), 3.51 (d, J=6.8 Hz, 2H), 3.45-3.41 (m, 1H), 3.28 (s, 3H), 3.14-3.03 (m, 2H), 2.89-2.81 (m, 1H), 1.88-1.83 (m, 2H), 1.76-1.73 (m, 1H), 1.63-1.60 (m, 1H), 1.22 (d, J=6.8 Hz, 3H).

Example 22: Preparation of (R)-2-(1-(4-(5-(3-amino-3H-spiro[benzofuran-2,4'-piperidin]-1'-yl)-6-(hydroxymethyl)pyrazin-2-ylthio)-3-chloropyridin-2-yl)azetidin-3-yl)propan-2-ol (Compound 72)

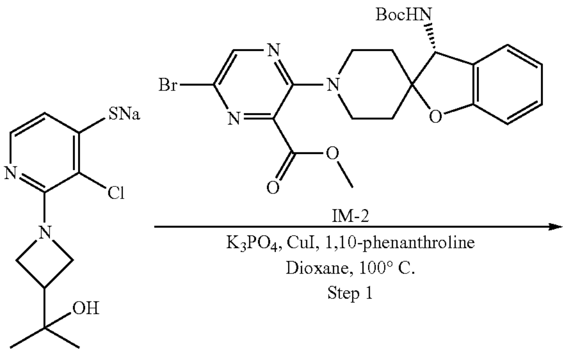

IM-2

12-3

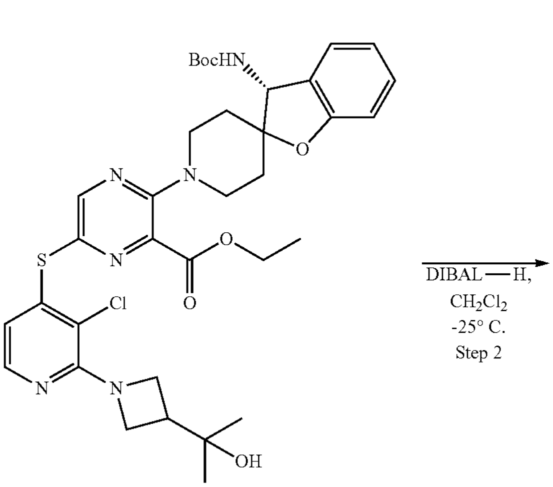

22-1

-continued

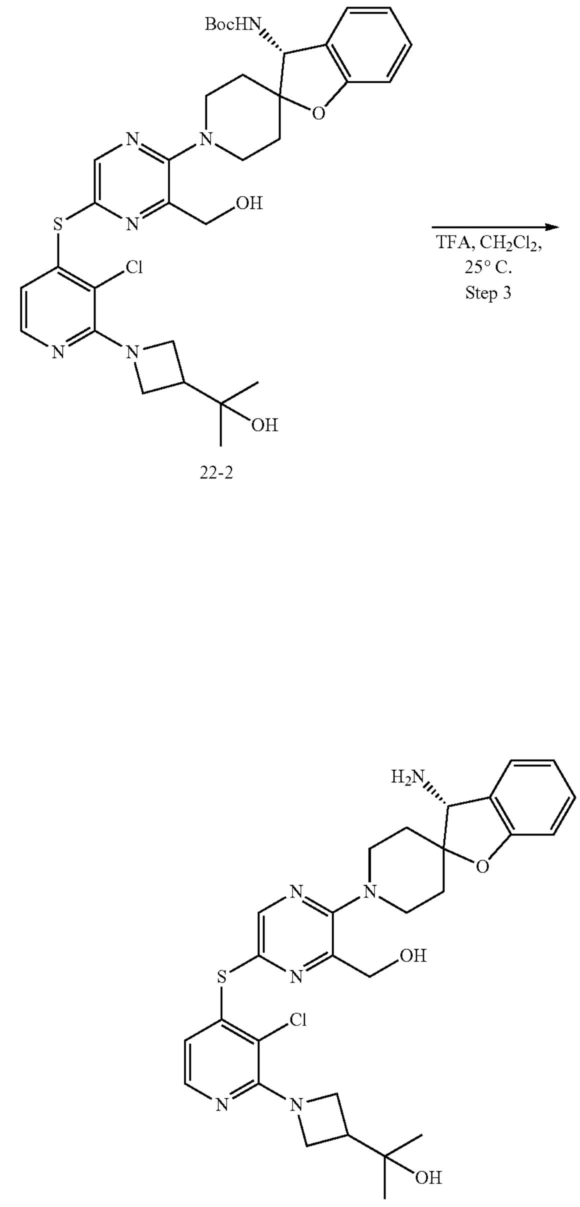

22-2

72

A crude product of Compound 72 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 72.

MS (ESI): m/z 569.2 $[M+H]^+$.

$^1$H-NMR (400 MHz, DMSO-$d_6$): δ 8.44 (s, 3H), 8.38 (s, 1H), 7.80 (d, J=5.4 Hz, 1H), 7.57 (d, J=7.4 Hz, 1H), 7.38 (t, J=7.4 Hz, 1H), 7.02 (dd, J=16.4, 8.0 Hz, 2H), 6.05 (d, J=5.4 Hz, 1H), 4.73-4.68 (m, 1H), 4.56 (s, 2H), 4.10 (d, J=7.6 Hz, 4H), 3.97-3.92 (m, 1H), 3.45-3.43 (m, 2H), 3.33-3.30 (m, 1H), 2.66-2.60 (m, 1H), 2.21-2.12 (m, 1H), 2.05-1.89 (m, 2H), 1.82-1.77 (m, 1H), 1.05 (s, 6H).

Example 23: Preparation of (S)-2-(1-(4-(5-(1-amino-1,3-dihydrospiro[indene-2,4'-piperidin]-1'-yl)-6-(hydroxymethyl)pyrazin-2-ylthio)-3-chloro-pyridin-2-yl)azetidin-3-yl)propan-2-ol (Compound 73)

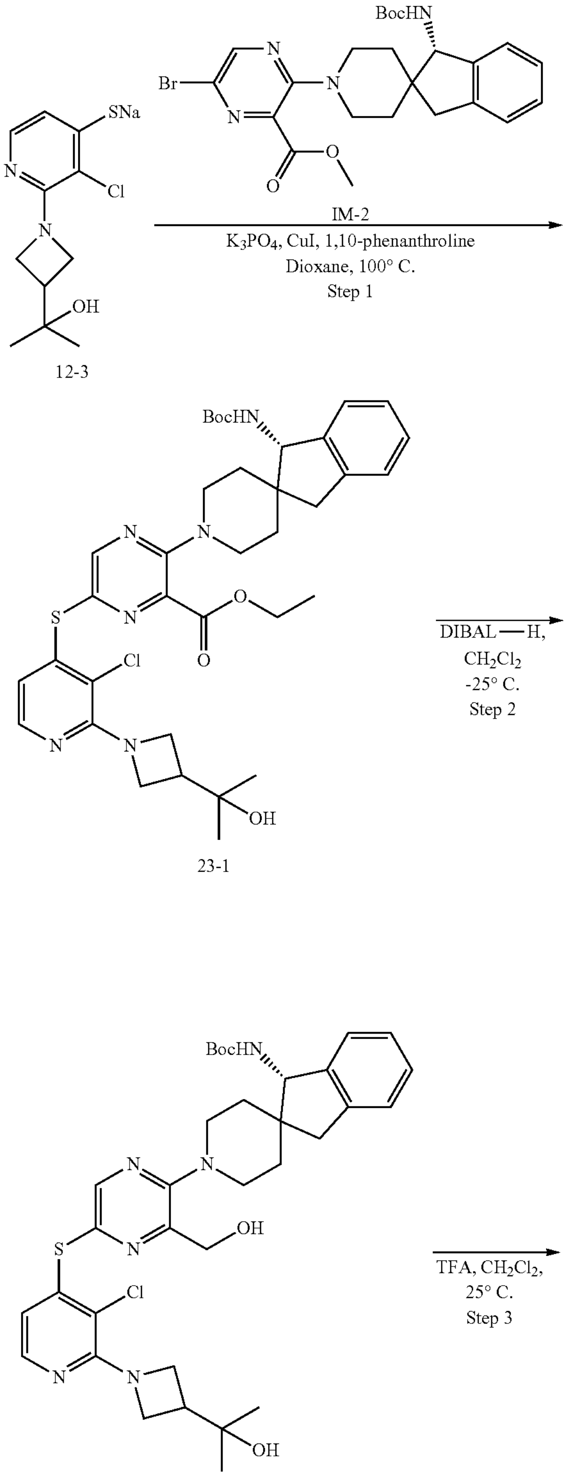

12-3

23-1

23-2

-continued

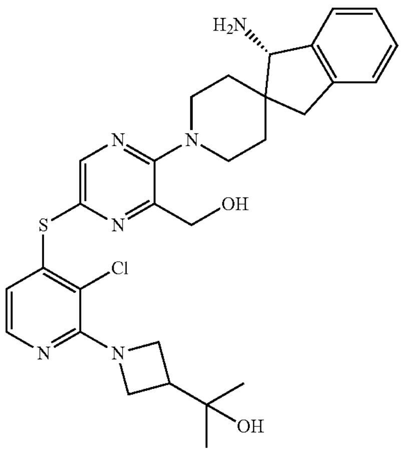

73

A crude product of Compound 73 was synthesized by similar methods described in Example 13. The crude product was purified by HPLC (mobile phase A: acetonitrile, mobile phase B: 0.050% aqueous solution of trifluoroacetic acid) to afford a trifluoroacetate salt of Compound 73.

MS (ESI): m/z 567.3 $[M+H]^+$.

$^1$H-NMR (400 MHz, DMSO-$d_6$): δ 8.35 (s, 1H), 8.23 (s, 3H), 7.80 (d, J=5.4 Hz, 1H), 7.51 (d, J=7.2 Hz, 1H), 7.40-7.29 (m, 3H), 6.03 (d, J=5.6 Hz, 1H), 4.54 (s, 2H), 4.44-4.40 (m, 1H), 4.08 (d, J=7.6 Hz, 4H), 4.01-3.95 (m, 1H), 3.87-3.84 (s, 1H), 3.29-3.19 (m, 2H), 3.17-3.13 (m, 1H), 3.04-3.00 (m, 1H), 2.65-2.58 (m, 1H), 1.89-1.80 (m, 2H), 1.61-1.51 (m, 2H), 1.05 (s, 6H).

Example 24: Preparation of 2-(1-(4-(5-(4-(1-aminoethyl)-4-methylpiperidin-1-yl)-6-(hydroxymethyl) pyrazin-2-ylthio)-3-chloropyridin-2-yl)azetidin-3-yl) propan-2-ol (Compound 74)

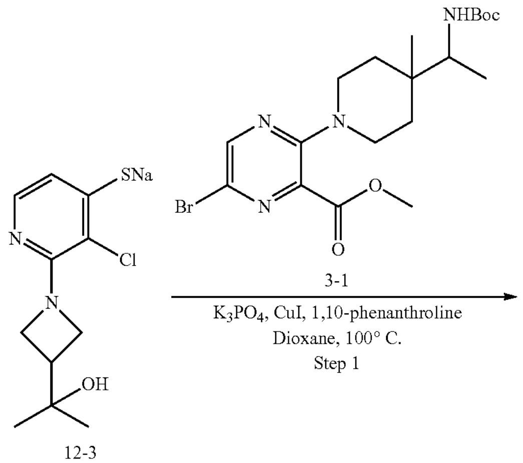

12-3, 3-1

-continued

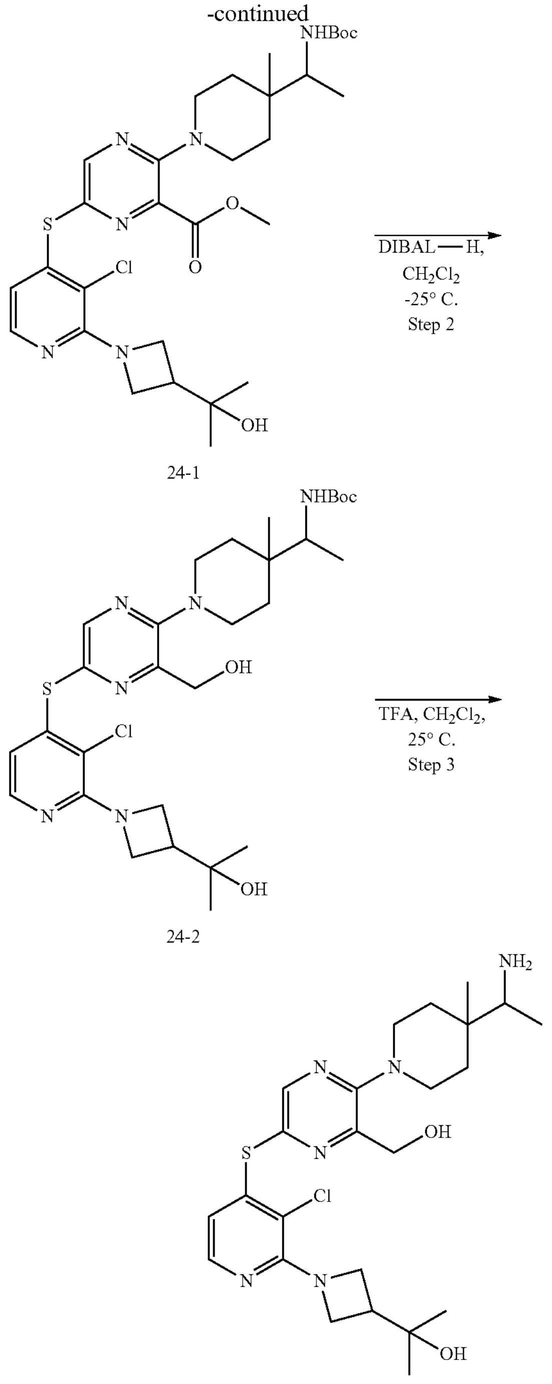

24-1, 24-2, 74

A crude product of Compound 74 was synthesized by similar methods described in Example 13. The crude product was purified by HPLC (mobile phase A: acetonitrile, mobile phase B: 0.050% aqueous solution of trifluoroacetic acid) to afford a trifluoroacetate salt of Compound 74.

MS (ESI): m/z 507.2 $[M+H]^+$.

$^1$H-NMR (400 MHz, DMSO-$d_6$): δ 8.33 (s, 1H), 7.79 (d, J=5.2 Hz, 1H), 7.69 (s, 3H), 6.01 (d, J=5.2 Hz, 1H), 4.51 (s, 2H), 4.08 (d, J=7.6 Hz, 4H), 3.85-3.78 (m, 2H), 3.25-3.10 (m, 3H), 2.64-2.58 (m, 1H), 1.69-1.53 (m, 3H), 1.44-1.41 (m, 1H), 1.14 (d, J=6.8 Hz, 3H), 1.05 (s, 6H), 1.01 (s, 3H).

Example 25: Preparation of (3-((3S,4S)-4-amino-3-methyl-2-oxa-8-azaspiro[4.5]decan-8-yl)-6-(3-chloro-2-(3-(methylsulfonylmethyl)azetidin-1-yl)pyridin-4-ylthio)-5-methylpyrazin-2-yl)methanol (Compound 75)

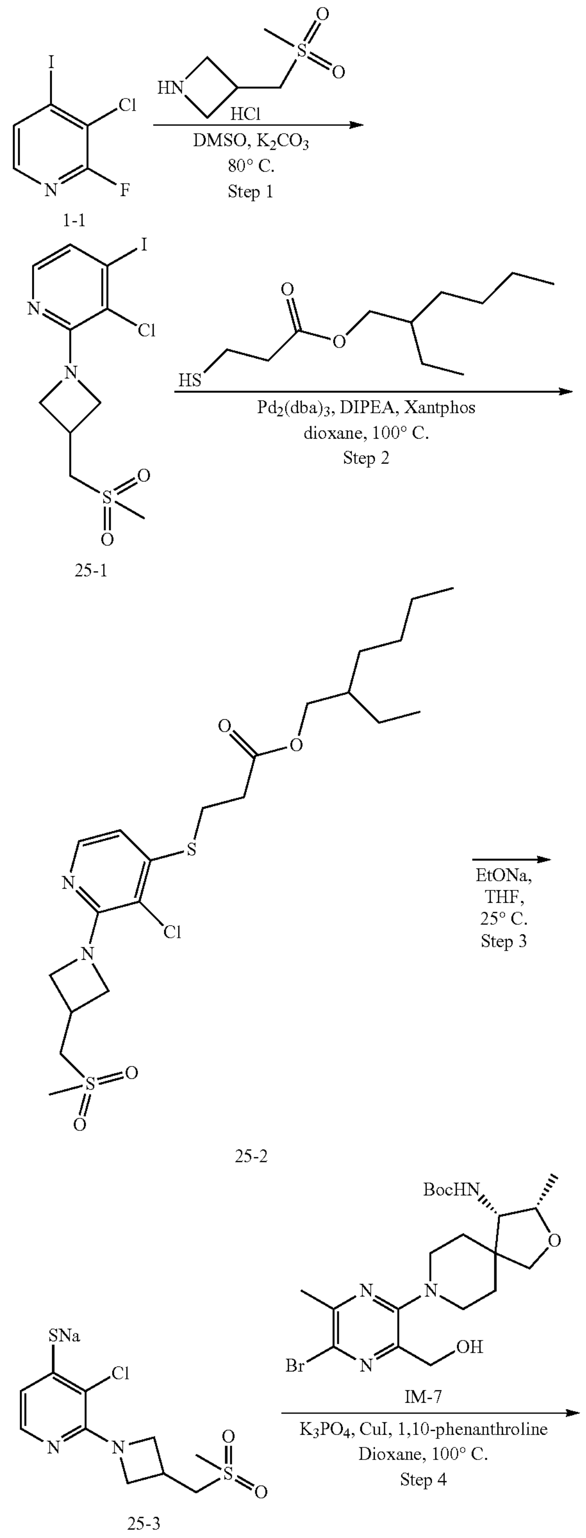

-continued

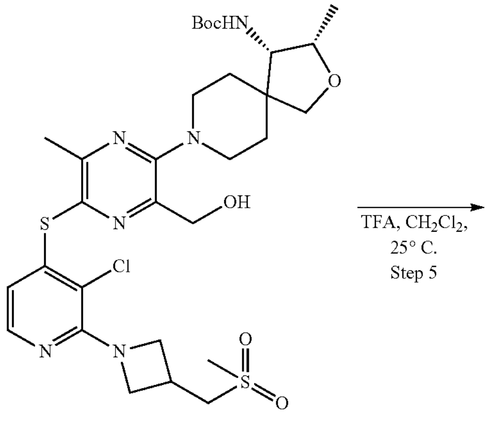

25-4

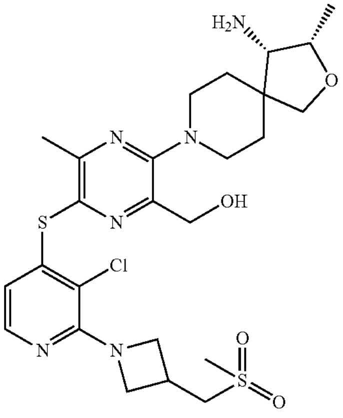

75

A crude product of Compound 75 was synthesized by similar methods described in Example 5. The crude product was purified by HPLC (mobile phase A: acetonitrile, mobile phase B: 0.05% aqueous solution of trifluoroacetic acid) to afford a trifluoroacetate salt of Compound 75.

MS (ESI): m/z 583.1 $[M+H]^+$.

$^1$H-NMR (400 MHz, CD3OD): δ 7.64-7.58 (m, 1H), 6.11-6.08 (m, 1H), 4.72-4.60 (m, 4H), 4.41-4.27 (m, 3H), 4.01-3.83 (m, 4H), 3.58 (d, J=7.6 Hz, 2H), 3.45 (d, J=4.0 Hz, 1H), 3.41-3.33 (m, 1H), 3.21-3.06 (m, 2H), 3.01 (s, 3H), 2.48 (s, 3H), 2.03-1.87 (m, 3H), 1.74-1.71 (m, 1H), 1.32 (d, J=6.4 Hz, 3H).

Example 26: Preparation of (3-((3S,4S)-4-amino-3-methyl-2-oxa-8-azaspiro[4.5]decan-8-yl)-6-(3-chloro-2-(3-(methylsulfonylmethyl)azetidin-1-yl)pyridin-4-ylthio)pyrazin-2-yl)methanol (Compound 76)

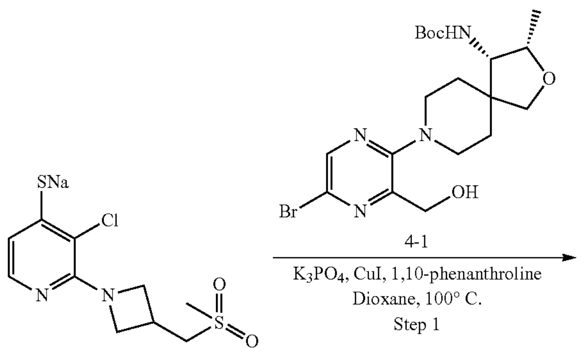

25-3

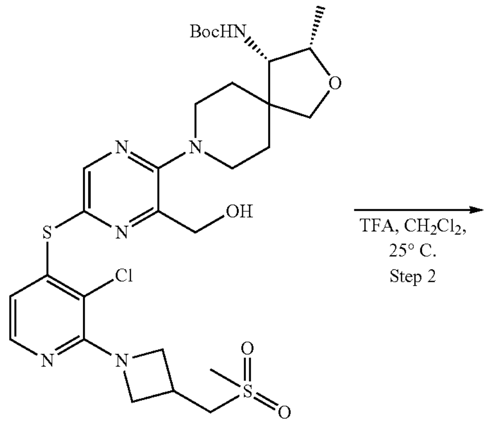

26-1

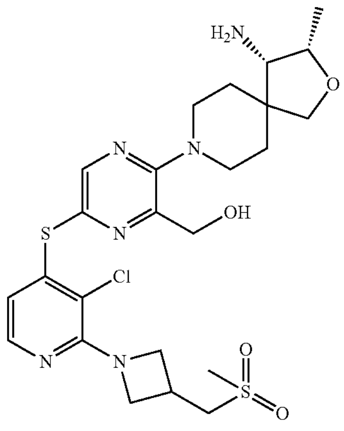

76

A crude product of Compound 76 was synthesized by similar methods described in Step 4 and Step 5 of Example 5. The crude product was purified by HPLC (mobile phase A: acetonitrile, mobile phase B: 0.05% aqueous solution of trifluoroacetic acid) to afford a trifluoroacetate salt of Compound 76.

MS (ESI): m/z 569.0 $[M+H]^+$.

$^1$H-NMR (400 MHz, $CD_3OD$): δ 8.32 (s, 1H), 7.66 (d, J=6.0 Hz, 1H), 6.22 (d, J=6.0 Hz, 1H), 4.66 (s, 2H), 4.62-4.58 (m, 2H), 4.32-4.25 (m, 3H), 3.97-3.84 (m, 4H), 3.56 (d, J=7.6 Hz, 2H), 3.45 (d, J=4.0 Hz, 1H), 3.38-3.32 (m, 1H), 3.20-3.07 (m, 2H), 3.00 (s, 3H), 1.99-1.88 (m, 3H), 1.77-1.68 (m, 1H), 1.31 (d, J=6.5 Hz, 3H).

Example 27: Preparation of (3-((3S,4S)-4-amino-3-methyl-2-oxa-8-azaspiro[4.5]decan-8-yl)-6-(3-chloro-2-(3-(hydroxymethyl)-3-methylazetidin-1-yl)pyridin-4-ylthio)pyrazin-2-yl)methanol (Compound 77)

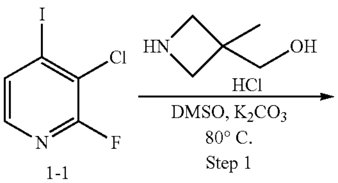

1-1

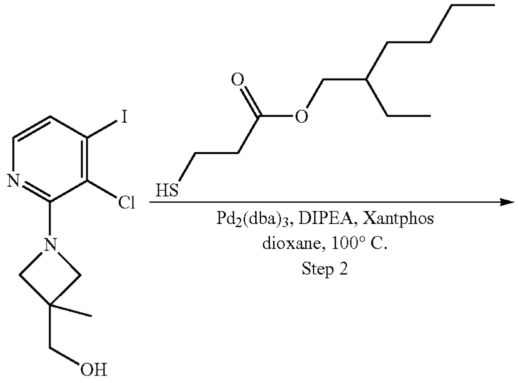

27-1

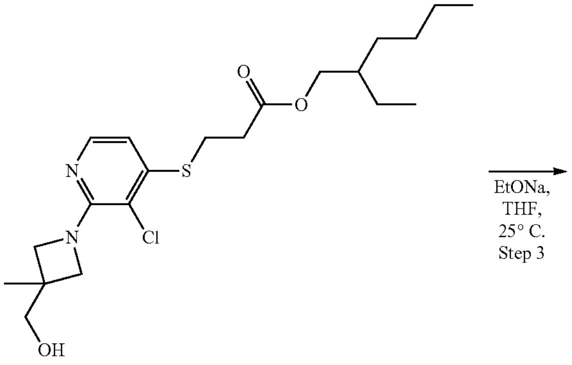

27-2

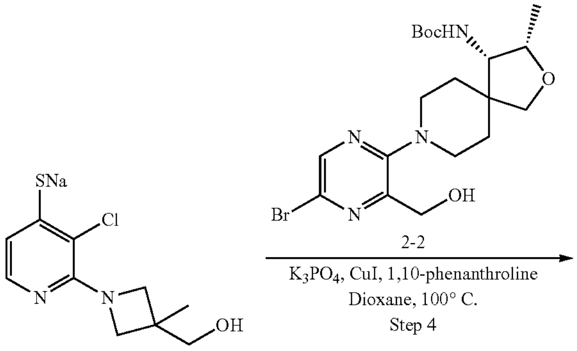

27-3

-continued

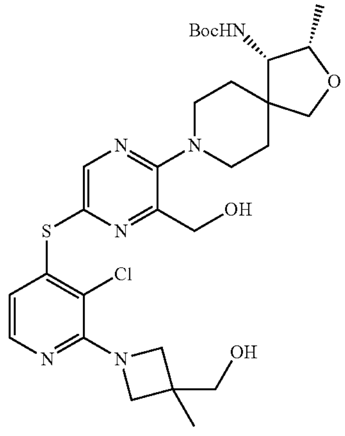

27-4

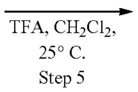

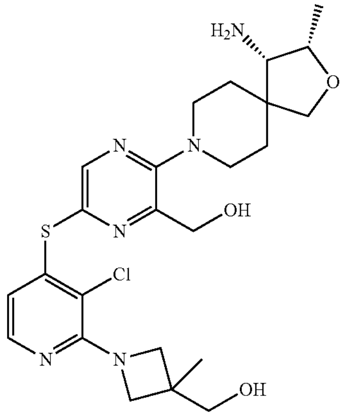

77

A crude product of Compound 77 was synthesized by similar methods described in Example 5. The crude product was purified by HPLC (mobile phase A: acetonitrile, mobile phase B: 0.05% aqueous solution of trifluoroacetic acid) to afford a trifluoroacetate salt of Compound 77.

MS (ESI): m/z 521.1 $[M+H]^+$.

$^1$H-NMR (400 MHz, DMSO-$d_6$): δ 8.34 (s, 1H), 7.95 (s, 3H), 7.79 (d, J=5.6 Hz, 1H), 6.03 (d, J=5.2 Hz, 1H), 4.52 (s, 2H), 4.25-4.16 (m, 1H), 4.03-4.00 (m, 2H), 3.93-3.81 (m, 3H), 3.76-3.73 (m, 2H), 3.71-3.68 (m, 1H), 3.48-3.40 (m, 3H), 3.13-3.03 (m, 2H), 1.88-1.76 (m, 2H), 1.76-1.71 (m, 1H), 1.65-1.55 (m, 1H), 1.22-1.21 (m, 6H).

Example 28: Preparation of 2-(1-(4-(5-((3S,4S)-4-amino-3-methyl-2-oxa-8-azaspiro[4.5]decan-8-yl)pyrazin-2-ylthio)-3-chloropyridin-2-yl)azetidin-3-yl)propan-2-ol (Compound 78)

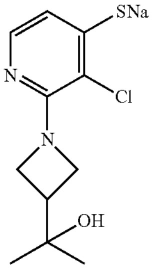

12-3

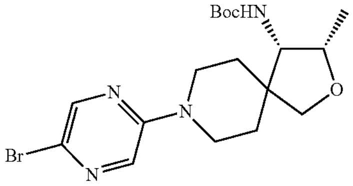

IM-6

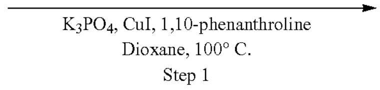

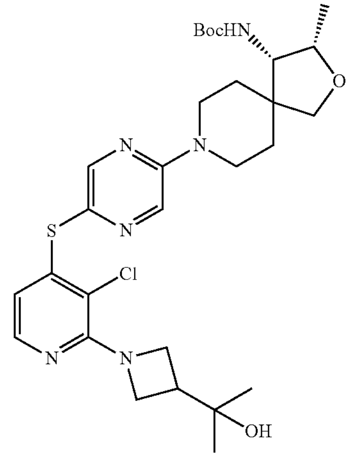

28-1

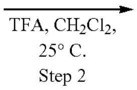

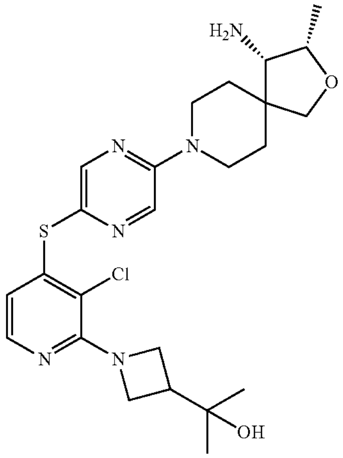

78

A crude product of Compound 78 was synthesized by similar methods described in Step 4 and Step 5 of Example 5. The crude product was purified by HPLC (mobile phase A: acetonitrile, mobile phase B: 0.05% aqueous solution of formic acid) to afford Compound 78.

MS (ESI): m/z 505.1 $[M+H]^+$.

$^1$H-NMR (400 MHz, DMSO-$d_6$): δ 8.48 (s, 1H), 8.29 (s, 1H), 8.24 (s, 1H), 7.78 (d, J=5.2 Hz, 1H), 5.92 (d, J=5.2 Hz, 1H), 4.12-4.03 (m, 5H), 4.00-3.95 (m, 2H), 3.75-3.70 (m, 1H), 3.55-3.53 (m, 1H), 3.37-3.34 (m, 2H), 3.05-3.00 (m, 1H), 2.65-2.58 (m, 1H), 1.79-1.50 (m, 4H), 1.12 (d, J=6.4 Hz, 3H), 1.05 (s, 6H).
Example 29: Preparation of (3-((3S,4S)-4-amino-3-methyl-2-oxa-8-azaspiro[4.5]decan-8-yl)-6-(3-chloro-2-(3-methyl-3-(methylsulfonylmethyl)azetidin-1-yl)pyridin-4-ylthio)pyrazin-2-yl)methanol (Compound 79)
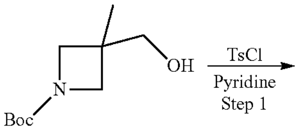
29-1
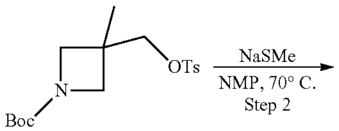
29-2
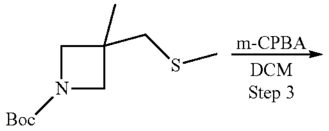
29-3
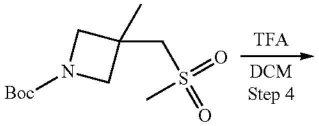
29-4
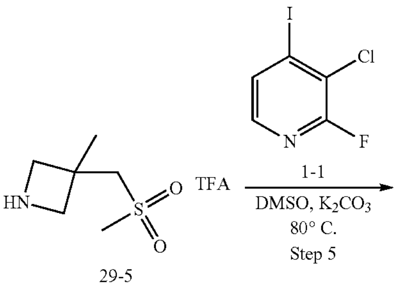
29-5
1-1
-continued
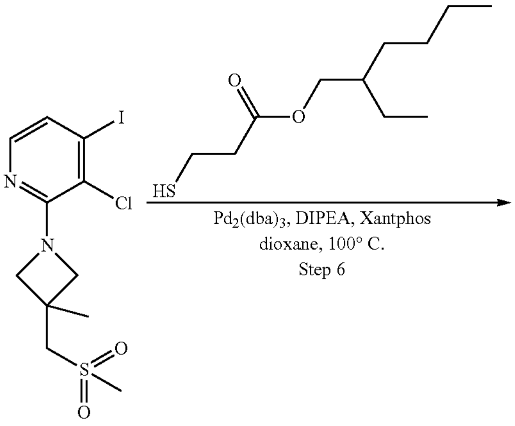
29-6
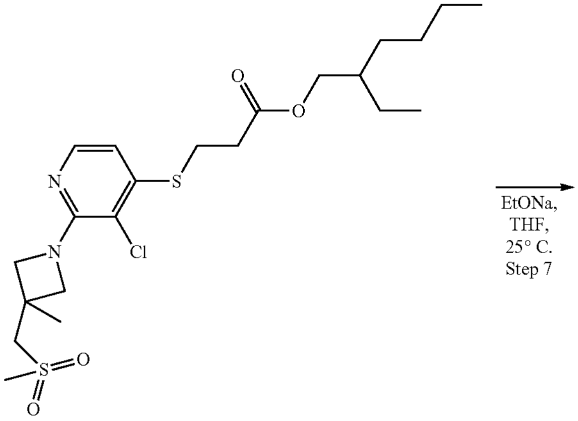
29-7
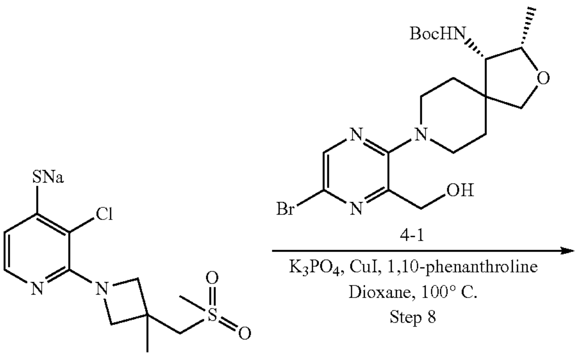
29-8

-continued

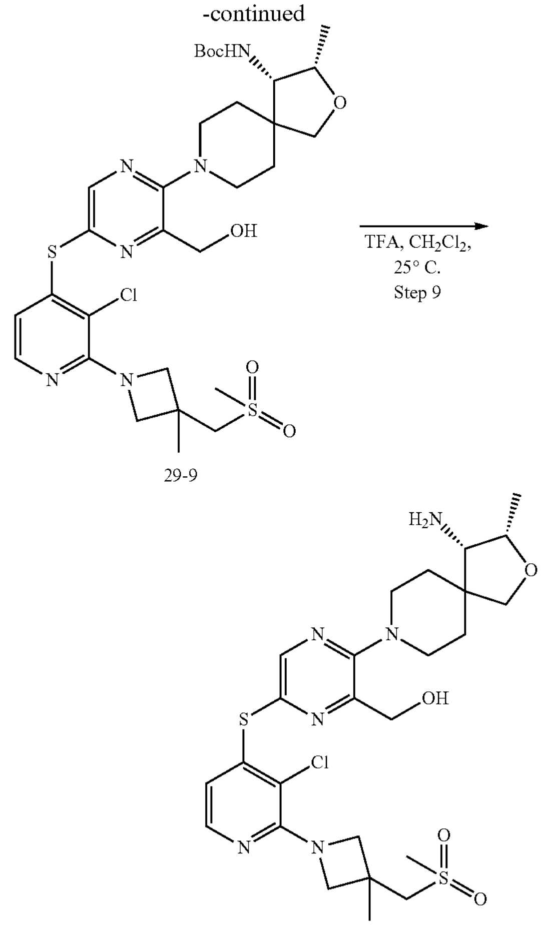

29-9

79

Step 1: Preparation of tert-butyl 3-methyl-3-(tosyloxymethyl)azetidine-1-carboxylate (Compound 29-2)

Compound 29-1 (1 g, 4.97 mmol) was dissolved in pyridine (10 mL) and cooled to 0° C., to which TsCl (516 mg, 5.96 mmol) was added. After the addition was complete, the reactants were warmed to 25° C. and reacted for 3 hours. After the reaction was complete, the resultant was quenched with water, and extracted with dichloromethane. The combined organic phase was dried, and concentrated to afford a crude product. The crude product was purified by column chromatography to afford Compound 29-2 (900 mg, yield 48%).

Step 2: Preparation of tert-butyl 3-methyl-3-(methylthiomethyl)azetidine-1-carboxylate (Compound 29-3)

Compound 29-2 (900 mg, 2.53 mmol) was dissolved in NMP (10 mL), and sodium thiomethoxide (355 mg, 5.06 mmol) was added at 20° C. After the addition was complete, the reactants were heated to 70° C. and reacted for 4 hours. After the reaction was complete, the resultant was cooled to room temperature, diluted with water, and extracted with ethyl acetate. The combined organic phase was dried, and concentrated to afford a crude product of Compound 29-3 (600 mg). The crude product was used directly in the next reaction step without purification.

Step 3: Preparation of tert-butyl 3-methyl-3-(methylsulfonylmethyl)azetidine-1-carboxylate (Compound 29-4)

Compound 29-3 (600 mg, 2.07 mmol) was dissolved in DCM (20 mL), and cooled to 5° C. m-CPBA (787 mg, 4.56 mmol) was added in batches. After the addition was complete, the reactants were warmed naturally to room temperature and reacted for 4 hours. After the reaction was complete, 15% aqueous solution of potassium carbonate (10 mL) was added and stirred for 5 minutes. After the liquid-liquid separation, the organic phase was washed with saturated saline, dried, concentrated to afford a crude product. The crude product was purified by column chromatography to afford Compound 29-4 (300 mg, yield 52%).

Step 4: Preparation of 3-methyl-3-(methylsulfonylmethyl)azetidine (Compound 29-5)

Compound 29-4 (300 mg, 1.14 mmol) was dissolved in DCM (2 mL), and TFA (1 mL) was added and reacted at 20° C. for 1 hour. After the reaction was complete, the resultant was concentrated to remove the solvent, thereby affording Compound 29-5 (300 mg).

Step 5 to Step 9: Preparation of (3-((3S,4S)-4-amino-3-methyl-2-oxa-8-azaspiro[4.5]decan-8-yl)-6-(3-chloro-2-(3-methyl-3-(methylsulfonylmethyl)azetidin-1-yl)pyridin-4-ylthio)pyrazin-2-yl)methanol (Compound 79)

In Step 5 to Step 9, a crude product of Compound 79 was synthesized by similar methods described in Example 5. The crude product was purified by HPLC (mobile phase A: acetonitrile, mobile phase B: 0.05% aqueous solution of formic acid) to afford Compound 79.

MS (ESI): m/z 583.2 $[M+H]^+$.

$^1$H-NMR (400 MHz, DMSO-$d_6$): δ 8.32 (s, 1H), 7.81 (d, J=5.2 Hz, 1H), 6.08 (d, J=5.2 Hz, 1H), 4.50 (s, 2H), 4.20 (d, J=8.4 Hz, 2H), 4.13-4.05 (m, 1H), 3.90 (d, J=8.4 Hz, 2H), 3.72-3.66 (m, 3H), 3.60 (s, 2H), 3.54 (d, J=8.8 Hz, 1H), 3.27-3.15 (m, 2H), 3.04 (d, J=4.8 Hz, 1H), 3.01 (m, 3H), 1.90-1.70 (m, 2H), 1.64-1.60 (m, 1H), 1.56-1.50 (m, 4H), 1.12 (d, J=6.4 Hz, 3H).

Example 30: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)azetidin-3-yl)-2-methylpropanenitrile (Compound 80)

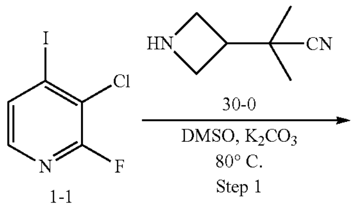

1-1

-continued

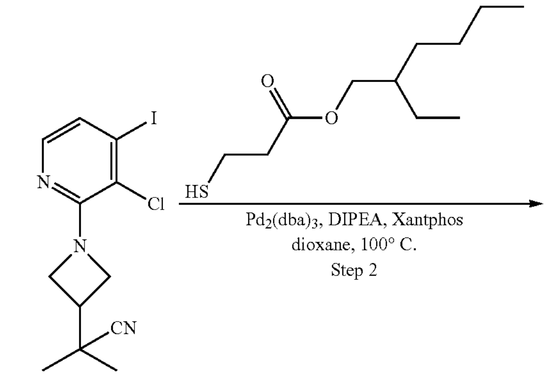

30-1

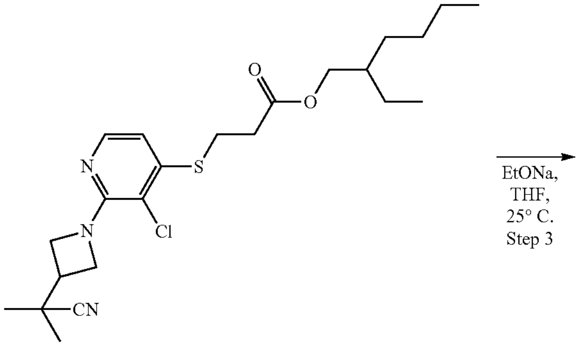

30-2

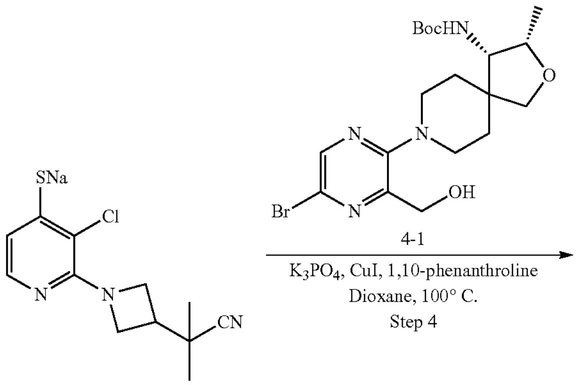

30-3

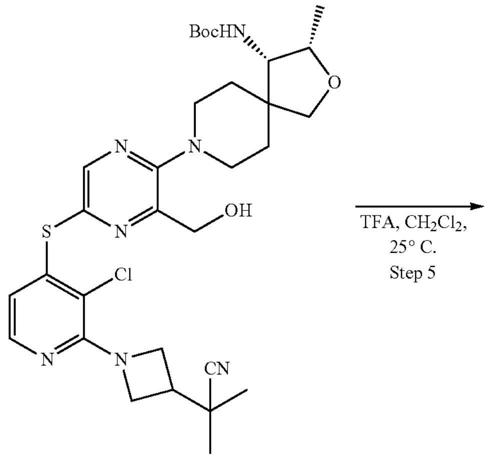

30-4

-continued

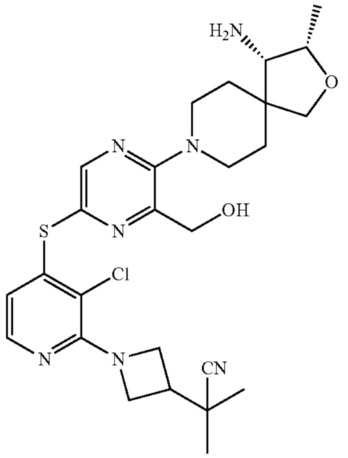

80

A crude product of Compound 80 was synthesized by similar methods described in Example 5. The crude product was purified by HPLC (mobile phase A: acetonitrile, mobile phase B: 0.05% aqueous solution of formic acid) to afford Compound 80.

MS (ESI): m/z 544.1 $[M+H]^+$.

$^1$H-NMR (400 MHz, DMSO-$d_6$): δ 8.33 (s, 1H), 8.26 (s, 1H), 7.83 (d, J=5.2 Hz, 1H), 6.09 (d, J=5.2 Hz, 1H), 5.56-5.49 (m, 1H), 4.51 (s, 2H), 4.29 (t, J=8.8 Hz, 2H), 4.11-4.06 (m, 1H), 4.03-3.97 (m, 2H), 3.72-3.63 (m, 3H), 3.52-3.50 (m, 1H), 3.23-3.17 (m, 2H), 2.96 (d, J=5.2 Hz, 1H), 2.82-2.75 (m, 2H), 1.87-1.79 (m, 1H), 1.76-1.68 (m, 1H), 1.62-1.49 (m, 2H), 1.29 (s, 6H), 1.09 (d, J=6.4 Hz, 3H).

Example 31: Preparation of 3-((4-(5-((3S,4S)-4-amino-3-methyl-2-oxa-8-azaspiro[4.5]decan-8-yl)-6-(hydroxymethyl)-3-methylpyrazin-2-ylthio)-3-chloropyridin-2-ylamino)methyl)oxetan-3-ol (Compound 81)

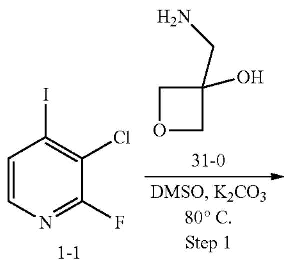

-continued

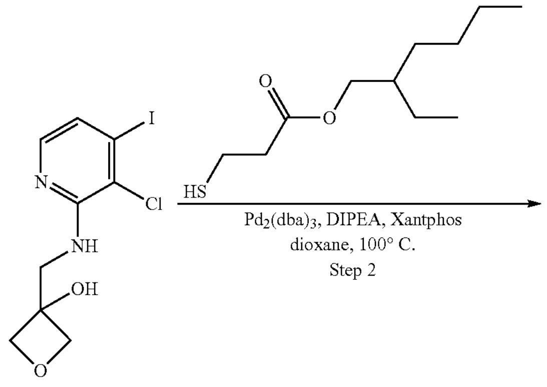

31-1

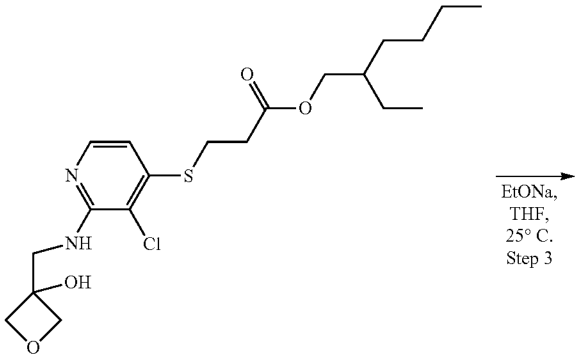

30-2

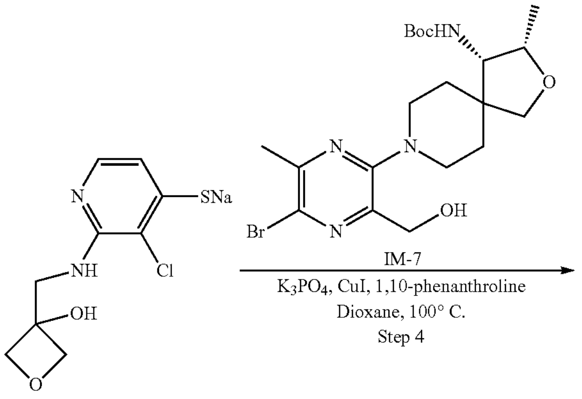

31-3

-continued

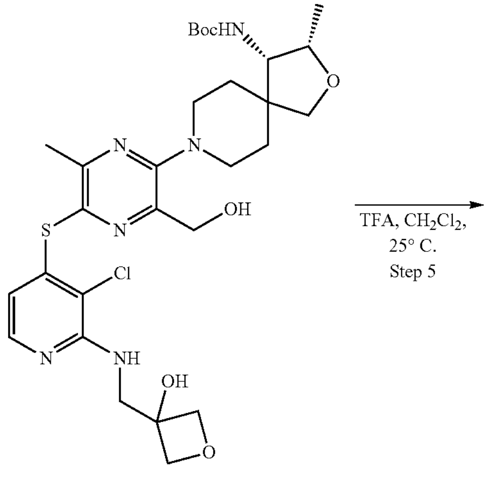

31-4

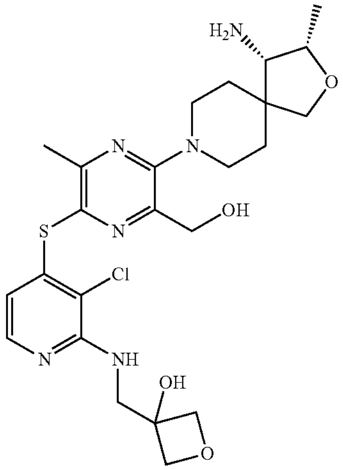

81

A crude product of Compound 81 was synthesized by similar methods described in Example 5. The crude product was purified by HPLC (mobile phase A: acetonitrile, mobile phase B: 0.05% aqueous solution of trifluoroacetic acid) to afford a trifluoroacetate salt of Compound 81.

MS (ESI): m/z 537.1 $[M+H]^+$.

$^1$H-NMR (400 MHz, $CD_3OD$): δ 7.61 (d, J=7.2 Hz, 1H), 6.23 (d, J=7.2 Hz, 1H), 4.65 (s, 2H), 4.63-4.28 (m, 2H), 4.18-4.10 (m, 1H), 4.05-3.90 (m, 3H), 3.89-3.84 (m, 1H), 3.67-3.60 (m, 3H), 3.50-3.43 (m, 2H), 3.24-3.09 (m, 2H), 2.52 (s, 3H), 2.03-1.80 (m, 3H), 1.76-1.66 (m, 1H), 1.33 (d, J=6.8 Hz, 3H).

Example 32: Preparation of 2-(1-(4-(5-((3S,4S)-4-amino-3-methyl-2-oxa-8-azaspiro[4.5]decan-8-yl)-6-(hydroxymethyl)-3-methylpyrazin-2-ylthio)-3-chloropyridin-2-yl)azetidin-3-yl)propan-2-ol (Compound 82)

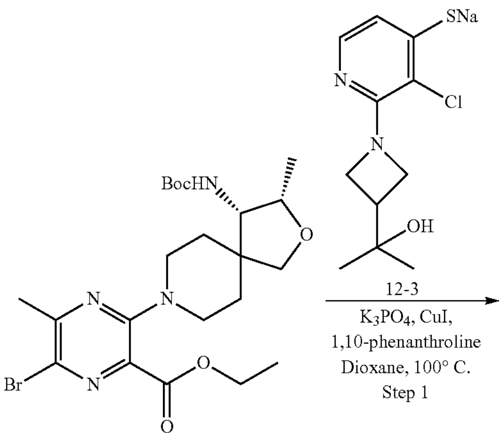

IM-1

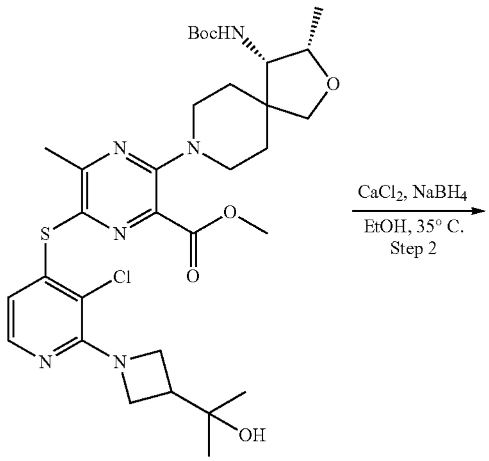

32-1

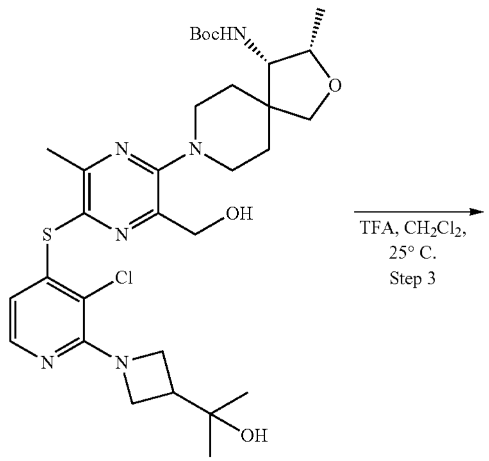

32-2

-continued

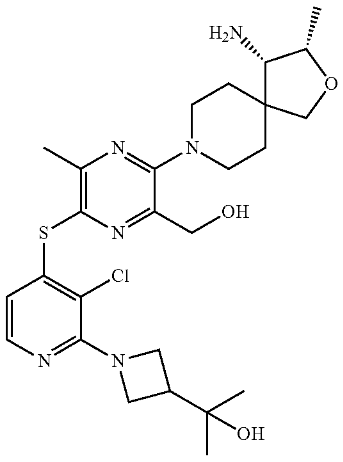

82

A crude product of Compound 82 was synthesized by similar methods described in Example 13. The crude product was purified by HPLC (mobile phase A: acetonitrile, mobile phase B: 0.050% aqueous solution of trifluoroacetic acid) to afford a trifluoroacetate salt of Compound 82.

MS (ESI): m/z 549.3$[M+H]^+$.

$^1$H-NMR (400 MHz, DMSO-$d_6$) δ 7.94 (s, 3H), 7.77 (d, J=5.4 Hz, 1H), 5.85 (d, J=5.4 Hz, 1H), 4.48 (s, 2H), 4.24-4.18 (m, 1H), 4.09-4.07 (m, 4H), 3.96-3.81 (m, 3H), 3.70-3.68 (m, 1H), 3.45-3.43 (m, 1H), 3.12-3.02 (m, 2H), 2.66-2.59 (m, 1H), 2.41 (s, 3H), 1.89-1.71 (m, 3H), 1.62-1.59 (m, 1H), 1.22 (d, J=6.4 Hz, 3H), 1.05 (s, 6H).

Example 33: Preparation of (3-((3S,4S)-4-amino-3-methyl-2-oxa-8-azaspiro[4.5]decan-8-yl)-6-(3-chloro-2-(3-(methoxymethyl)-3-methylazetidin-1-yl)pyridin-4-ylthio)pyrazin-2-yl)methanol (Compound 83)

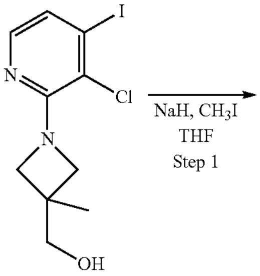

27-1

-continued
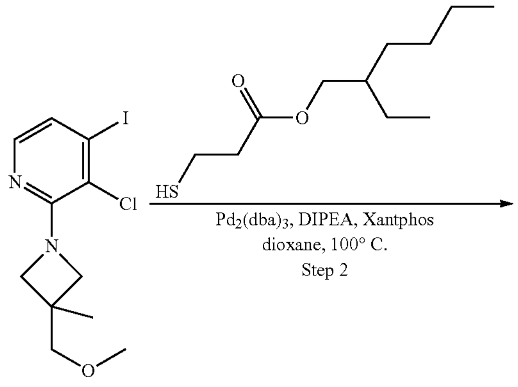
33-1
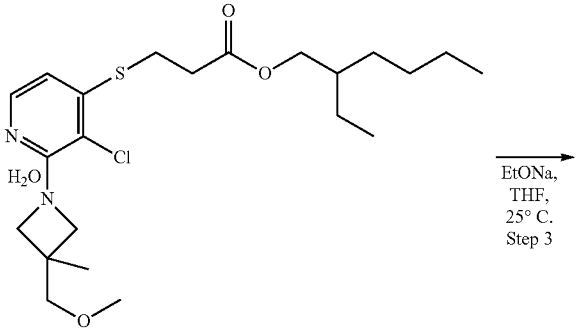
33-2
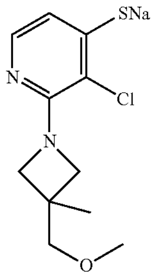
33-3
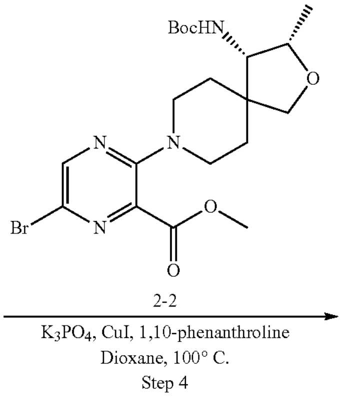
2-2
-continued
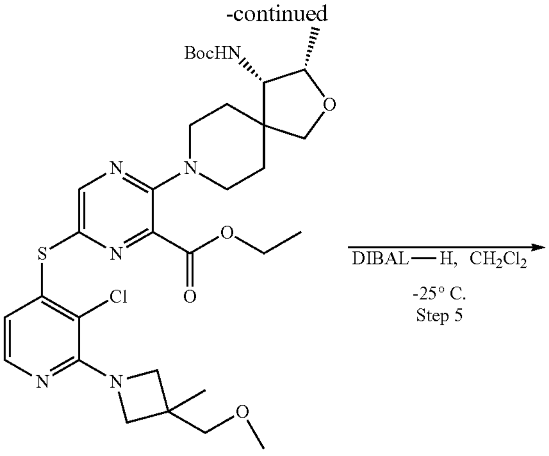
33-4
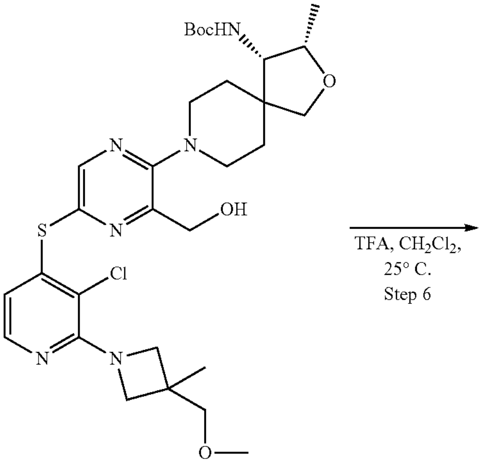
33-5
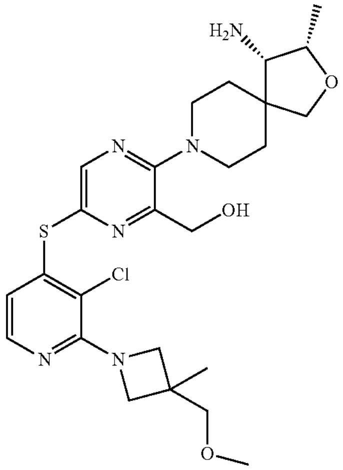
83
Step 1: Preparation of 3-chloro-4-iodo-2-(3-(methoxymethyl)-3-methylazetidin-1-yl)pyridine (Compound 33-1)
Compound 27-1 (0.30 g, 0.88 mmol) was dissolved in THF (3 mL). NaH (70.89 mg, 1.77 mmol) was added and reacted at 25° C. for 20 minutes, and then iodomethane (377.31 mg, 2.66 mmol) was added and reacted at 25° C. for hours. After the completion of the reaction was detected by LCMS, the reaction solution was added with water and extracted with ethyl acetate. The combined organic phase was dried, concentrated, and purified by thin layer chromatography to afford Compound 33-1 (100 mg, yield 32%).

Step 2 to Step 6: Preparation of (3-((3S,4S)-4-amino-3-methyl-2-oxa-8-azaspiro[4.5]decan-8-yl)-6-(3-chloro-2-(3-(methoxymethyl)-3-methylazetidin-1-yl)pyridin-4-ylthio)pyrazin-2-yl)methanol (Compound 83)

A crude product of Compound 83 was synthesized by similar methods described in Step 2 to Step 6 of Example 6. The crude product was purified by HPLC (mobile phase A: acetonitrile, mobile phase B: 0.05% aqueous solution of formic acid) to afford Compound 83.

MS (ESI): m/z 535.2 $[M+H]^+$.

$^1$H-NMR (400 MHz, $CD_3OD$): δ 8.27 (s, 1H), 7.68 (d, J=5.2 Hz, 1H), 6.07 (d, J=5.2 Hz, 1H), 4.66 (s, 2H), 4.28-4.16 (m, 1H), 4.09 (d, J=8.4 Hz, 2H), 3.85 (dd, J=8.4, 4.0 Hz, 3H), 3.77-3.63 (m, 3H), 3.41 (s, 2H), 3.39 (s, 3H), 3.29-3.12 (m, 2H), 3.03 (d, J=5.2 Hz, 1H), 1.99-1.81 (m, 2H), 1.77-1.65 (m, 2H), 1.31 (s, 3H), 1.22 (d, J=6.4 Hz, 3H).

Example 34: Preparation of 2-(1-(4-(5-(4-(1-amino-2-fluoroethyl)-4-methylpiperidin-1-yl)-6-(hydroxymethyl)pyrazin-2-ylthio)-3-chloropyridin-2-yl)azetidin-3-yl)propan-2-ol (Compound 84)

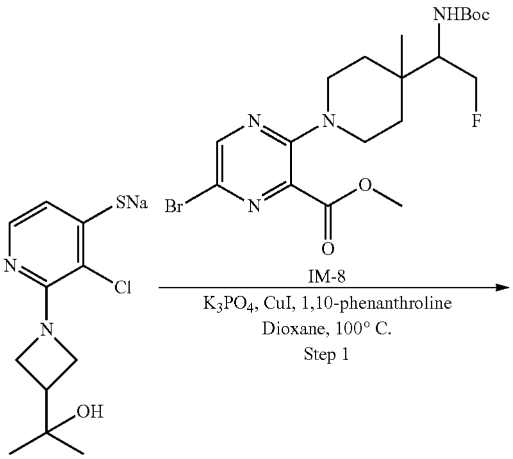

12-3

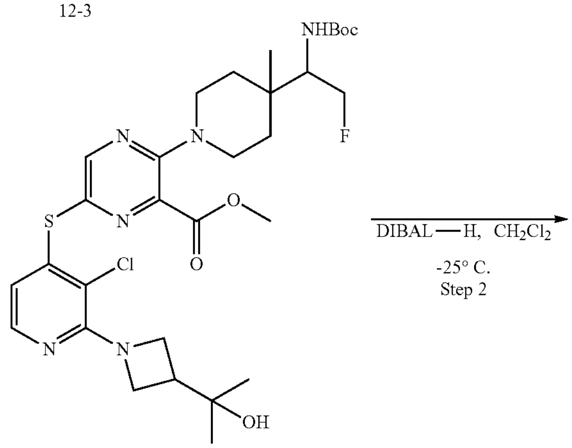

34-1

-continued

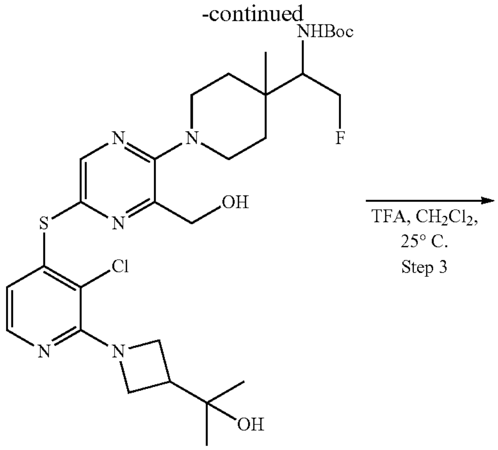

34-2

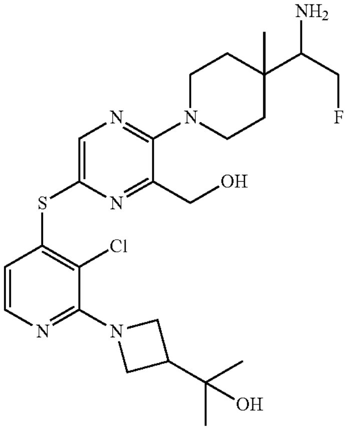

84

A crude product of Compound 84 was synthesized by similar methods described in Example 13. The crude product was purified by HPLC (mobile phase A: acetonitrile, mobile phase B: 0.050% aqueous solution of trifluoroacetic acid) to afford a trifluoroacetate salt of Compound 84.

MS (ESI): m/z 525.3 $[M+H]^+$.

$^1$H-NMR (400 MHz, $CD_3OD$): δ 8.33 (s, 1H), 7.60 (d, J=5.6 Hz, 1H), 6.22 (d, J=5.2 Hz, 1H), 4.81-4.70 (m, 2H), 4.67 (s, 2H), 4.53-4.33 (m, 4H), 3.93-3.77 (m, 2H), 3.51-3.37 (m, 2H), 3.25-3.16 (m, 1H), 2.88-2.73 (m, 1H), 1.91-1.56 (m, 4H), 1.19 (m, 9H).

Example 35: Preparation of (3-((3S,4S)-4-amino-3-methyl-2-oxa-8-azaspiro[4.5]decan-8-yl)-6-(3-chloro-2-(oxetan-3-ylmethoxy)pyridin-4-ylthio)pyrazin-2-yl)methanol (Compound 59)

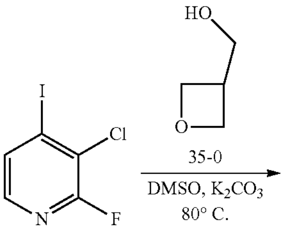

1-1

-continued

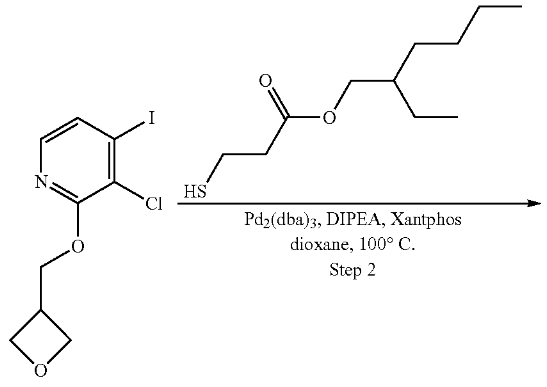

35-1

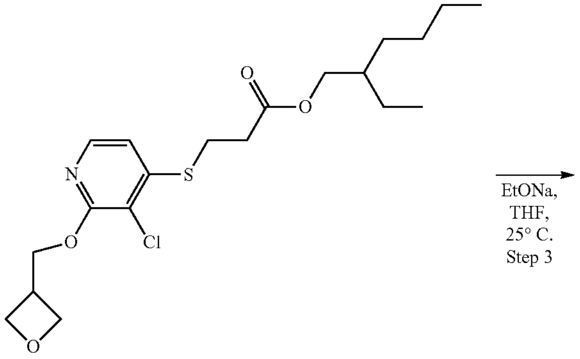

35-2

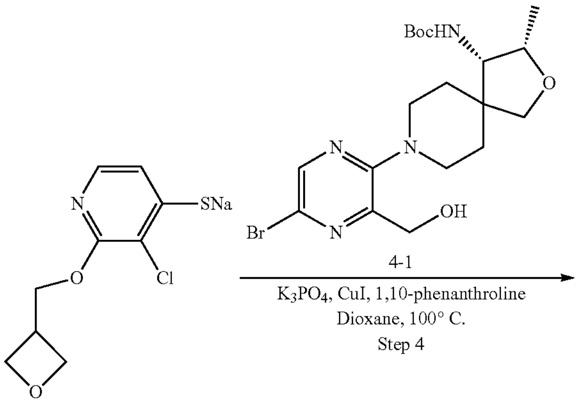

35-3

-continued

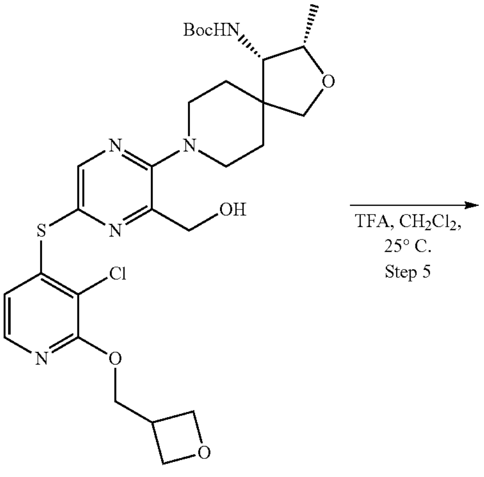

35-4

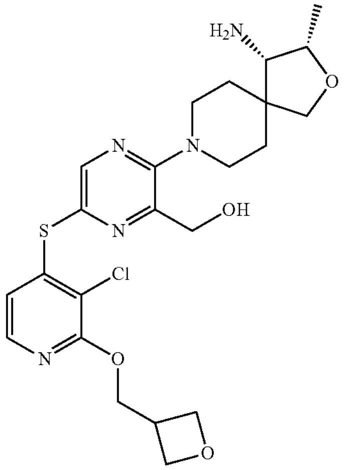

59

A crude product of Compound 59 was synthesized by similar methods described in Example 5. The crude product was purified by HPLC (mobile phase A: acetonitrile, mobile phase B: 0.05% aqueous solution of trifluoroacetic acid) to afford a trifluoroacetate salt of Compound 59.

MS (ESI): m/z 508.1 $[M+H]^+$.

$^1$H-NMR (400 MHz, $CD_3OD$-$d_4$): δ 8.39 (s, 1H), 7.94 (d, J=7.2 Hz, 1H), 6.90 (d, J=6.8 Hz, 1H), 4.94-4.93 (m, 1H), 4.71-4.65 (m, 3H), 4.59 (dd, J=13.2, 4.2 Hz, 1H), 4.42 (dd, J=13.6, 8.4 Hz, 1H), 4.34-4.27 (m, 1H), 4.01-3.86 (m, 4H), 3.77-3.71 (m, 2H), 3.46 (d, J=4.0 Hz, 1H), 3.24-3.10 (m, 2H), 2.72-2.66 (m, 1H), 2.02-1.87 (m, 3H), 1.76-1.73 (m, 1H), 1.32 (d, J=6.8 Hz, 3H).

Example 36: Preparation of 2-(1-(4-(3-amino-5-((3S,4S)-4-amino-3-methyl-2-oxa-8-azaspiro[4.5]decan-8-yl)pyrazin-2-ylthio)-3-chloropyridin-2-yl)azetidin-3-yl)propan-2-ol (Compound 85)

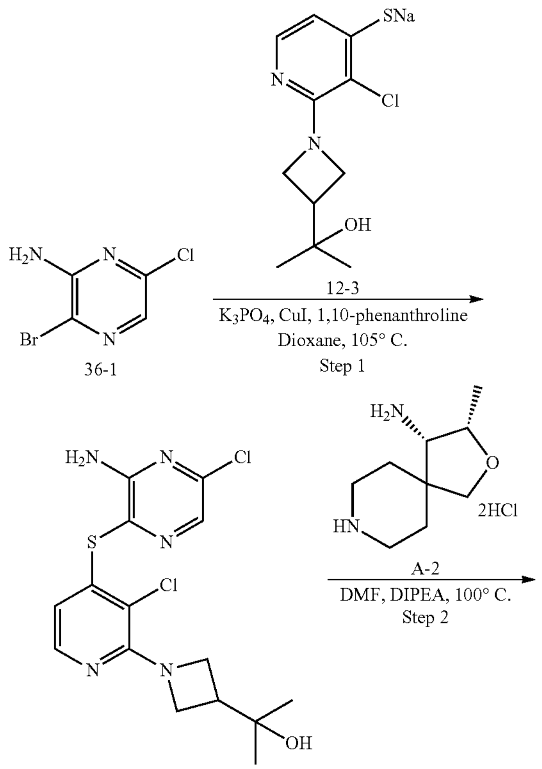

36-1

36-2

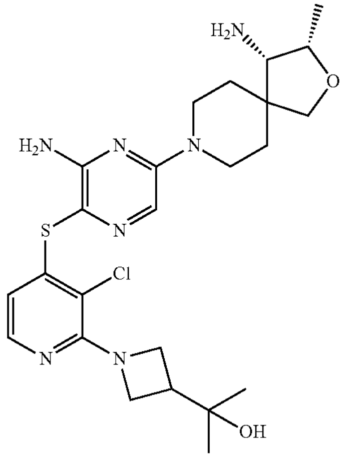
85

Step 1: Preparation of 2-(1-(4-(3-amino-5-chloropyrazin-2-ylthio)-3-chloropyridin-2-yl)azetidin-3-yl)propan-2-ol (Compound 36-2)

Compound 36-1 (135 mg, 647.66 μmol), Compound 12-3 (272.74 mg, 917.49 μmol), CuI (123.35 mg, 647.66 μmol), 1,10-phenanthroline (116.71 mg, 647.66 μmol), and $K_3PO_4$ (412.43 mg, 1.94 mmol) were added into 1,4-dioxane (8 mL), warmed to 105° C. in a microwave reactor, and reacted for 2 hours. The resultant was cooled to room temperature, and filtered to remove the insoluble. The filtrate was concentrated to afford a crude product. The crude product was purified by thin layer chromatography to afford Compound 36-2 (130 mg, yield 52%).

Step 2: Preparation of 2-(1-(4-(3-amino-5-((3S,4S)-4-amino-3-methyl-2-oxa-8-azaspiro[4.5]decan-8-yl)pyrazin-2-ylthio)-3-chloropyridin-2-yl)azetidin-3-yl)propan-2-ol (Compound 85)

Compound 36-2 (50 mg, 129.43 μmol), Compound A-2 (63 mg, 258.87 μmol), and DIPEA (134 mg, 1.04 mmol) were added into DMF (3 mL). The system was warmed to 100° C. and reacted for 16 hours. After the reaction was complete, the resultant was concentrated to afford a crude product. The crude product was purified by HPLC (mobile phase A: acetonitrile, mobile phase B: 0.05% aqueous solution of formic acid) to afford Compound 85 (8.10 mg, yield 11%).

MS (ESI): m/z 520.2 $[M+H]^+$.

$^1$H-NMR (400 MHz, DMSO-$d_6$): δ 7.76 (d, J=5.6 Hz, 1H), 7.63 (s, 1H), 6.14 (s, 2H), 5.84 (d, J=5.6 Hz, 1H), 4.10-4.00 (m, 6H), 3.90-3.78 (m, 3H), 3.67 (d, J=8.4 Hz, 1H), 3.49 (d, J=8.4 Hz, 1H), 2.92 (d, J=5.2 Hz, 1H), 2.66-2.56 (m, 1H), 1.76-1.42 (m, 4H), 1.08 (d, J=6.8 Hz, 3H), 1.05 (s, 6H).

Example 37: Preparation of (1-(4-(3-amino-5-((3S,4S)-4-amino-3-methyl-2-oxa-8-azaspiro[4.5]decan-8-yl)pyrazin-2-ylthio)-3-chloropyridin-2-yl)pyrrolidin-2-yl)methanol (Compound 86)

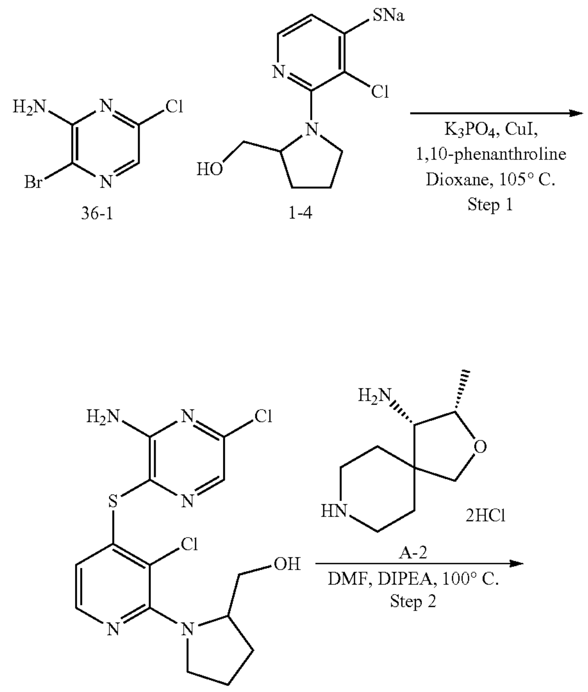

36-1 1-4

37-1

-continued

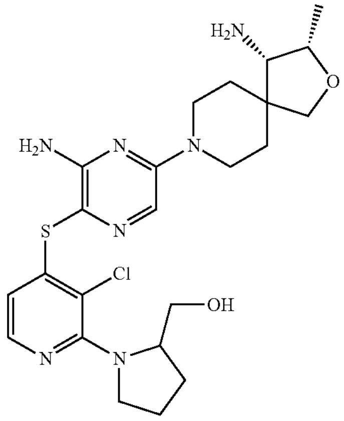

86

A crude product of Compound 86 was synthesized by similar methods described in Example 36. The crude product was purified by HPLC (mobile phase A: acetonitrile, mobile phase B: 0.05% aqueous solution of trifluoroacetic acid) to afford a trifluoroacetate salt of Compound 86.

MS (ESI): m/z 506.1 $[M+H]^+$.

$^1$H-NMR (400 MHz, DMSO-$d_6$): δ 7.98 (s, 3H), 7.80 (d, J=5.2 Hz, 1H), 7.69 (s, 1H), 6.23 (s, 2H), 5.92 (d, J=5.2 Hz, 1H), 4.46-4.39 (m, 1H), 4.25-4.18 (m, 2H), 4.16-4.12 (m, 1H), 3.88-3.80 (m, 2H), 3.69 (d, J=9.2 Hz, 1H), 3.52 (dd, J=10.4, 3.6 Hz, 1H), 3.43-3.34 (m, 2H), 3.22 (dd, J=10.4, 7.2 Hz, 1H), 3.13-3.00 (m, 2H), 2.08-1.99 (m, 1H), 1.97-1.89 (m, 1H), 1.86-1.78 (m, 1H), 1.70-1.67 (m, 4H), 1.57-1.54 (m, 1H), 1.22 (d, J=6.4 Hz, 3H).

Example 38: Preparation of (3S,4S)-8-(6-amino-5-(3-chloro-2-(3-(methylsulfonylmethyl)azetidin-1-yl)pyridin-4-ylthio)pyrazin-2-yl)-3-methyl-2-oxa-8-azaspiro[4.5]decan-4-amine (Compound 87)

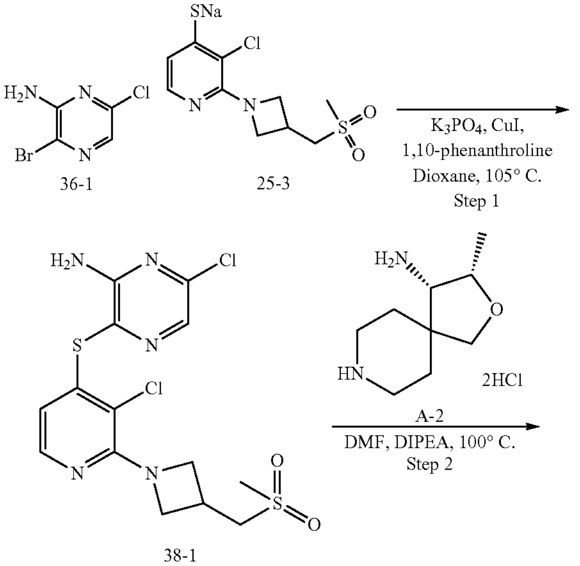

-continued

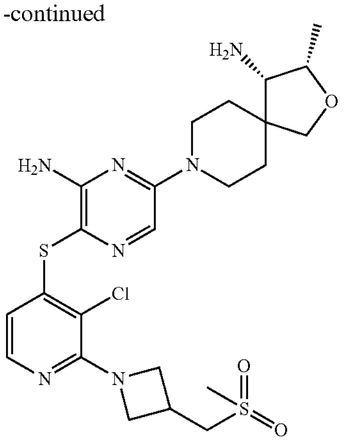

87

A crude product of Compound 87 was synthesized by similar methods described in Example 36. The crude product was purified by HPLC (mobile phase A: acetonitrile, mobile phase B: 0.05% aqueous solution of formic acid) to afford Compound 87.

MS (ESI): m/z 554.1 $[M+H]^+$.

$^1$H-NMR (400 MHz, DMSO-$d_6$): δ 7.79 (d, J=5.2 Hz, 1H), 7.63 (s, 1H), 6.14 (s, 2H), 5.91 (d, J=5.2 Hz, 1H), 4.31 (t, J=8.4 Hz, 2H), 4.10-4.03 (m, 1H), 4.03-3.96 (m, 2H), 3.87-3.79 (s, 2H), 3.66 (d, J=8.4 Hz, 1H), 3.53-3.47 (m, 3H), 3.43-3.38 (m, 1H), 3.20-3.07 (m, 2H), 2.98 (s, 3H), 2.89 (d, J=5.2 Hz, 1H), 1.76-1.69 (m, 1H), 1.64-1.58 (m, 1H), 1.53-1.42 (m, 2H), 1.08 (d, J=6.4 Hz, 3H).

Example 39: Preparation of (3-((3S,4S)-4-amino-3-methyl-2-oxa-8-azaspiro[4.5]decan-8-yl)-6-(3-chloro-2-(3-fluoro-3-(hydroxymethyl)azetidin-1-yl)pyridin-4-ylthio)pyrazin-2-yl)methanol (Compound 88)

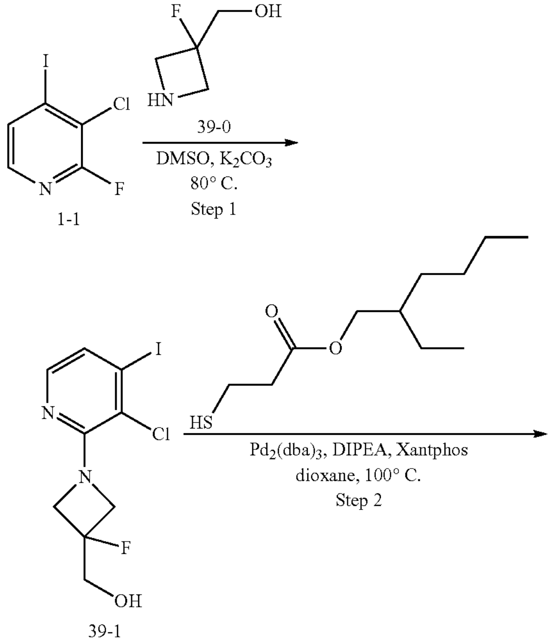

-continued
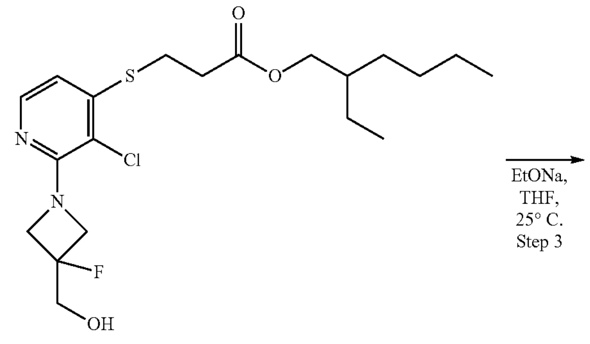
39-2
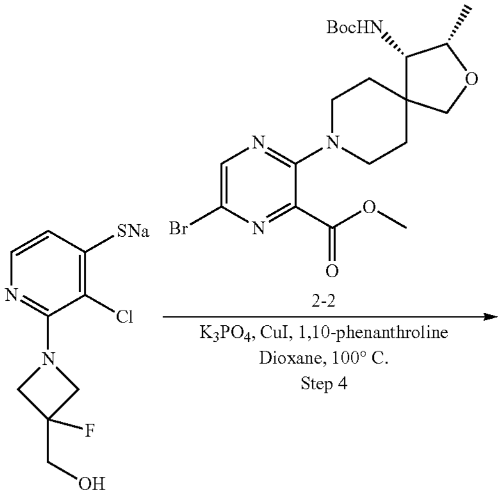
2-2
39-3
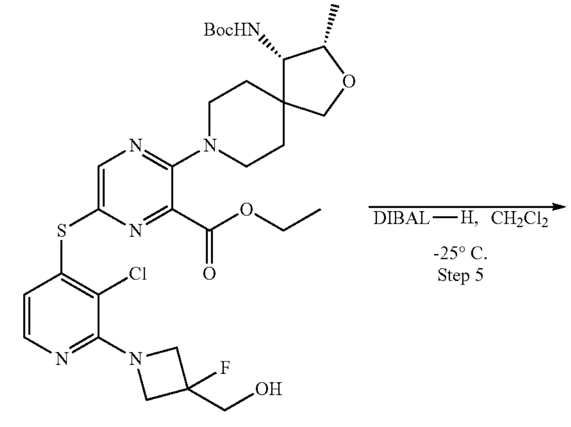
39-4
-continued
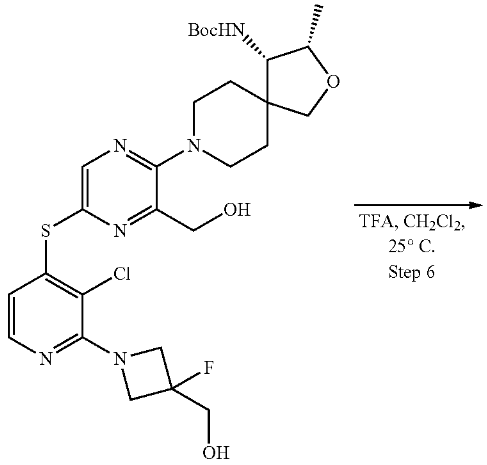
39-5
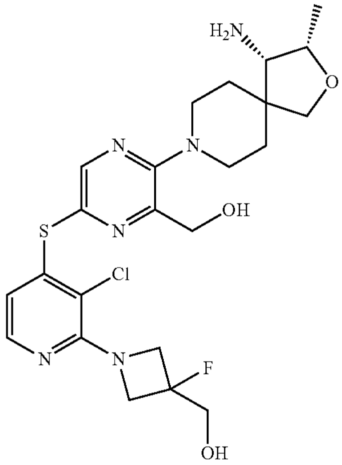
88
A crude product of Compound 88 was synthesized by similar methods described in Example 6. The crude product was purified by HPLC (mobile phase A: acetonitrile, mobile phase B: 0.05% aqueous solution of formic acid) to afford Compound 88.
MS (ESI): m/z 525.2 $[M+H]^+$.
$^1$H-NMR (400 MHz, $CD_3OD$): δ 8.35 (s, 1H), 7.95 (s, 3H), 7.86 (d, J=5.6 Hz, 1H), 6.15 (d, J=5.6 Hz, 1H), 4.52 (s, 2H), 4.33 (d, J=10.4 Hz, 1H), 4.28 (d, J=10.4 Hz, 1H), 4.24-4.10 (m, 4H), 3.9-3.60 (m, 6H), 3.48-3.38 (m, 1H), 3.17-3.30 (m, 2H), 1.92-1.55 (m, 4H), 1.22 (d, J=6.4 Hz, 3H).

Example 40: Preparation of 2-(1-(4-(5-((3S,4S)-4-amino-3-methyl-2-oxa-8-azaspiro[4.5]decan-8-yl)-6-(hydroxymethyl)pyrazin-2-ylthio)-3-fluoropyridin-2-yl)azetidin-3-yl)propan-2-ol (Compound 90)

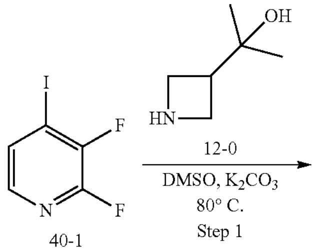

40-1

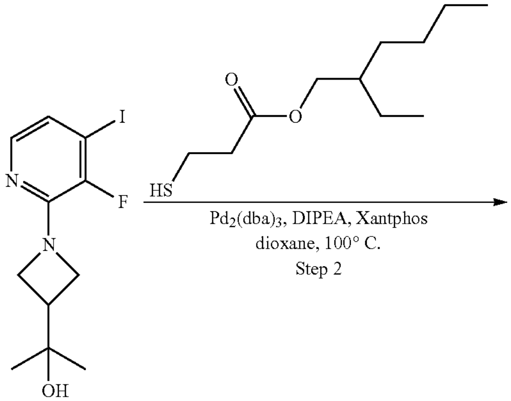

40-2

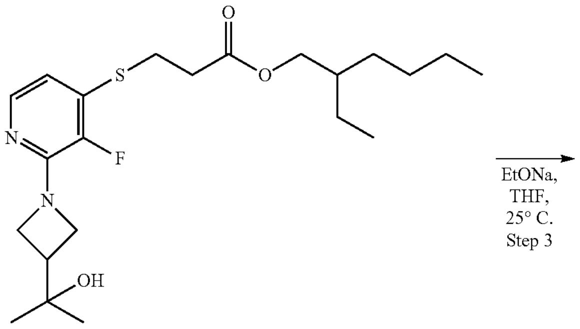

40-3

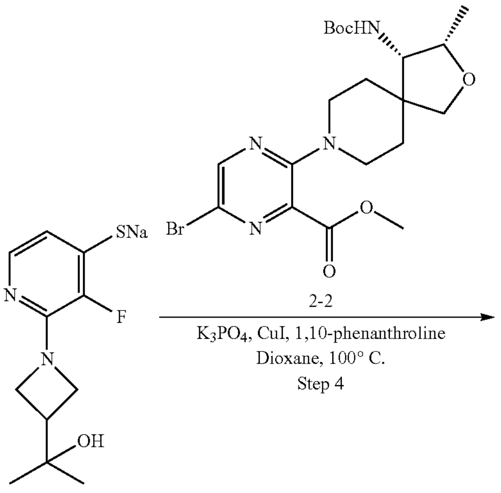

40-4

-continued

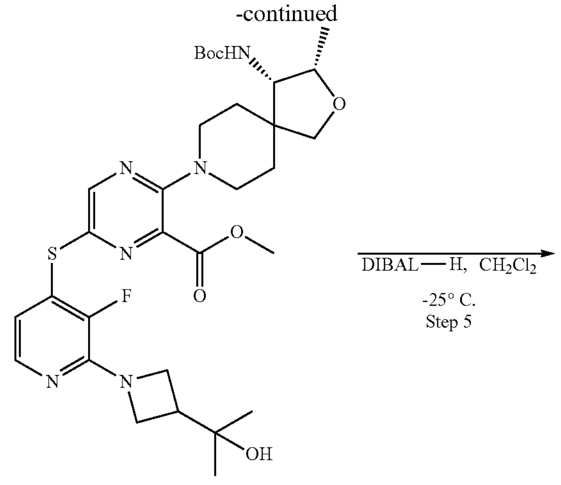

40-5

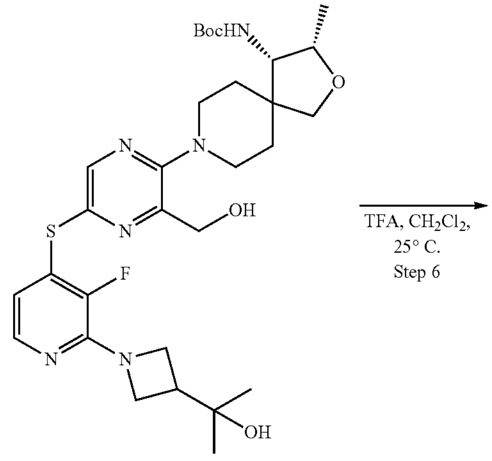

40-6

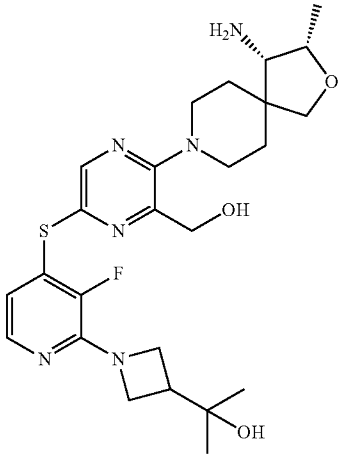

90

A crude product of Compound 90 was synthesized by similar methods described in Example 6. The crude product was purified by HPLC (mobile phase A: acetonitrile, mobile phase B: 0.05% aqueous solution of formic acid) to afford Compound 90.

MS (ESI): m/z 519.1 $[M+H]^+$.

$^1$H-NMR (400 MHz, DMSO-$d_6$): δ 8.23 (s, 1H), 7.61 (d, J=5.6 Hz, 1H), 6.40-6.05 (m, 1H), 4.64 (s, 2H), 4.28-4.17 (m, 1H), 4.17-4.03 (m, 4H), 3.85 (d, J=8.8 Hz, 1H), 3.71 (d,

J=8.8 Hz, 1H), 3.69-3.59 (m, 2H), 3.25-3.07 (m, 2H), 3.03 (d, J=5.2 Hz, 1H), 2.86-2.76 (m, 1H), 1.98-1.81 (m, 2H), 1.78-1.64 (m, 2H), 1.22 (d, J=6.8 Hz, 3H), 1.18 (s, 6H).

Example 41: Preparation of (R)-2-(1-(4-(5-(3-amino-5-fluoro-3H-spiro[benzofuran-2,4'-piperidin]-1'-yl)pyrazin-2-ylthio)-3-chloropyridin-2-yl)azetidin-3-yl)propan-2-ol (Compound 107)

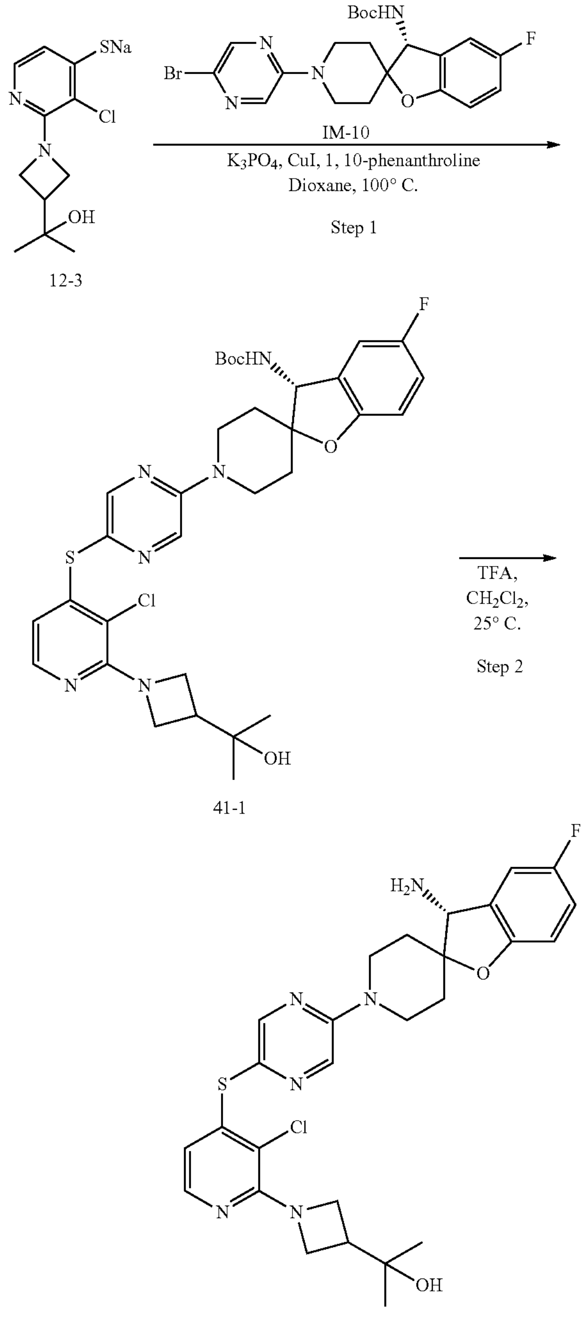

12-3

41-1

107

A crude product of Compound 107 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 107.

MS (ESI): m/z 557.0 $[M+H]^+$.

$^1$H-NMR (400 MHz, DMSO-$d_6$): δ 8.59 (d, J=0.8 Hz, 1H), 8.55 (s, 3H), 8.36 (d, J=0.8 Hz, TH), 7.80 (d, J=5.2 Hz, TH), 7.38 (dd, J=8.0, 2.8 Hz, TH), 7.23 (td, J=8.8, 2.8 Hz, TH), 7.01 (d, J=9.2, 4.4 Hz, 1H), 5.95 (d, J=5.2 Hz, 1H), 4.77-4.65 (m, 1H), 4.60-4.51 (m, 1H), 4.46-4.36 (m, 1H), 4.08 (d, J=7.6 Hz, 4H), 3.42-3.25 (m, 2H), 2.70-2.55 (m, 1H), 2.10-1.94 (m, 2H), 1.90-1.76 (m, 2H), 1.05 (s, 6H).

Example 42: Preparation of (3-((3S,4S)-4-amino-3-methyl-2-oxa-8-azaspiro[4.5]decan-8-yl)-6-(3-chloro-2-(3-(fluoromethyl)-3-(hydroxymethyl)azetidin-1-yl)pyridin-4-ylthio)pyrazin-2-yl)methanol (Compound 124)

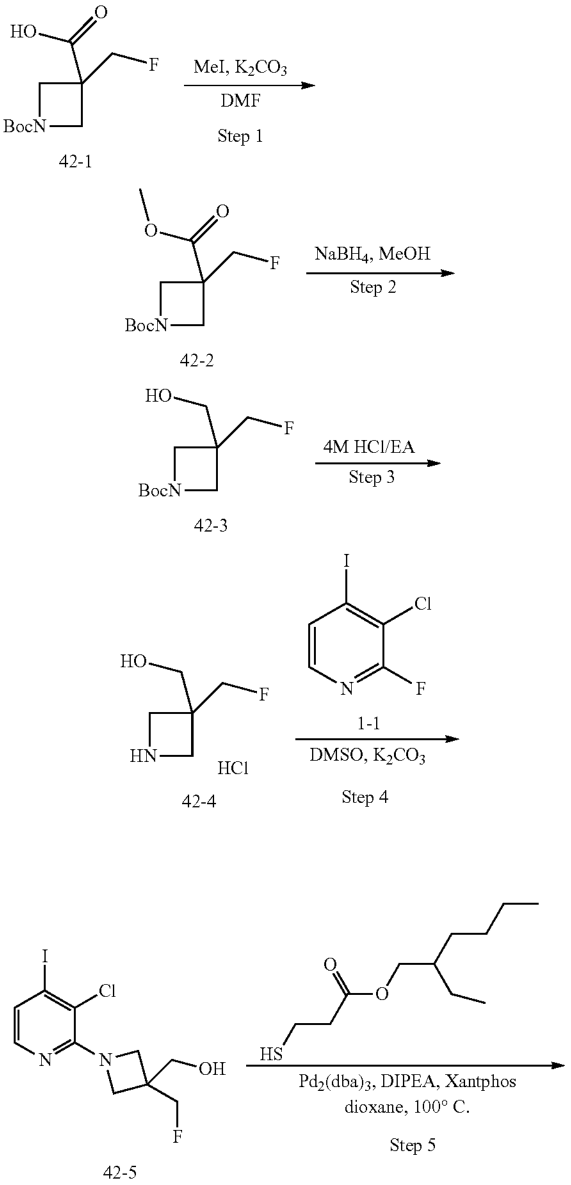

42-1

42-2

42-3

42-4

42-5

-continued

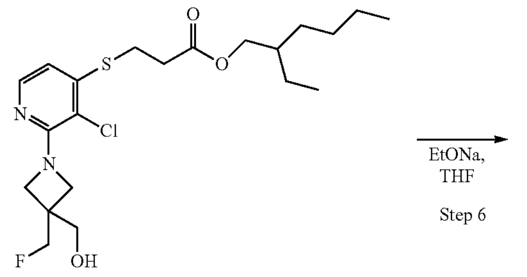

42-6

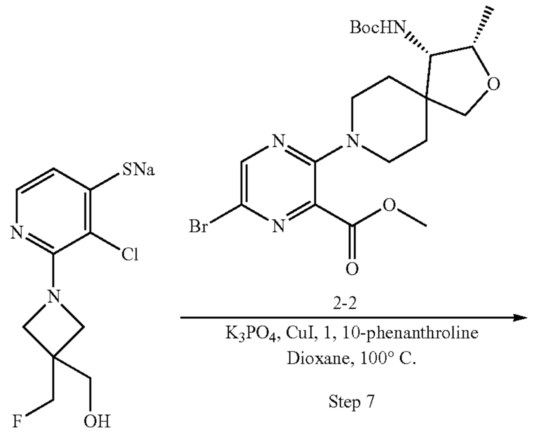

2-2

42-7

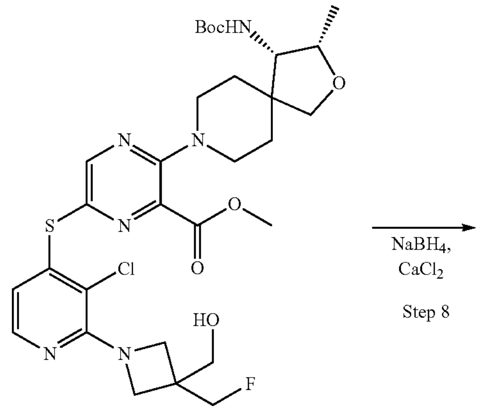

42-8

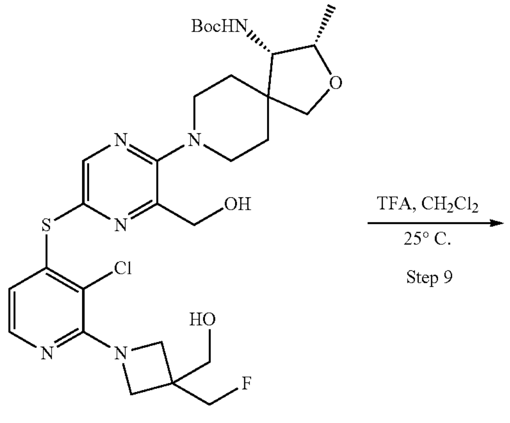

42-9

-continued

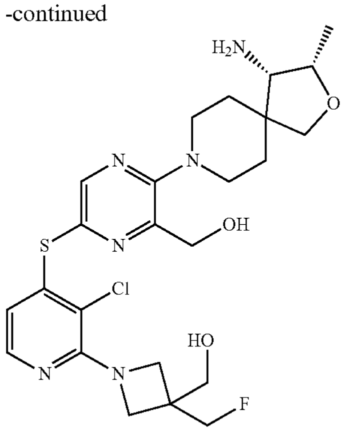

124

Step 1: Preparation of 1-tert-butyl 3-methyl 3-(fluoromethyl)azetidine-1,3-dicarboxylate (Compound 42-2)

Compound 42-1 (450 mg, 1.93 mmol) was dissolved in DMF (5 mL), and potassium carbonate (533 mg, 3.86 mmol) and iodomethane (411 mg, 2.89 mmol) were added and reacted at 25° C. for 2 hours. Saturated ammonium chloride was added to quench the reaction. The resultant was extracted with ethyl acetate. The combined organic phase was dried, concentrated under reduced pressure, and then purified by silica gel column chromatography to afford Compound 42-2 (345 mg, yield 72%).

Step 2: Preparation of tert-butyl 3-(fluoromethyl)-3-(hydroxymethyl)azetidine-1-carboxylate (Compound 42-3)

Compound 42-2 (320 mg, 1.29 mmol) was added into methanol (10 mL), and sodium borohydride (143 mg, 3.88 mmol) was added and reacted at 25° C. for 2 hours. After the reaction was complete, the resultant was cooled to room temperature. Water was added into the system to separate the organic phase. The organic phase was washed with saline, dried over anhydrous sodium sulfate, and filtered. The filtrate was concentrated to dryness to afford a crude product of Compound 42-3 (280 mg). The crude product was used directly in the next reaction step without purification.

Step 3: Preparation of (3-(fluoromethyl)azetidin-3-yl)methanol hydrochloride (Compound 42-4)

Compound 42-3 (280 mg, 1.27 mmol) was dissolved in a 4 M HCl/EA solution (5 mL) and reacted at 25° C. for 2 hours. The solvent was evacuated under reduced pressure to afford a crude product of Compound 42-4 (210 mg). The crude product was used directly in the next reaction step without purification.

Step 4 to Step 9: Preparation of (3-((3S,4S)-4-amino-3-methyl-2-oxa-8-azaspiro[4.5]decan-8-yl)-6-(3-chloro-2-(3-(fluoromethyl)-3-(hydroxymethyl)azetidin-1-yl)pyridin-4-ylthio)pyrazin-2-yl)methanol (Compound 124)

A crude product of Compound 124 was synthesized by similar methods described in Step 1 to Step 6 of Example 12.

The crude product was purified by HPLC (mobile phase A: acetonitrile, mobile phase B: 0.05% aqueous solution of trifluoroacetic acid) to afford a trifluoroacetate salt of Compound 124.

MS (ESI): m/z 538.9 $[M+H]^+$.

$^1$H-NMR (400 MHz, DMSO-$d_6$): δ 8.35 (s, 1H), 7.97 (brs, 3H), 7.81 (d, J=5.6 Hz, 1H), 6.06 (d, J=5.6 Hz, 1H), 4.65 (s, 1H), 4.53 (s, 1H), 4.52 (s, 2H), 4.25-4.17 (m, 1H), 4.05-3.78 (m, 7H), 3.69 (d, J=8.8 Hz, 1H), 3.60 (s, 2H), 3.38-3.34 (m, 1H), 3.17-3.02 (m, 2H), 1.92-1.79 (m, 2H), 1.79-1.70 (m, 1H), 1.65-1.54 (m, 1H), 1.21 (d, J=6.8 Hz, 3H).

Example 43: Preparation of (S)-2-(1-(4-(5-(5-amino-5,7-dihydrospiro[cyclopenta[b]pyridine-6,4'-piperidin]-1'-yl)-6-(hydroxymethyl)pyrazin-2-ylthio)-3-chloropyridin-2-yl)azetidin-3-yl)propan-2-ol (Compound 89)

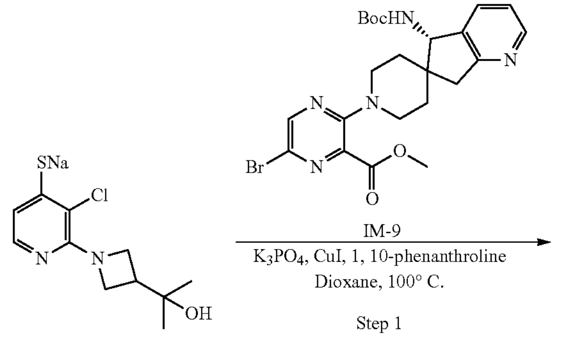

12-3

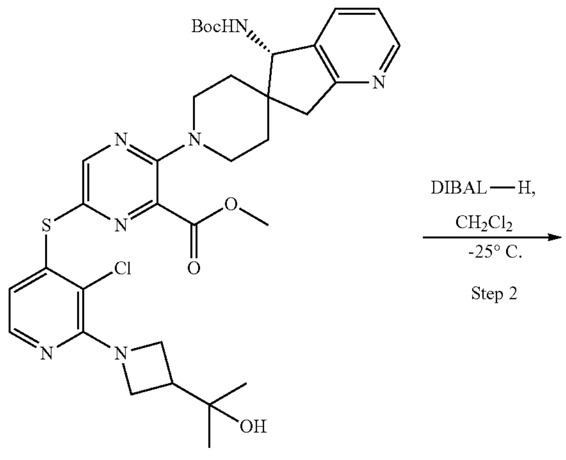

43-1

-continued

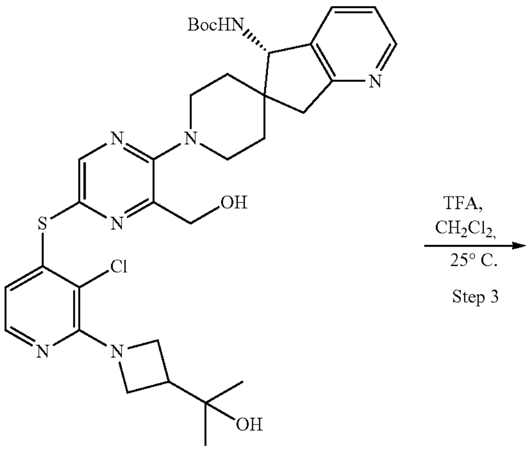

43-2

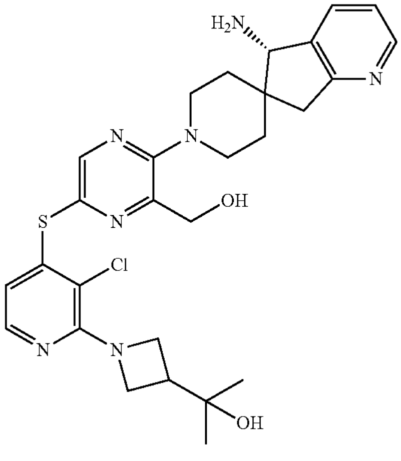

89

A crude product of Compound 89 was synthesized by similar methods described in Example 13. The crude product was purified by HPLC (mobile phase A: acetonitrile, mobile phase B: 0.050% aqueous solution of trifluoroacetic acid) to afford a trifluoroacetate salt of Compound 89.

MS (ESI): m/z 568.0 $[M+H]^+$.

$^1$H NMR (400 MHz, DMSO) δ 8.56 (dd, J=5.2, 1.6 Hz, 1H), 8.44 (br, 3H), 8.36 (s, 1H), 7.96 (d, J=7.6 Hz, 1H), 7.80 (d, J=5.6 Hz, 1H), 7.39 (dd, J=8.0, 5.2 Hz, 1H), 6.05 (d, J=5.2 Hz, 1H), 4.51 (s, 2H), 4.59-4.45 (m, 1H), 4.17-4.06 (m, 4H), 4.05-3.84 (m, 2H), 3.36-3.17 (m, 3H), 3.12 (d, J=17.2 Hz, 1H), 2.68-2.57 (m, 1H), 1.97-1.82 (m, 2H), 1.67-1.50 (m, 2H), 1.05 (s, 6H).

Example 44: Preparation of (R)-2-(1-(4-(5-(3-amino-3H-spiro[furo[2,3-b]pyridine-2,4'-piperidin]-1'-yl)-6-(hydroxymethyl)pyrazin-2-ylthio)-3-chloropyridin-2-yl)azetidin-3-yl)propan-2-ol (Compound 101)

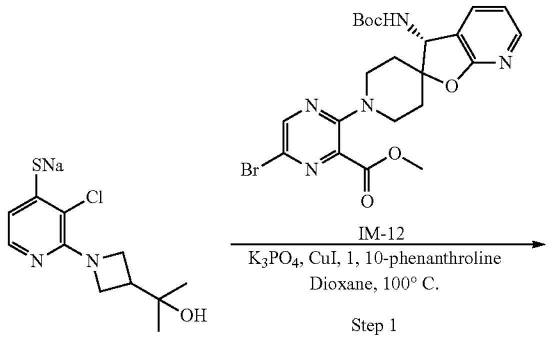

12-3

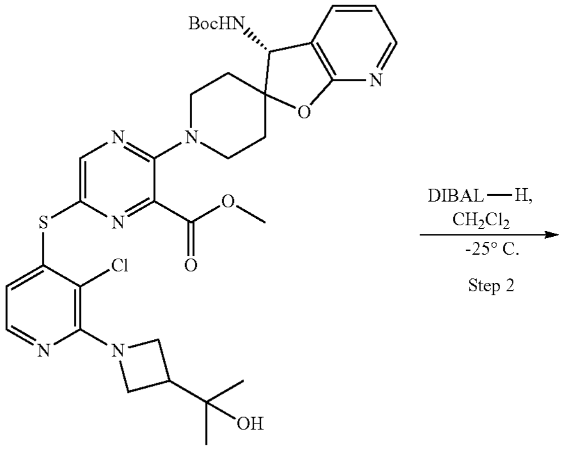

44-1

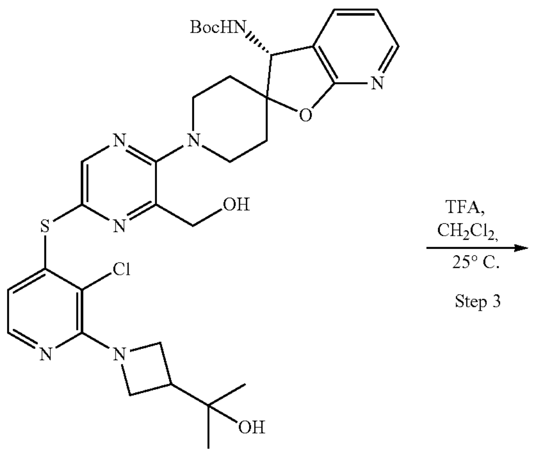

44-2

-continued

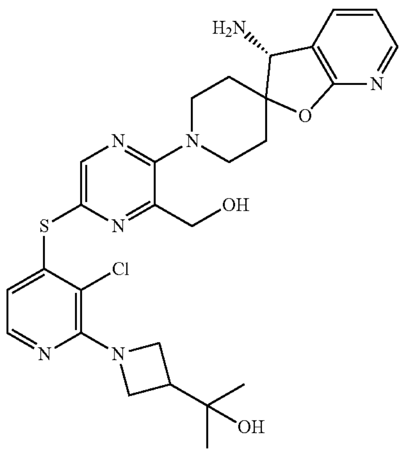

101

A crude product of Compound 101 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 101.

MS (ESI): m/z 570.0 $[M+H]^+$.

$^1$H-NMR (400 MHz, DMSO-$d_6$): δ 8.60 (brs, 3H), 8.39 (s, 1H), 8.22 (dd, J=5.2, 1.6 Hz, 1H), 7.97 (dd, J=7.2, 1.2 Hz, 1H), 7.80 (d, J=5.2 Hz, 1H), 7.09 (dd, J=7.6, 5.2 Hz, 1H), 6.06 (d, J=5.2 Hz, 1H), 4.84-4.73 (m, 1H), 4.57 (s, 2H), 4.20-4.10 (m, 1H), 4.08 (d, J=7.6 Hz, 4H), 4.02-3.94 (m, 1H), 3.44-3.28 (m, 2H), 2.70-2.57 (m, 1H), 2.25-2.12 (m, 1H), 2.08-1.90 (m, 2H), 1.90-1.77 (m, 1H), 1.05 (s, 6H).

Example 45: Preparation of (S)-2-(1-(4-(5-(5-amino-5,7-dihydrospiro[cyclopenta[b]pyridine-6,4'-piperidin]-1'-yl)pyrazin-2-ylthio)-3-chloropyridin-2-yl)azetidin-3-yl)propan-2-ol (Compound 103)

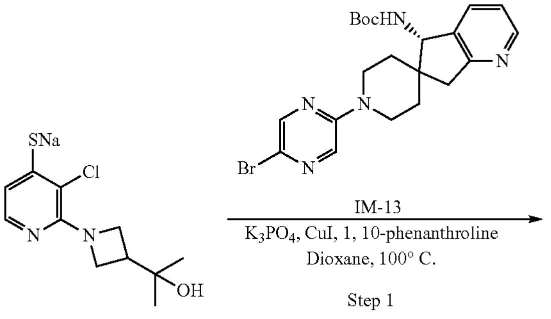

12-3

-continued

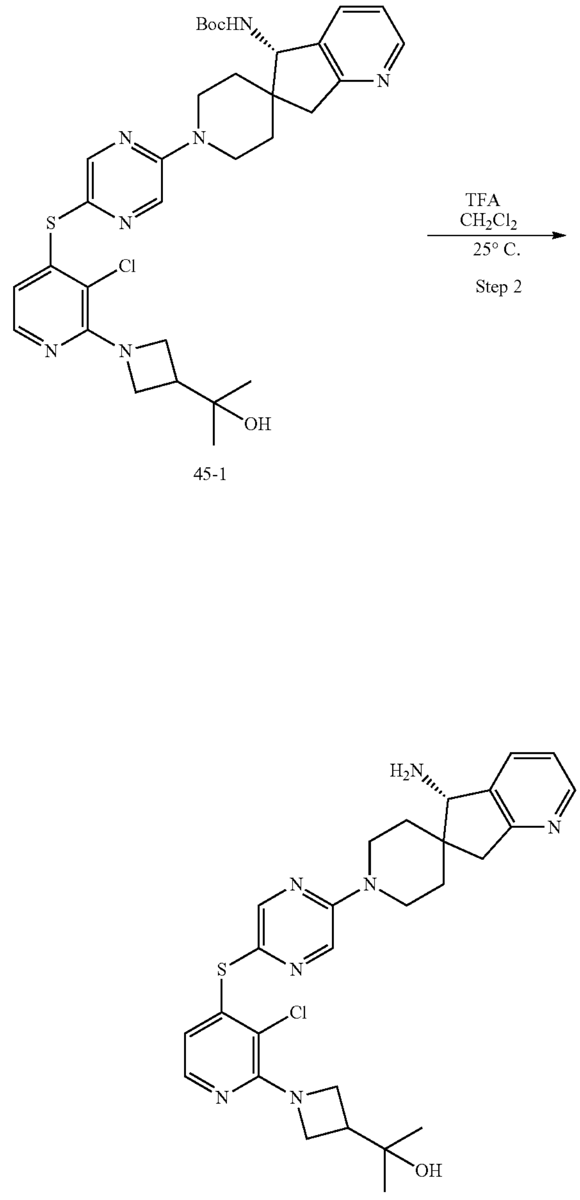

45-1

103

A crude product of Compound 103 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 103.

MS (ESI): m/z 538.0 $[M+H]^+$.

$^1$H-NMR (400 MHz, $CD_3OD$): δ 8.64-8.54 (m, 1H), 8.41 (d, J=1.2 Hz, 1H), 8.33 (d, J=1.2 Hz, 1H), 7.98 (d, J=7.6 Hz, 1H), 7.59 (d, J=6.4 Hz, 1H), 7.42 (dd, J=7.6, 5.2 Hz, 1H), 6.14 (d, J=6.4 Hz, 1H), 4.64-4.32 (m, 7H), 3.52-3.30 (m, 4H), 2.88-2.78 (m, 1H), 1.95-1.75 (m, 3H), 1.74-1.65 (m, 1H), 1.20 (s, 6H).

Example 46: Preparation of (S)-2-(1-(4-(3-amino-5-(5-amino-5,7-dihydrospiro[cyclopenta[b]pyridine-6,4'-piperidin]-1'-yl)pyrazin-2-ylthio)-3-chloropyridin-2-yl)azetidin-3-yl)propan-2-ol (Compound 115)

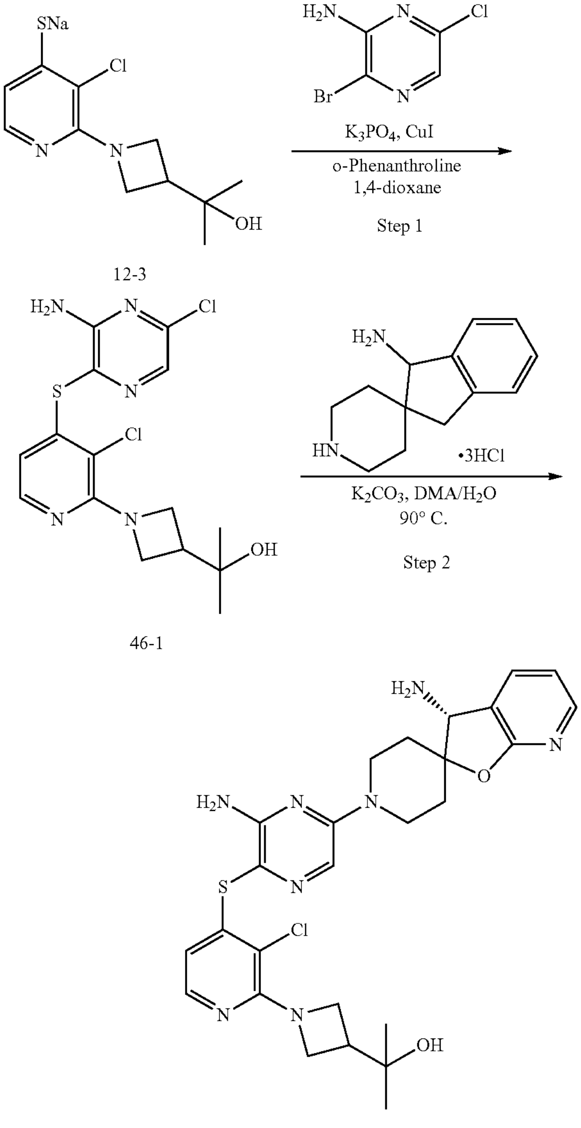

12-3

46-1

115

A crude product of Compound 115 was synthesized by similar methods described in Example 36. The crude product was purified by Pre-TLC (MeOH/DCM=1:5, V/V) to afford Compound 115.

MS (ESI): m/z 553.0$[M+H]^+$.

$^1$H NMR (400 MHz, DMSO) δ 8.31 (d, J=4.0 Hz, 1H), 7.77 (d, J=5.2 Hz, 1H), 7.71-7.61 (m, 2H), 7.21-7.13 (m, 1H), 6.15 (s, 2H), 5.86 (d, J=5.6 Hz, 1H), 4.44 (s, 1H), 4.30-4.17 (m, 2H), 4.12-3.99 (m, 4H), 3.89 (s, 1H), 3.22-3.06 (m, 3H), 2.75 (d, J=16.4 Hz, 1H), 2.67-2.56 (m, 1H), 1.82-1.62 (m, 2H), 1.57-1.48 (m, 1H), 1.18-1.07 (m, 1H), 1.05 (s, 6H).

Example 47: Preparation of 1-(4-(5-((3S,4S)-4-amino-3-methyl-2-oxa-8-azaspiro[4.5]decan-8-yl)-6-(hydroxymethyl)pyrazin-2-ylthio)-3-chloropyridin-2-yl)-3-(hydroxymethyl)azetidine-3-carbonitrile (Compound 126)

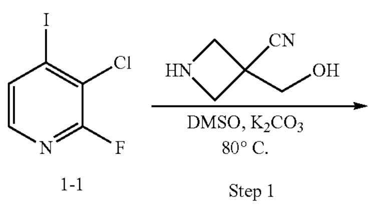

1-1

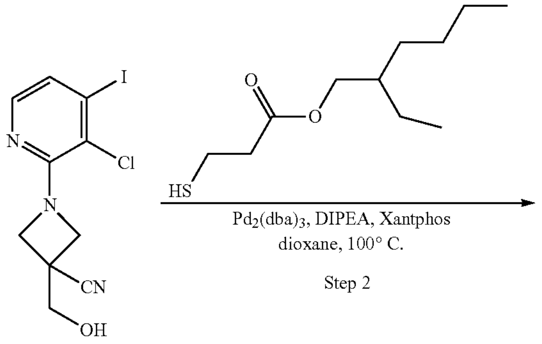

47-1

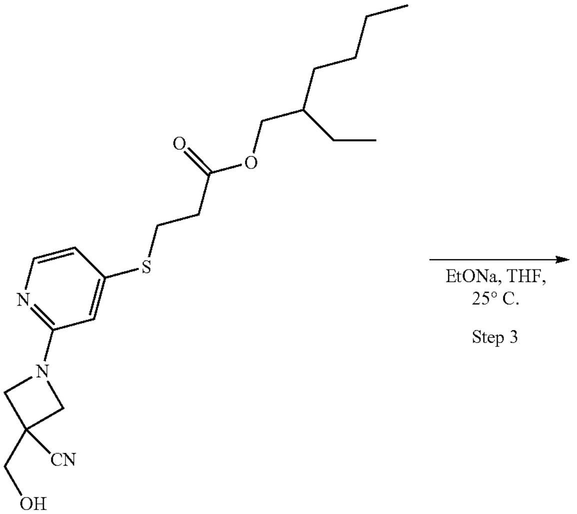

47-2

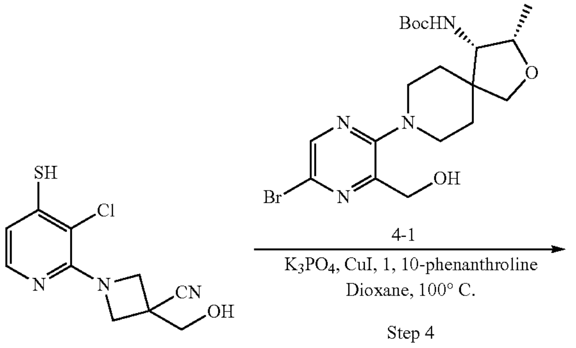

4-1

47-3

-continued

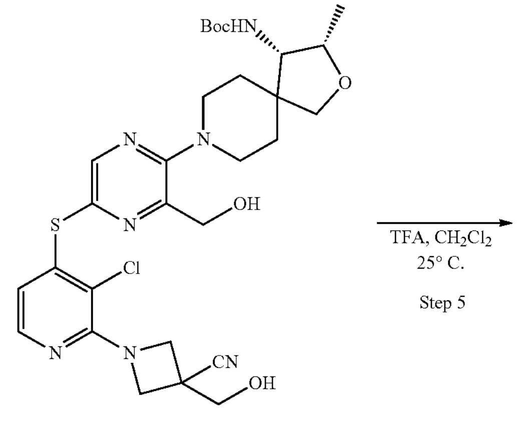

47-4

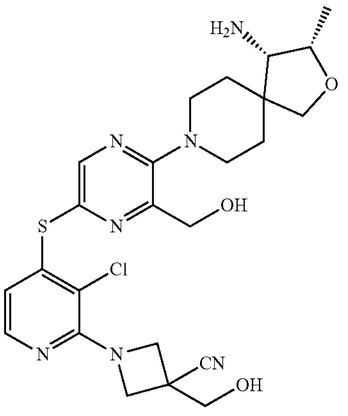

126

A crude product of Compound 126 was synthesized by similar methods described in Step 1 to Step 4 and Step 6 of Example 1, except that 3-(hydroxymethyl)azetidine-3-carbonitrile was used in Step 1 to replace 2-hydroxymethylpyrrolidine in Step 1 of Example 1 and that Compound 4-1 was used in Step 4 to replace Compound IM-1 in Step 4 of Example 1. The crude product was purified by HPLC (mobile phase A: acetonitrile, mobile phase B: 0.05% aqueous solution of trifluoroacetic acid) to afford a trifluoroacetate salt of Compound 126.

MS (ESI): m/z 532.0 $[M+H]^+$.

$^1$H-NMR (400 MHz, DMSO-$d_6$): δ 8.35 (s, 1H), 7.96 (s, 3H), 7.87 (d, J=5.6 Hz, 1H), 6.18 (d, J=5.6 Hz, 1H), 4.52 (s, 2H), 4.35 (d, J=8.4 Hz, 2H), 4.22 (d, J=8.8 Hz, 2H), 4.21-4.16 (m, 1H), 3.96-3.83 (m, 1H), 3.87 (d, J=8.8 Hz, 1H), 3.81 (s, 2H), 3.70 (d, J=8.8 Hz, 1H), 3.50-3.40 (m, 1H), 3.16-3.01 (m, 2H), 1.92-1.55 (m, 4H), 1.22 (d, J=6.4 Hz, 3H).

Example 48: Preparation of (1-(4-(5-((3S,4S)-4-amino-3-methyl-2-oxa-8-azaspiro[4.5]decan-8-yl)pyrazin-2-ylthio)-3-chloropyridin-2-yl)-3-fluoroazetidin-3-yl)methanol (Compound 138)

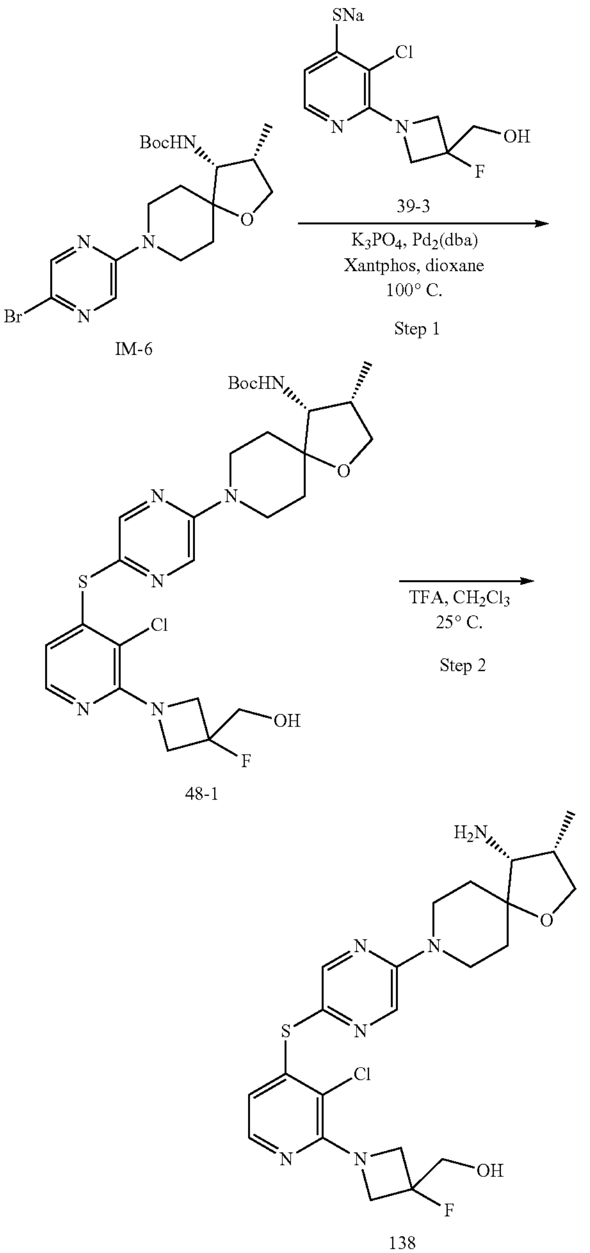

IM-6, 39-3, 48-1, 138

A crude product of Compound 138 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 138.

MS (ESI): m/z 495.0 $[M+H]^+$.

$^1$H-NMR (400 MHz, DMSO-$d_6$): δ 8.53 (s, 1H), 8.33 (s, 1H), 7.95 (s, 3H), 7.84 (d, J=5.6 Hz, 1H) 6.04 (d, J=5.2 Hz, 1H), 4.33-4.10 (m, 7H), 3.91-3.88 (m, 1H), 3.73-3.68 (m, 3H), 3.23-3.14 (m, 3H), 1.79-1.69 (m, 3H), 1.60-1.57 (m, 1H), 1.21 (d, J=6.8 Hz, 3H).

Example 49: Preparation of 2-(1-(4-(5-(4-amino-8-azadispiro[2.1.5.2]dodecan-8-yl)-6-(hydroxymethyl)pyrazin-2-ylthio)-3-chloropyridin-2-yl)azetidin-3-yl)propan-2-ol (Compound 139)

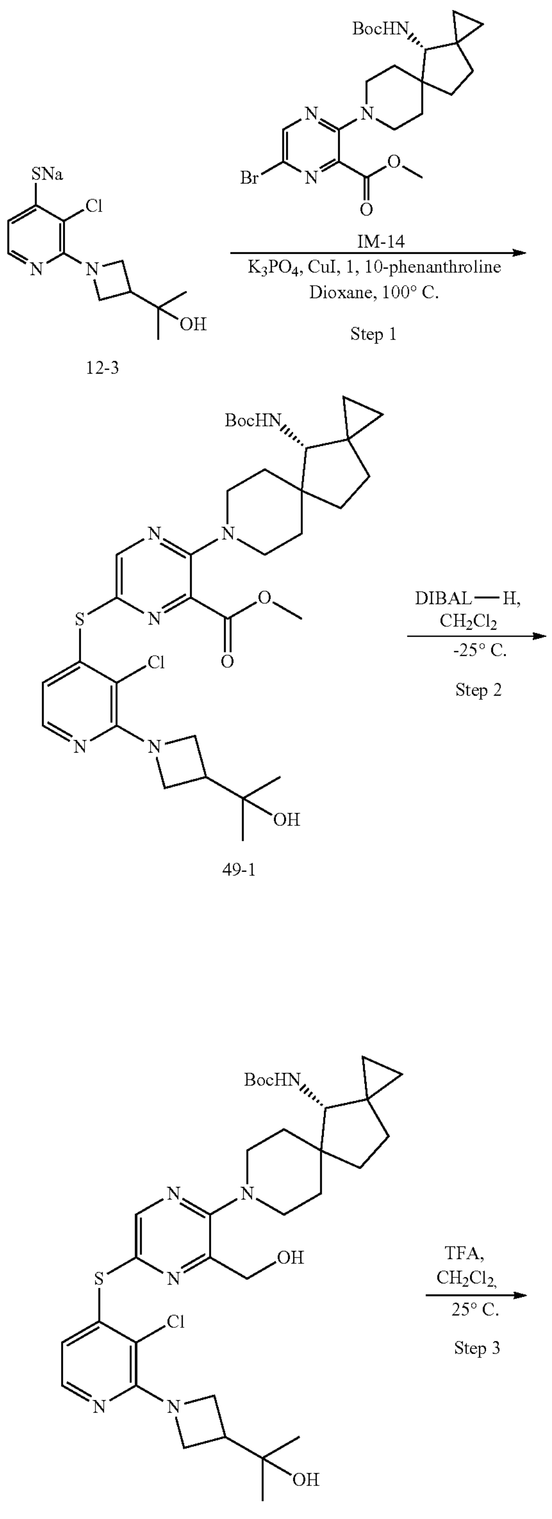

12-3, IM-14, 49-1, 49-2

-continued

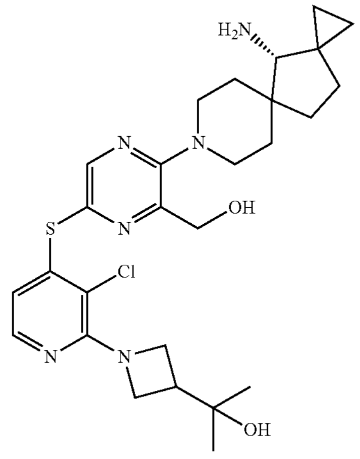

139

A crude product of Compound 139 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 139.

MS (ESI): m/z 545.0 $[M+H]^+$.

$^1$H-NMR (400 MHz, DMSO-$d_6$): δ 8.34 (s, 1H), 7.78 (d, J=5.2 Hz, 1H), 7.68 (brs, 3H), 6.01 (d, J=5.2 Hz, 1H), 4.52 (s, 2H), 4.07 (d, J=7.6 Hz, 4H), 3.90-3.70 (m, 2H), 3.35-3.24 (m, 1H), 3.22-3.12 (m, 1H), 2.94-2.82 (m, 1H), 2.66-2.58 (m, 1H), 2.05-1.70 (m, 6H), 1.66-1.50 (m, 2H), 1.05 (s, 6H), 1.00-0.90 (m, 1H), 0.84-0.73 (m, 1H), 0.64-0.53 (m, 1H), 0.53-0.45 (m, 1H).

Example 50: Preparation of (S)-2-(1-(4-(5-(5-amino-5,7-dihydrospiro[cyclopenta[b]pyridine-6,4'-piperidin]-1'-yl)-6-(hydroxymethyl)-3-methylpyrazin-2-ylthio)-3-chloropyridin-2-yl)azetidin-3-yl)propan-2-ol (Compound 140)

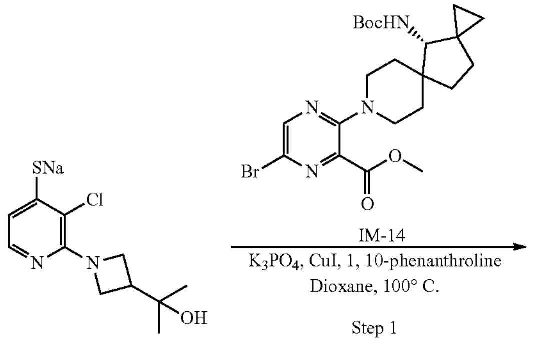

12-3

-continued

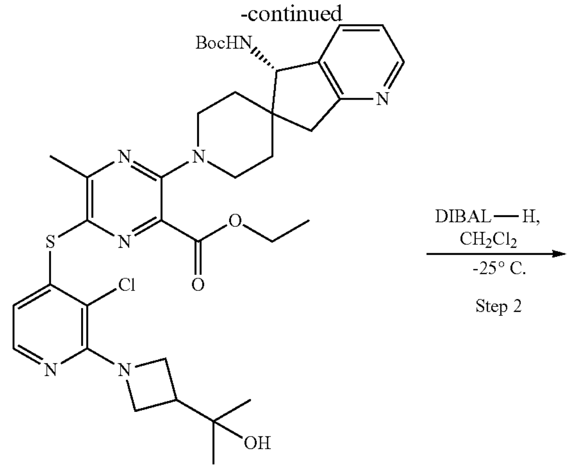

50-1

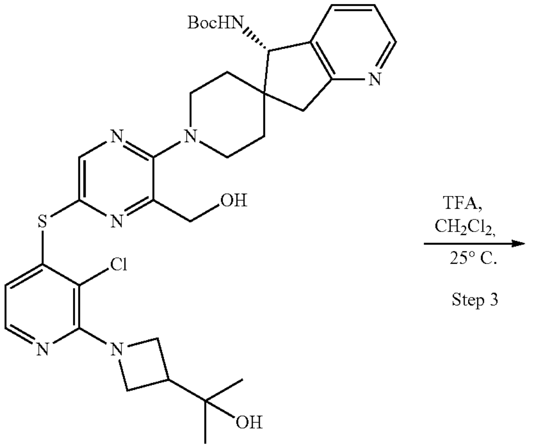

50-2

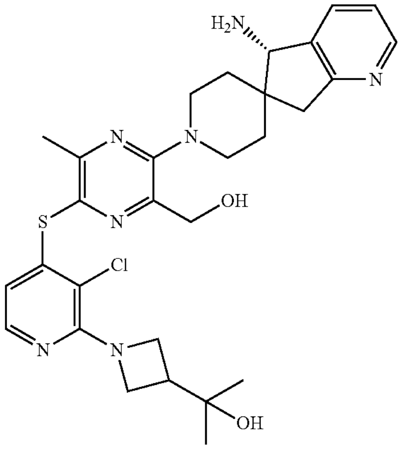

140

A crude product of Compound 140 was synthesized by similar methods described in Example 13. The crude product was purified by HPLC (mobile phase A: acetonitrile, mobile phase B: 0.05% aqueous solution of trifluoroacetic acid) to afford a trifluoroacetate salt of Compound 140.

MS (ESI): m/z 582.3 $[M+H]^+$.

$^1$H-NMR (400 MHz, DMSO-$d_6$): δ 8.55 (d, J=4.8 Hz, 1H), 8.38 (s, 3H), 7.93 (d, J=7.6 Hz, 1H), 7.77 (d, J=5.2 Hz, 1H), 7.37 (dd, J=4.8 Hz, 7.6 Hz, 1H), 5.87 (d, J=5.2 Hz, 1H), 4.50 (s, 3H), 4.10 (d, J=7.6 Hz, 2H), 4.06-3.92 (m, 2H), 3.28-3.20 (m, 3H), 3.12-3.08 (m, 1H), 2.66-2.59 (m, 1H), 252-2.50 (m, 2H), 2.42 (s, 3H), 1.92-1.83 (m, 2H), 1.64-1.55 (m, 2H), 1.05 (s, 6H).

Synthesis of Control Compounds 1 and 2 and TNO-155: Control Compound 1, Control Compound 2, and TNO-155 were synthesized with reference to the methods described in WO2019075265, WO2018013597, and WO2015107495, respectively.

Control Compound 1

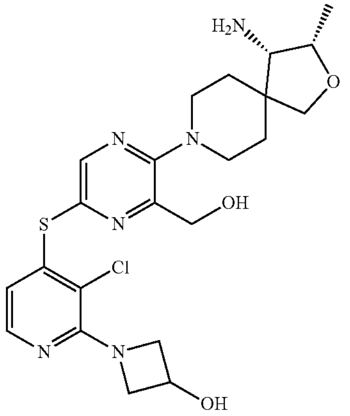

Control Compound 2

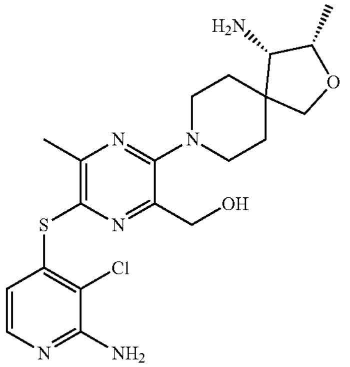

TNO-155

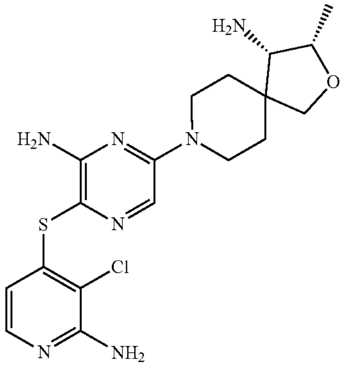

Test Example 1: Experiment on the Inhibition of In Vitro Enzyme Activity of SHP2 (Protein Phosphatase)

1. Experimental System:
   - phosphatase: recombinant full-length human PTPN11 (SHP2), active (SignalChem);
   - substrate: 6,8-difluoro-4-methylumbelliferyl phosphate (DiFMUP) (Invitrogen);
   - activating peptide: IRS1_pY1172(dPEG8)pY1222 (IRS1) (BPS Bioscience);
   - terminator: bpv(phen) (bpv) (Abcam).
2. Experimental Parameters:
   - SHP2 concentration: 0.5 nM;
   - DiFMUP concentration: 200 μM;
   - IRS-1 concentration: 0.5 μM;
   - bpv concentration: 160 μM;
   - buffer systems: 60 mM Hepes pH 7.2; 75 mM NaCl; 75 mM KCl; 0.05% surfactant P20; 1 mM EDTA; 5 mM DTT;
   - incubation duration of compound and enzyme: 60 minutes;
   - reaction time of enzyme and substrate: 30 minutes;
   - parameters for microplate reader: BMG PHERAstar fluorescence microplate reader at an excitation wavelength of 340 nm and an emission wavelength of 450 nm.
3. Experimental Steps:
   - Test group: A mixture of the test compound and the phosphatase SHP2 together with the activating peptide IRS-1 were incubated in the buffer system at room temperature for 60 minutes. The substrate DiFMUP was added to initiate the reaction and incubated at room temperature for 30 minutes. Thereafter, bpv was added to terminate the reaction. The reaction plate was placed in the microplate reader, and the fluorescence intensities of the wells in the plate were measured using an endpoint assay.

Negative group: The experimental method for the negative group was the same as that for the test group, except that the test compound was substituted with 0.05% aqueous solution of DMSO.

Blank group: The experimental method for the blank group was the same as that for the test group, except that the test compound was substituted with 0.05% aqueous solution of DMSO and that SHP2 was not added.

4. Data Processing:
   - The relative inhibitory activity was calculated for the test group at each concentration based on the following equation: inhibition rate (%)=100%−(the fluorescence intensity of the test group−the fluorescence intensity of the blank group)/(the fluorescence intensity of the negative group−the fluorescence intensity of the blank group)×100%. The half maximal inhibitory concentration ($IC_{50}$) of the compound was calculated by fitting the curve according to the four-parameter logistic model.
5. Experimental Results:
   - The inhibitory effects of the compounds on the SHP2 activity were determined by the above-mentioned method, and the results were listed in Table 1.

TABLE 1

Experimental results of the inhibition of the SHP2 enzyme activity

| Group | $IC_{50}$ (nM) |
|---|---|
| Example 1 | 6.03 |
| Example 2 | 1.82 |
| Example 3 | 3.48 |
| Example 4 | 4.10 |
| Example 5 | 1.22 |
| Example 6 | 1.76 |
| Example 7 | 4.60 |
| Example 8 | 0.88 |
| Example 9 | 1.30 |
| Example 10 | 1.22 |

TABLE 1-continued

| Experimental results of the inhibition of the SHP2 enzyme activity | |
|---|---|
| Group | $IC_{50}$ (nM) |
| Example 11 | 9.30 |
| Example 12 | 2.50 |
| Example 13 | 4.90 |
| Example 15 | 2.40 |
| Example 16 | 1.00 |
| Example 17 | 2.50 |
| Example 18 | 1.90 |
| Example 19 | 1.50 |
| Example 20 | 6.90 |
| Example 21 | 1.15 |
| Example 22 | 4.30 |
| Example 23 | 1.90 |
| Example 25 | 7.00 |
| Example 26 | 0.70 |
| Example 27 | 4.10 |
| Example 28 | 2.45 |
| Example 29 | 1.68 |
| Example 30 | 4.00 |
| Example 32 | 3.70 |
| Example 33 | 4.10 |
| Example 37 | 2.40 |
| Example 38 | 5.30 |
| Example 39 | 1.40 |
| Example 40 | 4.13 |
| Example 41 | 8.40 |
| Example 42 | 10.19 |
| Example 43 | 2.60 |
| Example 44 | 2.49 |
| Example 45 | 4.10 |
| Example 46 | 2.60 |
| Example 47 | 3.20 |
| Example 48 | 2.20 |
| Example 49 | 2.30 |
| Example 50 | 4.84 |

6. Conclusions:

In the experiment on the inhibition of the SHP2 enzyme activity, the compounds of the present disclosure exhibited a strong inhibitory activity.

Test Example 2: Experiment on the Inhibition of the Proliferation Activity of KYSE-520 Cell (Human Esophageal Squamous Cell Carcinoma Cell)

1. Experimental System:

cell: KYSE-520 (JCRB Cell Bank);

kit: CellTiter-Glo® Luminescent Cell Viability Assay Kit (Promega).

2. Experimental Parameters:

inoculation amount of cell: 1500 cells/well;

plating medium: KYSE-520: 1640+10% FBS;

dosing medium: KYSE-520: 1640+10% FBS;

incubation conditions for compound: 37° C., 5% $CO_2$;

incubation duration: 5 days;

detecting temperature: room temperature;

chemiluminescence detection using the BMG PHERAstar FS reader.

3. Experimental Steps:

Cells were cultured in a medium containing 10% fetal bovine serum under the culture conditions of 37° C. and 5% $CO_2$. An appropriate amount of cells were plated into a 96-well plate and cultured overnight in an incubator to allow the cells to adhere to the wall. The following day, the medium was removed and a complete medium containing a pre-diluted compound was added and incubated at 37° C. for 5 days. On the fifth day, the detection reagent CellTiter-Glo® was added into each well. Chemiluminescence was adopted to detect the relative luminescence units (RLUs) of the wells.

4. Data Processing:

The result of a well containing cell-free medium, treated with CellTiter-Glo®, was obtained as the blank value. Cell viability (%)=(sample RLU−blank RLU)/(vehicle RLU−blank RLU)×100%, and maximum inhibition rate (%)=100%−cell viability$_{max.\ conc.}$ (%). The half maximal inhibitory concentration ($IC_{50}$) of the compound was calculated by fitting the curve according to the four-parameter logistic model.

5. Experimental Results:

The inhibitory activities of the compounds of the present disclosure against KYSE-520 cell proliferation were determined by the above-mentioned method, and the results were listed in Table 2.

TABLE 2

| Results of inhibitory effects of the compounds on KYSE-520 cell proliferation | |
|---|---|
| Example No. | KYSE-520, $IC_{50}$ (μM) |
| Example 1 | 0.36 |
| Example 2 | 0.10 |
| Example 3 | 1.14 |
| Example 4 | 0.17 |
| Example 5 | 0.06 |
| Example 6 | 0.04 |
| Example 7 | 0.77 |
| Example 8 | 0.03 |
| Example 9 | 0.22 |
| Example 10 | 0.04 |
| Example 12 | 0.04 |
| Example 15 | 0.04 |
| Example 16 | 0.04 |
| Example 17 | 0.03 |
| Example 18 | 0.24 |
| Example 19 | 0.19 |
| Example 21 | 0.11 |
| Example 22 | 0.05 |
| Example 23 | 0.14 |
| Example 26 | 0.03 |
| Example 27 | 0.06 |
| Example 29 | 0.04 |
| Example 33 | 0.09 |
| Example 39 | 0.02 |
| Example 42 | 0.10 |
| Example 43 | 0.04 |
| Example 44 | 0.05 |
| Example 45 | 0.21 |
| Example 46 | 0.07 |
| Example 47 | 0.04 |
| Example 48 | 0.64 |
| Example 49 | 0.27 |

6. Conclusions:

The compounds of the present disclosure had a strong cell proliferation inhibitory activity against the KYSE-520 cells.

Test Example 3: Biochemical Assay for hERG Inhibition

1. Experimental System:

kit: Predictor™ hERG Fluorescence Polarization Assay Kit (ThermoFisher) containing:

Compound E4031 as a positive control;

hERG cell membrane;

affinity tracer; and hERG buffer.

2. Experimental Parameters:

hERG concentration: 1×;

tracer concentration: 1 nM;

incubation duration: 2 hours;

parameters for microplate reader: BMG PHERAstar FS fluorescence microplate reader.

3. Experimental Steps:

Test group: The test compounds at different concentrations were added into a microplate containing hERG cell membrane, and the tracer with a high affinity for hERG was then added into each well. The microplate was incubated at 25° C. for 2 hours before detection of the change in fluorescence polarization value (mP) (excitation wavelength: 540 nm; emission wavelength: 590 nm) using a multi-mode microplate reader.

Positive control group: The experimental method for the positive control group was the same as that for the test group, except that the test compound was replaced with 30 μM Compound E4031.

Blank control group: The experimental method for the blank control group was the same as that for the test group, except that the test compound was replaced with the hERG buffer and that the hERG cell membrane was not added.

4. Data Processing:

Based on the data ratios, the percentage inhibition (%) of the compounds of the present disclosure against hERG at different concentrations was calculated and the range of the half maximal inhibitory concentration ($IC_{50}$) of the compounds was determined. Percentage inhibition (%)=(1−(mP of the test compound−mP of the positive control group)/(mP of the blank control group−mP of the positive control group))×100%.

5. Experimental Results:

The inhibition of the compounds of the present disclosure against hERG was determined by the above-mentioned method, and the results were listed in Table 3.

TABLE 3

Results of hERG inhibition assay

| Example No. | $IC_{50}$ (μM) |
|---|---|
| Example 2 | >10 |
| Example 4 | >10 |
| Example 7 | >10 |
| Example 9 | >10 |
| Example 12 | >10 |
| Example 13 | >10 |
| Example 15 | >10 |
| Example 18 | >10 |
| Example 19 | >10 |
| Example 25 | >10 |
| Example 26 | >10 |
| Example 27 | >10 |
| Example 28 | >10 |
| Example 29 | >10 |
| Example 30 | >10 |
| Example 39 | >10 |
| Example 40 | >10 |
| Example 42 | >10 |
| Example 46 | >10 |
| Example 47 | >10 |
| Example 48 | >10 |

6. Conclusions:

The experimental results showed that the compounds of the present disclosure had low affinity for hERG, and had an $IC_{50}$ of greater than 10 NM for competition with the affinity tracer.

Test Example 4: Experiment on the Inhibition of the Proliferation Activity of NCI-H358 Cell (Human Non-Small Cell Lung Cancer Cell)

1. Experimental System:

cell: NCI-H358 (Nanjing CoBioer);

kit: CellTiter-Glo® Luminescent Cell Viability Assay Kit (Promega).

2. Experimental Parameters:

inoculation amount of cell: 1500 cells/well;

plating medium: NCI-H358: 1640+10% FBS;

dosing medium: NCI-H358: 1640+10% FBS;

incubation conditions for compounds: 37° C., 5% $CO_2$;

incubation duration: 5 days;

detecting temperature: room temperature;

chemiluminescence detection using the BMG PHERAstar FS reader.

3. Experimental Steps:

Cells were cultured in a medium containing 10% fetal bovine serum under the culture conditions of 37° C. and 5% $CO_2$. An appropriate amount of cells were plated into a 96-well plate and cultured overnight in an incubator to allow the cells to adhere to the wall. The following day, the medium was removed and a complete medium containing a pre-diluted compound was added and incubated at 37° C. for 5 days. On the fifth day, the detection reagent CellTiter-Glo® was added into each well. Chemiluminescence was adopted to detect the relative luminescence units (RLUs) of the wells.

4. Data Processing:

The result of a well containing cell-free medium, treated with CellTiter-Glo®, was obtained as the blank value. Cell viability (%)=(sample RLU−blank RLU)/(vehicle RLU−blank RLU)×100%, and maximum inhibition rate (%)=100%−cell viability$_{max.\ conc.}$ (%). The half maximal inhibitory concentration ($IC_{50}$) of the compound was calculated by fitting the curve according to the four-parameter logistic model.

5. Experimental Results:

The inhibitory activities of the compounds of the present disclosure against NCI-H358 cell proliferation were determined by the above-mentioned method, and the results were listed in Table 4.

TABLE 4

Results of inhibitory effects of the compounds on NCI-H358 cell proliferation

| Example No. | NCI-H358, $IC_{50}$ (μM) |
|---|---|
| Example 2 | 0.040 |
| Example 5 | 0.034 |
| Example 6 | 0.074 |
| Example 12 | 0.018 |
| Example 13 | 0.260 |
| Example 15 | 0.040 |
| Example 17 | 0.039 |
| Example 19 | 0.220 |
| Example 21 | 0.030 |
| Example 22 | 0.031 |
| Example 23 | 0.005 |
| Example 25 | 0.150 |
| Example 26 | 0.032 |
| Example 27 | 0.030 |
| Example 28 | 0.130 |
| Example 29 | 0.040 |
| Example 40 | 0.030 |
| Example 42 | 0.044 |
| Example 43 | 0.008 |

TABLE 4-continued

| Results of inhibitory effects of the compounds on NCI-H358 cell proliferation | |
|---|---|
| Example No. | NCI-H358, $IC_{50}$ (μM) |
| Example 44 | 0.050 |
| Example 46 | 0.028 |
| Example 47 | 0.023 |

6. Conclusions:

The experimental results showed that the compounds of the present disclosure had a strong cell proliferation inhibitory activity against the NCI-H358 cells.

Test Example 5: Biochemical Assay for CYP Enzyme (Cytochrome P450) Inhibition

1. Experimental System:

P450-Glo™ CYP1A2 Screening System, (Promega);
P450-Glo™ CYP2D6 Screening System, (Promega);
P450-Glo™ CYP3A4 Screening System, (Promega).

2. Test Instrument:

BMG PHERAstar FS Luminescent.

3. Experimental Method:

The experiments were carried out separately according to the instructions of the kits. The steps were as follows:

3.1. Inhibition Against CYP1A2:

Test group: The test compounds at different concentrations were added into a microplate, and Luciferin-ME (100 μM), $K_3PO_4$ (100 mM), and CYP1A2 (0.01 μmol/μL) were added into each well, and pre-incubated at room temperature for 10 min. Thereafter, an NADPH regeneration system was added. The mixture was reacted at room temperature for 30 min. Finally, an equal volume of detection buffer was added and incubated at room temperature for 20 min, followed by chemiluminescence detection.

Negative control group: The experimental method for the negative control group was the same as that for the test group, except that the test compound was not added.

Blank control group: The experimental method for the blank control group was the same as that for the test group, except that the test compound was not added and that CYP1A2 was replaced with CYP1A2 Membrance (0.01 μmol/μL).

3.2. Inhibition Against CYP2D6:

Test group: The test compounds at different concentrations were added into a microplate, and Luciferin-ME EGE (3 μM), $K_3PO_4$ (100 mM), and CYP2D6 (5 nM) were added into each well, and pre-incubated at room temperature for 10 min. Thereafter, an NADPH regeneration system was added. The mixture was reacted at 37° C. for 30 min. Finally, an equal volume of detection buffer was added and incubated at room temperature for 20 min, followed by chemiluminescence detection.

Negative control group: The experimental method for the negative control group was the same as that for the test group, except that the test compound was not added.

Blank control group: The experimental method for the blank control group was the same as that for the test group, except that the test compound was not added and that CYP2D6 was replaced with CYP2D6 Membrance (5 nM).

3.3. Inhibition Against CYP3A4:

Test group: The test compounds at different concentrations were added into a microplate, and Luciferin-IPA (3 NM), $K_3PO_4$ (100 mM), and CYP3A4 (2 nM) were added into each well, and pre-incubated at room temperature for 10 min. Thereafter, an NADPH regeneration system was added. The mixture was reacted at room temperature for 30 min. Finally, an equal volume of detection buffer was added and incubated at room temperature for 20 min, followed by chemiluminescence detection.

Negative control group: The experimental method for the negative control group was the same as that for the test group, except that the test compound was not added.

Blank control group: The experimental method for the blank control group was the same as that for the test group, except that the test compound was not added and that CYP3A4 was replaced with CYP3A4 Membrance (2 nM).

4. Data Processing:

Percentage inhibition=(1−(the chemiluminescent signal value of the test compound group at a certain test concentration−the chemiluminescent signal value of the blank control group)/(the chemiluminescent signal value of the negative control group−the chemiluminescent signal value of the blank control group))×100%.

When the percentage inhibition was between 30% and 80%, a single value or a value range of the half maximal inhibitory concentration ($IC_{50}$) of the compound against the CYP enzyme was estimated based on the following equation: $IC_{50}$=X×(1−percentage inhibition)/percentage inhibition, wherein X was the test concentration of the compound.

5. Experimental Results:

The inhibition of the compounds of the present disclosure against three types of CYPs was determined by the above-mentioned methods, and the results were listed in Table 5 below.

TABLE 5

Results of CYPs inhibition assay

| | $IC_{50}$ (μM) | | |
|---|---|---|---|
| Example No. | CYP1A2 | CYP2D6 | CYP3A4 |
| Control Compound 1 | >10 | 6.96 | >10 |
| Example 1 | >10 | >10 | >10 |
| Example 2 | >10 | >10 | >10 |
| Example 5 | >10 | >10 | >10 |
| Example 6 | >10 | >10 | >10 |
| Example 12 | >10 | >10 | >10 |
| Example 13 | >10 | >10 | >10 |
| Example 15 | >10 | >10 | >10 |
| Example 17 | >10 | >10 | >10 |
| Example 19 | >10 | >10 | >10 |
| Example 21 | >10 | >10 | >10 |
| Example 22 | >10 | >10 | >10 |
| Example 23 | >10 | >10 | >10 |
| Example 25 | >10 | >10 | >10 |
| Example 26 | >10 | >10 | >10 |
| Example 27 | >10 | >10 | >10 |
| Example 28 | >10 | >10 | >10 |
| Example 29 | >10 | >10 | >10 |
| Example 40 | >10 | >10 | >10 |
| Example 42 | >10 | >10 | >10 |
| Example 43 | >10 | >10 | >10 |
| Example 46 | >10 | >10 | >10 |
| Example 47 | >10 | >10 | >10 |

6. Conclusions:

The above results showed that the compounds of the present disclosure had no obvious inhibitory effects on all of the three main CYP subtypes, suggesting their relatively low potential drug interactions, which was better than that of the Control Compound 1.

Test Example 6: Pharmacokinetic (PK) Studies in SD Rat

The compound of Example 12 and Control Compound 2 were administered to male SD rats by intravenous injection (IV) and gavage (PO) respectively to estimate the pharmacokinetic properties. Dosing amounts for IV and PO routes were 1 mg/kg and 5 mg/kg, respectively. The solvent for IV route was 5% DMSO+5% Solutol (polyoxyl 15-hydroxystearate)+90% Saline (physiological saline), and the solvent for PO route was 0.5% MC (sodium methylcellulose). Blood was collected at various time points after IV and PO administration. The blood was anticoagulated using EDTA.K2, and centrifuged to obtain plasma samples. The plasma samples were preserved at −80° C.

The plasma samples were subjected to protein precipitation and then to the LC-MS/MS analysis. WinNonlin 6.3 software was used to calculate the pharmacokinetic parameters by non-compartmental model, and the results were listed in Table 6 below.

TABLE 6

In vivo pharmacokinetic parameters of the compounds in blood of rats

| Example No. | Route of Adminis-tration | Dose mg/kg | $AUC_{last}$ h * ng/mL | Cl ml/min/kg | $C_{max}$ ng/mL |
|---|---|---|---|---|---|
| Example 12 | IV | 1 | 1688 | 9.80 | 373 |
| | PO | 5 | 9676 | / | 1113 |
| Control | IV | 1 | 696 | 24.6 | 215 |
| Compound 2 | PO | 5 | 2763 | / | 363 |

Note:
the sign "/" means that it is not yet available.

Conclusions: Under the conditions of a dosing amount of 1 mg/kg by injection and a dosing amount of 5 mg/kg by mouth, the compound of Example 12 of the present disclosure exhibited high exposure in the rat plasma, which was much higher than that of Control Compound 2, and its clearance was much lower than that of Control Compound 2. The compound of Example 12 showed excellent pharmacokinetic properties.

Test Example 7: Pharmacokinetic (PK) Studies in Balb/c Mouse

The compound of Example 12, Control Compound 1, Control Compound 2, and TNO-155 were administered to female Balb/c mice by intravenous injection (IV) and gavage (PO) respectively to estimate the pharmacokinetic properties. Dosing amounts for IV and PO routes were 1 mg/kg and 10 mg/kg, respectively. The solvent for IV route was 5% DMSO+5% Solutol+90% Saline, and the solvent for PO route was 0.5% MC (sodium methylcellulose). Blood was collected at various time points after IV and PO administration. The blood from the test groups of the compound of Example 12, Control Compound 1, and Control Compound 2 was anticoagulated using EDTA.K2 and preserved at −80° C. The blood from the test groups of TNO-155 was anticoagulated using EDTA.K2 and centrifuged to obtain plasma samples, and the plasma samples were preserved at −80° C.

The blood or plasma samples were subjected to protein precipitation and then to the LC-MS/MS analysis. WinNonlin 6.3 software was used to calculate the pharmacokinetic parameters by non-compartmental model, and the results were listed in Table 7 below.

TABLE 7

In vivo pharmacokinetic parameters of the compounds in blood of Balb/c mice

| Example No. | Route of Adminis-tration | Dose mg/kg | $AUC_{last}$ h * ng/mL | Cl ml/min/kg | $T_{1/2}$ h |
|---|---|---|---|---|---|
| Example 12 | IV | 1 | 2593 | 6.23 | / |
| | PO | 10 | 12277 | / | 7.13 |
| Control | IV | 1 | 2195 | 7.21 | / |
| Compound 1 | PO | 10 | 8694 | / | 4.61 |
| Control | IV | 1 | 576 | 23.2 | / |
| Compound 2 | PO | 10 | 3869 | / | 5.08 |
| TNO-155 | IV | 1 | 672 | 24 | |
| | PO | 10 | 7914 | / | 1.69 |

Note:
the sign "/" means that it is not yet available.

Conclusions: Under the conditions of a dosing amount of 1 mg/kg by injection and a dosing amount of 10 mg/Kg by mouth, the compound of Example 12 of the present disclosure exhibited high exposure in the systemic circulation of mice, low clearance, and long half-life, with comprehensive properties remarkably superior to those of Control Compound 1, Control Compound 2, and TNO-155. The compound of Example 12 showed excellent pharmacokinetic properties.

Test Example 8: Pharmacokinetic (PK) Studies in Beagle Dog

The compound of Example 12, Control Compound 1, Control Compound 2, and TNO-155 were administered to male beagle dogs by intravenous injection (IV) and gavage (PO) respectively to estimate the pharmacokinetic properties. Dosing amounts for IV and PO routes were 0.5 mg/kg and 2.5 mg/kg. The solvent for IV route was 5% DMSO+5% Solutol+90% Saline, and the solvent for PO route was 0.5% MC (sodium methylcellulose). Blood was collected at various time points after IV and PO administration. The blood was anticoagulated using EDTA.K2, and centrifuged to obtain plasma samples. The plasma samples were preserved at −80° C.

The plasma samples were subjected to protein precipitation and then to the LC-MS/MS analysis. WinNonlin 6.3 software was used to calculate the pharmacokinetic parameters by non-compartmental model, and the results were listed in Table 8 below.

TABLE 8

In vivo pharmacokinetic parameters of the compounds in blood of beagle dogs

| Example No. | Route of Adminis-tration | Dose mg/kg | $AUC_{last}$ h * ng/mL | Cl ml/min/kg | $T_{1/2}$ h |
|---|---|---|---|---|---|
| Example 12 | IV | 0.5 | 3092 | 2.31 | / |
| | PO | 2.5 | 10976 | / | 24.5 |
| Control | IV | 0.5 | 1215 | 7.08 | / |
| Compound 1 | PO | 2.5 | 3910 | / | 10.5 |
| Control | IV | 0.5 | 614 | 13.2 | / |
| Compound 2 | PO | 2.5 | 2547 | / | 12.3 |
| TNO-155 | IV | 0.5 | 2353 | 3.43 | / |
| | PO | 2.5 | 10098 | / | 13.2 |

Note:
the sign "/" means that it is not yet available.

Conclusions: Under the conditions of a dosing amount of 0.5 mg/kg by injection and a dosing amount of 2.5 mg/Kg by mouth, the compound of Example 12 of the present disclosure exhibited high exposure in beagle dog plasma and had long half-life and low clearance, with comprehensive properties superior to those of Control Compound 1, Control Compound 2, and TNO-155. The compound of Example 12 showed excellent pharmacokinetic properties.

Test Example 9: Experiment on Tumor Inhibition in KYSE-520 Xenograft Model

1. Experimental Purpose:
   A CDX xenograft animal model was established by subcutaneously inoculating KYSE-520 cells in nu-nu mice. After tumor formation, the mice were orally administered once daily to evaluate the in vivo drug efficacy of different test compounds.
2. Reagents for Experiment:

| Name | Manufacturer | Storage Condition |
|---|---|---|
| RPMI1640 medium | Hyclone | 4° C. |
| Trypsase | Hyclone | −20° C. |
| Mycoplasma Detection Kit | Shanghai Yise Medical Technology Co., Ltd. | 4° C. |

3. Experimental Method:
   The KYSE-520 cells were subjected to monolayer in vitro culture. The culture conditions were as follows: 10% fetal bovine serum was added into the RPMI 1640 medium, and the cells were cultured in an incubator at 37° C. in air containing 5% $CO_2$. The cells were digested twice a week with tryptase for passaging. When the cells were in exponential growth phase, the cells were harvested and counted. The KYSE-520 cell strains cultured to the logarithmic growth phase were prepared into a single cell suspension (the cells were resuspended in PBS and mixed with Matrigel Matrix Phenol Red-free at a ratio of 1:1, and the final concentration of the cells was $5\times10^7$/ml). Each of the nude mice was inoculated with 0.1 ml subcutaneously into the right axilla of the nude mice to establish a xenograft model of nude mice with esophageal cancer. When the tumors grew to 130 $mm^3$, the nude mice were randomly divided into 5 groups and administered. The dosage regime was as shown in Table 9 (once-daily oral administration for 21 consecutive days). The vehicle was 5% DMSO+5% Solutol+90% $H_2O$.

The animals were monitored daily for health and mortality. Routine inspections included observing the influences of drug treatment on the animals' daily behaviors, such as actions and activities, food (water) intake, physical signs, or other abnormalities, and recording them accordingly.

Mice were weighed and tumor volumes were measured twice a week, and the data were recorded. The tumor volume (V) was calculated by the following equation: $V=\frac{1}{2}\times a\times b^2$, wherein a and b indicated the length and width, respectively. The volumes of xenograft tumors in mice were as shown in FIG. 1.

The anti-tumor efficacy was evaluated by tumor growth inhibition TGI (%). When the tumor did not regress, TGI (%) (tumor volume)$=[1-(TV_t-TV_0)/(CV_t-CV_0)]\times100\%$, $TV_0$ being the mean tumor volume of the test compound group at the time of grouping, $TV_t$ being the mean tumor volume of the test compound group on Day t after administration; $CV_0$ being the mean tumor volume of the vehicle group at the time of grouping; and $CV_t$ being the mean tumor volume of the vehicle group on Day t after administration. When the tumor regressed, TGI (%) (tumor volume) $=100\%-(TV_t-TV_0)/TV_0\times100\%$.

4. Experimental Results:

TABLE 9

Efficacy of the test compounds in KYSE-520 cell xenograft model (calculated by the tumor volume)

| Group | Qty. (Piece) | Dosage Regime | TGI (%) | P Value |
|---|---|---|---|---|
| G1 | 8 | Vehicle group | — | — |
| G2 | 8 | TNO155 (10 mpk) | 55.49 | <0.05 |
| G3 | 8 | TNO155 (30 mpk) | 72.74 | <0.05 |
| G4 | 8 | Compound of Example 12 (10 mpk) | 81.28 | <0.05 |
| G5 | 8 | Compound of Example 12 (30 mpk) | 96.93 | <0.05 |

Note:
the sign means that it is not yet available;
P < 0.05 indicates a significant difference as compared to the vehicle group.

5. Experimental Conclusions:
   The above data showed that after oral administration for 21 consecutive days, the compound of Example 12 of the present disclosure had a remarkable tumor inhibitory effect, with drug efficacy better than that of the positive control TNO-155 administered at the same dose.

Test Example 10: Experiment on Tumor Inhibition in NCI-H358 Xenograft Model

1. Experimental Purpose:
   A subcutaneous xenograft mouse model was established by subcutaneously inoculating human non-small cell lung cancer cells NCI-H358 into the right scapulae of Balb/c-nu mice. After tumor formation, the mice were orally administered to evaluate the in vivo drug efficacy of different test compounds.
2. Reagents for Experiment:

| Name | Manufacturer | Storage Condition |
|---|---|---|
| RPMI1640 medium | Hyclone | 4° C. |
| Trypsase | Hyclone | −20° C. |
| Mycoplasma Detection Kit | Shanghai Yise Medical Technology Co., Ltd. | 4° C. |

3. Experimental Method:
   The NCI-H358 cells were subjected to monolayer in vitro culture. The culture conditions were as follows: 10% fetal bovine serum was added into the RPMI 1640 medium, and the cells were cultured in an incubator at 37° C. in air containing 5% $CO_2$. The cells were digested twice/trice a week with pancreatin-EDTA for passaging. When the cells were in exponential growth phase, the cells were harvested, counted, and inoculated.

Before inoculated with tumor cells, the experimental mice were identified sequentially with numbered ear spikes specific to mice.

Every of the mice were subcutaneously inoculated with $1\times10^6$ NCI-H358 cells (suspended in 0.1 ml PBS+Matrigel Matrix) into the right scapulae. It was predicted that the mean tumor volume on Day 7 would be ~200 $mm^3$. Based on the measurement results on Day 7, thirty mice with regular shapes and uniform volumes of tumor were screened, randomly divided into 5 groups and administered according to the experimental scheme (the dosing regimen was as shown in Table 10 (lasting for 21 days)). The vehicle was 5% DMSO+5% Solutol+90% $H_2O$.

Figure 2:
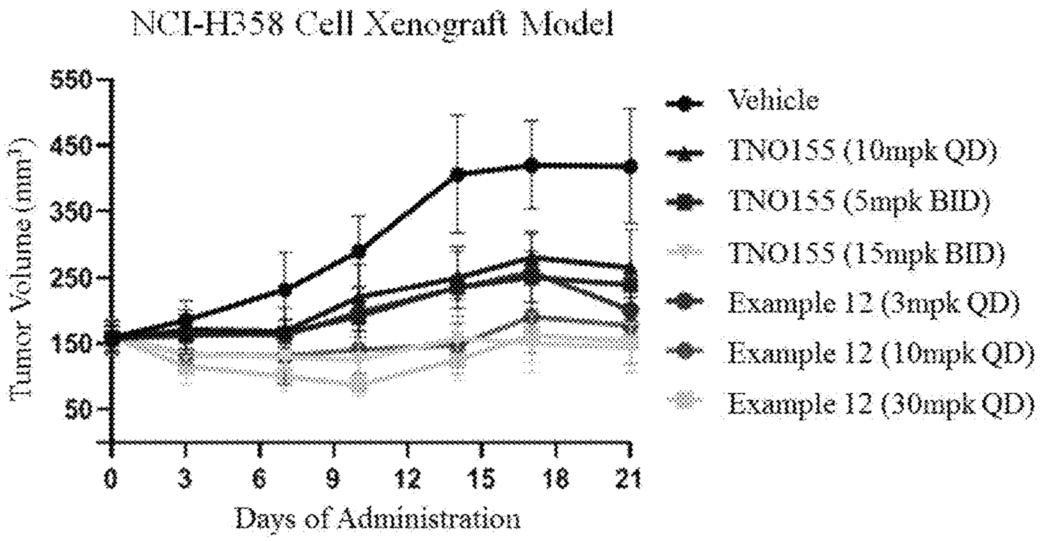
FIG. 2 shows the comparison of in vivo drug efficacy between positive control compound and compound of Example 12 in NCI-H358 cell xenograft model.

Mice were weighed and tumor volumes were measured trice a week, and the data were recorded. The tumor volume (V) was calculated by the following equation: $V=\frac{1}{2}\times a\times b^2$, wherein a and b indicated the length and width, respectively. The volumes of xenograft tumors in mice were as shown in FIG. 2.

The anti-tumor efficacy was evaluated by tumor growth inhibition TGI (%). When the tumor did not regress, TGI (%) (tumor volume)=$[1-(TV_t-TV_0)/(CV_t-CV_0)]\times100\%$, $TV_0$ being the mean tumor volume of the test compound group at the time of grouping, $TV_t$ being the mean tumor volume of the test compound group on Day t after administration; $CV_0$ being the mean tumor volume of the vehicle group at the time of grouping; and $CV_t$ being the mean tumor volume of the vehicle group on Day t after administration. When the tumor regressed, TGI (%) (tumor volume) $=100\%-(TV_t-TV_0)/TV_0\times100\%$.

If the tumor was smaller than its initial volume, i.e., $V_t<V_0$, it was defined as partial regression (PR) of the tumor. If the tumor disappeared completely, it was defined as complete regression (CR) of the tumor.

4. Experimental Results:

TABLE 10

Efficacy of the test compounds in NCI-H358 cell xenograft model (calculated by the tumor volume)

| Group | Qty. (Piece) | Dosage Regime | TGI (%) | P Value |
|---|---|---|---|---|
| G1 | 6 | Vehicle group | — | — |
| G2 | 6 | TNO155 (5 mpk/BID) | 68.59 | <0.05 |
| G3 | 6 | TNO155 (10 mpk/QD) | 58.49 | <0.05 |
| G4 | 6 | Compound of Example 12 (3 mpk/QD) | 84.35 | <0.05 |
| G5 | 6 | Compound of Example 12 (10 mpk/QD) | 93.14 | <0.05 |

Note:
the sign means that it is not yet available;
P < 0.05 indicates a significant difference as compared to the vehicle group;
BID indicates bis in die;
and QD indicates quaque die;
mpk indicates mg/kg.

5. Experimental Conclusions:

The above data showed that after oral administration for 21 consecutive days, the compound of Example 12 of the present disclosure had a remarkable tumor inhibitory effect, with drug efficacy better than that of the positive control TNO-155 administered at the same or higher dose.

Test Example 11: Kinase Selectivity Test

1. Experimental Purpose: Tests for selectivity of the compounds of the present disclosure for a plurality of kinases were carried out to assess the safety risk of the compounds of the present disclosure.

2. Test institution: ThermoFisher USA

3. Testing methods: LanthaScreen binding, Z'-LYTE, Adapta

4. Test targets: 100 targets in total

| Test Target | Test Target | Test Target | Test Target |
|---|---|---|---|
| ABL1 | JAK1 | RPS6KA4 (MSK2) | MAPK8 (JNK1) |
| AKT2 (PKB beta) | JAK2 | SGK (SGK1) | RAF1 (cRAF) Y340D Y341D |
| AKT3 (PKB gamma) | KDR (VEGFR2) | SRC | TTK |
| ALK | KIT | STK25 (YSK1) | WEE1 |
| AURKA (Aurora A) | LCK | SYK | ZAK |
| AXL | MAP4K4 (HGK) | TBK1 | DNA-PK |
| BTK | MAPK1 (ERK2) | TYRO3 (RSE) | DDR1 |
| CAMK4 (CaMKIV) | MAPK3 (ERK1) | YES1 | EPHA3 |
| CDK2/cyclin A | MAPKAPK2 | ZAP70 | DAPK2 |
| CHEKI (CHK1) | MARK2 | MAPK14 (p38 alpha) Direct | WNK3 |
| CHEK2 (CHK2) | MET (eMet) | CAMK1 (CaMK1) | ALKC1156Y |
| CSF1R (FMS) | NTRK1 (TRKA) | CDK7/cyclin H/MNAT1 | ALKLH96M |
| EGFR (ErbB1) | PDGFRA (PDGFR alpha) | CDK9/cyclin T1 | CASK |
| EGFR (ErbB1) T790M L858R | PHKG1 | DAPK1 | DYRK2 |
| ERBB2 (HER2) | PIM1 | PIK3CA/PIK3R1(p110 alpha/p85 alpha) | FGFR3 G697C |
| FGFR2 | PIM2 | NUAK1 (ARK5) | MAP4K1 (HPK1) |
| FGFR3 | PKN1 (PRK1) | PAK1 | KIT A829P |
| FGFR4 | PLK1 | BRAF | TNIK |
| FLT3 | PRKG1 | CDK8/cyclin C | AAK1 |
| FLT3 D835Y | PRKX | DMPK | ERN1 |
| FRAP1 (mTOR) | PTK2 (FAK) | MAP2K1 (MEK1) | MYO3A (MYO3 alpha) |
| GRK4 | RET | MAP2K2 (MEK2) | WNK1 |
| GSK3A (GSK3 alpha) | ROCK1 | MAP3K14 (NIK) | CDK6/cyclinD1 |
| GSK3B (GSK3 beta) | ROCK2 | MAP3K5 (ASK1) | AMPK (A1/B2/G2) |
| IGFIR | ROS1 | MAPK10 (JNK3) | CDK4/cyclinD1 |

5. Experimental Conclusions:

| | TNO-155 | | | Example 12 | | |
|---|---|---|---|---|---|---|
| | Inhibition (%) | | Inhibition (%) | Inhibition (%) | | Inhibition (%) |
| Target | Target 1 | Target 2 | Mean value | Target 1 | Target 2 | Mean value |
| EGFR (ErbB1) T790M L858R | 81 | 77 | 79 | 0 | 5 | 2 |
| FLT3 D835Y | 71 | 69 | 70 | 5 | 6 | 6 |
| FLT3 | 96 | 97 | 97 | 11 | 8 | 9 |
| GRK4 | 96 | 95 | 95 | 9 | 7 | 8 |
| GSK3A (GSK3 alpha) | 92 | 87 | 90 | 9 | 8 | 8 |
| GSK3B (GSK3 beta) | 96 | 96 | 96 | 7 | 7 | 7 |
| JAK2 | 61 | 57 | 59 | −7 | −2 | −4 |
| KDR (VEGFR2) | 73 | 73 | 73 | 3 | 4 | 3 |
| MAPKAPK2 | 106 | 107 | 106 | 31 | 27 | 29 |
| MET (cMet) | 42 | 40 | 41 | −1 | 16 | 7 |
| SGK (SGK1) | 62 | 57 | 60 | 1 | 2 | 1 |
| CAMK1 (CaMK1) | 55 | 46 | 51 | −9 | −16 | −12 |
| AAK1 | 49 | 46 | 48 | 3 | 0 | 1 |
| CDK8/ cyclin C | 89 | 89 | 89 | 7 | −3 | 2 |

The results showed that TNO-155 had a strong inhibitory effect on the above 14 kinase targets and a weak inhibitory effect on the remaining 86 targets; Example 12 had a weak inhibitory effect on all of the 100 kinase targets, indicating that Example 12 had good kinase selectivity and a low safety risk.

In conclusion, the present disclosure provides a series of highly active SHP2 phosphatase inhibitors with a novel structure, which show good drug efficacy in the KYSE-520 CDX mouse model and the NCI-1H358 CDX mouse model and have great potential for being developed into medications against tumor diseases.

In addition to the embodiments described herein, various modifications to the present disclosure will be apparent to those skilled in the art from the foregoing descriptions. Such modifications are also intended to fall within the scope of the appended claims. The reference literatures (including all patents, applications for patent, journals, books, and any other publications) cited in the present disclosure all are incorporated herein by reference in their entirety.

What is claimed is:

1. A compound having a structure of formula I or a pharmaceutically acceptable salt, ester, stereoisomer, tautomer, polymorph, solvate, isotope-labelled compound, metabolite, or prodrug thereof,

I

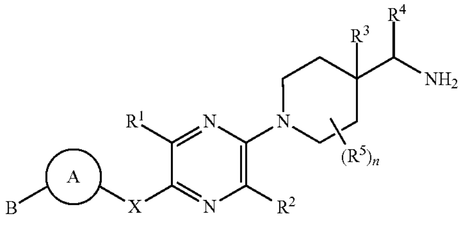

wherein

X is S;

$R^1$ is hydrogen;

$R^2$ is hydroxymethyl;

A is pyridinylene, wherein the pyridinylene is substituted by one chlorine

B is selected from the group consisting of

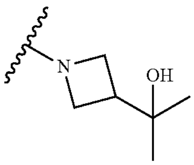
,
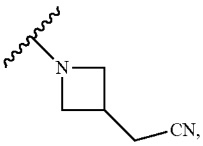

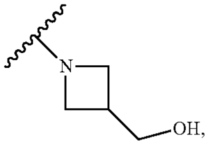

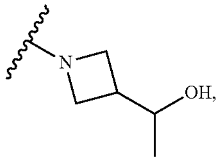

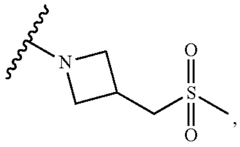
, and
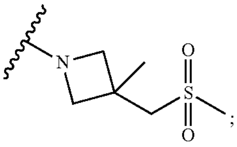
;

$R^3$ and $R^4$ together with the atoms to which they are linked form a ring,

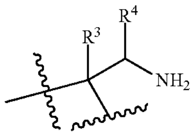

is

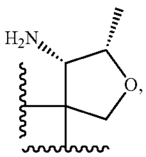

$R^5$ is hydrogen; and n is 1.

2. The compound or the pharmaceutically acceptable salt, ester, stereoisomer, tautomer, polymorph, solvate, isotope-labelled compound, metabolite, or prodrug thereof according to claim 1, wherein B is selected from the group consisting of

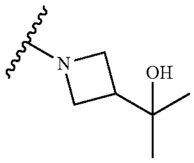
,
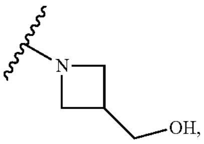
and

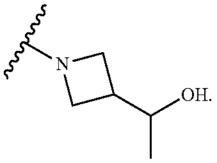

3. The compound or the pharmaceutically acceptable salt, ester, stereoisomer, tautomer, polymorph, solvate, isotope-labelled compound, metabolite, or prodrug thereof according to claim 1, wherein B is

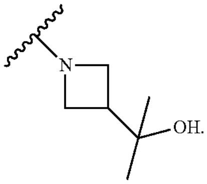 [SMILES: *N1CC(C(C)(C)O)C1]

4. A compound or a pharmaceutically acceptable salt, ester, stereoisomer, tautomer, polymorph, solvate, isotope-labelled compound, metabolite, or prodrug thereof, wherein the compound is one of the following compounds:

11

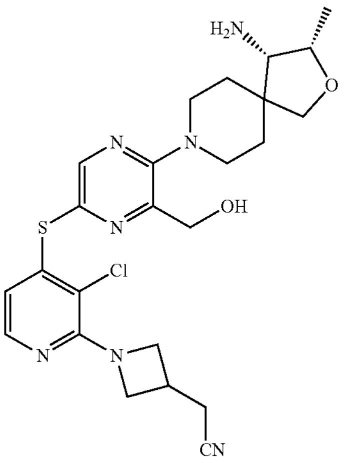

-continued

12

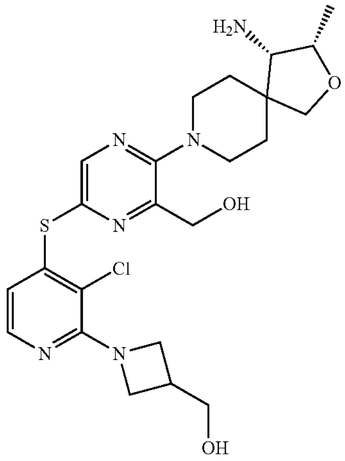

67

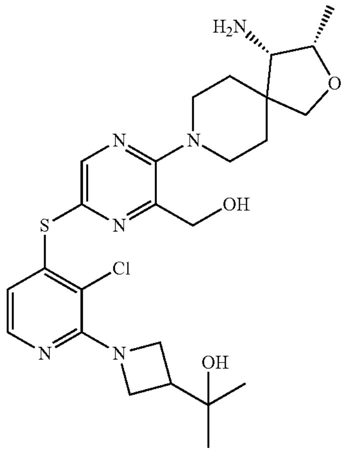

70

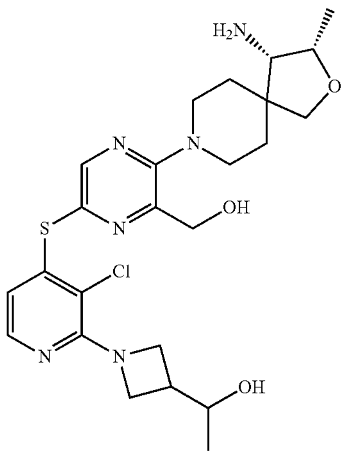

-continued

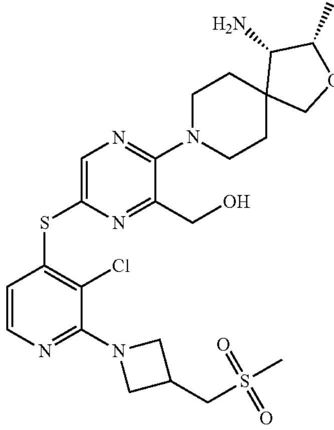

76

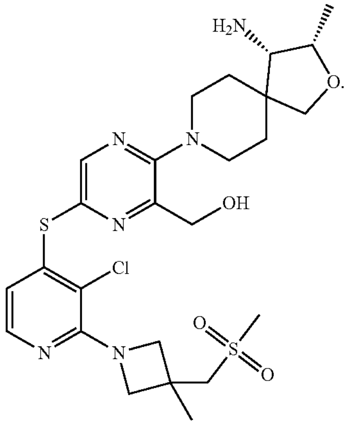

79

5. A pharmaceutical composition, comprising the compound or the pharmaceutically acceptable salt, ester, stereoisomer, tautomer, polymorph, solvate, isotope-labelled compound, metabolite, or prodrug thereof according to claim 1, and one or more pharmaceutically acceptable carriers.

6. A drug, comprising:

a) a container;

b) at least one of the compound or the pharmaceutically acceptable salt, ester, stereoisomer, tautomer, polymorph, solvate, isotope-labelled compound, metabolite, or prodrug thereof according to claim 1 held in the container; and c) an optional packaging and/or instruction.

7. A pharmaceutical composition, comprising the compound or the pharmaceutically acceptable salt, ester, stereoisomer, tautomer, polymorph, solvate, isotope-labelled compound, metabolite, or prodrug thereof according to claim 4, and one or more pharmaceutically acceptable carriers.

8. A drug, comprising:

a) a container;

b) at least one of the compound or the pharmaceutically acceptable salt, ester, stereoisomer, tautomer, polymorph, solvate, isotope-labelled compound, metabolite, or prodrug thereof according to claim 4 held in the container; and c) an optional packaging and/or instruction.

* * * * *